US012529062B2

(12) United States Patent
Price et al.

(10) Patent No.: US 12,529,062 B2
(45) Date of Patent: Jan. 20, 2026

(54) INIR12 TRANSGENIC MAIZE

(71) Applicant: INARI AGRICULTURE TECHNOLOGY, INC., Cambridge, MA (US)

(72) Inventors: Joshua L. Price, Cambridge, MA (US); Michael Andreas Kock, Rheinfelden (DE); Michael Lee Nuccio, Salem, NH (US); Frédéric Van Ex, Kortrijk (BE); Alexandra Elata, Arlington, MA (US); Daniel Rodriguez Leal, Belmont, MA (US)

(73) Assignee: INARI AGRICULTURE TECHNOLOGY, INC., Cambridge, MA (US)

( * ) Notice: Subject to any disclaimer, the term of this patent is extended or adjusted under 35 U.S.C. 154(b) by 369 days.

(21) Appl. No.: 17/806,435

(22) Filed: Jun. 10, 2022

(65) Prior Publication Data

US 2022/0364105 A1 Nov. 17, 2022

Related U.S. Application Data

(63) Continuation-in-part of application No. 17/303,116, filed on May 20, 2021, now Pat. No. 11,369,073, which is a continuation-in-part of application No. 17/302,739, filed on May 11, 2021, now Pat. No. 11,326,177, which is a continuation-in-part of application No. 17/248,936, filed on Feb. 12, 2021, now Pat. No. 11,359,210.

(60) Provisional application No. 63/199,949, filed on Feb. 4, 2021, provisional application No. 63/059,813, filed on Jul. 31, 2020, provisional application No. 63/059,916, filed on Jul. 31, 2020, provisional application No. 63/059,860, filed on Jul. 31, 2020, provisional application No. 63/059,963, filed on Jul. 31, 2020, provisional application No. 63/202,569, filed on Jun. 16, 2021.

(51) Int. Cl.
*C12N 15/82* (2006.01)
*A01H 6/46* (2018.01)

(52) U.S. Cl.
CPC ....... *C12N 15/8213* (2013.01); *A01H 6/4684* (2018.05)

(58) Field of Classification Search
CPC .......................... C12N 15/8213; A01H 6/4684
See application file for complete search history.

(56) References Cited

U.S. PATENT DOCUMENTS

| | | | |
|---|---|---|---|
| 6,825,400 B2 | 11/2004 | Behr et al. | |
| 7,956,246 B2 | 6/2011 | Bing et al. | |
| 8,232,456 B2 * | 7/2012 | Long | C12Q 1/6895 536/23.7 |
| 8,450,561 B2 | 5/2013 | Beazley et al. | |
| 8,455,720 B2 | 6/2013 | Long et al. | |
| 8,466,346 B2 | 6/2013 | Deframmond et al. | |
| 8,575,434 B2 | 11/2013 | Diehn et al. | |
| 8,680,363 B2 | 3/2014 | Bard et al. | |
| 9,187,756 B2 | 11/2015 | Nuccio | |
| 10,093,940 B2 | 10/2018 | Sastry-Dent et al. | |
| 10,538,774 B2 | 1/2020 | D'Halluin | |
| 11,041,172 B2 | 6/2021 | Cermak | |
| 11,326,177 B2 | 5/2022 | Price et al. | |
| 11,359,210 B2 | 6/2022 | Price et al. | |
| 11,369,073 B2 | 6/2022 | Price et al. | |
| 11,814,630 B2 | 11/2023 | Price et al. | |
| 2003/0088081 A1 | 5/2003 | Maliga | |
| 2010/0162428 A1 | 6/2010 | Brown | |
| 2013/0333071 A1 | 12/2013 | Boukharov et al. | |
| 2014/0162272 A1 | 6/2014 | Long et al. | |
| 2014/0196169 A1 | 7/2014 | D'Halluin et al. | |
| 2015/0059010 A1 | 2/2015 | Cigan et al. | |
| 2015/0082478 A1 | 3/2015 | Cigan et al. | |
| 2016/0333363 A1 | 11/2016 | Srivastava | |
| 2017/0166912 A1 | 6/2017 | Brower-Toland et al. | |
| 2018/0291386 A1 | 10/2018 | Chen et al. | |
| 2019/0112614 A1 | 4/2019 | Russell et al. | |
| 2019/0136249 A1 | 5/2019 | Sakai et al. | |
| 2019/0345512 A1 | 11/2019 | Moser et al. | |
| 2019/0352655 A1 | 11/2019 | Niu et al. | |

(Continued)

FOREIGN PATENT DOCUMENTS

| | | |
|---|---|---|
| CN | 104830860 B | 1/2018 |
| WO | 2018111553 A1 | 6/2018 |

(Continued)

OTHER PUBLICATIONS

Ward et al (Petition for Determination of Nonregulated Status for Insect-Resistant MIR 162 Maize. 1-268, Aug. 31, 2007) (Year: 2007).*

(Continued)

*Primary Examiner* — Wayne Zhong

(74) *Attorney, Agent, or Firm* — McKee, Voorhees & Sease, PLC

(57) ABSTRACT

Transgenic INIR12 maize plants comprising a vip3Aa19 or vip3Aa20 expression cassette linked to a secondary nopaline synthase terminator element which lack a selectable marker gene and/or which comprise modifications that provide for facile excision of the INIR12 transgenic locus from the maize plant genome are provided. Genomic DNA of INIR12 transgenic plants, detection of INIR12 plants and products thereof, methods of making INIR12 plants, and use of INIR12 plants to facilitate breeding are disclosed.

6 Claims, 14 Drawing Sheets

Figure 1:
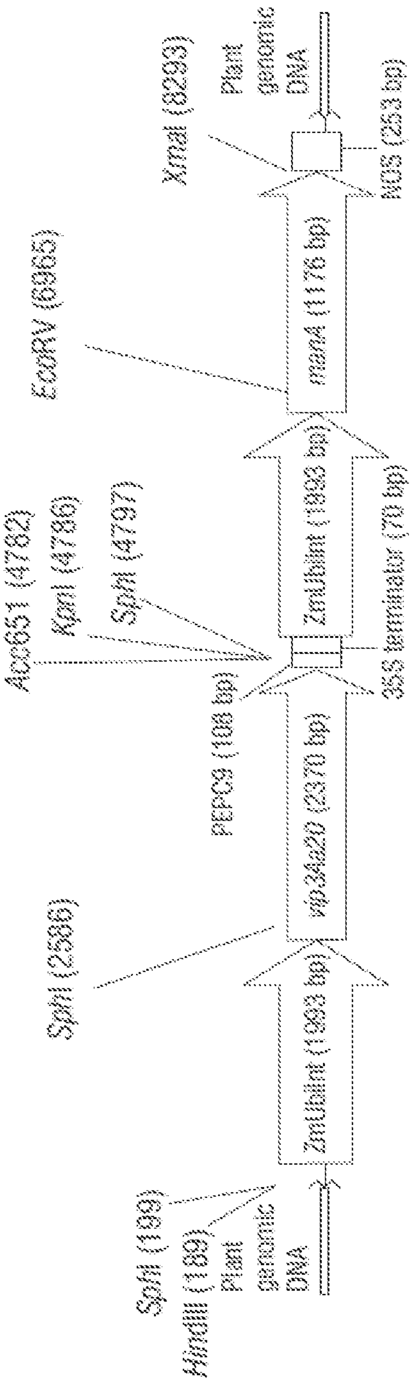

Specification includes a Sequence Listing.

(56) References Cited

U.S. PATENT DOCUMENTS

| | | | |
|---|---|---|---|
| 2020/0157554 A1 | 5/2020 | Cigan et al. |
| 2022/0251584 A1 | 8/2022 | Nuccio et al. |
| 2023/0265445 A1 | 8/2023 | Kock et al. |
| 2023/0313221 A1 | 10/2023 | Kock et al. |
| 2024/0011043 A1 | 1/2024 | Kock et al. |

FOREIGN PATENT DOCUMENTS

| | | |
|---|---|---|
| WO | 2019126627 A1 | 6/2019 |
| WO | 2022026375 A1 | 2/2022 |
| WO | 2022026379 A1 | 2/2022 |
| WO | 2022026390 A1 | 2/2022 |
| WO | 2022026395 A2 | 2/2022 |
| WO | 2022026554 A1 | 2/2022 |
| WO | 2023130031 A2 | 7/2023 |

OTHER PUBLICATIONS

Du et al (Construction of Marker-Free Genetically Modified Maize Using a Heat-Inducible Auto-Excision Vector. Genes, p. 1-17, 2019) (Year: 2019).*

Zhao et al (An alternative strategy for targeted gene replacement in plants using a dual-sgRNA/Cas9 design. Nature Scientific Report. 1-11, 2016) (Year: 2016).*

Zhao et al_2016_supplements (Year: 2016).*

Non-Final Office Action in U.S. Appl. No. 18/452,225, mailed Jun. 20, 2024, 42 pages.

Non-Final Office Action in U.S. Appl. No. 18/452,330, mailed Jun. 20, 2024, 44 pages.

Non-Final Office Action in U.S. Appl. No. 18/481,069, mailed Jun. 20, 2024, 21 pages.

Rudgers, G., "EXZACT Precision Technology: Scientific and Regulatory Advancements on Plant-Genome Editing with ZFNs," Dow AgroSciences, 2014, pp. 113-124.

Syngenta, "5307 Maize Syngenta Agrisure Duracade," Information for Operators, Updated Dec. 2020, 5 pages.

United States Environmental Protection Agency, "Non-PRIA Labeling and Formulation Amendment," Plant-Incorporated Protectant Label for Herculex RW Insect Protection, Sep. 25, 2015, 5 pages.

Du et al., "Construction of Marker-Free Genetically Modified Maize Using a Heat-Inducible Auto-Excision Vector", Genes, vol. 10, No. 374, pp. 1-17, 2019.

Stine, Harry H., "Request for Extension of Determination of Nonregulated Status to the Additional Regulated Article: Maize Line HCEM485", USDA Extension Petition (online), https://www.aphis.usda.gov/brs/aphisdocs/09_06301p_a3.pdf, pp. 1-3, Feb. 14, 2011.

U.S. Department of Agriculture, "BE Corn Crop Summary", USDA Report (online), https://www.ams.usda.gov/sites/defauiUfiles/media/BECornCropSummary.pdf, pp. 1-5, 2018.

International Searching Authority in connection with PCT/US21/43187 filed Jul. 26, 2021, "The International Search Report and the Written Opinion of the International Searching Authority, or the Declaration", 27 pages, mailed Jan. 6, 2022.

International Searching Authority in connection with PCT/US21/43161, Notification of Transmittal of the International Search Report and the Written Opinion of the International Searching Authority, or the Declaration, 23 pages, mailed Jan. 5, 2022.

U.S. Department of Agriculture, "Approval of AgrEvo Request (98-014-01p) Seeking Extension of Determination of Non-regulated Status for Glufosinate Resistant Soybean Transformation Event A5547-127", 6 pages Apr. 30, 1998.

U.S. Department of Agriculture, "Response to AgrEvo Petition 98-278-01p for Determination of Nonregulated Status for Canola Transformation Events MS8 and RF3 Genetically Engineered for Pollination Control and Tolerance to Glufosinate Herbicide", 4 pages Mar. 22, 1999.

U.S. Department of Agriculture, "Syngenta Petition 03-155-01p for Determination of Nonregulated Status for Lepitodopteran Resistant Cotton Event COT102", 3 pages May 2005.

Bortesi et al., "The CRISPR/Cas9 system for plant genome editing and beyond", Biotechnology Advances, vol. 33, pp. 41-52, Dec. 16, 2014.

Cho et al., "Nonallelic homologous recombination events responsible for copy number variation within an RNA silencing locus", Plant Direct, vol. 3, 16 pages, Aug. 5, 2019.

Luo et al., "Improperly Terminated, Unpolyadenylated mRNA of Sense Transgenes is Targeted by RDR6-Mediated RNA Silencing in *Arabidopsis*", The Plant Cell, vol. 19, pp. 943-958, Mar. 2007.

Srivastava et al., "Gene Stacking by recombinases", Plant Biotechnology Journal, vol. 14, pp. 471-482, 2016.

Xing et al., "Revealing frequent alternative polyadenylation and widespread low-level transcription read-through of novel plant transcription terminators", Plant Biotechnology Journal, vol. 8, pp. 772-782, 2010.

Young et al., "CRISPR-Cas9 Editing in Maize: Systematic Evaluation of Off-target Activity and Its Relevance in Crop Improvement", Scientific Reports, vol. 9, 11 pages, Apr. 15, 2019.

Ward, Dennis P., "Petition for Determination of Nonregulated Status for Insect-Resistant MIR162 Maize", Syngenta, pp. 1-268, Aug. 31, 2007.

Que et al., "Maize transformation technology development for commercial event generation", Frontiers in Plant Science, vol. 5, Article 379, pp. 1-19, 2014.

Begemann et al., "Precise insertion and guided editing of higher plant genomes using Cpf1 CRISPR nucleases," Scientific Reports Sep. 14, 2017, vol. 7, No. 11606, pp. 1-6.

Begemann et al., "Supplementary Data—Precise insertion and guided editing of higher plant genomes using Cpf1 CRISPR nucleases," Scientific Reports, Sep. 14, 2017, 18 pages.

Danilo et al., "The DFR locus: A smart landing pad for targeted transgene insertion in tomato," PLOS One, Dec. 6, 2018, vol. 13, No. 12, pp. 1-14.

Yau et al., "Less is more: strategies to remove marker genes from transgenic plants," BMC Biotechnology, 2013, vol. 13, No. 36, pp. 1-23.

Gleditzsch et al., "PAM identification by CRISPR-Cas effector complexes: diversified mechanisms and structures," RNA Biology, 2019, vol. 16, No. 4, pp. 504-517.

Gurusaran et al., "RepEx: Repeat extractor for biological sequences," Genomics, 2013, vol. 102, pp. 403-408.

International Search Report and Written Opinion in PCT/US2021/043192, mailed Jan. 27, 2022, 20 pages.

International Search Report and Written Opinion in PCT/US2021/043468, mailed Nov. 26, 2021, 15 pages.

International Search Report and Written Opinion in PCT/US21/43170, mailed Jan. 5, 2022, 20 pages.

Invitation to pay Additional Fees in PCT/US2022/82566, mailed Apr. 13, 2023, 4 pages.

Non-Final Office Action in U.S. Appl. No. 17/680,647, mailed Jun. 23, 2022, 11 pages.

Notice of Allowance in U.S. Appl. No. 17/680,647, mailed Apr. 27, 2023, 7 pages.

Shi et al., "ARGOS8 variants generated by CRISPR-Cas9 improve maize grain yield under field drought stress conditions," Plant Biotechnology Journal, 2017, vol. 15, pp. 207-216.

Srivastava et al., "Dual-targeting by CRISPR/Cas9 for precise excision of transgenes from rice genome," Plant Cell Tiss Organ Cult, Jan. 20, 2017, vol. 129, pp. 153-160.

Afzal et al., "Seed Production Technologies of Some Major Field Crops", 2019, 24 pages.

Gaudelli et al., "Programmable base editing of A-T to G-C in genomic DNA without DNA without DNA cleavage", vol. 551, Nov. 23, 2017, 24 pages.

Jacobs et al., "Targeted genome modifications in soybean with CRISPR/Cas9", BMC Biotechnology, 2015, 10 pages.

Official Journal of the European Union, Commission Implementing Decision (EU) 2017 | 2450, Dec. 21, 2017, 4 pages.

Kock, Michael Andreas, Non-Final Office Action from U.S. Appl. No. 18/007,019, mailed on Apr. 17, 2025, 198 pages.

(56) References Cited

OTHER PUBLICATIONS

Tang et al., "Class 2 CRISPR/Cas: an expanding biotechnology toolbox for and beyond genome editing", Cell & Bioscience, 2018, 13 pages.
Yau et al., "Less is more: strategies to remove marker genes from transgenic plants", BMC Biotechnology, 2013, 23 pages.
Cai et al., "CRISPR/Cas9-Mediated Deletion of Large Genomic Fragments in Soybean", International Journal of Molecular Sciences, 2018, 13 pages.
EFSA GMO Panel 2019, "Assessment of genetically modified maize Bt11×MIR162×MIR604×1507×5307×GA.21 and subcombinations, for food and feed uses, under Regulation (EC) No. 1829/2003 (application EFSA-GMO-DE-2011-103)", EFSA Journal, Feb. 27, 2019, 36 pages.
EFSA GMO Panel 2017, "Assessment of genetically modified maize 1507×59122×MON810×NK603 and subcombinations, for food and feed uses, under Regulation (EC) No. 1829/2003 (application EfSA-GMO-NL-2011-92)", EFSA Journal, Nov. 14, 2017, 29 pages.
Kock, Michael Andreas, Non-Final Office Action from U.S. Appl. No. 18/007,112, mailed on May 16, 2025, 167 pages.
Qi et al., "High-efficiency CRISPR/Cas9 multiplex gene editing using the glycine tRNA-processing system-based strategy in maize", BMC Biotechnology, 2016, 8 pages.

* cited by examiner

TACGTATACCTGCTGCAGCAGCATCTGCGTAAGCACAGCCTAGATATATGCTTCTGTGTGGACTGAAAGGAGACTT
TGTTTATCAATTAGTATACTCCCAAAAAACTGATGACACCAATGATGCAAATAGGCTGGGAATAGTCTGTCTAATA
GTTTGAGTGAATCATGTCACTGATAGTTTAAACTGAAGGCGGGAAACGACAATCTGATCATGAGCGGAGAATTAAG
GGAGTCACGTTATGACCCCCGCCGATGACGCGGGACAAGCCGTTTTACGTTTGGAACTGACAGAACCGCAACGTTG
AAGGAGCCACTCAGCAA

FIGURE 4

TCCTGTGTTGTTGGAACAGACTTCTGTCTCTTCTGGTGATCATAAATATTTAAATGAACCAGTTGTGTTGGAAAATG
TTGTTTTCTTTTGTCTCTAGACTGGAAAGCGGAGTTCTCGTCAACACGGTTCTTTCAACTAGGGATGAAAGTGGTAA
TCCGAATTGTTAGTACAAATTTAATATTTTAAAATAGATATGTATAAAATTTTATGTTGATCTTTTTTATGTTATCAA
GCACATTAGTATAAATTAGTATAAATATGAATAAAATATTACATAAAATGTTTTATGTATTATTTGGTCCCTACAACA
TAAATAGTTGAAAAAATTACTAAATTTGTTTTCGAATCTATATCGAAGTTTATATCTATTATTTAAGAAAAATATAGG
ATGAAAAGGTTTATCTTTTATGAATCTTTACAAGCTGGATCTTATAAACAAGAAAATAAATTTATATTGTAGATTTT
ATATCCTATTTATTCGCAATCAAAGAAAAGCGACTAAAAAACTGATTACCGAGTAAATACTGTTTCCAACCGTTTTC
GTCCCTACTATCAACGCCTTCTCCCAACCGCAGTCGATCTGTCCGTCTGTATCAGGCGCAGCGGCACCCCTGCTGTT
CGACTATCTAGACCATAGAATATTTTAGGTATACAATAATTTTAGTTCCACGCTAGAACATTTTAGTTAGAATAATA
ACAAGATTTGCTATTGATGTAGGACTCGCCCGTCACTGTCTAAAAAAGCATTCTGTCGGTCTTATTCTTTAGGCATC
AGCGGGTGTACTATCTCATTTTTCCTATCATATTCCTCAGTACTCTGTTAAGTATAAATGGTCTATTTTACATGATGA
ACTAATAAAACTAATTAAGGATCCTAACTTTTTGTGAAGGTAATTTGGATCATTATGCATTACCATCCTACGTATAC
CTGCTGCAGCAGCATCTGCGTAAGCACAGCCTAGATATATGCTTCTGTGTGGACTGAAAGGAGACTTTGTTTATCA
ATTAGTATACTCCCAAAAAACTGATGACACCAATGATGCAAATAGGCTGGGAATAGTCTGTCTAATAGTTTGAGTG
AATCATGTcactgatagtttaaactgaaggcgggaaacgacaatctgatcatgagcggagaattaagggagtcacgttatgaccccgccgatga
cgcgggacaagccgttttacgtttggaactgacagaaccgcaacgttgaaggagccactcagcaagctggtacaagcttgcatgcctgcagtgcagc
gtgacccggtcgtgcccctctctagagataatgagcattgcatgtctaagttataaaaaattaccacatattttttttgtcacacttgtttgaagtgcagtt
tatctatctttatacatatatttaaactttactctacgaataatataatctatagtactacaataatatcagtgttttagagaatcatataaatgaacagtt
agacatggtctaaaggacaattgagtattttgacaacaggactctacagttttatctttttagtgtgcatgtgttctcctttttttttgcaaatagcttcacc
tatataatacttcatccattttattagtacatccatttagggtttagggttaatggtttttatagactaattttttttagtacatctattttattctattttagcct
ctaaattaagaaaactaaaactctatttagtttttttatttaataatttagatataaaatagaataaaataaagtgactaaaaattaaacaaataccct
ttaagaaattaaaaaaactaaggaaacatttttcttgtttcgagtagataatgccagcctgttaaacgccgtcgacgagtctaacggacaccaaccag
cgaaccagcagcgtcgcgtcgggccaagcgaagcagacggcacggcatctctgtcgctgcctctggacccctctcgagagttccgctccaccgttgga
cttgctccgctgtcggcatccagaaattgcgtggcggagcggcagacgtgagccggcacggcaggcggcctcctcctcctctcacggcaccggcagct
acgggggattcctttcccaccgctccttcgctttcccttcctcgcccgccgtaataaatagacacccccctccacaccctctttccccaacctcgtgttgttc
ggagcgcacacacacacaaccagatctcccccaaatccacccgtcggcacctccgcttcaaggtacgccgctcgtcctcccccccccccctctctacc
ttctctagatcggcgttccggtccatggttagggcccggtagttctacttctgttcatgtttgtgttagatccgtgtttgtgttagatccgtgctgctagcgtt
cgtacacggatgcgacctgtacgtcagacacgttctgattgctaacttgccagtgtttctctttggggaatcctgggatggctctagccgttccgcagac
gggatcgatttcatgattttttttgtttcgttgcatagggtttggtttgcccttttcctttatttcaatatatgccgtgcacttgtttgtcgggtcatcttttcat
gcttttttttgtcttggttgtgatgatgtggtctggttgggcggtcgttctagatcggagtagaattctgtttcaaactacctggtggatttattaattttgga
tctgtatgtgtgtgccatacatattcatagttacgaattgaagatgatggatggaaatatcgatctaggataggtatacatgttgatgcgggttttactga
tgcatatacagagatgctttttgttcgcttggttgtgatgatgtggtgtggttgggcggtcgttcattcgttctagatcggagtagaatactgtttcaaact
acctggtgtatttattaattttggaactgtatgtgtgtgtcatacatcttcatagttacgagtttaagatggatggaaatatcgatctaggataggtatac
atgttgatgtgggttttactgatgcatatacatgatggcatatgcagcatctattcatatgctctaaccttgagtacctatctattataataaacaagtatg
ttttataattattttgatcttgatatacttggatgatggcatatgcagcagctatatgtggatttttttagccctgccttcatacgctatttatttgcttggtac
tgtttcttttgtcgatgctcaccctgttgtttggtgttacttctgcaggtcgactctagaggatccaccatgaacaagaacaacaccaagctgagcacccg
cgccctgccgagcttcatcgactacttcaacggcatctacggcttcgccaccggcatcaaggacatcatgaacatgatcttcaagaccgacaccggcg
gcgacctgaccctggacgagatcctgaagaaccagcagctgctgaacgacatcagcggcaagctggacggcgtgaacggcagcctgaacgacctga
tcgcccagggcaacctgaacaccgagctgagcaaggagatccttaagatcgccaacgagcagaaccaggtgctgaacgacgtgaacaacaagctg
gacgccatcaacaccatgctgcgcgtgtacctgccgaagatcaccagcatgctgagcgacgtgattaagcagaactacgccctgagcctgcagatcg
agtacctgagcaagcagctgcaggagatcagcgacaagctggacatcatcaacgtgaacgtcctgatcaacagcaccctgaccgagatcaccccgg
cctaccagcgcatcaagtacgtgaacgagaagttcgaagagctgaccttcgccaccgagaccagcagcaaggtgaagaaggacggcagcccggcc

FIG. 5A gacatcctggacgagctgaccgagctgaccgagctggcgaagagcgtgaccaagaacgacgtggacggcttcgagttctacctgaacaccttccacg
acgtgatggtgggcaacaacctgttcggccgcagcgccctgaagaccgccagcgagctgatcaccaaggagaacgtgaagaccagcggcagcgag
gtgggcaacgtgtacaacttcctgatcgtgctgaccgccctgcaggcccaggccttcctgaccctgaccacctgtcgcaagctgctgggcctggccgac
atcgactacaccagcatcatgaacgagcacttgaacaaggagaaggaggagttccgcgtgaacatcctgccgaccctgagcaacaccttcagcaac
ccgaactacgccaaggtgaagggcagcgacgaggacgccaagatgatcgtggaggctaagccgggccacgcgttgatcggcttcgagatcagcaac
gacagcatcaccgtgctgaaggtgtacgaggccaagctgaagcagaactaccaggtggacaaggacagcttgagcgaggtgatctacggcgacatg
gacaagctgctgtgtccggaccagagcgagcaaatctactacaccaacaacatcgtgttcccgaacgagtacgtgatcaccaagatcgacttcacca
agaagatgaagaccctgcgctacgaggtgaccgccaacttctacgacagcagcaccggcgagatcgacctgaacaagaagaaggtggagagcagc
gaggccgagtaccgcaccctgagcgcgaacgacgacggcgtctacatgccactgggcgtgatcagcgagaccttcctgaccccgatcaacggctttg
gcctgcaggccgacgagaacagccgcctgatcaccctgacctgtaagagctacctgcgcgagctgctgctagccaccgacctgagcaacaaggaga
ccaagctgatcgtgccaccgagcggcttcatcagcaacatcgtggagaacggcagcatcgaggaggacaacctggagccgtggaaggccaacaac
aagaacgcctacgtcgaccacaccggcggcgtgaacggcaccaaggccctgtacgtgcacaaggacggcggcatcagccagttcatcggcgacaag
ctgaagccgaagaccgagtacgtgatccagtacaccgtgaagggcaagccatcgattcacctgaaggacgagaacaccggctacatccactacgag
gacaccaacaacaacctggaggactaccagaccatcaacaagcgcttcaccaccggcaccgacctgaagggcgtgtacctgatcctgaagagccag
aacggcgacgaggcctggggcgacaacttcatcatcctggagatcagcccgagcgagaagctgctgagcccggagctgatcaacaccaacaactgg
accagcaccggcagcaccaacatcagcggcaacaccctgaccctgtaccagggcggccgcggcatcctgaagcagaacctgcagctggacagcttc
agcacctaccgcgtgtacttcagcgtgagcggcgacgccaacgtgcgcatccgcaactcccgcgaggtgctgttcgagaagaggtacatgagcggcg
ccaaggacgtgagcgagatgttcaccaccaagttcgagaaggacaacttctacatcgagctgagccagggcaacaacctgtacggcggcccgatcgt
gcacttctacgacgtgagcatcaagtaggagctctagatctgttctgcacaaagtggagtagtcagtcatcgatcaggaaccagacaccagacttttat
tcatacagtgaagtgaagtgaagtgcagtgcagtgagttgctggtttttgtacaacttagtatgtatttgtatttgtaaaatacttctatcaataaaatttc
taattcctaaaaccaaaatccaggggtaccagcttgcatgcctgcagtgcagcgtgacccggtcgtgcccctctctagagataatgagcattgcatgtc
taagttataaaaaattaccacatatttttttgtcacacttgtttgaagtgcagtttatctatctttatacatatatttaaactttactctacgaataatataa
tctatagtactacaataatatcagtgttttagagaatcatataaatgaacagttagacatggtctaaaggacaattgagtattttgacaacaggactct
acagttttatctttttagtgtgcatgtgttctcctttttttttgcaaatagcttcacctatataatacttcatccattttattagtacatccatttagggtttagg
gttaatggtttttatagactaatttttttagtacatctattttattctattttagcctctaaattaagaaaactaaaactctattttagtttttttatttaataat
ttagatataaaatagaataaaataaagtgactaaaaattaaacaaataccctttaagaaattaaaaaaactaaggaaacatttttcttgtttcgagta
gataatgccagcctgttaaacgccgtcgacgagtctaacggacaccaaccagcgaaccagcagcgtcgcgtcgggccaagcgaagcagacggcac
ggcatctctgtcgctgcctctggacccctctcgagagttccgctccaccgttggacttgctccgctgtcggcatccagaaattgcgtggcggagcggcag
acgtgagccggcacggcaggcggcctcctcctcctctcacggcaccggcagctacgggggattcctttcccaccgctccttcgctttcccttcctcgccc
gccgtaataaatagacacccccctccacaccctctttccccaacctcgtgttgttcggagcgcacacacacacaaccagatctcccccaaatccacccgt
cggcacctccgcttcaaggtacgccgctcgtcctcccccccccccctctctaccttctctagatcggcgttccggtccatggttagggcccggtagttct
acttctgttcatgtttgtgttagatccgtgtttgtgttagatccgtgctgctagcgttcgtacacggatgcgacctgtacgtcagacacgttctgattgcta
acttgccagtgtttctctttggggaatcctgggatggctctagccgttccgcagacgggatcgatttcatgattttttttgtttcgttgcatagggtttggttt
gcccttttcctttatttcaatatatgccgtgcacttgtttgtcgggtcatcttttcatgcttttttttgtcttggttgtgatgatgtggtctggttgggcggtcgt
tctagatcggagtagaattctgtttcaaactacctggtggatttattaattttggatctgtatgtgtgtgccatacatattcatagttacgaattgaagatg
atggatggaaatatcgatctaggataggtatacatgttgatgcgggttttactgatgcatatacagagatgctttttgttcgcttggttgtgatgatgtgg
tgtggttgggcggtcgttcattcgttctagatcggagtagaatactgtttcaaactacctggtgtatttattaattttggaactgtatgtgtgtgtcatacat
cttcatagttacgagtttaagatggatggaaatatcgatctaggataggtatacatgttgatgtgggttttactgatgcatatacatgatggcatatgca
gcatctattcatatgctctaaccttgagtacctatctattataataaacaagtatgttttataattattttgatcttgatatacttggatgatggcatatgca
gcagctatatgtggatttttttagccctgccttcatacgctatttatttgcttggtactgtttcttttgtcgatgctcaccctgttgtttggtgttacttctgcag
ggatccccgatcatgcaaaaactcattaactcagtgcaaaactatgcctggggcagcaaaacggcgttgactgaactttatggtatggaaaatccgtc
cagccagccgatggccgagctgtggatgggcgcacatccgaaaagcagttcacgagtgcagaatgccgccggagatatcgtttcactgcgtgatgtg

FIG. 5B attgagagtgataaatcgactctgctcggagaggccgttgccaaacgctttggcgaactgcctttcctgttcaaagtattatgcgcagcacagccactct
ccattcaggttcatccaaacaaacacaattctgaaatcggttttgccaaagaaaatgccgcaggtatcccgatggatgccgccgagcgtaactataaa
gatcctaaccacaagccggagctggtttttgcgctgacgcctttccttgcgatgaacgcgtttcgtgaattttccgagattgtctccctactccagccggt
cgcaggtgcacatccggcgattgctcactttttacaacagcctgatgccgaacgtttaagcgaactgttcgccagcctgttgaatatgcagggtgaaga
aaaatcccgcgcgctggcgatttaaaatcggccctcgatagccagcagggtgaaccgtggcaaacgattcgtttaatttctgaattttacccggaaga
cagcggtctgttctccccgctattgctgaatgtggtgaaattgaaccctggcgaagcgatgttcctgttcgctgaaacaccgcacgcttacctgcaaggc
gtggcgctggaagtgatggcaaactccgataacgtgctgcgtgcgggtctgacgcctaaatacattgatattccggaactggttgccaatgtgaaattc
gaagccaaaccggctaaccagttgttgacccagccggtgaaacaaggtgcagaactggacttcccgattccagtggatgattttgccttctcgctgcat
gaccttagtgataaagaaaccaccattagccagcagagtgccgccattttgttctgcgtcgaaggcgatgcaacgttgtggaaaggttctcagcagtta
cagcttaaaccgggtgaatcagcgtttattgccgccaacgaatcaccggtgactgtcaaaggccacggccgtttagcgcgtgtttacaacaagctgta
agagcttactgaaaaaattaacatctcttgctaagctgggagctcgatccgtcgacctgcagatcgttcaaacatttggcaataaagtttcttaagattg
aatcctgttgccggtcttgcgatgattatcatataatttctgttgaattacgttaagcatgtaataattaacatgtaatgcatgacgttatttatgagatgg
gtttttatgattagagtcccgcaattatacatttaatacgcgatagaaaacaaaatatagcgcgcaaactaggataaattatcgcgcgcggtgtcatct
atgttactagatccccgggtctagacaattcagtacattaaAAACGTCCGCCATGGTCTGAAGGCAACAGATAAGGCATACTGGG
CCTTGTGGTAGTTGTTTTACTGGGCCTTTTTGTATGATCTATAAAATTCACTGGGATCAACCCGGAGAGGAATGGC
AGCAGATGCAGTCCCCAGGGTCCTCCGTCGCCGCCTGAGCACCCGGCACCCGCGCTGAACCGGAGAGGGACGCG
CGGACGCCGTGCAGCTGGTGCGGAGGGGGCTGTGGCAGATGAGGATGAGACGCGTACGTGGCTGGGAAGGCCA
GCAGGCCACCGGGTCTTCGTCCAGCCCGGCGCGAGTGGACAGGACTAGAGATGGCAACGGTTACAAACCCGCTG
GGTTTTACCGTCCCAAACCCGTACCCGTGAAAAATATCTATGCCCATTAAAAAACCCGTACCCATGACGGGTTTGA
GATTTTGCCCAAACCCGTACCCATCGGGTTAACGGGTACCCATGGGTTACCCGCGGGTTTCATCTCCAATATACCTG
TTCTTCTCATAATCAATAAGTATCGTAATGATTAATGATATCATGATCCAAAATCTATGTAATGAACAACGAGTTCA
TGATTTGGTATAAAAATTATTAGTAGAGAGAATGAAATACAAATAATAAGTTGTATAATTAAGTGACCTTGCACTA
AGTTATCCATCCATCACATATATAACGCTAGTAAAAACTATAATATCAAGCAAGCAACACTCTCACCGACTACTGAT
ACATTCACCAATTGATAAAAAATATGAAGTAAATAAGGAATAACAAGTTTGTTGTTCGTTTATAAAATAAAATGAC
AATATGCACTAGGTTTGGTCGGGTTTAAAAAACCCACGGGTTCACGGGTTTGGGTACTATAGGAACAAACCCGTA
CCCATAAACCCATTGGGTACAGATTTATGCCCGTTAACAAACCCATGGGTATGAAAATTGACCCAAACCTATACCCT
AATGGGGTAAAAACCCATCGGGTTTCGGATTTCGGGTACCCATTGCCATCTCTAGACAGGACAACCTCGGCCGGTC
CTGTATGTAGGCCACCAGCATCGGCCAGTTGGTACATCCAGCCGGGGTCAGGTCACTTTTACTCGTCTCAATCAGA
CAATCACCGTCCACCAACGAACGCCAACGTTGTCACTTGTCAGGTCGGTTGAGACTTGTATTTTTTTTTGTCCTCCGT
AAAAATCGGTTCACCAG

FIG. 5C

TCCTGTGTTGTTGGAACAGACTTCTGTCTCTTCTGGTGATCATAAATATTTAAATGAACCAGTTGTGTTGGAAAATG
TTGTTTTCTTTTGTCTCTAGACTGGAAAGCGGAGTTCTCGTCAACACGGTTCTTTCAACTAGGGATGAAAGTGGTAA
TCCGAATTGTTAGTACAAATTTAATATTTTAAAATAGATATGTATAAAATTTTATGTTGATCTTTTTTATGTTATCAA
GCACATTAGTATAAATTAGTATAAATATGAATAAAATATTACATAAAATGTTTTATGTATTATTTGGTCCCTACAACA
TAAATAGTTGAAAAAATTACTAAATTTGTTTTCGAATCTATATCGAAGTTTATATCTATTATTTAAGAAAAATATAGG
ATGAAAAGGTTTATCTTTTATGAATCTTTACAAGCTGGATCTTATAAACAAGAAAATAAATTTATATTGTAGATTTT
ATATCCTATTTATTCGCAATCAAAGAAAAGCGACTAAAAAACTGATTACCGAGTAAATACTGTTTCCAACCGTTTTC
GTCCCTACTATCAACGCCTTCTCCCAACCGCAGTCGATCTGTCCGTCTGTATCAGGCGCAGCGGCACCCCTGCTGTT
CGACTATCTAGACCATAGAATATTTTAGGTATACAATAATTTTAGTTCCACGCTAGAACATTTTAGTTAGAATAATA
ACAAGATTTGCTATTGATGTAGGACTCGCCCGTCACTGTCTAAAAAAGCATTCTGTCGGTCTTATTCTTTAGGCATC
AGCGGGTGTACTATCTCATTTTTCCTATCATATTCCTCAGTACTCTGTTAAGTATAAATGGTCTATTTTACATGATGA
ACTAATAAAACTAATTAAGGATCCTAACTTTTTGTGAAGGTAATTTGGATCATTATGCATTACCATCCTACGTATAC
CTGCTGCAGCAGCATCTGCGTAAGCACAGCCTAGATATATGCTTCTGTGTGGACTGAAAGGAGACTTTGTTTATCA
ATTAGTATACTCCCAAAAAACTGATGACACCAATGATGCAAATAGGCTGGGAATAGTCTGTCTAATAGTTTGAGTG
AATCatgtcactgatttatagatcatacaaaaaggcccagttagtttaaactgaaggcgggaaacgacaatctgatca
tgagcggagaattaagggagtcacgttatgacccccgccgatgacgcgggacaagccgttttacgtttggaactgacagaaccgcaacgttgaagga
gccactcagcaagctggtacaagcttgcatgcctgcagtgcagcgtgacccggtcgtgcccctctctagagataatgagcattgcatgtctaagttata
aaaaattaccacatattttttttgtcacacttgtttgaagtgcagtttatctatctttatacatatatttaaactttactctacgaataatataatctatagta
ctacaataatatcagtgttttagagaatcatataaatgaacagttagacatggtctaaaggacaattgagtattttgacaacaggactctacagttttat
ctttttagtgtgcatgtgttctcctttttttttgcaaatagcttcacctatataatacttcatccattttattagtacatccatttagggtttagggttaatggtt
tttatagactaatttttttagtacatctattttattctattttagcctctaaattaagaaaactaaaactctatttttagtttttttatttaataatttagatataa
aatagaataaaataaagtgactaaaaattaaacaaataccctttaagaaattaaaaaaactaaggaaacatttttcttgtttcgagtagataatgcca
gcctgttaaacgccgtcgacgagtctaacggacaccaaccagcgaaccagcagcgtcgcgtcgggccaagcgaagcagacggcacggcatctctgt
cgctgcctctggacccctctcgagagttccgctccaccgttggacttgctccgctgtcggcatccagaaattgcgtggcggagcggcagacgtgagccg
gcacggcaggcggcctcctcctcctctcacggcaccggcagctacgggggattcctttcccaccgctccttcgctttcccttcctcgcccgccgtaataa
atagacacccctccacaccctctttccccaacctcgtgttgttcggagcgcacacacacacaaccagatctcccccaaatccacccgtcggcacctcc
gcttcaaggtacgccgctcgtcctcccccccccccctctctaccttctctagatcggcgttccggtccatggttagggcccggtagttctacttctgttcat
gtttgtgttagatccgtgtttgtgttagatccgtgctgctagcgttcgtacacggatgcgacctgtacgtcagacacgttctgattgctaacttgccagtgt
ttctctttggggaatcctgggatggctctagccgttccgcagacgggatcgatttcatgattttttttgtttcgttgcatagggtttggtttgcccttttccttt
atttcaatatatgccgtgcacttgtttgtcgggtcatcttttcatgcttttttttgtcttggttgtgatgatgtggtctggttgggcggtcgttctagatcggag
tagaattctgtttcaaactacctggtggatttattaattttggatctgtatgtgtgtgccatacatattcatagttacgaattgaagatgatggatggaaat
atcgatctaggataggtatacatgttgatgcgggttttactgatgcatatacagagatgctttttgttcgcttggttgtgatgatgtggtgtggttgggcgg
tcgttcattcgttctagatcggagtagaatactgtttcaaactacctggtgtatttattaattttggaactgtatgtgtgtgtcatacatcttcatagttacg
agtttaagatggatggaaatatcgatctaggataggtatacatgttgatgtgggttttactgatgcatatacatgatggcatatgcagcatctattcatat
gctctaaccttgagtacctatctattataataaacaagtatgttttataattattttgatcttgatatacttggatgatggcatatgcagcagctatatgtg
gatttttttagccctgccttcatacgctatttatttgcttggtactgtttcttttgtcgatgctcaccctgttgtttggtgttacttctgcaggtcgactctagag
gatccaccatgaacaagaacaacaccaagctgagcacccgcgccctgccgagcttcatcgactacttcaacggcatctacggcttcgccaccggcatc
aaggacatcatgaacatgatcttcaagaccgacaccggcggcgacctgaccctggacgagatcctgaagaaccagcagctgctgaacgacatcagc
ggcaagctggacggcgtgaacggcagcctgaacgacctgatcgcccagggcaacctgaacaccgagctgagcaaggagatccttaagatcgccaac
gagcagaaccaggtgctgaacgacgtgaacaacaagctggacgccatcaacaccatgctgcgcgtgtacctgccgaagatcaccagcatgctgagc
gacgtgattaagcagaactacgccctgagcctgcagatcgagtacctgagcaagcagctgcaggagatcagcgacaagctggacatcatcaacgtg
aacgtcctgatcaacagcaccctgaccgagatcaccccggcctaccagcgcatcaagtacgtgaacgagaagttcgaagagctgaccttcgccaccg
agaccagcagcaaggtgaagaaggacggcagcccggccgacatcctggacgagctgaccgagctgaccgagctggcgaagagcgtgaccaagaa

FIG. 6A cgacgtggacggcttcgagttctacctgaacaccttccacgacgtgatggtgggcaacaacctgttcggccgcagcgccctgaagaccgccagcgagc
tgatcaccaaggagaacgtgaagaccagcggcagcgaggtgggcaacgtgtacaacttcctgatcgtgctgaccgccctgcaggcccaggccttcct
gaccctgaccacctgtcgcaagctgctgggcctggccgacatcgactacaccagcatcatgaacgagcacttgaacaaggagaaggaggagttccgc
gtgaacatcctgccgaccctgagcaacaccttcagcaacccgaactacgccaaggtgaagggcagcgacgaggacgccaagatgatcgtggaggct
aagccgggccacgcgttgatcggcttcgagatcagcaacgacagcatcaccgtgctgaaggtgtacgaggccaagctgaagcagaactaccaggtg
gacaaggacagcttgagcgaggtgatctacggcgacatggacaagctgctgtgtccggaccagagcgagcaaatctactacaccaacaacatcgtgt
tcccgaacgagtacgtgatcaccaagatcgacttcaccaagaagatgaagaccctgcgctacgaggtgaccgccaacttctacgacagcagcaccgg
cgagatcgacctgaacaagaagaaggtggagagcagcgaggccgagtaccgcaccctgagcgcgaacgacgacggcgtctacatgccactgggcg
tgatcagcgagaccttcctgaccccgatcaacggctttggcctgcaggccgacgagaacagccgcctgatcaccctgacctgtaagagctacctgcgc
gagctgctgctagccaccgacctgagcaacaaggagaccaagctgatcgtgccaccgagcggcttcatcagcaacatcgtggagaacggcagcatc
gaggaggacaacctggagccgtggaaggccaacaacaagaacgcctacgtcgaccacaccggcggcgtgaacggcaccaaggccctgtacgtgca
caaggacggcggcatcagccagttcatcggcgacaagctgaagccgaagaccgagtacgtgatccagtacaccgtgaagggcaagccatcgattca
cctgaaggacgagaacaccggctacatccactacgaggacaccaacaacaacctggaggactaccagaccatcaacaagcgcttcaccaccggca
ccgacctgaagggcgtgtacctgatcctgaagagccagaacggcgacgaggcctggggcgacaacttcatcatcctggagatcagcccgagcgaga
agctgctgagcccggagctgatcaacaccaacaactggaccagcaccggcagcaccaacatcagcggcaacaccctgaccctgtaccagggcggcc
gcggcatcctgaagcagaacctgcagctggacagcttcagcacctaccgcgtgtacttcagcgtgagcggcgacgccaacgtgcgcatccgcaactc
ccgcgaggtgctgttcgagaagaggtacatgagcggcgccaaggacgtgagcgagatgttcaccaccaagttcgagaaggacaacttctacatcga
gctgagccagggcaacaacctgtacggcggcccgatcgtgcacttctacgacgtgagcatcaagtaggagctctagatctgttctgcacaaagtggag
tagtcagtcatcgatcaggaaccagacaccagacttttattcatacagtgaagtgaagtgaagtgcagtgcagtgagttgctggtttttgtacaactta
gtatgtatttgtatttgtaaaatacttctatcaataaaatttctaattcctaaaaccaaaatccaggggtaccagcttgcatgcctgcagtgcagcgtgac
ccggtcgtgcccctctctagagataatgagcattgcatgtctaagttataaaaaattaccacatattttttttgtcacacttgtttgaagtgcagtttatct
atctttatacatatatttaaactttactctacgaataatataatctatagtactacaataatatcagtgttttagagaatcatataaatgaacagttagac
atggtctaaaggacaattgagtattttgacaacaggactctacagttttatctttttagtgtgcatgtgttctccttttttttttgcaaatagcttcacctatat
aatacttcatccattttattagtacatccatttagggtttagggttaatggtttttatagactaattttttttagtacatctattttattctattttagcctctaaa
ttaagaaaactaaaactctattttagttttttttatttaataatttagatataaaatagaataaaataaagtgactaaaaattaaacaaataccctttaag
aaattaaaaaaaactaaggaaacatttttcttgtttcgagtagataatgccagcctgttaaacgccgtcgacgagtctaacggacaccaaccagcgaac
cagcagcgtcgcgtcgggccaagcgaagcagacggcacggcatctctgtcgctgcctctggacccctctcgagagttccgctccaccgttggacttgct
ccgctgtcggcatccagaaattgcgtggcggagcggcagacgtgagccggcacggcaggcggcctcctcctcctctcacggcaccggcagctacggg
ggattcctttcccaccgctccttcgctttcccttcctcgcccgccgtaataaatagacacccccctccacaccctctttccccaacctcgtgttgttcggagc
gcacacacacacaaccagatctcccccaaatccacccgtcggcacctccgcttcaaggtacgccgctcgtcctcccccccccccctctctaccttctct
agatcggcgttccggtccatggttagggcccggtagttctacttctgttcatgtttgtgttagatccgtgtttgtgttagatccgtgctgctagcgttcgtac
acggatgcgacctgtacgtcagacacgttctgattgctaacttgccagtgtttctctttggggaatcctgggatggctctagccgttccgcagacgggat
cgatttcatgattttttttgtttcgttgcatagggtttggtttgcccttttcctttatttcaatatatgccgtgcacttgtttgtcgggtcatcttttcatgcttttt
tttgtcttggttgtgatgatgtggtctggttgggcggtcgttctagatcggagtagaattctgtttcaaactacctggtggatttattaattttggatctgta
tgtgtgtgccatacatattcatagttacgaattgaagatgatggatggaaatatcgatctaggataggtatacatgttgatgcgggttttactgatgcat
atacagagatgctttttgttcgcttggttgtgatgatgtggtgtggttgggcggtcgttcattcgttctagatcggagtagaatactgtttcaaactacctg
gtgtatttattaattttggaactgtatgtgtgtgtcatacatcttcatagttacgagtttaagatggatggaaatatcgatctaggataggtatacatgttg
atgtgggttttactgatgcatatacatgatggcatatgcagcatctattcatatgctctaaccttgagtacctatctattataataaacaagtatgttttat
aattattttgatcttgatatacttggatgatggcatatgcagcagctatatgtggatttttttagccctgccttcatacgctatttatttgcttggtactgttt
cttttgtcgatgctcaccctgttgtttggtgttacttctgcagggatccccgatcatgcaaaaactcattaactcagtgcaaaactatgcctggggcagca
aaacggcgttgactgaactttatggtatggaaaatccgtccagccagccgatggccgagctgtggatgggcgcacatccgaaaagcagttcacgagt
gcagaatgccgccggagatatcgtttcactgcgtgatgtgattgagagtgataaatcgactctgctcggagaggccgttgccaaacgctttggcgaact
gcctttcctgttcaaagtattatgcgcagcacagccactctccattcaggttcatccaaacaaacacaattctgaaatcggttttgccaaagaaaatgcc

FIG. 6B gcaggtatcccgatggatgccgccgagcgtaactataaagatcctaaccacaagccggagctggtttttgcgctgacgcctttccttgcgatgaacgcg
tttcgtgaattttccgagattgtctccctactccagccggtcgcaggtgcacatccggcgattgctcactttttacaacagcctgatgccgaacgtttaag
cgaactgttcgccagcctgttgaatatgcagggtgaagaaaaatcccgcgcgctggcgattttaaaatcggccctcgatagccagcagggtgaaccgt
ggcaaacgattcgtttaatttctgaattttacccggaagacagcggtctgttctccccgctattgctgaatgtggtgaaattgaaccctggcgaagcgat
gttcctgttcgctgaaacaccgcacgcttacctgcaaggcgtggcgctggaagtgatggcaaactccgataacgtgctgcgtgcgggtctgacgccta
aatacattgatattccggaactggttgccaatgtgaaattcgaagccaaaccggctaaccagttgttgacccagccggtgaaacaaggtgcagaactg
gacttcccgattccagtggatgattttgccttctcgctgcatgaccttagtgataaagaaaccaccattagccagcagagtgccgccattttgttctgcgt
cgaaggcgatgcaacgttgtggaaaggttctcagcagttacagcttaaaccgggtgaatcagcgtttattgccgccaacgaatcaccggtgactgtca
aaggccacggccgtttagcgcgtgtttacaacaagctgtaagagcttactgaaaaaattaacatctcttgctaagctgggagctcgatccgtcgacctg
cagatcgttcaaacatttggcaataaagtttcttaagattgaatcctgttgccggtcttgcgatgattatcatataatttctgttgaattacgttaagcatg
taataattaacatgtaatgcatgacgttatttatgagatgggtttttatgattagagtcccgcaattatacatttaatacgcgatagaaaacaaaatata
gcgcgcaaactaggataaattatcgcgcgcggtgtcatctatgttactagatccccgggtctagacaattcagtacattaaAAACGTCCGCCATG
GTCTGAAGGCAACAGATAAGGCATACTGGGCCTTGTGGTAGTTGTTTTACTGGGCCTTTTTGTATGATCTATAAAA
TTCACTGGGATCAACCCGGAGAGGAATGGCAGCAGATGCAGTCCCCAGGGTCCTCCGTCGCCGCCTGAGCACCCG
GCACCCGCGCTGAACCGGAGAGGGACGCGCGGACGCCGTGCAGCTGGTGCGGAGGGGGCTGTGGCAGATGAG
GATGAGACGCGTACGTGGCTGGGAAGGCCAGCAGGCCACCGGGTCTTCGTCCAGCCCGGCGCGAGTGGACAGG
ACTAGAGATGGCAACGGTTACAAACCCGCTGGGTTTTACCGTCCCAAACCCGTACCCGTGAAAAATATCTATGCCC
ATTAAAAAACCCGTACCCATGACGGGTTTGAGATTTTGCCCAAACCCGTACCCATCGGGTTAACGGGTACCCATGG
GTTACCCGCGGGTTTCATCTCCAATATACCTGTTCTTCTCATAATCAATAAGTATCGTAATGATTAATGATATCATGA
TCCAAAATCTATGTAATGAACAACGAGTTCATGATTTGGTATAAAAATTATTAGTAGAGAGAATGAAATACAAATA
ATAAGTTGTATAATTAAGTGACCTTGCACTAAGTTATCCATCCATCACATATATAACGCTAGTAAAAACTATAATAT
CAAGCAAGCAACACTCTCACCGACTACTGATACATTCACCAATTGATAAAAAATATGAAGTAAATAAGGAATAACA
AGTTTGTTGTTCGTTTATAAAATAAAATGACAATATGCACTAGGTTTGGTCGGGTTTAAAAAACCCACGGGTTCAC
GGGTTTGGGTACTATAGGAACAAACCCGTACCCATAAACCCATTGGGTACAGATTTATGCCCGTTAACAAACCCAT
GGGTATGAAAATTGACCCAAACCTATACCCTAATGGGGTAAAAACCCATCGGGTTTCGGATTTCGGGTACCCATTG
CCATCTCTAGACAGGACAACCTCGGCCGGTCCTGTATGTAGGCCACCAGCATCGGCCAGTTGGTACATCCAGCCG
GGGTCAGGTCACTTTTACTCGTCTCAATCAGACAATCACCGTCCACCAACGAACGCCAACGTTGTCACTTGTCAGGT
CGGTTGAGACTTGTATTTTTTTTTGTCCTCCGTAAAAATCGGTTCACCAG

FIG. 6C

TCCTGTGTTGTTGGAACAGACTTCTGTCTCTTCTGGTGATCATAAATATTTAAATGAACCAGTTGTGTTGGAAAATG
TTGTTTTCTTTTGTCTCTAGACTGGAAAGCGGAGTTCTCGTCAACACGGTTCTTTCAACTAGGGATGAAAGTGGTAA
TCCGAATTGTTAGTACAAATTTAATATTTTAAAATAGATATGTATAAAATTTTATGTTGATCTTTTTTATGTTATCAA
GCACATTAGTATAAATTAGTATAAATATGAATAAAATATTACATAAAATGTTTTATGTATTATTTGGTCCCTACAACA
TAAATAGTTGAAAAAATTACTAAATTTGTTTTCGAATCTATATCGAAGTTTATATCTATTATTTAAGAAAAATATAGG
ATGAAAAGGTTTATCTTTTATGAATCTTTACAAGCTGGATCTTATAAACAAGAAAATAAATTTATATTGTAGATTTT
ATATCCTATTTATTCGCAATCAAAGAAAAGCGACTAAAAAACTGATTACCGAGTAAATACTGTTTCCAACCGTTTTC
GTCCCTACTATCAACGCCTTCTCCCAACCGCAGTCGATCTGTCCGTCTGTATCAGGCGCAGCGGCACCCCTGCTGTT
CGACTATCTAGACCATAGAATATTTTAGGTATACAATAATTTTAGTTCCACGCTAGAACATTTTAGTTAGAATAATA
ACAAGATTTGCTATTGATGTAGGACTCGCCCGTCACTGTCTAAAAAAGCATTCTGTCGGTCTTATTCTTTAGGCATC
AGCGGGTGTACTATCTCATTTTTCCTATCATATTCCTCAGTACTCTGTTAAGTATAAATGGTCTATTTTACATGATGA
ACTAATAAAACTAATTAAGGATCCTAACTTTTTGTGAAGGTAATTTGGATCATTATGCATTACCATCCTACGTATAC
CTGCTGCAGCAGCATCTGCGTAAGCACAGCCTAGATATATGCTTCTGTGTGGACTGAAAGGAGACTTTGTTTATCA
ATTAGTATACTCCCAAAAAACTGATGACACCAATGATGCAAATAGGCTGGGAATAGTCTGTCTAATAGTTTGAGTG
AATCATGTcactgattaaactgaaggcgggaaacgacaatctgatcatgagcggagaattaagggagtcacgttatgacccccgccgatgacgcg
ggacaagccgttttacgtttggaactgacagaaccgcaacgttgaaggagccactcagcaagctggtacaagcttgcatgcctgcagtgcagcgtga
cccggtcgtgcccctctctagagataatgagcattgcatgtctaagttataaaaaattaccacatattttttttgtcacacttgtttgaagtgcagtttatct
atctttatacatatatttaaactttactctacgaataatataatctatagtactacaataatatcagtgttttagagaatcatataaatgaacagttagac
atggtctaaaggacaattgagtattttgacaacaggactctacagttttatctttttagtgtgcatgtgttctcctttttttttgcaaatagcttcacctatat
aatacttcatccattttattagtacatccatttagggtttagggttaatggtttttatagactaatttttttagtacatctattttattctattttagcctctaaa
ttaagaaaactaaaactctatttagtttttttatttaataatttagatataaaatagaataaaataaagtgactaaaaattaaacaaataccctttaag
aaattaaaaaaactaaggaaacatttttcttgtttcgagtagataatgccagcctgttaaacgccgtcgacgagtctaacggacaccaaccagcgaac
cagcagcgtcgcgtcgggccaagcgaagcagacggcacggcatctctgtcgctgcctctggacccctctcgagagttccgctccaccgttggacttgct
ccgctgtcggcatccagaaattgcgtggcggagcggcagacgtgagccggcacggcaggcggcctcctcctcctctcacggcaccggcagctacggg
ggattcctttcccaccgctccttcgctttcccttcctcgcccgccgtaataaatagacacccccctccacaccctctttccccaacctcgtgttgttcggagc
gcacacacacacaaccagatctcccccaaatccacccgtcggcacctccgcttcaaggtacgccgctcgtcctcccccccccccctctctaccttctct
agatcggcgttccggtccatggttagggcccggtagttctacttctgttcatgtttgtgttagatccgtgtttgtgttagatccgtgctgctagcgttcgtac
acggatgcgacctgtacgtcagacacgttctgattgctaacttgccagtgtttctctttggggaatcctgggatggctctagccgttccgcagacgggat
cgatttcatgattttttttgtttcgttgcatagggtttggtttgcccttttcctttatttcaatatatgccgtgcacttgtttgtcgggtcatcttttcatgctttttt
tttgtcttggttgtgatgatgtggtctggttgggcggtcgttctagatcggagtagaattctgtttcaaactacctggtggatttattaattttggatctgta
tgtgtgtgccatacatattcatagttacgaattgaagatgatggatggaaatatcgatctaggataggtatacatgttgatgcgggttttactgatgcat
atacagagatgctttttgttcgcttggttgtgatgatgtggtgtggttgggcggtcgttcattcgttctagatcggagtagaatactgtttcaaactacctg
gtgtatttattaattttggaactgtatgtgtgtgtcatacatcttcatagttacgagtttaagatggatggaaatatcgatctaggataggtatacatgttg
atgtgggttttactgatgcatatacatgatggcatatgcagcatctattcatatgctctaaccttgagtacctatctattataataaacaagtatgttttat
aattattttgatcttgatatacttggatgatggcatatgcagcagctatatgtggattttttttagccctgccttcatacgctatttatttgcttggtactgttt
cttttgtcgatgctcaccctgttgtttggtgttacttctgcaggtcgactctagaggatccaccatgaacaagaacaacaccaagctgagcacccgcgcc
ctgccgagcttcatcgactacttcaacggcatctacggcttcgccaccggcatcaaggacatcatgaacatgatcttcaagaccgacaccggcggcga
cctgaccctggacgagatcctgaagaaccagcagctgctgaacgacatcagcggcaagctggacggcgtgaacggcagcctgaacgacctgatcgc
ccagggcaacctgaacaccgagctgagcaaggagatccttaagatcgccaacgagcagaaccaggtgctgaacgacgtgaacaacaagctggacg
ccatcaacaccatgctgcgcgtgtacctgccgaagatcaccagcatgctgagcgacgtgattaagcagaactacgccctgagcctgcagatcgagta
cctgagcaagcagctgcaggagatcagcgacaagctggacatcatcaacgtgaacgtcctgatcaacagcaccctgaccgagatcaccccggccta
ccagcgcatcaagtacgtgaacgagaagttcgaagagctgaccttcgccaccgagaccagcagcaaggtgaagaaggacggcagcccggccgaca

FIG. 7A tcctggacgagctgaccgagctgaccgagctggcgaagagcgtgaccaagaacgacgtggacggcttcgagttctacctgaacaccttccacgacgt
gatggtgggcaacaacctgttcggccgcagcgccctgaagaccgccagcgagctgatcaccaaggagaacgtgaagaccagcggcagcgaggtgg
gcaacgtgtacaacttcctgatcgtgctgaccgccctgcaggcccaggccttcctgaccctgaccacctgtcgcaagctgctgggcctggccgacatcg
actacaccagcatcatgaacgagcacttgaacaaggagaaggaggagttccgcgtgaacatcctgccgaccctgagcaacaccttcagcaacccga
actacgccaaggtgaagggcagcgacgaggacgccaagatgatcgtggaggctaagccgggccacgcgttgatcggcttcgagatcagcaacgac
agcatcaccgtgctgaaggtgtacgaggccaagctgaagcagaactaccaggtggacaaggacagcttgagcgaggtgatctacggcgacatggac
aagctgctgtgtccggaccagagcgagcaaatctactacaccaacaacatcgtgttcccgaacgagtacgtgatcaccaagatcgacttcaccaaga
agatgaagaccctgcgctacgaggtgaccgccaacttctacgacagcagcaccggcgagatcgacctgaacaagaagaaggtggagagcagcgag
gccgagtaccgcaccctgagcgcgaacgacgacggcgtctacatgccactgggcgtgatcagcgagaccttcctgaccccgatcaacggctttggcct
gcaggccgacgagaacagccgcctgatcaccctgacctgtaagagctacctgcgcgagctgctgctagccaccgacctgagcaacaaggagaccaa
gctgatcgtgccaccgagcggcttcatcagcaacatcgtggagaacggcagcatcgaggaggacaacctggagccgtggaaggccaacaacaaga
acgcctacgtcgaccacaccggcggcgtgaacggcaccaaggccctgtacgtgcacaaggacggcggcatcagccagttcatcggcgacaagctga
agccgaagaccgagtacgtgatccagtacaccgtgaagggcaagccatcgattcacctgaaggacgagaacaccggctacatccactacgaggaca
ccaacaacaacctggaggactaccagaccatcaacaagcgcttcaccaccggcaccgacctgaagggcgtgtacctgatcctgaagagccagaacg
gcgacgaggcctggggcgacaacttcatcatcctggagatcagcccgagcgagaagctgctgagcccggagctgatcaacaccaacaactggacca
gcaccggcagcaccaacatcagcggcaacaccctgaccctgtaccagggcggccgcggcatcctgaagcagaacctgcagctggacagcttcagca
cctaccgcgtgtacttcagcgtgagcggcgacgccaacgtgcgcatccgcaactcccgcgaggtgctgttcgagaagaggtacatgagcggcgccaa
ggacgtgagcgagatgttcaccaccaagttcgagaaggacaacttctacatcgagctgagccagggcaacaacctgtacggcggcccgatcgtgcac
ttctacgacgtgagcatcaagtaggagctctagatctgttctgcacaaagtggagtagtcagtcatcgatcaggaaccagacaccagacttttattcat
acagtgaagtgaagtgaagtgcagtgcagtgagttgctggtttttgtacaacttagtatgtatttgtatttgtaaaatacttctatcaataaaatttctaat
tcctaaaaccatcaaacatttggcaataaagtttcttaagattgaatcctgttgccggtcttgcgatgattatcatataatttctgttgaattacgttaagc
atgtaataattaacatgtaatgcatgacgttatttatgagatgggtttttatgattagagtcccgcaattatacatttaatacgcgatagaaaacaaaat
atagcgcgcaaactaggataaattatcgcgcgcggtgtcatctatgttactagatccccgggtctagacaattcagtacattaaAAACGTCCGCC
ATGGTCTGAAGGCAACAGATAAGGCATACTGGGCCTTGTGGTAGTTGTTTTACTGGGCCTTTTTGTATGATCTATA
AAATTCACTGGGATCAACCCGGAGAGGAATGGCAGCAGATGCAGTCCCCAGGGTCCTCCGTCGCCGCCTGAGCAC
CCGGCACCCGCGCTGAACCGGAGAGGGACGCGCGGACGCCGTGCAGCTGGTGCGGAGGGGGCTGTGGCAGATG
AGGATGAGACGCGTACGTGGCTGGGAAGGCCAGCAGGCCACCGGGTCTTCGTCCAGCCCGGCGCGAGTGGACA
GGACTAGAGATGGCAACGGTTACAAACCCGCTGGGTTTTACCGTCCCAAACCCGTACCCGTGAAAAATATCTATGC
CCATTAAAAAACCCGTACCCATGACGGGTTTGAGATTTTGCCCAAACCCGTACCCATCGGGTTAACGGGTACCCAT
GGGTTACCCGCGGGTTTCATCTCCAATATACCTGTTCTTCTCATAATCAATAAGTATCGTAATGATTAATGATATCAT
GATCCAAAATCTATGTAATGAACAACGAGTTCATGATTTGGTATAAAAATTATTAGTAGAGAGAATGAAATACAAA
TAATAAGTTGTATAATTAAGTGACCTTGCACTAAGTTATCCATCCATCACATATATAACGCTAGTAAAAACTATAAT
ATCAAGCAAGCAACACTCTCACCGACTACTGATACATTCACCAATTGATAAAAAATATGAAGTAAATAAGGAATAA
CAAGTTTGTTGTTCGTTTATAAAATAAAATGACAATATGCACTAGGTTTGGTCGGGTTTAAAAAACCCACGGGTTC
ACGGGTTTGGGTACTATAGGAACAAACCCGTACCCATAAACCCATTGGGTACAGATTTATGCCCGTTAACAAACCC
ATGGGTATGAAAATTGACCCAAACCTATACCCTAATGGGGTAAAAACCCATCGGGTTTCGGATTTCGGGTACCCAT
TGCCATCTCTAGACAGGACAACCTCGGCCGGTCCTGTATGTAGGCCACCAGCATCGGCCAGTTGGTACATCCAGCC
GGGGTCAGGTCACTTTTACTCGTCTCAATCAGACAATCACCGTCCACCAACGAACGCCAACGTTGTCACTTGTCAG
GTCGGTTGAGACTTGTATTTTTTTTTGTCCTCCGTAAAAATCGGTTCACCAG

FIG. 7B

SEQUENCE LISTING

```
<160> NUMBER OF SEQ ID NOS: 167

<210> SEQ ID NO 1
<211> LENGTH: 10579
<212> TYPE: DNA
<213> ORGANISM: Artificial
<220> FEATURE:
<223> OTHER INFORMATION: synthetic

<400> SEQUENCE: 1

tcctgtgttg ttggaacaga cttctgtctc ttctggtgat cataaatatt taaatgaacc     60

agttgtgttg gaaaatgttg ttttcttttg tctctagact ggaaagcgga gttctcgtca    120

acacggttct ttcaactagg gatgaaagtg gtaatccgaa ttgttagtac aaatttaata    180

ttttaaaata gatatgtata aaattttatg ttgatctttt ttatgttatc aagcacatta    240

gtataaatta gtataaatat gaataaaata ttacataaaa tgttttatgt attatttggt    300

ccctacaaca taaatagttg aaaaaattac taaatttgtt ttcgaatcta tatcgaagtt    360

tatatctatt atttaagaaa aatataggat gaaaaggttt atcttttatg aatctttaca    420

agctggatct tataaacaag aaaataaatt tatattgtag attttatatc ctatttattc    480

gcaatcaaag aaaagcgact aaaaaactga ttaccgagta aatactgttt ccaaccgttt    540

tcgtccctac tatcaacgcc ttctcccaac cgcagtcgat ctgtccgtct gtatcaggcg    600

cagcggcacc cctgctgttc gactatctag accatagaat attttaggta tacaataatt    660

ttagttccac gctagaacat tttagttaga ataataacaa gatttgctat tgatgtagga    720

ctcgcccgtc actgtctaaa aaagcattct gtcggtctta ttctttaggc atcagcgggt    780

gtactatctc atttttccta tcatattcct cagtactctg ttaagtataa atggtctatt    840

ttacatgatg aactaataaa actaattaag gatcctaact ttttgtgaag gtaatttgga    900

tcattatgca ttaccatcct acgtatacct gctgcagcag catctgcgta agcacagcct    960

agatatatgc ttctgtgtgg actgaaagga gactttgttt atcaattagt atactcccaa   1020

aaaactgatg acaccaatga tgcaaatagg ctgggaatag tctgtctaat agtttgagtg   1080

aatcatgtca ctgatagttt aaactgaagg cgggaaacga caatctgatc atgagcggag   1140

aattaaggga gtcacgttat gacccccgcc gatgacgcgg gacaagccgt tttacgtttg   1200

gaactgacag aaccgcaacg ttgaaggagc cactcagcaa gctggtacaa gcttgcatgc   1260

ctgcagtgca gcgtgacccg gtcgtgcccc tctctagaga taatgagcat tgcatgtcta   1320

agttataaaa aattaccaca tatttttttt gtcacacttg tttgaagtgc agtttatcta   1380
```

-continued

```
tctttataca tatatttaaa ctttactcta cgaataatat aatctatagt actacaataa   1440
tatcagtgtt ttagagaatc atataaatga acagttagac atggtctaaa ggacaattga   1500
gtattttgac aacaggactc tacagtttta tctttttagt gtgcatgtgt tctccttttt   1560
ttttgcaaat agcttcacct atataatact tcatccattt tattagtaca tccatttagg   1620
gtttagggtt aatggttttt atagactaat ttttttagta catctatttt attctatttt   1680
agcctctaaa ttaagaaaac taaaactcta ttttagtttt tttatttaat aatttagata   1740
taaaatagaa taaaataaag tgactaaaaa ttaaacaaat accctttaag aaattaaaaa   1800
aactaaggaa acatttttct tgtttcgagt agataatgcc agcctgttaa acgccgtcga   1860
cgagtctaac ggacaccaac cagcgaacca gcagcgtcgc gtcgggccaa gcgaagcaga   1920
cggcacggca tctctgtcgc tgcctctgga cccctctcga gagttccgct ccaccgttgg   1980
acttgctccg ctgtcggcat ccagaaattg cgtggcggag cggcagacgt gagccggcac   2040
ggcaggcggc ctcctcctcc tctcacggca ccggcagcta cgggggattc ctttcccacc   2100
gctccttcgc tttcccttcc tcgcccgccg taataaatag acaccccctc cacaccctct   2160
ttccccaacc tcgtgttgtt cggagcgcac acacacacaa ccagatctcc cccaaatcca   2220
cccgtcggca cctccgcttc aaggtacgcc gctcgtcctc cccccccccc cctctctacc   2280
ttctctagat cggcgttccg gtccatggtt agggcccggt agttctactt ctgttcatgt   2340
ttgtgttaga tccgtgtttg tgttagatcc gtgctgctag cgttcgtaca cggatgcgac   2400
ctgtacgtca gacacgttct gattgctaac ttgccagtgt ttctctttgg ggaatcctgg   2460
gatggctcta gccgttccgc agacgggatc gatttcatga ttttttttgt ttcgttgcat   2520
agggtttggt ttgccctttt cctttatttc aatatatgcc gtgcacttgt ttgtcgggtc   2580
atcttttcat gctttttttt gtcttggttg tgatgatgtg gtctggttgg gcggtcgttc   2640
tagatcggag tagaattctg tttcaaacta cctggtggat ttattaattt tggatctgta   2700
tgtgtgtgcc atacatattc atagttacga attgaagatg atggatggaa atatcgatct   2760
aggataggta tacatgttga tgcgggtttt actgatgcat atacagagat gctttttgtt   2820
cgcttggttg tgatgatgtg gtgtggttgg gcggtcgttc attcgttcta gatcggagta   2880
gaatactgtt tcaaactacc tggtgtattt attaattttg gaactgtatg tgtgtgtcat   2940
acatcttcat agttacgagt ttaagatgga tggaaatatc gatctaggat aggtatacat   3000
gttgatgtgg gttttactga tgcatataca tgatggcata tgcagcatct attcatatgc   3060
tctaaccttg agtacctatc tattataata aacaagtatg ttttataatt attttgatct   3120
tgatatactt ggatgatggc atatgcagca gctatatgtg gattttttta gccctgcctt   3180
catacgctat ttatttgctt ggtactgttt cttttgtcga tgctcaccct gttgtttggt   3240
gttacttctg caggtcgact ctagaggatc caccatgaac aagaacaaca ccaagctgag   3300
cacccgcgcc ctgccgagct tcatcgacta cttcaacggc atctacggct tcgccaccgg   3360
catcaaggac atcatgaaca tgatcttcaa gaccgacacc ggcggcgacc tgaccctgga   3420
cgagatcctg aagaaccagc agctgctgaa cgacatcagc ggcaagctgg acggcgtgaa   3480
cggcagcctg aacgacctga tcgcccaggg caacctgaac accgagctga gcaaggagat   3540
ccttaagatc gccaacgagc agaaccaggt gctgaacgac gtgaacaaca agctggacgc   3600
catcaacacc atgctgcgcg tgtacctgcc gaagatcacc agcatgctga gcgacgtgat   3660
gaagcagaac tacgccctga gcctgcagat cgagtacctg agcaagcagc tgcaggagat   3720
```

```
cagcgacaag ctggacatca tcaacgtgaa cgtcctgatc aacagcaccc tgaccgagat   3780
caccccggcc taccagcgca tcaagtacgt gaacgagaag ttcgaagagc tgaccttcgc   3840
caccgagacc agcagcaagg tgaagaagga cggcagcccg gccgacatcc tggacgagct   3900
gaccgagctg accgagctgg cgaagagcgt gaccaagaac gacgtggacg gcttcgagtt   3960
ctacctgaac accttccacg acgtgatggt gggcaacaac ctgttcggcc gcagcgccct   4020
gaagaccgcc agcgagctga tcaccaagga gaacgtgaag accagcggca gcgaggtggg   4080
caacgtgtac aacttcctga tcgtgctgac cgccctgcag gcccaggcct tcctgaccct   4140
gaccacctgt cgcaagctgc tgggcctggc cgacatcgac tacaccagca tcatgaacga   4200
gcacttgaac aaggagaagg aggagttccg cgtgaacatc ctgccgaccc tgagcaacac   4260
cttcagcaac ccgaactacg ccaaggtgaa gggcagcgac gaggacgcca agatgatcgt   4320
ggaggctaag ccgggccacg cgttgatcgg cttcgagatc agcaacgaca gcatcaccgt   4380
gctgaaggtg tacgaggcca agctgaagca gaactaccag gtggacaagg acagcttgag   4440
cgaggtgatc tacggcgaca tggacaagct gctgtgtccg gaccagagcg agcaaatcta   4500
ctacaccaac aacatcgtgt tcccgaacga gtacgtgatc accaagatcg acttcaccaa   4560
gaagatgaag accctgcgct acgaggtgac cgccaacttc tacgacagca gcaccggcga   4620
gatcgacctg aacaagaaga aggtggagag cagcgaggcc gagtaccgca ccctgagcgc   4680
gaacgacgac ggcgtctaca tgccactggg cgtgatcagc gagaccttcc tgaccccgat   4740
caacggcttt ggcctgcagg ccgacgagaa cagccgcctg atcaccctga cctgtaagag   4800
ctacctgcgc gagctgctgc tagccaccga cctgagcaac aaggagacca agctgatcgt   4860
gccaccgagc ggcttcatca gcaacatcgt ggagaacggc agcatcgagg aggacaacct   4920
ggagccgtgg aaggccaaca acaagaacgc ctacgtggac cacaccggcg gcgtgaacgg   4980
caccaaggcc ctgtacgtgc acaaggacgg cggcatcagc cagttcatcg gcgacaagct   5040
gaagccgaag accgagtacg tgatccagta caccgtgaag ggcaagccat cgattcacct   5100
gaaggacgag aacaccggct acatccacta cgaggacacc aacaacaacc tggaggacta   5160
ccagaccatc aacaagcgct tcaccaccgg caccgacctg aagggcgtgt acctgatcct   5220
gaagagccag aacggcgacg aggcctgggg cgacaacttc atcatcctgg agatcagccc   5280
gagcgagaag ctgctgagcc cggagctgat caacaccaac aactggacca gcaccggcag   5340
caccaacatc agcggcaaca ccctgaccct gtaccagggc ggccgcggca tcctgaagca   5400
gaacctgcag ctggacagct tcagcaccta ccgcgtgtac ttcagcgtga gcggcgacgc   5460
caacgtgcgc atccgcaact cccgcgaggt gctgttcgag aagaggtaca tgagcggcgc   5520
caaggacgtg agcgagatgt tcaccaccaa gttcgagaag gacaacttct acatcgagct   5580
gagccagggc aacaacctgt acggcggccc gatcgtgcac ttctacgacg tgagcatcaa   5640
gtaggagctc tagatctgtt ctgcacaaag tggagtagtc agtcatcgat caggaaccag   5700
acaccagact tttattcata cagtgaagtg aagtgaagtg cagtgcagtg agttgctggt   5760
ttttgtacaa cttagtatgt atttgtattt gtaaaatact tctatcaata aaatttctaa   5820
ttcctaaaac caaaatccag ggtaccagc ttgcatgcct gcagtgcagc gtgacccggt   5880
cgtgcccctc tctagagata atgagcattg catgtctaag ttataaaaaa ttaccacata   5940
tttttttgt cacacttgtt tgaagtgcag tttatctatc tttatacata tatttaaact   6000
ttactctacg aataatataa tctatagtac tacaataata tcagtgtttt agagaatcat   6060
ataaatgaac agttagacat ggtctaaagg acaattgagt attttgacaa caggactcta   6120
```

-continued

```
cagttttatc tttttagtgt gcatgtgttc tccttttttt ttgcaaatag cttcacctat   6180
ataatacttc atccatttta ttagtacatc catttagggt ttagggttaa tggtttttat   6240
agactaattt ttttagtaca tctattttat tctattttag cctctaaatt aagaaaaacta   6300
aaactctatt ttagtttttt tatttaataa tttagatata aaatagaata aaataaagtg   6360
actaaaaatt aaacaaatac cctttaagaa attaaaaaaa ctaaggaaac atttttcttg   6420
tttcgagtag ataatgccag cctgttaaac gccgtcgacg agtctaacgg acaccaacca   6480
gcgaaccagc agcgtcgcgt cgggccaagc gaagcagacg gcacggcatc tctgtcgctg   6540
cctctggacc cctctcgaga gttccgctcc accgttggac ttgctccgct gtcggcatcc   6600
agaaattgcg tggcggagcg gcagacgtga gccggcacgg caggcggcct cctcctcctc   6660
tcacggcacc ggcagctacg gggggattcct ttcccaccgc tccttcgctt tcccttcctc   6720
gcccgccgta ataaatagac acccccctcca caccctcttt ccccaacctc gtgttgttcg   6780
gagcgcacac acacacaacc agatctcccc caaatccacc cgtcggcacc tccgcttcaa   6840
ggtacgccgc tcgtcctccc cccccccccc tctctacctt ctctagatcg gcgttccggt   6900
ccatggttag ggcccggtag ttctacttct gttcatgttt gtgttagatc cgtgtttgtg   6960
ttagatccgt gctgctagcg ttcgtacacg gatgcgacct gtacgtcaga cacgttctga   7020
ttgctaactt gccagtgttt ctctttgggg aatcctggga tggctctagc cgttccgcag   7080
acgggatcga tttcatgatt ttttttgttt cgttgcatag ggtttggttt gccctttttcc   7140
tttatttcaa tatatgccgt gcacttgttt gtcgggtcat cttttcatgc ttttttttgt   7200
cttggttgtg atgatgtggt ctggttgggc ggtcgttcta gatcggagta gaattctgtt   7260
tcaaactacc tggtggattt attaattttg gatctgtatg tgtgtgccat acatattcat   7320
agttacgaat tgaagatgat ggatggaaat atcgatctag gataggtata catgttgatg   7380
cgggttttac tgatgcatat acagagatgc tttttgttcg cttggttgtg atgatgtggt   7440
gtggttgggc ggtcgttcat tcgttctaga tcggagtaga atactgtttc aaactacctg   7500
gtgtatttat taattttgga actgtatgtg tgtgtcatac atcttcatag ttacgagttt   7560
aagatggatg gaaatatcga tctaggatag gtatacatgt tgatgtgggt tttactgatg   7620
catatacatg atggcatatg cagcatctat tcatatgctc taaccttgag tacctatcta   7680
ttataataaa caagtatgtt ttataattat tttgatcttg atatacttgg atgatggcat   7740
atgcagcagc tatatgtgga tttttttagc cctgccttca tacgctattt atttgcttgg   7800
tactgtttct tttgtcgatg ctcaccctgt tgtttggtgt tacttctgca gggatccccg   7860
atcatgcaaa aactcattaa ctcagtgcaa aactatgcct ggggcagcaa aacggcgttg   7920
actgaacttt atggtatgga aaatccgtcc agccagccga tggccgagct gtggatgggc   7980
gcacatccga aaagcagttc acgagtgcag aatgccgccg gagatatcgt ttcactgcgt   8040
gatgtgattg agagtgataa atcgactctg ctcggagagg ccgttgccaa acgctttggc   8100
gaactgcctt tcctgttcaa agtattatgc gcagcacagc cactctccat tcaggttcat   8160
ccaaacaaac acaattctga aatcggtttt gccaaagaaa atgccgcagg tatcccgatg   8220
gatgccgccg agcgtaacta taaagatcct aaccacaagc cggagctggt ttttgcgctg   8280
acgcctttcc ttgcgatgaa cgcgtttcgt gaattttccg agattgtctc cctactccag   8340
ccggtcgcag gtgcacatcc ggcgattgct cactttttac aacagcctga tgccgaacgt   8400
ttaagcgaac tgttcgccag cctgttgaat atgcagggtg aagaaaaatc ccgcgcgctg   8460
```

```
gcgattttaa aatcggccct cgatagccag cagggtgaac cgtggcaaac gattcgttta   8520
atttctgaat tttacccgga agacagcggt ctgttctccc cgctattgct gaatgtggtg   8580
aaattgaacc ctggcgaagc gatgttcctg ttcgctgaaa caccgcacgc ttacctgcaa   8640
ggcgtggcgc tggaagtgat ggcaaactcc gataacgtgc tgcgtgcggg tctgacgcct   8700
aaatacattg atattccgga actggttgcc aatgtgaaat tcgaagccaa accggctaac   8760
cagttgttga cccagccggt gaaacaaggt gcagaactgg acttcccgat tccagtggat   8820
gattttgcct tctcgctgca tgaccttagt gataaagaaa ccaccattag ccagcagagt   8880
gccgccattt tgttctgcgt cgaaggcgat gcaacgttgt ggaaaggttc tcagcagtta   8940
cagcttaaac cgggtgaatc agcgtttatt gccgccaacg aatcaccggt gactgtcaaa   9000
ggccacggcc gtttagcgcg tgtttacaac aagctgtaag agcttactga aaaaattaac   9060
atctcttgct aagctgggag ctcgatccgt cgacctgcag atcgttcaaa catttggcaa   9120
taaagtttct taagattgaa tcctgttgcc ggtcttgcga tgattatcat ataatttctg   9180
ttgaattacg ttaagcatgt aataattaac atgtaatgca tgacgttatt tatgagatgg   9240
gtttttatga ttagagtccc gcaattatac atttaatacg cgatagaaaa caaaatatag   9300
cgcgcaaact aggataaatt atcgcgcgcg gtgtcatcta tgttactaga tccccgggtc   9360
tagacaattc agtacattaa aaacgtccgc catggtctga aggcaacaga taaggcatac   9420
tgggccttgt ggtagttgtt ttactgggcc tttttgtatg atctataaaa ttcactggga   9480
tcaacccgga gaggaatggc agcagatgca gtccccaggg tcctccgtcg ccgcctgagc   9540
acccggcacc cgcgctgaac cggagaggga cgcgcggacg ccgtgcagct ggtgcggagg   9600
gggctgtggc agatgaggat gagacgcgta cgtggctggg aaggccagca ggccaccggg   9660
tcttcgtcca gcccggcgcg agtggacagg actagagatg gcaacggtta caaacccgct   9720
gggttttacc gtcccaaacc cgtacccgtg aaaaatatct atgcccatta aaaaacccgt   9780
acccatgacg ggtttgagat tttgcccaaa cccgtaccca tcgggttaac gggtacccat   9840
gggttacccg cgggtttcat ctccaatata cctgttcttc tcataatcaa taagtatcgt   9900
aatgattaat gatatcatga tccaaaatct atgtaatgaa caacgagttc atgatttggt   9960
ataaaaatta ttagtagaga gaatgaaata caaataataa gttgtataat taagtgacct  10020
tgcactaagt tatccatcca tcacatatat aacgctagta aaaactataa tatcaagcaa  10080
gcaacactct caccgactac tgatacattc accaattgat aaaaaatatg aagtaaataa  10140
ggaataacaa gtttgttgtt cgtttataaa ataaaatgac aatatgcact aggtttggtc  10200
gggtttaaaa aacccacggg ttcacgggtt tgggtactat aggaacaaac ccgtacccat  10260
aaacccattg ggtacagatt tatgcccgtt aacaaaccca tgggtatgaa aattgaccca  10320
aacctatacc ctaatggggt aaaaacccat cgggtttcgg atttcgggta cccattgcca  10380
tctctagaca ggacaacctc ggccggtcct gtatgtaggc caccagcatc ggccagttgg  10440
tacatccagc cggggtcagg tcacttttac tcgtctcaat cagacaatca ccgtccacca  10500
acgaacgcca acgttgtcac ttgtcaggtc ggttgagact tgtatttttt tttgtcctcc  10560
gtaaaaatcg gttcaccag                                                10579
```

<210> SEQ ID NO 2
<211> LENGTH: 7314
<212> TYPE: DNA
<213> ORGANISM: Artificial
<220> FEATURE:
<223> OTHER INFORMATION: synthetic

```
<220> FEATURE:
<221> NAME/KEY: misc_feature
<222> LOCATION: (5831)..(5842)
<223> OTHER INFORMATION: n is absent or is a, c, g, or t

<400> SEQUENCE: 2

tcctgtgttg ttggaacaga cttctgtctc ttctggtgat cataaatatt taaatgaacc     60

agttgtgttg gaaaatgttg ttttcttttg tctctagact ggaaagcgga gttctcgtca    120

acacggttct ttcaactagg gatgaaagtg gtaatccgaa ttgttagtac aaatttaata    180

ttttaaaata gatatgtata aaattttatg ttgatctttt ttatgttatc aagcacatta    240

gtataaatta gtataaatat gaataaaata ttacataaaa tgttttatgt attatttggt    300

ccctacaaca taaatagttg aaaaaattac taaatttgtt ttcgaatcta tatcgaagtt    360

tatatctatt atttaagaaa aatataggat gaaaaggttt atcttttatg aatctttaca    420

agctggatct tataaacaag aaaataaatt tatattgtag attttatatc ctatttattc    480

gcaatcaaag aaaagcgact aaaaaactga ttaccgagta aatactgttt ccaaccgttt    540

tcgtccctac tatcaacgcc ttctcccaac cgcagtcgat ctgtccgtct gtatcaggcg    600

cagcggcacc cctgctgttc gactatctag accatagaat attttaggta tacaataatt    660

ttagttccac gctagaacat tttagttaga ataataacaa gatttgctat tgatgtagga    720

ctcgcccgtc actgtctaaa aaagcattct gtcggtctta ttctttaggc atcagcgggt    780

gtactatctc atttttccta tcatattcct cagtactctg ttaagtataa atggtctatt    840

ttacatgatg aactaataaa actaattaag gatcctaact ttttgtgaag gtaatttgga    900

tcattatgca ttaccatcct acgtatacct gctgcagcag catctgcgta agcacagcct    960

agatatatgc ttctgtgtgg actgaaagga gactttgttt atcaattagt atactcccaa   1020

aaaactgatg acaccaatga tgcaaatagg ctgggaatag tctgtctaat agtttgagtg   1080

aatcatgtca ctgatagttt aaactgaagg cgggaaacga caatctgatc atgagcggag   1140

aattaaggga gtcacgttat gaccccccgcc gatgacgcgg gacaagccgt tttacgtttg   1200

gaactgacag aaccgcaacg ttgaaggagc cactcagcaa gctggtacaa gcttgcatgc   1260

ctgcagtgca gcgtgacccg gtcgtgcccc tctctagaga taatgagcat tgcatgtcta   1320

agttataaaa aattaccaca tatttttttt gtcacacttg tttgaagtgc agtttatcta   1380

tctttataca tatatttaaa ctttactcta cgaataatat aatctatagt actacaataa   1440

tatcagtgtt ttagagaatc atataaatga acagttagac atggtctaaa ggacaattga   1500

gtattttgac aacaggactc tacagtttta tctttttagt gtgcatgtgt tctccttttt   1560

ttttgcaaat agcttcacct atataatact tcatccattt tattagtaca tccatttagg   1620

gtttagggtt aatggttttt atagactaat ttttttagta catctatttt attctatttt   1680

agcctctaaa ttaagaaaac taaaactcta ttttagtttt tttatttaat aatttagata   1740

taaaatagaa taaaataaag tgactaaaaa ttaaacaaat accctttaag aaattaaaaa   1800

aactaaggaa acatttttct tgtttcgagt agataatgcc agcctgttaa acgccgtcga   1860

cgagtctaac ggacaccaac cagcgaacca gcagcgtcgc gtcgggccaa gcgaagcaga   1920

cggcacggca tctctgtcgc tgcctctgga cccctctcga gagttccgct ccaccgttgg   1980

acttgctccg ctgtcggcat ccagaaattg cgtggcggag cggcagacgt gagccggcac   2040

ggcaggcggc ctcctcctcc tctcacggca ccggcagcta cgggggattc ctttcccacc   2100

gctccttcgc tttcccttcc tcgcccgccg taataaatag acaccccctc cacaccctct   2160
```

```
ttccccaacc tcgtgttgtt cggagcgcac acacacacaa ccagatctcc cccaaatcca   2220
cccgtcggca cctccgcttc aaggtacgcc gctcgtcctc cccccccccc cctctctacc   2280
ttctctagat cggcgttccg gtccatggtt agggcccggt agttctactt ctgttcatgt   2340
ttgtgttaga tccgtgtttg tgttagatcc gtgctgctag cgttcgtaca cggatgcgac   2400
ctgtacgtca gacacgttct gattgctaac ttgccagtgt ttctctttgg ggaatcctgg   2460
gatggctcta gccgttccgc agacgggatc gatttcatga ttttttttgt ttcgttgcat   2520
agggtttggt ttgccctttt cctttatttc aatatatgcc gtgcacttgt ttgtcgggtc   2580
atcttttcat gctttttttt gtcttggttg tgatgatgtg gtctggttgg gcggtcgttc   2640
tagatcggag tagaattctg tttcaaacta cctggtggat ttattaattt tggatctgta   2700
tgtgtgtgcc atacatattc atagttacga attgaagatg atggatggaa atatcgatct   2760
aggataggta tacatgttga tgcgggtttt actgatgcat atacagagat gctttttgtt   2820
cgcttggttg tgatgatgtg gtgtggttgg gcggtcgttc attcgttcta gatcggagta   2880
gaatactgtt tcaaactacc tggtgtattt attaattttg gaactgtatg tgtgtgtcat   2940
acatcttcat agttacgagt ttaagatgga tggaaatatc gatctaggat aggtatacat   3000
gttgatgtgg gttttactga tgcatataca tgatggcata tgcagcatct attcatatgc   3060
tctaaccttg agtacctatc tattataata aacaagtatg ttttataatt attttgatct   3120
tgatatactt ggatgatggc atatgcagca gctatatgtg gatttttta gccctgcctt   3180
catacgctat ttatttgctt ggtactgttt cttttgtcga tgctcaccct gttgtttggt   3240
gttacttctg caggtcgact ctagaggatc caccatgaac aagaacaaca ccaagctgag   3300
cacccgcgcc ctgccgagct tcatcgacta cttcaacggc atctacggct tcgccaccgg   3360
catcaaggac atcatgaaca tgatcttcaa gaccgacacc ggcggcgacc tgaccctgga   3420
cgagatcctg aagaaccagc agctgctgaa cgacatcagc ggcaagctgg acggcgtgaa   3480
cggcagcctg aacgacctga tcgcccaggg caacctgaac accgagctga gcaaggagat   3540
ccttaagatc gccaacgagc agaaccaggt gctgaacgac gtgaacaaca agctggacgc   3600
catcaacacc atgctgcgcg tgtacctgcc gaagatcacc agcatgctga gcgacgtgat   3660
gaagcagaac tacgccctga gcctgcagat cgagtacctg agcaagcagc tgcaggagat   3720
cagcgacaag ctggacatca tcaacgtgaa cgtcctgatc aacagcaccc tgaccgagat   3780
cacccccggcc taccagcgca tcaagtacgt gaacgagaag ttcgaagagc tgaccttcgc   3840
caccgagacc agcagcaagg tgaagaagga cggcagcccg gccgacatcc tggacgagct   3900
gaccgagctg accgagctgg cgaagagcgt gaccaagaac gacgtggacg gcttcgagtt   3960
ctacctgaac accttccacg acgtgatggt gggcaacaac ctgttcggcc gcagcgccct   4020
gaagaccgcc agcgagctga tcaccaagga gaacgtgaag accagcggca gcgaggtggg   4080
caacgtgtac aacttcctga tcgtgctgac cgccctgcag gcccaggcct tcctgaccct   4140
gaccacctgt cgcaagctgc tgggcctggc cgacatcgac tacaccagca tcatgaacga   4200
gcacttgaac aaggagaagg aggagttccg cgtgaacatc ctgccgaccc tgagcaacac   4260
cttcagcaac ccgaactacg ccaaggtgaa gggcagcgac gaggacgcca agatgatcgt   4320
ggaggctaag ccgggccacg cgttgatcgg cttcgagatc agcaacgaca gcatcaccgt   4380
gctgaaggtg tacgaggcca agctgaagca gaactaccag gtggacaagg acagcttgag   4440
cgaggtgatc tacggcgaca tggacaagct gctgtgtccg gaccagagcg agcaaatcta   4500
ctacaccaac aacatcgtgt tcccgaacga gtacgtgatc accaagatcg acttcaccaa   4560
```

```
gaagatgaag accctgcgct acgaggtgac cgccaacttc tacgacagca gcaccggcga   4620
gatcgacctg aacaagaaga aggtggagag cagcgaggcc gagtaccgca ccctgagcgc   4680
gaacgacgac ggcgtctaca tgccactggg cgtgatcagc gagaccttcc tgaccccgat   4740
caacggcttt ggcctgcagg ccgacgagaa cagccgcctg atcaccctga cctgtaagag   4800
ctacctgcgc gagctgctgc tagccaccga cctgagcaac aaggagacca agctgatcgt   4860
gccaccgagc ggcttcatca gcaacatcgt ggagaacggc agcatcgagg aggacaacct   4920
ggagccgtgg aaggccaaca acaagaacgc ctacgtggac cacaccggcg gcgtgaacgg   4980
caccaaggcc ctgtacgtgc acaaggacgg cggcatcagc cagttcatcg gcgacaagct   5040
gaagccgaag accgagtacg tgatccagta caccgtgaag ggcaagccat cgattcacct   5100
gaaggacgag aacaccggct acatccacta cgaggacacc aacaacaacc tggaggacta   5160
ccagaccatc aacaagcgct tcaccaccgg caccgacctg aagggcgtgt acctgatcct   5220
gaagagccag aacggcgacg aggcctgggg cgacaacttc atcatcctgg agatcagccc   5280
gagcgagaag ctgctgagcc cggagctgat caacaccaac aactggacca gcaccggcag   5340
caccaacatc agcggcaaca ccctgaccct gtaccagggc ggccgcggca tcctgaagca   5400
gaacctgcag ctggacagct tcagcaccta ccgcgtgtac ttcagcgtga gcggcgacgc   5460
caacgtgcgc atccgcaact cccgcgaggt gctgttcgag aagaggtaca tgagcggcgc   5520
caaggacgtg agcgagatgt tcaccaccaa gttcgagaag gacaacttct acatcgagct   5580
gagccagggc aacaacctgt acggcggccc gatcgtgcac ttctacgacg tgagcatcaa   5640
gtaggagctc tagatctgtt ctgcacaaag tggagtagtc agtcatcgat caggaaccag   5700
acaccagact tttattcata cagtgaagtg aagtgaagtg cagtgcagtg agttgctggt   5760
ttttgtacaa cttagtatgt atttgtattt gtaaaatact tctatcaata aaatttctaa   5820
ttcctaaaac nnnnnnnnnn nnaaacattt ggcaataaag tttcttaaga ttgaatcctg   5880
ttgccggtct tgcgatgatt atcatataat ttctgttgaa ttacgttaag catgtaataa   5940
ttaacatgta atgcatgacg ttatttatga gatgggtttt tatgattaga gtcccgcaat   6000
tatacattta atacgcgata gaaaacaaaa tatagcgcgc aaactaggat aaattatcgc   6060
gcgcggtgtc atctatgtta ctagatcccc gggtctagac aattcagtac attaaaaacg   6120
tccgccatgg tctgaaggca acagataagg catactgggc cttgtggtag ttgttttact   6180
gggccttttt gtatgatcta taaaattcac tgggatcaac ccggagagga atggcagcag   6240
atgcagtccc cagggtcctc cgtcgccgcc tgagcacccg gcacccgcgc tgaaccggag   6300
agggacgcgc ggacgccgtg cagctggtgc ggagggggct gtggcagatg aggatgagac   6360
gcgtacgtgg ctgggaaggc cagcaggcca ccgggtcttc gtccagcccg gcgcgagtgg   6420
acaggactag agatggcaac ggttacaaac ccgctgggtt ttaccgtccc aaacccgtac   6480
ccgtgaaaaa tatctatgcc cattaaaaaa cccgtaccca tgacgggttt gagattttgc   6540
ccaaacccgt acccatcggg ttaacgggta cccatgggtt acccgcgggt ttcatctcca   6600
atatacctgt tcttctcata atcaataagt atcgtaatga ttaatgatat catgatccaa   6660
aatctatgta atgaacaacg agttcatgat ttggtataaa aattattagt agagagaatg   6720
aaatacaaat aataagttgt ataattaagt gaccttgcac taagttatcc atccatcaca   6780
tatataacgc tagtaaaaac tataatatca agcaagcaac actctcaccg actactgata   6840
cattcaccaa ttgataaaaa atatgaagta aataaggaat aacaagtttg ttgttcgttt   6900
```

ataaaataaa atgacaatat gcactaggtt tggtcgggtt taaaaaaccc acgggttcac 6960
gggtttgggt actataggaa caaacccgta cccataaacc cattgggtac agatttatgc 7020
ccgttaacaa acccatgggt atgaaaattg acccaaacct ataccctaat ggggtaaaaa 7080
cccatcgggt ttcggatttc gggtacccat tgccatctct agacaggaca acctcggccg 7140
gtcctgtatg taggccacca gcatcggcca gttggtacat ccagccgggg tcaggtcact 7200
tttactcgtc tcaatcagac aatcaccgtc caccaacgaa cgccaacgtt gtcacttgtc 7260
aggtcggttg agacttgtat tttttttgt cctccgtaaa aatcggttca ccag 7314

<210> SEQ ID NO 3
<211> LENGTH: 7314
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1081)..(1104)
<223> OTHER INFORMATION: n is absent or is a, c, g, or t
<220> FEATURE:
<221> NAME/KEY: misc_feature
<222> LOCATION: (5831)..(5842)
<223> OTHER INFORMATION: n is absent or is a, c, g, or t

<400> SEQUENCE: 3
tcctgtgttg ttggaacaga cttctgtctc ttctggtgat cataaatatt taaatgaacc 60
agttgtgttg gaaaatgttg ttttcttttg tctctagact ggaaagcgga gttctcgtca 120
acacggttct ttcaactagg gatgaaagtg gtaatccgaa ttgttagtac aaatttaata 180
ttttaaaata gatatgtata aaattttatg ttgatctttt ttatgttatc aagcacatta 240
gtataaatta gtataaatat gaataaaata ttacataaaa tgttttatgt attatttggt 300
ccctacaaca taaatagttg aaaaaattac taaatttgtt ttcgaatcta tatcgaagtt 360
tatatctatt atttaagaaa aatataggat gaaaaggttt atcttttatg aatctttaca 420
agctggatct tataaacaag aaaataaatt tatattgtag attttatatc ctatttattc 480
gcaatcaaag aaaagcgact aaaaaactga ttaccgagta aatactgttt ccaaccgttt 540
tcgtccctac tatcaacgcc ttctcccaac cgcagtcgat ctgtccgtct gtatcaggcg 600
cagcggcacc cctgctgttc gactatctag accatagaat attttaggta tacaataatt 660
ttagttccac gctagaacat tttagttaga ataataacaa gatttgctat tgatgtagga 720
ctcgcccgtc actgtctaaa aagcattct gtcggtctta ttctttaggc atcagcgggt 780
gtactatctc atttttccta tcatattcct cagtactctg ttaagtataa atggtctatt 840
ttacatgatg aactaataaa actaattaag gatcctaact ttttgtgaag gtaatttgga 900
tcattatgca ttaccatcct acgtatacct gctgcagcag catctgcgta agcacagcct 960
agatatatgc ttctgtgtgg actgaaagga gactttgttt atcaattagt atactcccaa 1020
aaaactgatg acaccaatga tgcaaatagg ctgggaatag tctgtctaat agtttgagtg 1080
nnnnnnnnnn nnnnnnnnnn nnnntgaagg cgggaaacga caatctgatc atgagcggag 1140
aattaaggga gtcacgttat gaccccccgcc gatgacgcgg gacaagccgt tttacgtttg 1200
gaactgacag aaccgcaacg ttgaaggagc cactcagcaa gctggtacaa gcttgcatgc 1260
ctgcagtgca gcgtgacccg gtcgtgcccc tctctagaga taatgagcat tgcatgtcta 1320
agttataaaa aattaccaca tattttttt gtcacacttg tttgaagtgc agtttatcta 1380
tctttataca tatatttaaa ctttactcta cgaataatat aatctatagt actacaataa 1440

-continued

```
tatcagtgtt ttagagaatc atataaatga acagttagac atggtctaaa ggacaattga   1500
gtattttgac aacaggactc tacagtttta tctttttagt gtgcatgtgt tctccttttt   1560
ttttgcaaat agcttcacct atataatact tcatccattt tattagtaca tccatttagg   1620
gtttagggtt aatggttttt atagactaat ttttttagta catctatttt attctatttt   1680
agcctctaaa ttaagaaaac taaaactcta ttttagtttt tttatttaat aatttagata   1740
taaaatagaa taaaataaag tgactaaaaa ttaaacaaat accctttaag aaattaaaaa   1800
aactaaggaa acattttttct tgtttcgagt agataatgcc agcctgttaa acgccgtcga   1860
cgagtctaac ggacaccaac cagcgaacca gcagcgtcgc gtcgggccaa gcgaagcaga   1920
cggcacggca tctctgtcgc tgcctctgga cccctctcga gagttccgct ccaccgttgg   1980
acttgctccg ctgtcggcat ccagaaattg cgtggcggag cggcagacgt gagccggcac   2040
ggcaggcggc ctcctcctcc tctcacggca ccggcagcta cgggggattc ctttcccacc   2100
gctccttcgc tttcccttcc tcgcccgccg taataaatag acacccccctc cacaccctct   2160
ttccccaacc tcgtgttgtt cggagcgcac acacacacaa ccagatctcc cccaaatcca   2220
cccgtcggca cctccgcttc aaggtacgcc gctcgtcctc cccccccccc cctctctacc   2280
ttctctagat cggcgttccg gtccatggtt agggcccggt agttctactt ctgttcatgt   2340
ttgtgttaga tccgtgtttg tgttagatcc gtgctgctag cgttcgtaca cggatgcgac   2400
ctgtacgtca gacacgttct gattgctaac ttgccagtgt ttctctttgg ggaatcctgg   2460
gatggctcta gccgttccgc agacgggatc gatttcatga ttttttttgt ttcgttgcat   2520
agggtttggt ttgccctttt cctttatttc aatatatgcc gtgcacttgt ttgtcgggtc   2580
atcttttcat gctttttttt gtcttggttg tgatgatgtg gtctggttgg gcggtcgttc   2640
tagatcggag tagaattctg tttcaaacta cctggtggat ttattaattt tggatctgta   2700
tgtgtgtgcc atacatattc atagttacga attgaagatg atggatggaa atatcgatct   2760
aggataggta tacatgttga tgcgggtttt actgatgcat atacagagat gctttttgtt   2820
cgcttggttg tgatgatgtg gtgtggttgg gcggtcgttc attcgttcta gatcggagta   2880
gaatactgtt tcaaactacc tggtgtattt attaattttg gaactgtatg tgtgtgtcat   2940
acatcttcat agttacgagt ttaagatgga tggaaatatc gatctaggat aggtatacat   3000
gttgatgtgg gttttactga tgcatataca tgatggcata tgcagcatct attcatatgc   3060
tctaaccttg agtacctatc tattataata aacaagtatg ttttataatt attttgatct   3120
tgatatactt ggatgatggc atatgcagca gctatatgtg gatttttttta gccctgcctt   3180
catacgctat ttatttgctt ggtactgttt cttttgtcga tgctcaccct gttgtttggt   3240
gttacttctg caggtcgact ctagaggatc caccatgaac aagaacaaca ccaagctgag   3300
cacccgcgcc ctgccgagct tcatcgacta cttcaacggc atctacggct tcgccaccgg   3360
catcaaggac atcatgaaca tgatcttcaa gaccgacacc ggcggcgacc tgaccctgga   3420
cgagatcctg aagaaccagc agctgctgaa cgacatcagc ggcaagctgg acggcgtgaa   3480
cggcagcctg aacgacctga tcgcccaggg caacctgaac accgagctga gcaaggagat   3540
ccttaagatc gccaacgagc agaaccaggt gctgaacgac gtgaacaaca agctggacgc   3600
catcaacacc atgctgcgcg tgtacctgcc gaagatcacc agcatgctga gcgacgtgat   3660
gaagcagaac tacgccctga gcctgcagat cgagtacctg agcaagcagc tgcaggagat   3720
cagcgacaag ctggacatca tcaacgtgaa cgtcctgatc aacagcaccc tgaccgagat   3780
```

```
caccccggcc taccagcgca tcaagtacgt gaacgagaag ttcgaagagc tgaccttcgc   3840
caccgagacc agcagcaagg tgaagaagga cggcagcccg gccgacatcc tggacgagct   3900
gaccgagctg accgagctgg cgaagagcgt gaccaagaac gacgtggacg gcttcgagtt   3960
ctacctgaac accttccacg acgtgatggt gggcaacaac ctgttcggcc gcagcgccct   4020
gaagaccgcc agcgagctga tcaccaagga gaacgtgaag accagcggca gcgaggtggg   4080
caacgtgtac aacttcctga tcgtgctgac cgccctgcag gcccaggcct tcctgaccct   4140
gaccacctgt cgcaagctgc tgggcctggc cgacatcgac tacaccagca tcatgaacga   4200
gcacttgaac aaggagaagg aggagttccg cgtgaacatc ctgccgaccc tgagcaacac   4260
cttcagcaac ccgaactacg ccaaggtgaa gggcagcgac gaggacgcca agatgatcgt   4320
ggaggctaag ccgggccacg cgttgatcgg cttcgagatc agcaacgaca gcatcaccgt   4380
gctgaaggtg tacgaggcca agctgaagca gaactaccag gtggacaagg acagcttgag   4440
cgaggtgatc tacggcgaca tggacaagct gctgtgtccg gaccagagcg agcaaatcta   4500
ctacaccaac aacatcgtgt tcccgaacga gtacgtgatc accaagatcg acttcaccaa   4560
gaagatgaag accctgcgct acgaggtgac cgccaacttc tacgacagca gcaccggcga   4620
gatcgacctg aacaagaaga aggtggagag cagcgaggcc gagtaccgca ccctgagcgc   4680
gaacgacgac ggcgtctaca tgccactggg cgtgatcagc gagaccttcc tgaccccgat   4740
caacggcttt ggcctgcagg ccgacgagaa cagccgcctg atcaccctga cctgtaagag   4800
ctacctgcgc gagctgctgc tagccaccga cctgagcaac aaggagacca agctgatcgt   4860
gccaccgagc ggcttcatca gcaacatcgt ggagaacggc agcatcgagg aggacaacct   4920
ggagccgtgg aaggccaaca acaagaacgc ctacgtggac cacaccggcg gcgtgaacgg   4980
caccaaggcc ctgtacgtgc acaaggacgg cggcatcagc cagttcatcg gcgacaagct   5040
gaagccgaag accgagtacg tgatccagta caccgtgaag ggcaagccat cgattcacct   5100
gaaggacgag aacaccggct acatccacta cgaggacacc aacaacaacc tggaggacta   5160
ccagaccatc aacaagcgct tcaccaccgg caccgacctg aagggcgtgt acctgatcct   5220
gaagagccag aacggcgacg aggcctgggg cgacaacttc atcatcctgg agatcagccc   5280
gagcgagaag ctgctgagcc cggagctgat caacaccaac aactggacca gcaccggcag   5340
caccaacatc agcggcaaca ccctgaccct gtaccagggc ggccgcggca tcctgaagca   5400
gaacctgcag ctggacagct tcagcaccta ccgcgtgtac ttcagcgtga gcggcgacgc   5460
caacgtgcgc atccgcaact cccgcgaggt gctgttcgag aagaggtaca tgagcggcgc   5520
caaggacgtg agcgagatgt tcaccaccaa gttcgagaag gacaacttct acatcgagct   5580
gagccagggc aacaacctgt acggcggccc gatcgtgcac ttctacgacg tgagcatcaa   5640
gtaggagctc tagatctgtt ctgcacaaag tggagtagtc agtcatcgat caggaaccag   5700
acaccagact tttattcata cagtgaagtg aagtgaagtg cagtgcagtg agttgctggt   5760
ttttgtacaa cttagtatgt atttgtattt gtaaaatact tctatcaata aaatttctaa   5820
ttcctaaaac nnnnnnnnnn nnaaacattt ggcaataaag tttcttaaga ttgaatcctg   5880
ttgccggtct tgcgatgatt atcatataat ttctgttgaa ttacgttaag catgtaataa   5940
ttaacatgta atgcatgacg ttatttatga gatgggtttt tatgattaga gtcccgcaat   6000
tatacattta atacgcgata gaaaacaaaa tatagcgcgc aaactaggat aaattatcgc   6060
gcgcggtgtc atctatgtta ctagatcccc gggtctagac aattcagtac attaaaaacg   6120
tccgccatgg tctgaaggca acagataagg catactgggc cttgtggtag ttgttttact   6180
```

gggcctttttt gtatgatcta taaaattcac tgggatcaac ccggagagga atggcagcag 6240
atgcagtccc cagggtcctc cgtcgccgcc tgagcacccg gcacccgcgc tgaaccggag 6300
agggacgcgc ggacgccgtg cagctggtgc ggagggggct gtggcagatg aggatgagac 6360
gcgtacgtgg ctgggaaggc cagcaggcca ccgggtcttc gtccagcccg gcgcgagtgg 6420
acaggactag agatggcaac ggttacaaac ccgctgggtt ttaccgtccc aaacccgtac 6480
ccgtgaaaaa tatctatgcc cattaaaaaa cccgtaccca tgacgggttt gagattttgc 6540
ccaaacccgt acccatcggg ttaacgggta cccatgggtt acccgcgggt ttcatctcca 6600
atatacctgt tcttctcata atcaataagt atcgtaatga ttaatgatat catgatccaa 6660
aatctatgta atgaacaacg agttcatgat ttggtataaa aattattagt agagagaatg 6720
aaatacaaat aataagttgt ataattaagt gaccttgcac taagttatcc atccatcaca 6780
tatataacgc tagtaaaaac tataatatca agcaagcaac actctcaccg actactgata 6840
cattcaccaa ttgataaaaa atatgaagta aataaggaat aacaagtttg ttgttcgttt 6900
ataaaataaa atgacaatat gcactaggtt tggtcgggtt taaaaaaccc acgggttcac 6960
gggtttgggt actataggaa caaacccgta cccataaacc cattgggtac agatttatgc 7020
ccgttaacaa acccatgggt atgaaaattg acccaaacct ataccctaat ggggtaaaaa 7080
cccatcgggt ttcggatttc gggtacccat tgccatctct agacaggaca acctcggccg 7140
gtcctgtatg taggccacca gcatcggcca gttggtacat ccagccgggg tcaggtcact 7200
tttactcgtc tcaatcagac aatcaccgtc caccaacgaa cgccaacgtt gtcacttgtc 7260
aggtcggttg agacttgtat tttttttgt cctccgtaaa aatcggttca ccag 7314

<210> SEQ ID NO 4
<211> LENGTH: 7239
<212> TYPE: DNA
<213> ORGANISM: Artificial
<220> FEATURE:
<223> OTHER INFORMATION: synthetic

<400> SEQUENCE: 4
tcctgtgttg ttggaacaga cttctgtctc ttctggtgat cataaatatt taaatgaacc 60
agttgtgttg gaaaatgttg ttttcttttg tctctagact ggaaagcgga gttctcgtca 120
acacggttct ttcaactagg gatgaaagtg gtaatccgaa ttgttagtac aaatttaata 180
ttttaaaata gatatgtata aaattttatg ttgatctttt ttatgttatc aagcacatta 240
gtataaatta gtataaatat gaataaaata ttacataaaa tgttttatgt attatttggt 300
ccctacaaca taaatagttg aaaaaattac taaatttgtt ttcgaatcta tatcgaagtt 360
tatatctatt atttaagaaa aatataggat gaaaaggttt atcttttatg aatctttaca 420
agctggatct tataaacaag aaaataaatt tatattgtag attttatatc ctatttattc 480
gcaatcaaag aaaagcgact aaaaaactga ttaccgagta aatactgttt ccaaccgttt 540
tcgtccctac tatcaacgcc ttctcccaac cgcagtcgat ctgtccgtct gtatcaggcg 600
cagcggcacc cctgctgttc gactatctag accatagaat attttaggta tacaataatt 660
ttagttccac gctagaacat tttagttaga ataataacaa gatttgctat tgatgtagga 720
ctcgcccgtc actgtctaaa aaagcattct gtcggtctta ttctttaggc atcagcgggt 780
gtactatctc atttttccta tcatattcct cagtactctg ttaagtataa atggtctatt 840
ttacatgatg aactaataaa actaattaag gatcctaact ttttgtgaag gtaatttgga 900

-continued

```
tcattatgca ttaccatcct acgtatacct gctgcagcag catctgcgta agcacagcct    960
agatatatgc ttctgtgtgg actgaaagga gactttgttt atcaattagt atactcccat   1020
agtttaaact gaaggcggga aacgacaatc tgatcatgag cggagaatta agggagtcac   1080
gttatgaccc ccgccgatga cgcgggacaa gccgttttac gtttggaact gacagaaccg   1140
caacgttgaa ggagccactc agcaagctgg tacaagcttg catgcctgca gtgcagcgtg   1200
acccggtcgt gcccctctct agagataatg agcattgcat gtctaagtta taaaaaatta   1260
ccacatattt tttttgtcac acttgtttga agtgcagttt atctatcttt atacatatat   1320
ttaaacttta ctctacgaat aatataatct atagtactac aataatatca gtgttttaga   1380
gaatcatata aatgaacagt tagacatggt ctaaaggaca attgagtatt ttgacaacag   1440
gactctacag ttttatcttt ttagtgtgca tgtgttctcc tttttttttg caaatagctt   1500
cacctatata atacttcatc cattttatta gtacatccat ttagggttta gggttaatgg   1560
tttttataga ctaatttttt tagtacatct attttattct attttagcct ctaaattaag   1620
aaaactaaaa ctctatttta gtttttttat ttaataattt agatataaaa tagaataaaa   1680
taaagtgact aaaaattaaa caaataccct ttaagaaatt aaaaaaacta aggaaacatt   1740
tttcttgttt cgagtagata atgccagcct gttaaacgcc gtcgacgagt ctaacggaca   1800
ccaaccagcg aaccagcagc gtcgcgtcgg gccaagcgaa gcagacggca cggcatctct   1860
gtcgctgcct ctggacccct ctcgagagtt ccgctccacc gttggacttg ctccgctgtc   1920
ggcatccaga aattgcgtgg cggagcggca gacgtgagcc ggcacggcag gcggcctcct   1980
cctcctctca cggcaccggc agctacgggg gattcctttc ccaccgctcc ttcgctttcc   2040
cttcctcgcc cgccgtaata aatagacacc ccctccacac cctctttccc caacctcgtg   2100
ttgttcggag cgcacacaca cacaaccaga tctcccccaa atccacccgt cggcacctcc   2160
gcttcaaggt acgccgctcg tcctcccccc cccccccctct ctaccttctc tagatcggcg   2220
ttccggtcca tggttagggc ccggtagttc tacttctgtt catgtttgtg ttagatccgt   2280
gtttgtgtta gatccgtgct gctagcgttc gtacacggat gcgacctgta cgtcagacac   2340
gttctgattg ctaacttgcc agtgtttctc tttggggaat cctgggatgg ctctagccgt   2400
tccgcagacg ggatcgattt catgattttt tttgtttcgt tgcatagggt ttggtttgcc   2460
cttttccttt atttcaatat atgccgtgca cttgtttgtc gggtcatctt ttcatgcttt   2520
tttttgtctt ggttgtgatg atgtggtctg gttgggcggt cgttctagat cggagtagaa   2580
ttctgtttca aactacctgg tggatttatt aattttggat ctgtatgtgt gtgccataca   2640
tattcatagt tacgaattga agatgatgga tggaaatatc gatctaggat aggtatacat   2700
gttgatgcgg gttttactga tgcatataca gagatgcttt ttgttcgctt ggttgtgatg   2760
atgtggtgtg gttgggcggt cgttcattcg ttctagatcg gagtagaata ctgtttcaaa   2820
ctacctggtg tatttattaa ttttggaact gtatgtgtgt gtcatacatc ttcatagtta   2880
cgagtttaag atggatggaa atatcgatct aggataggta tacatgttga tgtgggtttt   2940
actgatgcat atacatgatg gcatatgcag catctattca tatgctctaa ccttgagtac   3000
ctatctatta taataaacaa gtatgtttta taattatttt gatcttgata tacttggatg   3060
atggcatatg cagcagctat atgtggattt ttttagccct gccttcatac gctatttatt   3120
tgcttggtac tgtttctttt gtcgatgctc accctgttgt ttggtgttac ttctgcaggt   3180
cgactctaga ggatccacca tgaacaagaa caacaccaag ctgagcaccc gcgccctgcc   3240
gagcttcatc gactacttca acggcatcta cggcttcgcc accggcatca aggacatcat   3300
```

```
gaacatgatc ttcaagaccg acaccggcgg cgacctgacc ctggacgaga tcctgaagaa   3360
ccagcagctg ctgaacgaca tcagcggcaa gctggacggc gtgaacggca gcctgaacga   3420
cctgatcgcc cagggcaacc tgaacaccga gctgagcaag gagatcctta agatcgccaa   3480
cgagcagaac caggtgctga acgacgtgaa caacaagctg gacgccatca acaccatgct   3540
gcgcgtgtac ctgccgaaga tcaccagcat gctgagcgac gtgatgaagc agaactacgc   3600
cctgagcctg cagatcgagt acctgagcaa gcagctgcag gagatcagcg acaagctgga   3660
catcatcaac gtgaacgtcc tgatcaacag caccctgacc gagatcaccc cggcctacca   3720
gcgcatcaag tacgtgaacg agaagttcga agagctgacc ttcgccaccg agaccagcag   3780
caaggtgaag aaggacggca gcccggccga catcctggac gagctgaccg agctgaccga   3840
gctggcgaag agcgtgacca agaacgacgt ggacggcttc gagttctacc tgaacacctt   3900
ccacgacgtg atggtgggca acaacctgtt cggccgcagc gccctgaaga ccgccagcga   3960
gctgatcacc aaggagaacg tgaagaccag cggcagcgag gtgggcaacg tgtacaactt   4020
cctgatcgtg ctgaccgccc tgcaggccca ggccttcctg accctgacca cctgtcgcaa   4080
gctgctgggc ctggccgaca tcgactacac cagcatcatg aacgagcact tgaacaagga   4140
gaaggaggag ttccgcgtga acatcctgcc gaccctgagc aacaccttca gcaacccgaa   4200
ctacgccaag gtgaagggca gcgacgagga cgccaagatg atcgtggagg ctaagccggg   4260
ccacgcgttg atcggcttcg agatcagcaa cgacagcatc accgtgctga aggtgtacga   4320
ggccaagctg aagcagaact accaggtgga caaggacagc ttgagcgagg tgatctacgg   4380
cgacatggac aagctgctgt gtccggacca gagcgagcaa atctactaca ccaacaacat   4440
cgtgttcccg aacgagtacg tgatcaccaa gatcgacttc accaagaaga tgaagaccct   4500
gcgctacgag gtgaccgcca acttctacga cagcagcacc ggcgagatcg acctgaacaa   4560
gaagaaggtg gagagcagcg aggccgagta ccgcaccctg agcgcgaacg acgacggcgt   4620
ctacatgcca ctgggcgtga tcagcgagac cttcctgacc ccgatcaacg gctttggcct   4680
gcaggccgac gagaacagcc gcctgatcac cctgacctgt aagagctacc tgcgcgagct   4740
gctgctagcc accgacctga gcaacaagga gaccaagctg atcgtgccac cgagcggctt   4800
catcagcaac atcgtggaga acggcagcat cgaggaggac aacctggagc cgtggaaggc   4860
caacaacaag aacgcctacg tggaccacac cggcggcgtg aacggcacca aggccctgta   4920
cgtgcacaag gacggcggca tcagccagtt catcggcgac aagctgaagc cgaagaccga   4980
gtacgtgatc cagtacaccg tgaagggcaa gccatcgatt cacctgaagg acgagaacac   5040
cggctacatc cactacgagg acaccaacaa caacctggag gactaccaga ccatcaacaa   5100
gcgcttcacc accggcaccg acctgaaggg cgtgtacctg atcctgaaga gccagaacgg   5160
cgacgaggcc tggggcgaca acttcatcat cctggagatc agcccgagcg agaagctgct   5220
gagcccggag ctgatcaaca ccaacaactg gaccagcacc ggcagcacca acatcagcgg   5280
caacaccctg accctgtacc agggcggccg cggcatcctg aagcagaacc tgcagctgga   5340
cagcttcagc acctaccgcg tgtacttcag cgtgagcggc gacgccaacg tgcgcatccg   5400
caactcccgc gaggtgctgt tcgagaagag gtacatgagc ggcgccaagg acgtgagcga   5460
gatgttcacc accaagttcg agaaggacaa cttctacatc gagctgagcc agggcaacaa   5520
cctgtacggc ggcccgatcg tgcacttcta cgacgtgagc atcaagtagg agctctagat   5580
ctgttctgca caaagtggag tagtcagtca tcgatcagga accagacacc agacttttat   5640
```

```
tcatacagtg aagtgaagtg aagtgcagtg cagtgagttg ctggtttttg tacaacttag   5700
tatgtatttg tatttgtaaa atacttctat caataaaatt tctaattcct aaaaccaaaa   5760
ttcgttcaaa catttggcaa taaagtttct taagattgaa tcctgttgcc ggtcttgcga   5820
tgattatcat ataatttctg ttgaattacg ttaagcatgt aataattaac atgtaatgca   5880
tgacgttatt tatgagatgg gtttttatga ttagagtccc gcaattatac atttaatacg   5940
cgatagaaaa caaaatatag cgcgcaaact aggataaatt atcgcgcgcg gtgtcatcta   6000
tgttactaga tccccgggtc tagacaattc agtacattaa aaacgtccgc catggtctga   6060
aggcaacaga taaggcatac tgggccttgt ggtagttgtt ttactgggcc tttttgtatg   6120
atctataaaa ttcactggga tcaacccgga gaggaatggc agcagatgca gtccccaggg   6180
tcctccgtcg ccgcctgagc acccggcacc cgcgctgaac cggagaggga cgcgcggacg   6240
ccgtgcagct ggtgcggagg gggctgtggc agatgaggat gagacgcgta cgtggctggg   6300
aaggccagca ggccaccggg tcttcgtcca gcccggcgcg agtggacagg actagagatg   6360
gcaacggtta caaacccgct gggttttacc gtcccaaacc cgtacccgtg aaaaatatct   6420
atgcccatta aaaaacccgt acccatgacg ggtttgagat tttgcccaaa cccgtaccca   6480
tcgggttaac gggtacccat gggttacccg cgggtttcat ctccaatata cctgttcttc   6540
tcataatcaa taagtatcgt aatgattaat gatatcatga tccaaaatct atgtaatgaa   6600
caacgagttc atgatttggt ataaaaatta ttagtagaga gaatgaaata caaataataa   6660
gttgtataat taagtgacct tgcactaagt tatccatcca tcacatatat aacgctagta   6720
aaaactataa tatcaagcaa gcaacactct caccgactac tgatacattc accaattgat   6780
aaaaaatatg aagtaaataa ggaataacaa gtttgttgtt cgtttataaa ataaaatgac   6840
aatatgcact aggtttggtc gggtttaaaa aacccacggg ttcacgggtt tgggtactat   6900
aggaacaaac ccgtacccat aaacccattg ggtacagatt tatgcccgtt aacaaaccca   6960
tgggtatgaa aattgaccca aacctatacc ctaatggggt aaaaacccat cgggtttcgg   7020
atttcgggta cccattgcca tctctagaca ggacaacctc ggccggtcct gtatgtaggc   7080
caccagcatc ggccagttgg tacatccagc cggggtcagg tcacttttac tcgtctcaat   7140
cagacaatca ccgtccacca acgaacgcca acgttgtcac ttgtcaggtc ggttgagact   7200
tgtatttttt tttgtcctcc gtaaaaatcg gttcaccag                          7239
```

```
<210> SEQ ID NO 5
<211> LENGTH: 7235
<212> TYPE: DNA
<213> ORGANISM: Artificial
<220> FEATURE:
<223> OTHER INFORMATION: synthetic

<400> SEQUENCE: 5
```

```
tcctgtgttg ttggaacaga cttctgtctc ttctggtgat cataaatatt taaatgaacc     60
agttgtgttg gaaaatgttg ttttcttttg tctctagact ggaaagcgga gttctcgtca    120
acacggttct ttcaactagg gatgaaagtg gtaatccgaa ttgttagtac aaatttaata    180
ttttaaaata gatatgtata aaattttatg ttgatctttt ttatgttatc aagcacatta    240
gtataaatta gtataaatat gaataaaata ttacataaaa tgttttatgt attatttggt    300
ccctacaaca taaatagttg aaaaaattac taaatttgtt ttcgaatcta tatcgaagtt    360
tatatctatt atttaagaaa aatataggat gaaaaggttt atcttttatg aatctttaca    420
agctggatct tataaacaag aaaataaatt tatattgtag attttatatc ctatttattc    480
```

```
gcaatcaaag aaaagcgact aaaaaactga ttaccgagta aatactgttt ccaaccgttt    540
tcgtccctac tatcaacgcc ttctcccaac cgcagtcgat ctgtccgtct gtatcaggcg    600
cagcggcacc cctgctgttc gactatctag accatagaat attttaggta tacaataatt    660
ttagttccac gctagaacat tttagttaga ataataacaa gatttgctat tgatgtagga    720
ctcgcccgtc actgtctaaa aaagcattct gtcggtctta ttctttaggc atcagcgggt    780
gtactatctc atttttccta tcatattcct cagtactctg ttaagtataa atggtctatt    840
ttacatgatg aactaataaa actaattaag gatcctaact ttttgtgaag gtaatttgga    900
tcattatgca ttaccatcct acgtatacct gctgcagcag catctgcgta agcacagcct    960
agatatatgc ttctgtgtgg actgaaagga gactttgttt atcaattagt atactcccat   1020
taaactgaag gcgggaaacg acaatctgat catgagcgga gaattaaggg agtcacgtta   1080
tgacccccgc cgatgacgcg ggacaagccg ttttacgttt ggaactgaca gaaccgcaac   1140
gttgaaggag ccactcagca agctggtaca agcttgcatg cctgcagtgc agcgtgaccc   1200
ggtcgtgccc ctctctagag ataatgagca ttgcatgtct aagttataaa aaattaccac   1260
atattttttt tgtcacactt gtttgaagtg cagtttatct atctttatac atatatttaa   1320
actttactct acgaataata taatctatag tactacaata atatcagtgt tttagagaat   1380
catataaatg aacagttaga catggtctaa aggacaattg agtattttga caacaggact   1440
ctacagtttt atctttttag tgtgcatgtg ttctcctttt tttttgcaaa tagcttcacc   1500
tatataatac ttcatccatt ttattagtac atccatttag ggtttagggt taatggtttt   1560
tatagactaa ttttttagt acatctattt tattctattt tagcctctaa attaagaaaa   1620
ctaaaactct attttagttt ttttatttaa taatttagat ataaaataga ataaaataaa   1680
gtgactaaaa attaaacaaa taccctttaa gaaattaaaa aaactaagga aacatttttc   1740
ttgtttcgag tagataatgc cagcctgtta aacgccgtcg acgagtctaa cggacaccaa   1800
ccagcgaacc agcagcgtcg cgtcgggcca agcgaagcag acggcacggc atctctgtcg   1860
ctgcctctgg acccctctcg agagttccgc tccaccgttg gacttgctcc gctgtcggca   1920
tccagaaatt gcgtggcgga gcggcagacg tgagccggca cggcaggcgg cctcctcctc   1980
ctctcacggc accggcagct acgggggatt cctttcccac cgctccttcg ctttcccttc   2040
ctcgcccgcc gtaataaata gacacccccct ccacaccctc tttccccaac ctcgtgttgt   2100
tcggagcgca cacacacaca accagatctc ccccaaatcc acccgtcggc acctccgctt   2160
caaggtacgc cgctcgtcct cccccccccc ccctctctac cttctctaga tcggcgttcc   2220
ggtccatggt tagggcccgg tagttctact tctgttcatg tttgtgttag atccgtgttt   2280
gtgttagatc cgtgctgcta gcgttcgtac acggatgcga cctgtacgtc agacacgttc   2340
tgattgctaa cttgccagtg tttctctttg gggaatcctg ggatggctct agccgttccg   2400
cagacgggat cgatttcatg attttttttg tttcgttgca tagggtttgg tttgcccttt   2460
tcctttattt caatatatgc cgtgcacttg tttgtcgggt catcttttca tgcttttttt   2520
tgtcttggtt gtgatgatgt ggtctggttg ggcggtcgtt ctagatcgga gtagaattct   2580
gtttcaaact acctggtgga tttattaatt ttggatctgt atgtgtgtgc catacatatt   2640
catagttacg aattgaagat gatggatgga aatatcgatc taggataggt atacatgttg   2700
atgcgggttt tactgatgca tatacagaga tgctttttgt tcgcttggtt gtgatgatgt   2760
ggtgtggttg ggcggtcgtt cattcgttct agatcggagt agaatactgt ttcaaactac   2820
```

ctggtgtatt tattaatttt ggaactgtat gtgtgtgtca tacatcttca tagttacgag 2880
tttaagatgg atggaaatat cgatctagga taggtataca tgttgatgtg ggttttactg 2940
atgcatatac atgatggcat atgcagcatc tattcatatg ctctaacctt gagtacctat 3000
ctattataat aaacaagtat gttttataat tattttgatc ttgatatact tggatgatgg 3060
catatgcagc agctatatgt ggattttttt agccctgcct tcatacgcta tttatttgct 3120
tggtactgtt tcttttgtcg atgctcaccc tgttgtttgg tgttacttct gcaggtcgac 3180
tctagaggat ccaccatgaa caagaacaac accaagctga gcacccgcgc cctgccgagc 3240
ttcatcgact acttcaacgg catctacggc ttcgccaccg gcatcaagga catcatgaac 3300
atgatcttca agaccgacac cggcggcgac ctgaccctgg acgagatcct gaagaaccag 3360
cagctgctga acgacatcag cggcaagctg gacggcgtga acggcagcct gaacgacctg 3420
atcgcccagg gcaacctgaa caccgagctg agcaaggaga tccttaagat cgccaacgag 3480
cagaaccagg tgctgaacga cgtgaacaac aagctggacg ccatcaacac catgctgcgc 3540
gtgtacctgc cgaagatcac cagcatgctg agcgacgtga tgaagcagaa ctacgccctg 3600
agcctgcaga tcgagtacct gagcaagcag ctgcaggaga tcagcgacaa gctggacatc 3660
atcaacgtga acgtcctgat caacagcacc ctgaccgaga tcacccccggc ctaccagcgc 3720
atcaagtacg tgaacgagaa gttcgaagag ctgaccttcg ccaccgagac cagcagcaag 3780
gtgaagaagg acggcagccc ggccgacatc ctggacgagc tgaccgagct gaccgagctg 3840
gcgaagagcg tgaccaagaa cgacgtggac ggcttcgagt tctacctgaa caccttccac 3900
gacgtgatgg tgggcaacaa cctgttcggc cgcagcgccc tgaagaccgc cagcgagctg 3960
atcaccaagg agaacgtgaa gaccagcggc agcgaggtgg gcaacgtgta caacttcctg 4020
atcgtgctga ccgccctgca ggcccaggcc ttcctgaccc tgaccacctg tcgcaagctg 4080
ctgggcctgg ccgacatcga ctacaccagc atcatgaacg agcacttgaa caaggagaag 4140
gaggagttcc gcgtgaacat cctgccgacc ctgagcaaca ccttcagcaa cccgaactac 4200
gccaaggtga agggcagcga cgaggacgcc aagatgatcg tggaggctaa gccgggccac 4260
gcgttgatcg gcttcgagat cagcaacgac agcatcaccg tgctgaaggt gtacgaggcc 4320
aagctgaagc agaactacca ggtggacaag gacagcttga gcgaggtgat ctacggcgac 4380
atggacaagc tgctgtgtcc ggaccagagc gagcaaatct actacaccaa caacatcgtg 4440
ttcccgaacg agtacgtgat caccaagatc gacttcacca agaagatgaa gaccctgcgc 4500
tacgaggtga ccgccaactt ctacgacagc agcaccggcg agatcgacct gaacaagaag 4560
aaggtggaga gcagcgaggc cgagtaccgc accctgagcg cgaacgacga cggcgtctac 4620
atgccactgg gcgtgatcag cgagaccttc ctgaccccga tcaacggctt tggcctgcag 4680
gccgacgaga acagccgcct gatcaccctg acctgtaaga gctacctgcg cgagctgctg 4740
ctagccaccg acctgagcaa caaggagacc aagctgatcg tgccaccgag cggcttcatc 4800
agcaacatcg tggagaacgg cagcatcgag gaggacaacc tggagccgtg gaaggccaac 4860
aacaagaacg cctacgtgga ccacaccggc ggcgtgaacg gcaccaaggc cctgtacgtg 4920
cacaaggacg gcggcatcag ccagttcatc ggcgacaagc tgaagccgaa gaccgagtac 4980
gtgatccagt acaccgtgaa gggcaagcca tcgattcacc tgaaggacga gaacaccggc 5040
tacatccact acgaggacac caacaacaac ctggaggact accagaccat caacaagcgc 5100
ttcaccaccg gcaccgacct gaagggcgtg tacctgatcc tgaagagcca gaacggcgac 5160
gaggcctggg gcgacaactt catcatcctg gagatcagcc cgagcgagaa gctgctgagc 5220

```
ccggagctga tcaacaccaa caactggacc agcaccggca gcaccaacat cagcggcaac   5280
accctgaccc tgtaccaggg cggccgcggc atcctgaagc agaacctgca gctggacagc   5340
ttcagcacct accgcgtgta cttcagcgtg agcggcgacg ccaacgtgcg catccgcaac   5400
tcccgcgagg tgctgttcga gaagaggtac atgagcggcg ccaaggacgt gagcgagatg   5460
ttcaccacca agttcgagaa ggacaacttc tacatcgagc tgagccaggg caacaacctg   5520
tacggcggcc cgatcgtgca cttctacgac gtgagcatca agtaggagct ctagatctgt   5580
tctgcacaaa gtggagtagt cagtcatcga tcaggaacca gacaccagac ttttattcat   5640
acagtgaagt gaagtgaagt gcagtgcagt gagttgctgg tttttgtaca acttagtatg   5700
tatttgtatt tgtaaaatac ttctatcaat aaaatttcta attcctaaaa ccaaaattcg   5760
ttcaaacatt tggcaataaa gtttcttaag attgaatcct gttgccggtc ttgcgatgat   5820
tatcatataa tttctgttga attacgttaa gcatgtaata attaacatgt aatgcatgac   5880
gttatttatg agatgggttt ttatgattag agtcccgcaa ttatacattt aatacgcgat   5940
agaaaacaaa atatagcgcg caaactagga taaattatcg cgcgcggtgt catctatgtt   6000
actagatccc cgggtctaga caattcagta cattaaaaac gtccgccatg gtctgaaggc   6060
aacagataag gcatactggg ccttgtggta gttgttttac tgggcctttt tgtatgatct   6120
ataaaattca ctgggatcaa cccggagagg aatggcagca gatgcagtcc ccagggtcct   6180
ccgtcgccgc ctgagcaccc ggcacccgcg ctgaaccgga gagggacgcg cggacgccgt   6240
gcagctggtg cggagggggc tgtggcagat gaggatgaga cgcgtacgtg gctgggaagg   6300
ccagcaggcc accgggtctt cgtccagccc ggcgcgagtg gacaggacta gagatggcaa   6360
cggttacaaa cccgctgggt tttaccgtcc caaacccgta cccgtgaaaa atatctatgc   6420
ccattaaaaa acccgtaccc atgacgggtt tgagattttg cccaaacccg tacccatcgg   6480
gttaacgggt acccatgggt tacccgcggg tttcatctcc aatatacctg ttcttctcat   6540
aatcaataag tatcgtaatg attaatgata tcatgatcca aaatctatgt aatgaacaac   6600
gagttcatga tttggtataa aaattattag tagagagaat gaaatacaaa taataagttg   6660
tataattaag tgaccttgca ctaagttatc catccatcac atatataacg ctagtaaaaa   6720
ctataatatc aagcaagcaa cactctcacc gactactgat acattcacca attgataaaa   6780
aatatgaagt aaataaggaa taacaagttt gttgttcgtt tataaaataa aatgacaata   6840
tgcactaggt ttggtcgggt ttaaaaaacc cacgggttca cgggtttggg tactatagga   6900
acaaacccgt acccataaac ccattgggta cagatttatg cccgttaaca aacccatggg   6960
tatgaaaatt gacccaaacc tataccctaa tggggtaaaa acccatcggg tttcggattt   7020
cgggtaccca ttgccatctc tagacaggac aacctcggcc ggtcctgtat gtaggccacc   7080
agcatcggcc agttggtaca tccagccggg gtcaggtcac ttttactcgt ctcaatcaga   7140
caatcaccgt ccaccaacga acgccaacgt tgtcacttgt caggtcggtt gagacttgta   7200
tttttttttg tcctccgtaa aaatcggttc accag                              7235
```

<210> SEQ ID NO 6
<211> LENGTH: 7310
<212> TYPE: DNA
<213> ORGANISM: Artificial
<220> FEATURE:
<223> OTHER INFORMATION: synthetic

<400> SEQUENCE: 6

-continued

```
tcctgtgttg ttggaacaga cttctgtctc ttctggtgat cataaatatt taaatgaacc     60
agttgtgttg gaaaatgttg ttttcttttg tctctagact ggaaagcgga gttctcgtca    120
acacggttct ttcaactagg gatgaaagtg gtaatccgaa ttgttagtac aaatttaata    180
ttttaaaata gatatgtata aaattttatg ttgatctttt ttatgttatc aagcacatta    240
gtataaatta gtataaatat gaataaaata ttacataaaa tgttttatgt attatttggt    300
ccctacaaca taaatagttg aaaaaattac taaatttgtt ttcgaatcta tatcgaagtt    360
tatatctatt atttaagaaa aatataggat gaaaaggttt atcttttatg aatctttaca    420
agctggatct tataaacaag aaaataaatt tatattgtag attttatatc ctatttattc    480
gcaatcaaag aaaagcgact aaaaaactga ttaccgagta aatactgttt ccaaccgttt    540
tcgtccctac tatcaacgcc ttctcccaac cgcagtcgat ctgtccgtct gtatcaggcg    600
cagcggcacc cctgctgttc gactatctag accatagaat attttaggta tacaataatt    660
ttagttccac gctagaacat tttagttaga ataataacaa gatttgctat tgatgtagga    720
ctcgcccgtc actgtctaaa aaagcattct gtcggtctta ttctttaggc atcagcgggt    780
gtactatctc atttttccta tcatattcct cagtactctg ttaagtataa atggtctatt    840
ttacatgatg aactaataaa actaattaag gatcctaact ttttgtgaag gtaatttgga    900
tcattatgca ttaccatcct acgtatacct gctgcagcag catctgcgta agcacagcct    960
agatatatgc ttctgtgtgg actgaaagga gactttgttt atcaattagt atactcccaa   1020
aaaactgatg acaccaatga tgcaaatagg ctgggaatag tctgtctaat agtttgagtg   1080
aatcatgtca tagtttaaac tgaaggcggg aaacgacaat ctgatcatga gcggagaatt   1140
aagggagtca cgttatgacc cccgccgatg acgcgggaca agccgtttta cgtttggaac   1200
tgacagaacc gcaacgttga aggagccact cagcaagctg gtacaagctt gcatgcctgc   1260
agtgcagcgt gacccggtcg tgcccctctc tagagataat gagcattgca tgtctaagtt   1320
ataaaaaatt accacatatt ttttttgtca cacttgtttg aagtgcagtt tatctatctt   1380
tatacatata tttaaacttt actctacgaa taatataatc tatagtacta caataatatc   1440
agtgttttag agaatcatat aaatgaacag ttagacatgg tctaaaggac aattgagtat   1500
tttgacaaca ggactctaca gttttatctt tttagtgtgc atgtgttctc cttttttttt   1560
gcaaatagct tcacctatat aatacttcat ccattttatt agtacatcca tttagggttt   1620
agggttaatg gtttttatag actaattttt ttagtacatc tattttattc tattttagcc   1680
tctaaattaa gaaaactaaa actctatttt agttttttta tttaataatt tagatataaa   1740
atagaataaa ataaagtgac taaaaattaa acaaataccc tttaagaaat taaaaaaact   1800
aaggaaacat ttttcttgtt tcgagtagat aatgccagcc tgttaaacgc cgtcgacgag   1860
tctaacggac accaaccagc gaaccagcag cgtcgcgtcg ggccaagcga agcagacggc   1920
acggcatctc tgtcgctgcc tctggacccc tctcgagagt tccgctccac cgttggactt   1980
gctccgctgt cggcatccag aaattgcgtg gcggagcggc agacgtgagc cggcacggca   2040
ggcggcctcc tcctcctctc acggcaccgg cagctacggg ggattccttt cccaccgctc   2100
cttcgctttc ccttcctcgc ccgccgtaat aaatagacac cccctccaca ccctctttcc   2160
ccaacctcgt gttgttcgga gcgcacacac acacaaccag atctccccca aatccacccg   2220
tcggcacctc cgcttcaagg tacgccgctc gtcctccccc ccccccctc tctaccttct   2280
ctagatcggc gttccggtcc atggttaggg cccggtagtt ctacttctgt tcatgtttgt   2340
gttagatccg tgtttgtgtt agatccgtgc tgctagcgtt cgtacacgga tgcgacctgt   2400
```

```
acgtcagaca cgttctgatt gctaacttgc cagtgtttct ctttggggaa tcctgggatg   2460
gctctagccg ttccgcagac gggatcgatt tcatgatttt ttttgtttcg ttgcataggg   2520
tttggtttgc ccttttcctt tatttcaata tatgccgtgc acttgtttgt cgggtcatct   2580
tttcatgctt ttttttgtct tggttgtgat gatgtggtct ggttgggcgg tcgttctaga   2640
tcggagtaga attctgtttc aaactacctg gtggatttat taattttgga tctgtatgtg   2700
tgtgccatac atattcatag ttacgaattg aagatgatgg atggaaatat cgatctagga   2760
taggtataca tgttgatgcg ggttttactg atgcatatac agagatgctt tttgttcgct   2820
tggttgtgat gatgtggtgt ggttgggcgg tcgttcattc gttctagatc ggagtagaat   2880
actgtttcaa actacctggt gtatttatta attttggaac tgtatgtgtg tgtcatacat   2940
cttcatagtt acgagtttaa gatggatgga aatatcgatc taggataggt atacatgttg   3000
atgtgggttt tactgatgca tatacatgat ggcatatgca gcatctattc atatgctcta   3060
accttgagta cctatctatt ataataaaca agtatgtttt ataattattt tgatcttgat   3120
atacttggat gatggcatat gcagcagcta tatgtggatt tttttagccc tgccttcata   3180
cgctatttat ttgcttggta ctgtttcttt tgtcgatgct caccctgttg tttggtgtta   3240
cttctgcagg tcgactctag aggatccacc atgaacaaga acaacaccaa gctgagcacc   3300
cgcgccctgc cgagcttcat cgactacttc aacggcatct acggcttcgc caccggcatc   3360
aaggacatca tgaacatgat cttcaagacc gacaccggcg gcgacctgac cctggacgag   3420
atcctgaaga accagcagct gctgaacgac atcagcggca agctggacgg cgtgaacggc   3480
agcctgaacg acctgatcgc ccagggcaac ctgaacaccg agctgagcaa ggagatcctt   3540
aagatcgcca acgagcagaa ccaggtgctg aacgacgtga acaacaagct ggacgccatc   3600
aacaccatgc tgcgcgtgta cctgccgaag atcaccagca tgctgagcga cgtgatgaag   3660
cagaactacg ccctgagcct gcagatcgag tacctgagca agcagctgca ggagatcagc   3720
gacaagctgg acatcatcaa cgtgaacgtc ctgatcaaca gcaccctgac cgagatcacc   3780
ccggcctacc agcgcatcaa gtacgtgaac gagaagttcg aagagctgac cttcgccacc   3840
gagaccagca gcaaggtgaa gaaggacggc agcccggccg acatcctgga cgagctgacc   3900
gagctgaccg agctggcgaa gagcgtgacc aagaacgacg tggacggctt cgagttctac   3960
ctgaacacct tccacgacgt gatggtgggc aacaacctgt tcggccgcag cgccctgaag   4020
accgccagcg agctgatcac caaggagaac gtgaagacca gcggcagcga ggtgggcaac   4080
gtgtacaact tcctgatcgt gctgaccgcc ctgcaggccc aggccttcct gaccctgacc   4140
acctgtcgca agctgctggg cctggccgac atcgactaca ccagcatcat gaacgagcac   4200
ttgaacaagg agaaggagga gttccgcgtg aacatcctgc cgaccctgag caacaccttc   4260
agcaacccga actacgccaa ggtgaagggc agcgacgagg acgccaagat gatcgtggag   4320
gctaagccgg gccacgcgtt gatcggcttc gagatcagca acgacagcat caccgtgctg   4380
aaggtgtacg aggccaagct gaagcagaac taccaggtgg acaaggacag cttgagcgag   4440
gtgatctacg gcgacatgga caagctgctg tgtccggacc agagcgagca aatctactac   4500
accaacaaca tcgtgttccc gaacgagtac gtgatcacca agatcgactt caccaagaag   4560
atgaagaccc tgcgctacga ggtgaccgcc aacttctacg acagcagcac cggcgagatc   4620
gacctgaaca agaagaaggt ggagagcagc gaggccgagt accgcaccct gagcgcgaac   4680
gacgacggcg tctacatgcc actgggcgtg atcagcgaga ccttcctgac cccgatcaac   4740
```

```
ggctttggcc tgcaggccga cgagaacagc cgcctgatca ccctgacctg taagagctac   4800
ctgcgcgagc tgctgctagc caccgacctg agcaacaagg agaccaagct gatcgtgcca   4860
ccgagcggct tcatcagcaa catcgtggag aacggcagca tcgaggagga caacctggag   4920
ccgtggaagg ccaacaacaa gaacgcctac gtggaccaca ccggcggcgt gaacggcacc   4980
aaggccctgt acgtgcacaa ggacggcggc atcagccagt tcatcggcga caagctgaag   5040
ccgaagaccg agtacgtgat ccagtacacc gtgaagggca agccatcgat tcacctgaag   5100
gacgagaaca ccggctacat ccactacgag gacaccaaca acaacctgga ggactaccag   5160
accatcaaca agcgcttcac caccggcacc gacctgaagg gcgtgtacct gatcctgaag   5220
agccagaacg gcgacgaggc ctggggcgac aacttcatca tcctggagat cagcccgagc   5280
gagaagctgc tgagcccgga gctgatcaac accaacaact ggaccagcac cggcagcacc   5340
aacatcagcg gcaacaccct gaccctgtac cagggcggcc gcggcatcct gaagcagaac   5400
ctgcagctgg acagcttcag cacctaccgc gtgtacttca gcgtgagcgg cgacgccaac   5460
gtgcgcatcc gcaactcccg cgaggtgctg ttcgagaaga ggtacatgag cggcgccaag   5520
gacgtgagcg agatgttcac caccaagttc gagaaggaca acttctacat cgagctgagc   5580
cagggcaaca acctgtacgg cggcccgatc gtgcacttct acgacgtgag catcaagtag   5640
gagctctaga tctgttctgc acaaagtgga gtagtcagtc atcgatcagg aaccagacac   5700
cagactttta ttcatacagt gaagtgaagt gaagtgcagt gcagtgagtt gctggttttt   5760
gtacaactta gtatgtattt gtatttgtaa aatacttcta tcaataaaat ttctaattcc   5820
taaaaccaaa attcgttcaa acatttggca ataaagtttc ttaagattga atcctgttgc   5880
cggtcttgcg atgattatca tataatttct gttgaattac gttaagcatg taataattaa   5940
catgtaatgc atgacgttat ttatgagatg ggtttttatg attagagtcc cgcaattata   6000
catttaatac gcgatagaaa acaaaatata gcgcgcaaac taggataaat tatcgcgcgc   6060
ggtgtcatct atgttactag atccccgggt ctagacaatt cagtacatta aaaacgtccg   6120
ccatggtctg aaggcaacag ataaggcata ctgggccttg tggtagttgt tttactgggc   6180
ctttttgtat gatctataaa attcactggg atcaacccgg agaggaatgg cagcagatgc   6240
agtccccagg gtcctccgtc gccgcctgag cacccggcac ccgcgctgaa ccggagaggg   6300
acgcgcggac gccgtgcagc tggtgcggag ggggctgtgg cagatgagga tgagacgcgt   6360
acgtggctgg gaaggccagc aggccaccgg gtcttcgtcc agcccggcgc gagtggacag   6420
gactagagat ggcaacggtt acaaacccgc tgggttttac cgtcccaaac ccgtacccgt   6480
gaaaaatatc tatgcccatt aaaaaacccg tacccatgac gggtttgaga ttttgcccaa   6540
acccgtaccc atcgggttaa cggtacccca tgggttaccc gcgggtttca tctccaatat   6600
acctgttctt ctcataatca ataagtatcg taatgattaa tgatatcatg atccaaaatc   6660
tatgtaatga acaacgagtt catgatttgg tataaaaatt attagtagag agaatgaaat   6720
acaaataata agttgtataa ttaagtgacc ttgcactaag ttatccatcc atcacatata   6780
taacgctagt aaaaactata atatcaagca agcaacactc tcaccgacta ctgatacatt   6840
caccaattga taaaaaatat gaagtaaata aggaataaca agtttgttgt tcgtttataa   6900
aataaaatga caatatgcac taggtttggt cgggtttaaa aaacccacgg gttcacgggt   6960
ttgggtacta taggaacaaa cccgtaccca taaacccatt gggtacagat ttatgcccgt   7020
taacaaaccc atgggtatga aaattgaccc aaacctatac cctaatgggg taaaaaccca   7080
tcgggtttcg gatttcgggt acccattgcc atctctagac aggacaacct cggccggtcc   7140
```

tgtatgtagg ccaccagcat cggccagttg gtacatccag ccggggtcag gtcactttta 7200
ctcgtctcaa tcagacaatc accgtccacc aacgaacgcc aacgttgtca cttgtcaggt 7260
cggttgagac ttgtattttt ttttgtcctc cgtaaaaatc ggttcaccag 7310

<210> SEQ ID NO 7
<211> LENGTH: 24
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (3)..(22)
<223> OTHER INFORMATION: n is absent or is a, c, g, or t

<400> SEQUENCE: 7
aannnnnnnn nnnnnnnnnn nnac 24

<210> SEQ ID NO 8
<211> LENGTH: 24
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (8)..(17)
<223> OTHER INFORMATION: n is absent or is a, c, g, or t

<400> SEQUENCE: 8
aatcatgnnn nnnnnnnttt aaac 24

<210> SEQ ID NO 9
<211> LENGTH: 24
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (10)..(15)
<223> OTHER INFORMATION: n is absent or is a, c, g, or t

<400> SEQUENCE: 9
aatcatgtcn nnnnnagttt aaac 24

<210> SEQ ID NO 10
<211> LENGTH: 16
<212> TYPE: DNA
<213> ORGANISM: Artificial
<220> FEATURE:
<223> OTHER INFORMATION: synthetic

<400> SEQUENCE: 10
aatcatgtgt ttaaac 16

<210> SEQ ID NO 11
<211> LENGTH: 16
<212> TYPE: DNA
<213> ORGANISM: Artificial
<220> FEATURE:
<223> OTHER INFORMATION: synthetic

<400> SEQUENCE: 11
aatcatgagt ttaaac 16

<210> SEQ ID NO 12
<211> LENGTH: 16
<212> TYPE: DNA
<213> ORGANISM: Artificial
<220> FEATURE:
<223> OTHER INFORMATION: synthetic

<400> SEQUENCE: 12
aatcatgtct ttaaac 16

<210> SEQ ID NO 13
<211> LENGTH: 14
<212> TYPE: DNA
<213> ORGANISM: Artificial
<220> FEATURE:
<223> OTHER INFORMATION: synthetic

<400> SEQUENCE: 13
aatcatgttt aaac 14

<210> SEQ ID NO 14
<211> LENGTH: 14
<212> TYPE: DNA
<213> ORGANISM: Artificial
<220> FEATURE:
<223> OTHER INFORMATION: synthetic

<400> SEQUENCE: 14
aatcaagttt aaac 14

<210> SEQ ID NO 15
<211> LENGTH: 14
<212> TYPE: DNA
<213> ORGANISM: Artificial
<220> FEATURE:
<223> OTHER INFORMATION: synthetic

<400> SEQUENCE: 15
aatcatgtct aaac 14

<210> SEQ ID NO 16
<211> LENGTH: 18
<212> TYPE: DNA
<213> ORGANISM: Artificial
<220> FEATURE:
<223> OTHER INFORMATION: synthetic

<400> SEQUENCE: 16
aatcatgtca gtttaaac 18

<210> SEQ ID NO 17
<211> LENGTH: 18
<212> TYPE: DNA
<213> ORGANISM: Artificial
<220> FEATURE:
<223> OTHER INFORMATION: synthetic

<400> SEQUENCE: 17
aatcatgtta gtttaaac 18

<210> SEQ ID NO 18
<211> LENGTH: 18
<212> TYPE: DNA
<213> ORGANISM: Artificial
<220> FEATURE:
<223> OTHER INFORMATION: synthetic

<400> SEQUENCE: 18
aatcatgtca gtttaaac 18

<210> SEQ ID NO 19
<211> LENGTH: 24
<212> TYPE: DNA
<213> ORGANISM: Artificial
<220> FEATURE:
<223> OTHER INFORMATION: synthetic

<400> SEQUENCE: 19
aatcatgtca tagtttaaac tgaa 24

<210> SEQ ID NO 20
<211> LENGTH: 23
<212> TYPE: DNA
<213> ORGANISM: Artificial
<220> FEATURE:
<223> OTHER INFORMATION: synthetic

<400> SEQUENCE: 20
ccgccttcag tttaaactat cag 23

<210> SEQ ID NO 21
<211> LENGTH: 23
<212> TYPE: DNA
<213> ORGANISM: Artificial
<220> FEATURE:
<223> OTHER INFORMATION: synthetic

<400> SEQUENCE: 21
catcattggt gtcatcagtt ttt 23

<210> SEQ ID NO 22
<211> LENGTH: 23
<212> TYPE: DNA
<213> ORGANISM: Artificial
<220> FEATURE:
<223> OTHER INFORMATION: synthetic

<400> SEQUENCE: 22
agtgaatcat gtcactgata gtt 23

<210> SEQ ID NO 23
<211> LENGTH: 23
<212> TYPE: DNA
<213> ORGANISM: Artificial
<220> FEATURE:
<223> OTHER INFORMATION: synthetic

<400> SEQUENCE: 23
taattcctaa aaccaaaatc cag 23

<210> SEQ ID NO 24
<211> LENGTH: 23
<212> TYPE: DNA
<213> ORGANISM: Artificial
<220> FEATURE:
<223> OTHER INFORMATION: synthetic

<400> SEQUENCE: 24
ttgccaaatg tttgaacgat ctg 23

<210> SEQ ID NO 25

<211> LENGTH: 29
<212> TYPE: DNA
<213> ORGANISM: Artificial
<220> FEATURE:
<223> OTHER INFORMATION: synthetic

<400> SEQUENCE: 25
taaaaccaaa attcgttcaa acatttggc 29

<210> SEQ ID NO 26
<211> LENGTH: 26
<212> TYPE: DNA
<213> ORGANISM: Artificial
<220> FEATURE:
<223> OTHER INFORMATION: synthetic

<400> SEQUENCE: 26
tttaatgtac tgaattgtct agaccc 26

<210> SEQ ID NO 27
<211> LENGTH: 27
<212> TYPE: DNA
<213> ORGANISM: Artificial
<220> FEATURE:
<223> OTHER INFORMATION: synthetic

<400> SEQUENCE: 27
tttatagatc atacaaaaag gcccagt 27

<210> SEQ ID NO 28
<211> LENGTH: 27
<212> TYPE: DNA
<213> ORGANISM: Artificial
<220> FEATURE:
<223> OTHER INFORMATION: synthetic

<400> SEQUENCE: 28
tttaatgtac tgaattgtct agacccg 27

<210> SEQ ID NO 29
<211> LENGTH: 7309
<212> TYPE: DNA
<213> ORGANISM: Artificial
<220> FEATURE:
<223> OTHER INFORMATION: synthetic

<400> SEQUENCE: 29
tcctgtgttg ttggaacaga cttctgtctc ttctggtgat cataaatatt taaatgaacc 60
agttgtgttg gaaaatgttg ttttcttttg tctctagact ggaaagcgga gttctcgtca 120
acacggttct ttcaactagg gatgaaagtg gtaatccgaa ttgttagtac aaatttaata 180
ttttaaaata gatatgtata aaattttatg ttgatctttt ttatgttatc aagcacatta 240
gtataaatta gtataaatat gaataaaata ttacataaaa tgttttatgt attatttggt 300
ccctacaaca taaatagttg aaaaaattac taaatttgtt ttcgaatcta tatcgaagtt 360
tatatctatt atttaagaaa aatataggat gaaaaggttt atcttttatg aatctttaca 420
agctggatct tataaacaag aaaataaatt tatattgtag attttatatc ctatttattc 480
gcaatcaaag aaaagcgact aaaaaactga ttaccgagta aatactgttt ccaaccgttt 540
tcgtccctac tatcaacgcc ttctcccaac cgcagtcgat ctgtccgtct gtatcaggcg 600
cagcggcacc cctgctgttc gactatctag accatagaat attttaggta tacaataatt 660
ttagttccac gctagaacat tttagttaga ataataacaa gatttgctat tgatgtagga 720

```
ctcgcccgtc actgtctaaa aaagcattct gtcggtctta ttctttaggc atcagcgggt    780
gtactatctc atttttccta tcatattcct cagtactctg ttaagtataa atggtctatt    840
ttacatgatg aactaataaa actaattaag gatcctaact ttttgtgaag gtaatttgga    900
tcattatgca ttaccatcct acgtatacct gctgcagcag catctgcgta agcacagcct    960
agatatatgc ttctgtgtgg actgaaagga gactttgttt atcaattagt atactcccaa   1020
aaaactgatg acaccaatga tgcaaatagg ctgggaatag tctgtctaat agtttgagtg   1080
aatcatgtca ctgattaaac tgaaggcggg aaacgacaat ctgatcatga gcggagaatt   1140
aagggagtca cgttatgacc cccgccgatg acgcgggaca agccgtttta cgtttggaac   1200
tgacagaacc gcaacgttga aggagccact cagcaagctg gtacaagctt gcatgcctgc   1260
agtgcagcgt gacccggtcg tgcccctctc tagagataat gagcattgca tgtctaagtt   1320
ataaaaaatt accacatatt ttttttgtca cacttgtttg aagtgcagtt tatctatctt   1380
tatacatata tttaaacttt actctacgaa taatataatc tatagtacta caataatatc   1440
agtgttttag agaatcatat aaatgaacag ttagacatgg tctaaaggac aattgagtat   1500
tttgacaaca ggactctaca gttttatctt tttagtgtgc atgtgttctc cttttttttt   1560
gcaaatagct tcacctatat aatacttcat ccattttatt agtacatcca tttagggttt   1620
agggttaatg gtttttatag actaattttt ttagtacatc tattttattc tattttagcc   1680
tctaaattaa gaaaactaaa actctatttt agttttttta tttaataatt tagatataaa   1740
atagaataaa ataaagtgac taaaaattaa acaaataccc tttaagaaat taaaaaaact   1800
aaggaaacat ttttcttgtt tcgagtagat aatgccagcc tgttaaacgc cgtcgacgag   1860
tctaacggac accaaccagc gaaccagcag cgtcgcgtcg ggccaagcga agcagacggc   1920
acggcatctc tgtcgctgcc tctggacccc tctcgagagt tccgctccac cgttggactt   1980
gctccgctgt cggcatccag aaattgcgtg gcggagcggc agacgtgagc cggcacggca   2040
ggcggcctcc tcctcctctc acggcaccgg cagctacggg ggattccttt cccaccgctc   2100
cttcgctttc ccttcctcgc ccgccgtaat aaatagacac cccctccaca ccctctttcc   2160
ccaacctcgt gttgttcgga gcgcacacac acacaaccag atctccccca aatccacccg   2220
tcggcacctc cgcttcaagg tacgccgctc gtcctccccc ccccccccctc tctaccttct   2280
ctagatcggc gttccggtcc atggttaggg cccggtagtt ctacttctgt tcatgtttgt   2340
gttagatccg tgtttgtgtt agatccgtgc tgctagcgtt cgtacacgga tgcgacctgt   2400
acgtcagaca cgttctgatt gctaacttgc cagtgtttct ctttggggaa tcctgggatg   2460
gctctagccg ttccgcagac gggatcgatt tcatgatttt ttttgtttcg ttgcataggg   2520
tttggtttgc cctttttcctt tatttcaata tatgccgtgc acttgtttgt cgggtcatct   2580
tttcatgctt ttttttgtct tggttgtgat gatgtggtct ggttgggcgg tcgttctaga   2640
tcggagtaga attctgtttc aaactacctg gtggatttat taattttgga tctgtatgtg   2700
tgtgccatac atattcatag ttacgaattg aagatgatgg atggaaatat cgatctagga   2760
taggtataca tgttgatgcg ggttttactg atgcatatac agagatgctt tttgttcgct   2820
tggttgtgat gatgtggtgt ggttgggcgg tcgttcattc gttctagatc ggagtagaat   2880
actgtttcaa actacctggt gtatttatta attttggaac tgtatgtgtg tgtcatacat   2940
cttcatagtt acgagtttaa gatggatgga aatatcgatc taggataggt atacatgttg   3000
atgtgggttt tactgatgca tatacatgat ggcatatgca gcatctattc atatgctcta   3060
```

-continued

```
accttgagta cctatctatt ataataaaca agtatgtttt ataattattt tgatcttgat   3120
atacttggat gatggcatat gcagcagcta tatgtggatt tttttagccc tgccttcata   3180
cgctatttat ttgcttggta ctgtttcttt tgtcgatgct caccctgttg tttggtgtta   3240
cttctgcagg tcgactctag aggatccacc atgaacaaga acaacaccaa gctgagcacc   3300
cgcgccctgc cgagcttcat cgactacttc aacggcatct acggcttcgc caccggcatc   3360
aaggacatca tgaacatgat cttcaagacc gacaccggcg gcgacctgac cctggacgag   3420
atcctgaaga accagcagct gctgaacgac atcagcggca agctggacgg cgtgaacggc   3480
agcctgaacg acctgatcgc ccagggcaac ctgaacaccg agctgagcaa ggagatcctt   3540
aagatcgcca acgagcagaa ccaggtgctg aacgacgtga acaacaagct ggacgccatc   3600
aacaccatgc tgcgcgtgta cctgccgaag atcaccagca tgctgagcga cgtgatgaag   3660
cagaactacg ccctgagcct gcagatcgag tacctgagca agcagctgca ggagatcagc   3720
gacaagctgg acatcatcaa cgtgaacgtc ctgatcaaca gcaccctgac cgagatcacc   3780
ccggcctacc agcgcatcaa gtacgtgaac gagaagttcg aagagctgac cttcgccacc   3840
gagaccagca gcaaggtgaa gaaggacggc agcccggccg acatcctgga cgagctgacc   3900
gagctgaccg agctggcgaa gagcgtgacc aagaacgacg tggacggctt cgagttctac   3960
ctgaacacct tccacgacgt gatggtgggc aacaacctgt tcggccgcag cgccctgaag   4020
accgccagcg agctgatcac caaggagaac gtgaagacca gcggcagcga ggtgggcaac   4080
gtgtacaact tcctgatcgt gctgaccgcc ctgcaggccc aggccttcct gaccctgacc   4140
acctgtcgca agctgctggg cctggccgac atcgactaca ccagcatcat gaacgagcac   4200
ttgaacaagg agaaggagga gttccgcgtg aacatcctgc cgaccctgag caacaccttc   4260
agcaacccga actacgccaa ggtgaagggc agcgacgagg acgccaagat gatcgtggag   4320
gctaagccgg gccacgcgtt gatcggcttc gagatcagca acgacagcat caccgtgctg   4380
aaggtgtacg aggccaagct gaagcagaac taccaggtgg acaaggacag cttgagcgag   4440
gtgatctacg gcgacatgga caagctgctg tgtccggacc agagcgagca aatctactac   4500
accaacaaca tcgtgttccc gaacgagtac gtgatcacca agatcgactt caccaagaag   4560
atgaagaccc tgcgctacga ggtgaccgcc aacttctacg acagcagcac cggcgagatc   4620
gacctgaaca agaagaaggt ggagagcagc gaggccgagt accgcaccct gagcgcgaac   4680
gacgacggcg tctacatgcc actgggcgtg atcagcgaga ccttcctgac cccgatcaac   4740
ggctttggcc tgcaggccga cgagaacagc cgcctgatca ccctgacctg taagagctac   4800
ctgcgcgagc tgctgctagc caccgacctg agcaacaagg agaccaagct gatcgtgcca   4860
ccgagcggct tcatcagcaa catcgtggag aacggcagca tcgaggagga caacctggag   4920
ccgtggaagg ccaacaacaa gaacgcctac gtggaccaca ccggcggcgt gaacggcacc   4980
aaggccctgt acgtgcacaa ggacggcggc atcagccagt tcatcggcga caagctgaag   5040
ccgaagaccg agtacgtgat ccagtacacc gtgaagggca agccatcgat tcacctgaag   5100
gacgagaaca ccggctacat ccactacgag gacaccaaca acaacctgga ggactaccag   5160
accatcaaca agcgcttcac caccggcacc gacctgaagg gcgtgtacct gatcctgaag   5220
agccagaacg gcgacgaggc ctggggcgac aacttcatca tcctggagat cagcccgagc   5280
gagaagctgc tgagcccgga gctgatcaac accaacaact ggaccagcac cggcagcacc   5340
aacatcagcg gcaacaccct gaccctgtac cagggcggcc gcggcatcct gaagcagaac   5400
ctgcagctgg acagcttcag cacctaccgc gtgtacttca gcgtgagcgg cgacgccaac   5460
```

```
gtgcgcatcc gcaactcccg cgaggtgctg ttcgagaaga ggtacatgag cggcgccaag   5520
gacgtgagcg agatgttcac caccaagttc gagaaggaca acttctacat cgagctgagc   5580
cagggcaaca acctgtacgg cggcccgatc gtgcacttct acgacgtgag catcaagtag   5640
gagctctaga tctgttctgc acaaagtgga gtagtcagtc atcgatcagg aaccagacac   5700
cagactttta ttcatacagt gaagtgaagt gaagtgcagt gcagtgagtt gctggttttt   5760
gtacaactta gtatgtattt gtatttgtaa aatacttcta tcaataaaat ttctaattcc   5820
taaaaccaaa attcgttcaa acatttggca ataaagtttc ttaagattga atcctgttgc   5880
cggtcttgcg atgattatca tataatttct gttgaattac gttaagcatg taataattaa   5940
catgtaatgc atgacgttat ttatgagatg ggtttttatg attagagtcc cgcaattata   6000
catttaatac gcgatagaaa acaaaatata gcgcgcaaac taggataaat tatcgcgcgc   6060
ggtgtcatct atgttactag atccccgggt ctagacaatt cagtacatta aaaacgtccg   6120
ccatggtctg aaggcaacag ataaggcata ctgggccttg tggtagttgt tttactgggc   6180
ctttttgtat gatctataaa attcactggg atcaacccgg agaggaatgg cagcagatgc   6240
agtccccagg gtcctccgtc gccgcctgag cacccggcac ccgcgctgaa ccggagaggg   6300
acgcgcggac gccgtgcagc tggtgcggag ggggctgtgg cagatgagga tgagacgcgt   6360
acgtggctgg gaaggccagc aggccaccgg gtcttcgtcc agcccggcgc gagtggacag   6420
gactagagat ggcaacggtt acaaacccgc tgggttttac cgtcccaaac ccgtacccgt   6480
gaaaaatatc tatgcccatt aaaaaacccg tacccatgac gggtttgaga ttttgcccaa   6540
acccgtaccc atcgggttaa cggtacccca tgggttaccc gcgggtttca tctccaatat   6600
acctgttctt ctcataatca ataagtatcg taatgattaa tgatatcatg atccaaaatc   6660
tatgtaatga acaacgagtt catgatttgg tataaaaatt attagtagag agaatgaaat   6720
acaaataata agttgtataa ttaagtgacc ttgcactaag ttatccatcc atcacatata   6780
taacgctagt aaaaactata atatcaagca agcaacactc tcaccgacta ctgatacatt   6840
caccaattga taaaaaatat gaagtaaata aggaataaca agtttgttgt tcgtttataa   6900
aataaaatga caatatgcac taggtttggt cgggtttaaa aaacccacgg gttcacgggt   6960
ttgggtacta taggaacaaa cccgtaccca taaacccatt gggtacagat ttatgcccgt   7020
taacaaaccc atgggtatga aaattgaccc aaacctatac cctaatgggg taaaaaccca   7080
tcgggtttcg gatttcgggt acccattgcc atctctagac aggacaacct cggccggtcc   7140
tgtatgtagg ccaccagcat cggccagttg gtacatccag ccggggtcag gtcactttta   7200
ctcgtctcaa tcagacaatc accgtccacc aacgaacgcc aacgttgtca cttgtcaggt   7260
cggttgagac ttgtattttt ttttgtcctc cgtaaaaatc ggttcacca              7309
```

<210> SEQ ID NO 30
<211> LENGTH: 27
<212> TYPE: DNA
<213> ORGANISM: Artificial
<220> FEATURE:
<223> OTHER INFORMATION: synthetic

<400> SEQUENCE: 30

```
tttgcatcat tggtgtcatc agttttt                                         27
```

<210> SEQ ID NO 31
<211> LENGTH: 27
<212> TYPE: DNA

<213> ORGANISM: Artificial
<220> FEATURE:
<223> OTHER INFORMATION: synthetic

<400> SEQUENCE: 31
tttcccgcct tcagtttaaa ctatcag 27

<210> SEQ ID NO 32
<211> LENGTH: 1243
<212> TYPE: DNA
<213> ORGANISM: Artificial
<220> FEATURE:
<223> OTHER INFORMATION: synthetic

<400> SEQUENCE: 32
tcgcaatcaa agaaaagcga ctaaaaaact gattaccgag taaatactgt ttccaaccgt 60
tttcgtccct actatcaacg ccttctccca accgcagtcg atctgtccgt ctgtatcagg 120
cgcagcggca cccctgctgt tcgactatct agaccataga atattttagg tatacaataa 180
ttttagttcc acgctagaac attttagtta gaataataac aagatttgct attgatgtag 240
gactcgcccg tcactgtcta aaaaagcatt ctgtcggtct tattctttag gcatcagcgg 300
gtgtactatc tcatttttcc tatcatattc ctcagtactc tgttaagtat aaatggtcta 360
ttttacatga tgaactaata aaactaatta aggatcctaa ctttttgtga aggtaatttg 420
gatcattatg cattaccatc ctacgtatac ctgctgcagc agcatctgcg taagcacagc 480
ctagatatat gcttctgtgt ggactgaaag gagactttgt ttatcaatta gtatactccc 540
aaaaaactga tgacaccaat gatgcaaata ggctgggaat agtctgtcta atagtttgag 600
tgaatcatgt cactgattta tagatcatac aaaaaggccc agttagttta aactgaaggc 660
gggaaacgac aatctgatca tgagcggaga attaagggag tcacgttatg acccccgccg 720
atgacgcggg acaagccgtt ttacgtttgg aactgacaga accgcaacgt tgaaggagcc 780
actcagcaag ctggtacaag cttgcatgcc tgcagtgcag cgtgacccgg tcgtgcccct 840
ctctagagat aatgagcatt gcatgtctaa gttataaaaa attaccacat attttttttg 900
tcacacttgt ttgaagtgca gtttatctat ctttatacat atatttaaac tttactctac 960
gaataatata atctatagta ctacaataat atcagtgttt tagagaatca tataaatgaa 1020
cagttagaca tggtctaaag gacaattgag tattttgaca acaggactct acagttttat 1080
ctttttagtg tgcatgtgtt ctcctttttt tttgcaaata gcttcaccta tataatactt 1140
catccatttt attagtacat ccatttaggg tttagggtta atggttttta tagactaatt 1200
tttttagtac atctatttta ttctatttta gcctctaaat taa 1243

<210> SEQ ID NO 33
<211> LENGTH: 25
<212> TYPE: DNA
<213> ORGANISM: Artificial
<220> FEATURE:
<223> OTHER INFORMATION: synthetic

<400> SEQUENCE: 33
ttttatgtat tatttggtcc ctaca 25

<210> SEQ ID NO 34
<211> LENGTH: 25
<212> TYPE: DNA
<213> ORGANISM: Artificial
<220> FEATURE:
<223> OTHER INFORMATION: synthetic

<400> SEQUENCE: 34
gtcgacggcg tttaacaggc tggca 25

<210> SEQ ID NO 35
<211> LENGTH: 25
<212> TYPE: DNA
<213> ORGANISM: Artificial
<220> FEATURE:
<223> OTHER INFORMATION: synthetic

<400> SEQUENCE: 35
ggcaacaacc tgtacggcgg cccga 25

<210> SEQ ID NO 36
<211> LENGTH: 25
<212> TYPE: DNA
<213> ORGANISM: Artificial
<220> FEATURE:
<223> OTHER INFORMATION: synthetic

<400> SEQUENCE: 36
gttgccttca gaccatggcg gacgt 25

<210> SEQ ID NO 37
<211> LENGTH: 47
<212> TYPE: DNA
<213> ORGANISM: Artificial
<220> FEATURE:
<223> OTHER INFORMATION: synthetic

<400> SEQUENCE: 37
atgtcactga tttatagatc atacaaaaag gcccagttag tttaaac 47

<210> SEQ ID NO 38
<211> LENGTH: 1307
<212> TYPE: PRT
<213> ORGANISM: Unknown
<220> FEATURE:
<223> OTHER INFORMATION: Acidaminococcus sp.

<400> SEQUENCE: 38

Met Thr Gln Phe Glu Gly Phe Thr Asn Leu Tyr Gln Val Ser Lys Thr
1 5 10 15

Leu Arg Phe Glu Leu Ile Pro Gln Gly Lys Thr Leu Lys His Ile Gln
20 25 30

Glu Gln Gly Phe Ile Glu Glu Asp Lys Ala Arg Asn Asp His Tyr Lys
35 40 45

Glu Leu Lys Pro Ile Ile Asp Arg Ile Tyr Lys Thr Tyr Ala Asp Gln
50 55 60

Cys Leu Gln Leu Val Gln Leu Asp Trp Glu Asn Leu Ser Ala Ala Ile
65 70 75 80

Asp Ser Tyr Arg Lys Glu Lys Thr Glu Glu Thr Arg Asn Ala Leu Ile
85 90 95

Glu Glu Gln Ala Thr Tyr Arg Asn Ala Ile His Asp Tyr Phe Ile Gly
100 105 110

Arg Thr Asp Asn Leu Thr Asp Ala Ile Asn Lys Arg His Ala Glu Ile
115 120 125

Tyr Lys Gly Leu Phe Lys Ala Glu Leu Phe Asn Gly Lys Val Leu Lys
130 135 140

Gln Leu Gly Thr Val Thr Thr Thr Glu His Glu Asn Ala Leu Leu Arg

```
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Ser Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575
```

```
Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
    850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990
```

```
Glu Asn Leu Asn Phe Gly Phe Lys  Ser Lys Arg Thr Gly  Ile Ala Glu
        995                 1000                 1005

Lys Ala  Val Tyr Gln Gln Phe  Glu Lys Met Leu Ile  Asp Lys Leu
    1010                 1015                 1020

Asn Cys  Leu Val Leu Lys Asp  Tyr Pro Ala Glu Lys  Val Gly Gly
    1025                 1030                 1035

Val Leu  Asn Pro Tyr Gln Leu  Thr Asp Gln Phe Thr  Ser Phe Ala
    1040                 1045                 1050

Lys Met  Gly Thr Gln Ser Gly  Phe Leu Phe Tyr Val  Pro Ala Pro
    1055                 1060                 1065

Tyr Thr  Ser Lys Ile Asp Pro  Leu Thr Gly Phe Val  Asp Pro Phe
    1070                 1075                 1080

Val Trp  Lys Thr Ile Lys Asn  His Glu Ser Arg Lys  His Phe Leu
    1085                 1090                 1095

Glu Gly  Phe Asp Phe Leu His  Tyr Asp Val Lys Thr  Gly Asp Phe
    1100                 1105                 1110

Ile Leu  His Phe Lys Met Asn  Arg Asn Leu Ser Phe  Gln Arg Gly
    1115                 1120                 1125

Leu Pro  Gly Phe Met Pro Ala  Trp Asp Ile Val Phe  Glu Lys Asn
    1130                 1135                 1140

Glu Thr  Gln Phe Asp Ala Lys  Gly Thr Pro Phe Ile  Ala Gly Lys
    1145                 1150                 1155

Arg Ile  Val Pro Val Ile Glu  Asn His Arg Phe Thr  Gly Arg Tyr
    1160                 1165                 1170

Arg Asp  Leu Tyr Pro Ala Asn  Glu Leu Ile Ala Leu  Leu Glu Glu
    1175                 1180                 1185

Lys Gly  Ile Val Phe Arg Asp  Gly Ser Asn Ile Leu  Pro Lys Leu
    1190                 1195                 1200

Leu Glu  Asn Asp Asp Ser His  Ala Ile Asp Thr Met  Val Ala Leu
    1205                 1210                 1215

Ile Arg  Ser Val Leu Gln Met  Arg Asn Ser Asn Ala  Ala Thr Gly
    1220                 1225                 1230

Glu Asp  Tyr Ile Asn Ser Pro  Val Arg Asp Leu Asn  Gly Val Cys
    1235                 1240                 1245

Phe Asp  Ser Arg Phe Gln Asn  Pro Glu Trp Pro Met  Asp Ala Asp
    1250                 1255                 1260

Ala Asn  Gly Ala Tyr His Ile  Ala Leu Lys Gly Gln  Leu Leu Leu
    1265                 1270                 1275

Asn His  Leu Lys Glu Ser Lys  Asp Leu Lys Leu Gln  Asn Gly Ile
    1280                 1285                 1290

Ser Asn  Gln Asp Trp Leu Ala  Tyr Ile Gln Glu Leu  Arg Asn
    1295                 1300                 1305
```

<210> SEQ ID NO 39
<211> LENGTH: 20
<212> TYPE: DNA
<213> ORGANISM: Artificial
<220> FEATURE:
<223> OTHER INFORMATION: synthetic

<400> SEQUENCE: 39
atgtcactga ttaaactgaa 20

<210> SEQ ID NO 40
<211> LENGTH: 40
<212> TYPE: DNA

<213> ORGANISM: Artificial
<220> FEATURE:
<223> OTHER INFORMATION: synthetic

<400> SEQUENCE: 40
tgagtgaatc atgtcactga ttaaactgaa ggcgggaaac 40

<210> SEQ ID NO 41
<211> LENGTH: 20
<212> TYPE: DNA
<213> ORGANISM: Artificial
<220> FEATURE:
<223> OTHER INFORMATION: synthetic

<400> SEQUENCE: 41
cctaaaacca tcaaacattt 20

<210> SEQ ID NO 42
<211> LENGTH: 39
<212> TYPE: DNA
<213> ORGANISM: Artificial
<220> FEATURE:
<223> OTHER INFORMATION: synthetic

<400> SEQUENCE: 42
atttctaatt cctaaaacca tcaaacattt ggcaataaa 39

<210> SEQ ID NO 43
<211> LENGTH: 7302
<212> TYPE: DNA
<213> ORGANISM: Artificial
<220> FEATURE:
<223> OTHER INFORMATION: synthetic

<400> SEQUENCE: 43
tcctgtgttg ttggaacaga cttctgtctc ttctggtgat cataaatatt taaatgaacc 60
agttgtgttg gaaaatgttg ttttcttttg tctctagact ggaaagcgga gttctcgtca 120
acacggttct ttcaactagg gatgaaagtg gtaatccgaa ttgttagtac aaatttaata 180
ttttaaaata gatatgtata aaattttatg ttgatctttt ttatgttatc aagcacatta 240
gtataaatta gtataaatat gaataaaata ttacataaaa tgttttatgt attatttggt 300
ccctacaaca taaatagttg aaaaaattac taaatttgtt ttcgaatcta tatcgaagtt 360
tatatctatt atttaagaaa aatataggat gaaaaggttt atcttttatg aatctttaca 420
agctggatct tataaacaag aaaataaatt tatattgtag attttatatc ctatttattc 480
gcaatcaaag aaaagcgact aaaaaactga ttaccgagta aatactgttt ccaaccgttt 540
tcgtccctac tatcaacgcc ttctcccaac cgcagtcgat ctgtccgtct gtatcaggcg 600
cagcggcacc cctgctgttc gactatctag accatagaat attttaggta tacaataatt 660
ttagttccac gctagaacat tttagttaga ataataacaa gatttgctat tgatgtagga 720
ctcgcccgtc actgtctaaa aaagcattct gtcggtctta ttctttaggc atcagcgggt 780
gtactatctc atttttccta tcatattcct cagtactctg ttaagtataa atggtctatt 840
ttacatgatg aactaataaa actaattaag gatcctaact ttttgtgaag gtaatttgga 900
tcattatgca ttaccatcct acgtatacct gctgcagcag catctgcgta agcacagcct 960
agatatatgc ttctgtgtgg actgaaagga gactttgttt atcaattagt atactcccaa 1020
aaaactgatg acaccaatga tgcaaatagg ctgggaatag tctgtctaat agtttgagtg 1080
aatcatgtca ctgattaaac tgaaggcggg aaacgacaat ctgatcatga gcggagaatt 1140

```
aagggagtca cgttatgacc cccgccgatg acgcgggaca agccgtttta cgtttggaac   1200
tgacagaacc gcaacgttga aggagccact cagcaagctg gtacaagctt gcatgcctgc   1260
agtgcagcgt gacccggtcg tgcccctctc tagagataat gagcattgca tgtctaagtt   1320
ataaaaaatt accacatatt ttttttgtca cacttgtttg aagtgcagtt tatctatctt   1380
tatacatata tttaaacttt actctacgaa taatataatc tatagtacta caataatatc   1440
agtgttttag agaatcatat aaatgaacag ttagacatgg tctaaaggac aattgagtat   1500
tttgacaaca ggactctaca gttttatctt tttagtgtgc atgtgttctc cttttttttt   1560
gcaaatagct tcacctatat aatacttcat ccattttatt agtacatcca tttagggttt   1620
agggttaatg gtttttatag actaattttt ttagtacatc tattttattc tattttagcc   1680
tctaaattaa gaaaactaaa actctatttt agttttttta tttaataatt tagatataaa   1740
atagaataaa ataaagtgac taaaaattaa acaaataccc tttaagaaat taaaaaaact   1800
aaggaaacat ttttcttgtt tcgagtagat aatgccagcc tgttaaacgc cgtcgacgag   1860
tctaacggac accaaccagc gaaccagcag cgtcgcgtcg ggccaagcga agcagacggc   1920
acggcatctc tgtcgctgcc tctggacccc tctcgagagt tccgctccac cgttggactt   1980
gctccgctgt cggcatccag aaattgcgtg gcggagcggc agacgtgagc cggcacggca   2040
ggcggcctcc tcctcctctc acggcaccgg cagctacggg ggattccttt cccaccgctc   2100
cttcgctttc ccttcctcgc ccgccgtaat aaatagacac cccctccaca ccctctttcc   2160
ccaacctcgt gttgttcgga gcgcacacac acacaaccag atctccccca aatccacccg   2220
tcggcacctc cgcttcaagg tacgccgctc gtcctccccc ccccccccctc tctaccttct   2280
ctagatcggc gttccggtcc atggttaggg cccggtagtt ctacttctgt tcatgtttgt   2340
gttagatccg tgtttgtgtt agatccgtgc tgctagcgtt cgtacacgga tgcgacctgt   2400
acgtcagaca cgttctgatt gctaacttgc cagtgtttct ctttggggaa tcctgggatg   2460
gctctagccg ttccgcagac gggatcgatt tcatgatttt ttttgtttcg ttgcataggg   2520
tttggtttgc cctttttcctt tatttcaata tatgccgtgc acttgtttgt cgggtcatct   2580
tttcatgctt ttttttgtct tggttgtgat gatgtggtct ggttgggcgg tcgttctaga   2640
tcggagtaga attctgtttc aaactacctg gtggatttat taattttgga tctgtatgtg   2700
tgtgccatac atattcatag ttacgaattg aagatgatgg atggaaatat cgatctagga   2760
taggtataca tgttgatgcg ggttttactg atgcatatac agagatgctt tttgttcgct   2820
tggttgtgat gatgtggtgt ggttgggcgg tcgttcattc gttctagatc ggagtagaat   2880
actgtttcaa actacctggt gtatttatta attttggaac tgtatgtgtg tgtcatacat   2940
cttcatagtt acgagtttaa gatggatgga aatatcgatc taggataggt atacatgttg   3000
atgtgggttt tactgatgca tatacatgat ggcatatgca gcatctattc atatgctcta   3060
accttgagta cctatctatt ataataaaca agtatgtttt ataattattt tgatcttgat   3120
atacttggat gatggcatat gcagcagcta tatgtggatt tttttagccc tgccttcata   3180
cgctatttat ttgcttggta ctgtttcttt tgtcgatgct caccctgttg tttggtgtta   3240
cttctgcagg tcgactctag aggatccacc atgaacaaga acaacaccaa gctgagcacc   3300
cgcgccctgc cgagcttcat cgactacttc aacggcatct acggcttcgc caccggcatc   3360
aaggacatca tgaacatgat cttcaagacc gacaccggcg gcgacctgac cctggacgag   3420
atcctgaaga accagcagct gctgaacgac atcagcggca agctggacgg cgtgaacggc   3480
```

-continued

```
agcctgaacg acctgatcgc ccagggcaac ctgaacaccg agctgagcaa ggagatcctt   3540
aagatcgcca acgagcagaa ccaggtgctg aacgacgtga acaacaagct ggacgccatc   3600
aacaccatgc tgcgcgtgta cctgccgaag atcaccagca tgctgagcga cgtgatgaag   3660
cagaactacg ccctgagcct gcagatcgag tacctgagca agcagctgca ggagatcagc   3720
gacaagctgg acatcatcaa cgtgaacgtc ctgatcaaca gcaccctgac cgagatcacc   3780
ccggcctacc agcgcatcaa gtacgtgaac gagaagttcg aagagctgac cttcgccacc   3840
gagaccagca gcaaggtgaa gaaggacggc agcccggccg acatcctgga cgagctgacc   3900
gagctgaccg agctggcgaa gagcgtgacc aagaacgacg tggacggctt cgagttctac   3960
ctgaacacct tccacgacgt gatggtgggc aacaacctgt tcggccgcag cgccctgaag   4020
accgccagcg agctgatcac caaggagaac gtgaagacca gcggcagcga ggtgggcaac   4080
gtgtacaact tcctgatcgt gctgaccgcc ctgcaggccc aggccttcct gaccctgacc   4140
acctgtcgca agctgctggg cctggccgac atcgactaca ccagcatcat gaacgagcac   4200
ttgaacaagg agaaggagga gttccgcgtg aacatcctgc cgaccctgag caacaccttc   4260
agcaacccga actacgccaa ggtgaagggc agcgacgagg acgccaagat gatcgtggag   4320
gctaagccgg gccacgcgtt gatcggcttc gagatcagca acgacagcat caccgtgctg   4380
aaggtgtacg aggccaagct gaagcagaac taccaggtgg acaaggacag cttgagcgag   4440
gtgatctacg gcgacatgga caagctgctg tgtccggacc agagcgagca aatctactac   4500
accaacaaca tcgtgttccc gaacgagtac gtgatcacca agatcgactt caccaagaag   4560
atgaagaccc tgcgctacga ggtgaccgcc aacttctacg acagcagcac cggcgagatc   4620
gacctgaaca agaagaaggt ggagagcagc gaggccgagt accgcaccct gagcgcgaac   4680
gacgacggcg tctacatgcc actgggcgtg atcagcgaga ccttcctgac cccgatcaac   4740
ggctttggcc tgcaggccga cgagaacagc cgcctgatca ccctgacctg taagagctac   4800
ctgcgcgagc tgctgctagc caccgacctg agcaacaagg agaccaagct gatcgtgcca   4860
ccgagcggct tcatcagcaa catcgtggag aacggcagca tcgaggagga caacctggag   4920
ccgtggaagg ccaacaacaa gaacgcctac gtggaccaca ccggcggcgt gaacggcacc   4980
aaggccctgt acgtgcacaa ggacggcggc atcagccagt tcatcggcga caagctgaag   5040
ccgaagaccg agtacgtgat ccagtacacc gtgaagggca agccatcgat tcacctgaag   5100
gacgagaaca ccggctacat ccactacgag gacaccaaca acaacctgga ggactaccag   5160
accatcaaca agcgcttcac caccggcacc gacctgaagg gcgtgtacct gatcctgaag   5220
agccagaacg gcgacgaggc ctggggcgac aacttcatca tcctggagat cagcccgagc   5280
gagaagctgc tgagcccgga gctgatcaac accaacaact ggaccagcac cggcagcacc   5340
aacatcagcg gcaacaccct gaccctgtac cagggcggcc gcggcatcct gaagcagaac   5400
ctgcagctgg acagcttcag cacctaccgc gtgtacttca gcgtgagcgg cgacgccaac   5460
gtgcgcatcc gcaactcccg cgaggtgctg ttcgagaaga ggtacatgag cggcgccaag   5520
gacgtgagcg agatgttcac caccaagttc gagaaggaca acttctacat cgagctgagc   5580
cagggcaaca acctgtacgg cggcccgatc gtgcacttct acgacgtgag catcaagtag   5640
gagctctaga tctgttctgc acaaagtgga gtagtcagtc atcgatcagg aaccagacac   5700
cagactttta ttcatacagt gaagtgaagt gaagtgcagt gcagtgagtt gctggttttt   5760
gtacaactta gtatgtattt gtatttgtaa aatacttcta tcaataaaat ttctaattcc   5820
taaaaccatc aaacatttgg caataaagtt tcttaagatt gaatcctgtt gccggtcttg   5880
```

```
cgatgattat catataattt ctgttgaatt acgttaagca tgtaataatt aacatgtaat   5940

gcatgacgtt atttatgaga tgggttttta tgattagagt cccgcaatta tacatttaat   6000

acgcgataga aaacaaaata tagcgcgcaa actaggataa attatcgcgc gcggtgtcat   6060

ctatgttact agatccccgg gtctagacaa ttcagtacat taaaaacgtc cgccatggtc   6120

tgaaggcaac agataaggca tactgggcct tgtggtagtt gttttactgg cctttttgt    6180

atgatctata aaattcactg ggatcaaccc ggagaggaat ggcagcagat gcagtcccca   6240

gggtcctccg tcgccgcctg agcacccggc acccgcgctg aaccggagag ggacgcgcgg   6300

acgccgtgca gctggtgcgg agggggctgt ggcagatgag gatgagacgc gtacgtggct   6360

gggaaggcca gcaggccacc gggtcttcgt ccagcccggc gcgagtggac aggactagag   6420

atggcaacgg ttacaaaccc gctgggtttt accgtcccaa acccgtaccc gtgaaaaata   6480

tctatgccca ttaaaaaacc cgtacccatg acgggtttga gattttgccc aaacccgtac   6540

ccatcgggtt aacgggtacc catgggttac ccgcgggttt catctccaat atacctgttc   6600

ttctcataat caataagtat cgtaatgatt aatgatatca tgatccaaaa tctatgtaat   6660

gaacaacgag ttcatgattt ggtataaaaa ttattagtag agagaatgaa atacaaataa   6720

taagttgtat aattaagtga ccttgcacta agttatccat ccatcacata tataacgcta   6780

gtaaaaacta taatatcaag caagcaacac tctcaccgac tactgataca ttcaccaatt   6840

gataaaaaat atgaagtaaa taaggaataa caagtttgtt gttcgtttat aaaataaaat   6900

gacaatatgc actaggtttg gtcgggttta aaaaacccac gggttcacgg gtttgggtac   6960

tataggaaca aacccgtacc cataaaccca ttgggtacag atttatgccc gttaacaaac   7020

ccatgggtat gaaaattgac ccaaacctat accctaatgg ggtaaaaacc catcgggttt   7080

cggatttcgg gtacccattg ccatctctag acaggacaac ctcggccggt cctgtatgta   7140

ggccaccagc atcggccagt tggtacatcc agccggggtc aggtcacttt tactcgtctc   7200

aatcagacaa tcaccgtcca ccaacgaacg ccaacgttgt cacttgtcag gtcggttgag   7260

acttgtattt ttttttgtcc tccgtaaaaa tcggttcacc ag                      7302
```

<210> SEQ ID NO 44
<211> LENGTH: 10606
<212> TYPE: DNA
<213> ORGANISM: Artificial
<220> FEATURE:
<223> OTHER INFORMATION: synthetic

<400> SEQUENCE: 44

```
tcctgtgttg ttggaacaga cttctgtctc ttctggtgat cataaatatt taaatgaacc     60

agttgtgttg gaaaatgttg ttttcttttg tctctagact ggaaagcgga gttctcgtca    120

acacggttct ttcaactagg gatgaaagtg gtaatccgaa ttgttagtac aaatttaata    180

ttttaaaata gatatgtata aaattttatg ttgatctttt ttatgttatc aagcacatta    240

gtataaatta gtataaatat gaataaaata ttacataaaa tgttttatgt attatttggt    300

ccctacaaca taaatagttg aaaaaattac taaatttgtt ttcgaatcta tatcgaagtt    360

tatatctatt atttaagaaa aatataggat gaaaaggttt atcttttatg aatctttaca    420

agctggatct tataaacaag aaaataaatt tatattgtag attttatatc ctatttattc    480

gcaatcaaag aaaagcgact aaaaaactga ttaccgagta aatactgttt ccaaccgttt    540

tcgtccctac tatcaacgcc ttctcccaac cgcagtcgat ctgtccgtct gtatcaggcg    600
```

-continued

```
cagcggcacc cctgctgttc gactatctag accatagaat attttaggta tacaataatt    660
ttagttccac gctagaacat tttagttaga ataataacaa gatttgctat tgatgtagga    720
ctcgcccgtc actgtctaaa aaagcattct gtcggtctta ttctttaggc atcagcgggt    780
gtactatctc atttttccta tcatattcct cagtactctg ttaagtataa atggtctatt    840
ttacatgatg aactaataaa actaattaag gatcctaact ttttgtgaag gtaatttgga    900
tcattatgca ttaccatcct acgtatacct gctgcagcag catctgcgta agcacagcct    960
agatatatgc ttctgtgtgg actgaaagga gactttgttt atcaattagt atactcccaa   1020
aaaactgatg acaccaatga tgcaaatagg ctgggaatag tctgtctaat agtttgagtg   1080
aatcatgtca ctgatttata gatcatacaa aaaggcccag ttagtttaaa ctgaaggcgg   1140
gaaacgacaa tctgatcatg agcggagaat taagggagtc acgttatgac ccccgccgat   1200
gacgcgggac aagccgtttt acgtttggaa ctgacagaac cgcaacgttg aaggagccac   1260
tcagcaagct ggtacaagct tgcatgcctg cagtgcagcg tgacccggtc gtgcccctct   1320
ctagagataa tgagcattgc atgtctaagt tataaaaaat taccacatat ttttttgtc   1380
acacttgttt gaagtgcagt ttatctatct ttatacatat atttaaactt tactctacga   1440
ataatataat ctatagtact acaataatat cagtgtttta gagaatcata taaatgaaca   1500
gttagacatg gtctaaagga caattgagta ttttgacaac aggactctac agttttatct   1560
ttttagtgtg catgtgttct cctttttttt tgcaaatagc ttcacctata taatacttca   1620
tccattttat tagtacatcc atttagggtt tagggttaat ggtttttata gactaatttt   1680
tttagtacat ctattttatt ctattttagc ctctaaatta agaaaactaa aactctattt   1740
tagttttttt atttaataat ttagatataa aatagaataa aataaagtga ctaaaaatta   1800
aacaaatacc ctttaagaaa ttaaaaaaac taaggaaaca tttttcttgt ttcgagtaga   1860
taatgccagc ctgttaaacg ccgtcgacga gtctaacgga caccaaccag cgaaccagca   1920
gcgtcgcgtc gggccaagcg aagcagacgg cacggcatct ctgtcgctgc ctctggaccc   1980
ctctcgagag ttccgctcca ccgttggact tgctccgctg tcggcatcca gaaattgcgt   2040
ggcggagcgg cagacgtgag ccggcacggc aggcggcctc ctcctcctct cacggcaccg   2100
gcagctacgg gggattcctt tcccaccgct ccttcgcttt cccttcctcg cccgccgtaa   2160
taaatagaca ccccctccac accctctttc cccaacctcg tgttgttcgg agcgcacaca   2220
cacacaacca gatctccccc aaatccaccc gtcggcacct ccgcttcaag gtacgccgct   2280
cgtcctcccc cccccccct ctctaccttc tctagatcgg cgttccggtc catggttagg   2340
gcccggtagt tctacttctg ttcatgtttg tgttagatcc gtgtttgtgt tagatccgtg   2400
ctgctagcgt tcgtacacgg atgcgacctg tacgtcagac acgttctgat tgctaacttg   2460
ccagtgtttc tctttgggga atcctgggat ggctctagcc gttccgcaga cgggatcgat   2520
ttcatgattt tttttgtttc gttgcatagg gtttggtttg cccttttcct ttatttcaat   2580
atatgccgtg cacttgtttg tcgggtcatc ttttcatgct ttttttgtc ttggttgtga   2640
tgatgtggtc tggttgggcg gtcgttctag atcggagtag aattctgttt caaactacct   2700
ggtggattta ttaattttgg atctgtatgt gtgtgccata catattcata gttacgaatt   2760
gaagatgatg gatggaaata tcgatctagg ataggtatac atgttgatgc gggttttact   2820
gatgcatata cagagatgct tttgttcgc ttggttgtga tgatgtggtg tggttgggcg   2880
gtcgttcatt cgttctagat cggagtagaa tactgtttca aactacctgg tgtatttatt   2940
aattttggaa ctgtatgtgt gtgtcataca tcttcatagt tacgagttta agatggatgg   3000
```

aaatatcgat ctaggatagg tatacatgtt gatgtgggtt ttactgatgc atatacatga 3060
tggcatatgc agcatctatt catatgctct aaccttgagt acctatctat tataataaac 3120
aagtatgttt tataattatt ttgatcttga tatacttgga tgatggcata tgcagcagct 3180
atatgtggat ttttttagcc ctgccttcat acgctattta tttgcttggt actgtttctt 3240
ttgtcgatgc tcaccctgtt gtttggtgtt acttctgcag gtcgactcta gaggatccac 3300
catgaacaag aacaacacca agctgagcac ccgcgccctg ccgagcttca tcgactactt 3360
caacggcatc tacggcttcg ccaccggcat caaggacatc atgaacatga tcttcaagac 3420
cgacaccggc ggcgacctga ccctggacga gatcctgaag aaccagcagc tgctgaacga 3480
catcagcggc aagctggacg gcgtgaacgg cagcctgaac gacctgatcg cccagggcaa 3540
cctgaacacc gagctgagca aggagatcct taagatcgcc aacgagcaga accaggtgct 3600
gaacgacgtg aacaacaagc tggacgccat caacaccatg ctgcgcgtgt acctgccgaa 3660
gatcaccagc atgctgagcg acgtgatgaa gcagaactac gccctgagcc tgcagatcga 3720
gtacctgagc aagcagctgc aggagatcag cgacaagctg gacatcatca acgtgaacgt 3780
cctgatcaac agcaccctga ccgagatcac cccggcctac cagcgcatca agtacgtgaa 3840
cgagaagttc gaagagctga ccttcgccac cgagaccagc agcaaggtga agaaggacgg 3900
cagcccggcc gacatcctgg acgagctgac cgagctgacc gagctggcga agagcgtgac 3960
caagaacgac gtggacggct tcgagttcta cctgaacacc ttccacgacg tgatggtggg 4020
caacaacctg ttcggccgca gcgccctgaa gaccgccagc gagctgatca ccaaggagaa 4080
cgtgaagacc agcggcagcg aggtgggcaa cgtgtacaac ttcctgatcg tgctgaccgc 4140
cctgcaggcc caggccttcc tgaccctgac cacctgtcgc aagctgctgg gcctggccga 4200
catcgactac accagcatca tgaacgagca cttgaacaag gagaaggagg agttccgcgt 4260
gaacatcctg ccgaccctga gcaacacctt cagcaacccg aactacgcca aggtgaaggg 4320
cagcgacgag gacgccaaga tgatcgtgga ggctaagccg ggccacgcgt tgatcggctt 4380
cgagatcagc aacgacagca tcaccgtgct gaaggtgtac gaggccaagc tgaagcagaa 4440
ctaccaggtg gacaaggaca gcttgagcga ggtgatctac ggcgacatgg acaagctgct 4500
gtgtccggac cagagcgagc aaatctacta caccaacaac atcgtgttcc cgaacgagta 4560
cgtgatcacc aagatcgact tcaccaagaa gatgaagacc ctgcgctacg aggtgaccgc 4620
caacttctac gacagcagca ccggcgagat cgacctgaac aagaagaagg tggagagcag 4680
cgaggccgag taccgcaccc tgagcgcgaa cgacgacggc gtctacatgc cactgggcgt 4740
gatcagcgag accttcctga ccccgatcaa cggctttggc ctgcaggccg acgagaacag 4800
ccgcctgatc accctgacct gtaagagcta cctgcgcgag ctgctgctag ccaccgacct 4860
gagcaacaag gagaccaagc tgatcgtgcc accgagcggc ttcatcagca acatcgtgga 4920
gaacggcagc atcgaggagg acaacctgga gccgtggaag gccaacaaca agaacgccta 4980
cgtggaccac accggcggcg tgaacggcac caaggccctg tacgtgcaca aggacggcgg 5040
catcagccag ttcatcggcg acaagctgaa gccgaagacc gagtacgtga tccagtacac 5100
cgtgaagggc aagccatcga ttcacctgaa ggacgagaac accggctaca tccactacga 5160
ggacaccaac aacaacctgg aggactacca gaccatcaac aagcgcttca ccaccggcac 5220
cgacctgaag ggcgtgtacc tgatcctgaa gagccagaac ggcgacgagg cctggggcga 5280
caacttcatc atcctggaga tcagcccgag cgagaagctg ctgagcccgg agctgatcaa 5340

-continued

```
caccaacaac tggaccagca ccggcagcac caacatcagc ggcaacaccc tgaccctgta   5400
ccagggcggc cgcggcatcc tgaagcagaa cctgcagctg gacagcttca gcacctaccg   5460
cgtgtacttc agcgtgagcg gcgacgccaa cgtgcgcatc cgcaactccc gcgaggtgct   5520
gttcgagaag aggtacatga gcggcgccaa ggacgtgagc gagatgttca ccaccaagtt   5580
cgagaaggac aacttctaca tcgagctgag ccagggcaac aacctgtacg gcggcccgat   5640
cgtgcacttc tacgacgtga gcatcaagta ggagctctag atctgttctg cacaaagtgg   5700
agtagtcagt catcgatcag gaaccagaca ccagactttt attcatacag tgaagtgaag   5760
tgaagtgcag tgcagtgagt tgctggtttt tgtacaactt agtatgtatt tgtatttgta   5820
aaatacttct atcaataaaa tttctaattc ctaaaaccaa aatccagggg taccagcttg   5880
catgcctgca gtgcagcgtg acccggtcgt gcccctctct agagataatg agcattgcat   5940
gtctaagtta taaaaaatta ccacatattt tttttgtcac acttgtttga agtgcagttt   6000
atctatcttt atacatatat ttaaacttta ctctacgaat aatataatct atagtactac   6060
aataatatca gtgttttaga gaatcatata aatgaacagt tagacatggt ctaaaggaca   6120
attgagtatt ttgacaacag gactctacag ttttatcttt ttagtgtgca tgtgttctcc   6180
tttttttttg caaatagctt cacctatata atacttcatc cattttatta gtacatccat   6240
ttagggttta gggttaatgg tttttataga ctaatttttt tagtacatct attttattct   6300
attttagcct ctaaattaag aaaactaaaa ctctatttta gtttttttat ttaataattt   6360
agatataaaa tagaataaaa taaagtgact aaaaattaaa caaataccct ttaagaaatt   6420
aaaaaaacta aggaaacatt tttcttgttt cgagtagata atgccagcct gttaaacgcc   6480
gtcgacgagt ctaacggaca ccaaccagcg aaccagcagc gtcgcgtcgg gccaagcgaa   6540
gcagacggca cggcatctct gtcgctgcct ctggacccct ctcgagagtt ccgctccacc   6600
gttggacttg ctccgctgtc ggcatccaga aattgcgtgg cggagcggca gacgtgagcc   6660
ggcacggcag gcggcctcct cctcctctca cggcaccggc agctacgggg gattcctttc   6720
ccaccgctcc ttcgctttcc cttcctcgcc cgccgtaata aatagacacc ccctccacac   6780
cctctttccc caacctcgtg ttgttcggag cgcacacaca cacaaccaga tctcccccaa   6840
atccacccgt cggcacctcc gcttcaaggt acgccgctcg tcctcccccc cccccctct    6900
ctaccttctc tagatcggcg ttccggtcca tggttagggc ccggtagttc tacttctgtt   6960
catgtttgtg ttagatccgt gtttgtgtta gatccgtgct gctagcgttc gtacacggat   7020
gcgacctgta cgtcagacac gttctgattg ctaacttgcc agtgtttctc tttggggaat   7080
cctgggatgg ctctagccgt tccgcagacg ggatcgattt catgattttt tttgtttcgt   7140
tgcatagggt ttggtttgcc cttttccttt atttcaatat atgccgtgca cttgtttgtc   7200
gggtcatctt ttcatgcttt tttttgtctt ggttgtgatg atgtggtctg gttgggcggt   7260
cgttctagat cggagtagaa ttctgtttca aactacctgg tggatttatt aattttggat   7320
ctgtatgtgt gtgccataca tattcatagt tacgaattga agatgatgga tggaaatatc   7380
gatctaggat aggtatacat gttgatgcgg gttttactga tgcatataca gagatgcttt   7440
ttgttcgctt ggttgtgatg atgtggtgtg gttgggcggt cgttcattcg ttctagatcg   7500
gagtagaata ctgtttcaaa ctacctggtg tatttattaa ttttggaact gtatgtgtgt   7560
gtcatacatc ttcatagtta cgagtttaag atggatggaa atatcgatct aggataggta   7620
tacatgttga tgtgggtttt actgatgcat atacatgatg gcatatgcag catctattca   7680
tatgctctaa ccttgagtac ctatctatta taataaacaa gtatgtttta taattatttt   7740
```

```
gatcttgata tacttggatg atggcatatg cagcagctat atgtggattt ttttagccct   7800
gccttcatac gctatttatt tgcttggtac tgtttctttt gtcgatgctc accctgttgt   7860
ttggtgttac ttctgcaggg atccccgatc atgcaaaaac tcattaactc agtgcaaaac   7920
tatgcctggg gcagcaaaac ggcgttgact gaactttatg gtatggaaaa tccgtccagc   7980
cagccgatgg ccgagctgtg gatgggcgca catccgaaaa gcagttcacg agtgcagaat   8040
gccgccggag atatcgtttc actgcgtgat gtgattgaga gtgataaatc gactctgctc   8100
ggagaggccg ttgccaaacg ctttggcgaa ctgcctttcc tgttcaaagt attatgcgca   8160
gcacagccac tctccattca ggttcatcca aacaaacaca attctgaaat cggttttgcc   8220
aaagaaaatg ccgcaggtat cccgatggat gccgccgagc gtaactataa agatcctaac   8280
cacaagccgg agctggtttt tgcgctgacg cctttccttg cgatgaacgc gtttcgtgaa   8340
ttttccgaga ttgtctccct actccagccg gtcgcaggtg cacatccggc gattgctcac   8400
tttttacaac agcctgatgc cgaacgttta agcgaactgt tcgccagcct gttgaatatg   8460
cagggtgaag aaaaatcccg cgcgctggcg attttaaaat cggccctcga tagccagcag   8520
ggtgaaccgt ggcaaacgat tcgtttaatt tctgaatttt acccggaaga cagcggtctg   8580
ttctccccgc tattgctgaa tgtggtgaaa ttgaaccctg gcgaagcgat gttcctgttc   8640
gctgaaacac cgcacgctta cctgcaaggc gtggcgctgg aagtgatggc aaactccgat   8700
aacgtgctgc gtgcgggtct gacgcctaaa tacattgata ttccggaact ggttgccaat   8760
gtgaaattcg aagccaaacc ggctaaccag ttgttgaccc agccggtgaa acaaggtgca   8820
gaactggact tcccgattcc agtggatgat tttgccttct cgctgcatga ccttagtgat   8880
aaagaaacca ccattagcca gcagagtgcc gccattttgt tctgcgtcga aggcgatgca   8940
acgttgtgga aaggttctca gcagttacag cttaaaccgg gtgaatcagc gtttattgcc   9000
gccaacgaat caccggtgac tgtcaaaggc cacggccgtt tagcgcgtgt ttacaacaag   9060
ctgtaagagc ttactgaaaa aattaacatc tcttgctaag ctgggagctc gatccgtcga   9120
cctgcagatc gttcaaacat ttggcaataa agtttcttaa gattgaatcc tgttgccggt   9180
cttgcgatga ttatcatata atttctgttg aattacgtta agcatgtaat aattaacatg   9240
taatgcatga cgttatttat gagatgggtt tttatgatta gagtcccgca attatacatt   9300
taatacgcga tagaaaacaa aatatagcgc gcaaactagg ataaattatc gcgcgcggtg   9360
tcatctatgt tactagatcc ccgggtctag acaattcagt acattaaaaa cgtccgccat   9420
ggtctgaagg caacagataa ggcatactgg gccttgtggt agttgtttta ctgggccttt   9480
ttgtatgatc tataaaattc actgggatca acccggagag gaatggcagc agatgcagtc   9540
cccagggtcc tccgtcgccg cctgagcacc cggcacccgc gctgaaccgg agagggacgc   9600
gcggacgccg tgcagctggt gcggaggggg ctgtggcaga tgaggatgag acgcgtacgt   9660
ggctgggaag gccagcaggc caccgggtct tcgtccagcc cggcgcgagt ggacaggact   9720
agagatggca acggttacaa acccgctggg ttttaccgtc ccaaacccgt acccgtgaaa   9780
aatatctatg cccattaaaa aacccgtacc catgacgggt ttgagatttt gcccaaaccc   9840
gtacccatcg ggttaacggg tacccatggg ttacccgcgg gtttcatctc caatatacct   9900
gttcttctca taatcaataa gtatcgtaat gattaatgat atcatgatcc aaaatctatg   9960
taatgaacaa cgagttcatg atttggtata aaaattatta gtagagagaa tgaaatacaa  10020
ataataagtt gtataattaa gtgaccttgc actaagttat ccatccatca catatataac  10080
```

```
gctagtaaaa actataatat caagcaagca acactctcac cgactactga tacattcacc  10140

aattgataaa aaatatgaag taaataagga ataacaagtt tgttgttcgt ttataaaata  10200

aaatgacaat atgcactagg tttggtcggg tttaaaaaac ccacgggttc acgggtttgg  10260

gtactatagg aacaaacccg tacccataaa cccattgggt acagatttat gcccgttaac  10320

aaacccatgg gtatgaaaat tgacccaaac ctatacccta atggggtaaa aacccatcgg  10380

gtttcggatt tcgggtaccc attgccatct ctagacagga caacctcggc cggtcctgta  10440

tgtaggccac cagcatcggc cagttggtac atccagccgg ggtcaggtca cttttactcg  10500

tctcaatcag acaatcaccg tccaccaacg aacgccaacg ttgtcacttg tcaggtcggt  10560

tgagacttgt atttttttt gtcctccgta aaaatcggtt caccag                 10606
```

<210> SEQ ID NO 45
<211> LENGTH: 7333
<212> TYPE: DNA
<213> ORGANISM: Artificial
<220> FEATURE:
<223> OTHER INFORMATION: synthetic

<400> SEQUENCE: 45

```
tcctgtgttg ttggaacaga cttctgtctc ttctggtgat cataaatatt taaatgaacc     60

agttgtgttg gaaaatgttg ttttcttttg tctctagact ggaaagcgga gttctcgtca    120

acacggttct ttcaactagg gatgaaagtg gtaatccgaa ttgttagtac aaatttaata    180

ttttaaaata gatatgtata aaattttatg ttgatctttt ttatgttatc aagcacatta    240

gtataaatta gtataaatat gaataaaata ttacataaaa tgttttatgt attatttggt    300

ccctacaaca taaatagttg aaaaaattac taaatttgtt ttcgaatcta tatcgaagtt    360

tatatctatt atttaagaaa aatataggat gaaaaggttt atcttttatg aatctttaca    420

agctggatct tataaacaag aaaataaatt tatattgtag attttatatc ctatttattc    480

gcaatcaaag aaaagcgact aaaaaactga ttaccgagta aatactgttt ccaaccgttt    540

tcgtccctac tatcaacgcc ttctcccaac cgcagtcgat ctgtccgtct gtatcaggcg    600

cagcggcacc cctgctgttc gactatctag accatagaat attttaggta tacaataatt    660

ttagttccac gctagaacat tttagttaga ataataacaa gatttgctat tgatgtagga    720

ctcgcccgtc actgtctaaa aaagcattct gtcggtctta ttctttaggc atcagcgggt    780

gtactatctc atttttccta tcatattcct cagtactctg ttaagtataa atggtctatt    840

ttacatgatg aactaataaa actaattaag gatcctaact ttttgtgaag gtaatttgga    900

tcattatgca ttaccatcct acgtatacct gctgcagcag catctgcgta agcacagcct    960

agatatatgc ttctgtgtgg actgaaagga gactttgttt atcaattagt atactcccaa   1020

aaaactgatg acaccaatga tgcaaatagg ctgggaatag tctgtctaat agtttgagtg   1080

aatcatgtca ctgatttata gatcatacaa aaaggcccag ttagtttaaa ctgaaggcgg   1140

gaaacgacaa tctgatcatg agcggagaat taagggagtc acgttatgac ccccgccgat   1200

gacgcgggac aagccgtttt acgtttggaa ctgacagaac cgcaacgttg aaggagccac   1260

tcagcaagct ggtacaagct tgcatgcctg cagtgcagcg tgacccggtc gtgcccctct   1320

ctagagataa tgagcattgc atgtctaagt tataaaaaat taccacatat ttttttgtc   1380

acacttgttt gaagtgcagt ttatctatct ttatacatat atttaaactt tactctacga   1440

ataatataat ctatagtact acaataatat cagtgtttta gagaatcata taaatgaaca   1500

gttagacatg gtctaaagga caattgagta ttttgacaac aggactctac agttttatct   1560
```

```
ttttagtgtg catgtgttct cctttttttt tgcaaatagc ttcacctata taatacttca   1620
tccattttat tagtacatcc atttagggtt tagggttaat ggtttttata gactaatttt   1680
tttagtacat ctattttatt ctattttagc ctctaaatta agaaaactaa aactctattt   1740
tagtttttt atttaataat ttagatataa aatagaataa aataaagtga ctaaaaatta    1800
aacaaatacc ctttaagaaa ttaaaaaaac taaggaaaca tttttcttgt ttcgagtaga   1860
taatgccagc ctgttaaacg ccgtcgacga gtctaacgga caccaaccag cgaaccagca   1920
gcgtcgcgtc gggccaagcg aagcagacgg cacggcatct ctgtcgctgc ctctggaccc   1980
ctctcgagag ttccgctcca ccgttggact tgctccgctg tcggcatcca gaaattgcgt   2040
ggcggagcgg cagacgtgag ccggcacggc aggcggcctc ctcctcctct cacggcaccg   2100
gcagctacgg gggattcctt tcccaccgct ccttcgcttt cccttcctcg cccgccgtaa   2160
taaatagaca ccccctccac accctctttc cccaacctcg tgttgttcgg agcgcacaca   2220
cacacaacca gatctccccc aaatccaccc gtcggcacct ccgcttcaag gtacgccgct   2280
cgtcctcccc ccccccccct ctctaccttc tctagatcgg cgttccggtc catggttagg   2340
gcccggtagt tctacttctg ttcatgtttg tgttagatcc gtgtttgtgt tagatccgtg   2400
ctgctagcgt tcgtacacgg atgcgacctg tacgtcagac acgttctgat tgctaacttg   2460
ccagtgtttc tctttgggga atcctgggat ggctctagcc gttccgcaga cgggatcgat   2520
ttcatgattt tttttgtttc gttgcatagg gtttggtttg ccctttttcct ttatttcaat   2580
atatgccgtg cacttgtttg tcgggtcatc ttttcatgct ttttttgtc ttggttgtga    2640
tgatgtggtc tggttgggcg gtcgttctag atcggagtag aattctgttt caaactacct   2700
ggtggattta ttaattttgg atctgtatgt gtgtgccata catattcata gttacgaatt   2760
gaagatgatg gatggaaata tcgatctagg ataggtatac atgttgatgc gggttttact   2820
gatgcatata cagagatgct tttgttcgc ttggttgtga tgatgtggtg tggttgggcg    2880
gtcgttcatt cgttctagat cggagtagaa tactgtttca aactacctgg tgtatttatt   2940
aattttggaa ctgtatgtgt gtgtcataca tcttcatagt tacgagttta agatggatgg   3000
aaatatcgat ctaggatagg tatacatgtt gatgtgggtt ttactgatgc atatacatga   3060
tggcatatgc agcatctatt catatgctct aaccttgagt acctatctat tataataaac   3120
aagtatgttt tataattatt ttgatcttga tatacttgga tgatggcata tgcagcagct   3180
atatgtggat ttttttagcc ctgccttcat acgctattta tttgcttggt actgtttctt   3240
ttgtcgatgc tcaccctgtt gtttggtgtt acttctgcag gtcgactcta gaggatccac   3300
catgaacaag aacaacacca agctgagcac ccgcgccctg ccgagcttca tcgactactt   3360
caacggcatc tacggcttcg ccaccggcat caaggacatc atgaacatga tcttcaagac   3420
cgacaccggc ggcgacctga ccctggacga gatcctgaag aaccagcagc tgctgaacga   3480
catcagcggc aagctggacg gcgtgaacgg cagcctgaac gacctgatcg cccagggcaa   3540
cctgaacacc gagctgagca aggagatcct taagatcgcc aacgagcaga accaggtgct   3600
gaacgacgtg aacaacaagc tggacgccat caacaccatg ctgcgcgtgt acctgccgaa   3660
gatcaccagc atgctgagcg acgtgatgaa gcagaactac gccctgagcc tgcagatcga   3720
gtacctgagc aagcagctgc aggagatcag cgacaagctg gacatcatca acgtgaacgt   3780
cctgatcaac agcaccctga ccgagatcac ccccggcctac cagcgcatca agtacgtgaa   3840
cgagaagttc gaagagctga ccttcgccac cgagaccagc agcaaggtga agaaggacgg   3900
```

cagcccggcc gacatcctgg acgagctgac cgagctgacc gagctggcga agagcgtgac 3960
caagaacgac gtggacggct tcgagttcta cctgaacacc ttccacgacg tgatggtggg 4020
caacaacctg ttcggccgca gcgccctgaa gaccgccagc gagctgatca ccaaggagaa 4080
cgtgaagacc agcggcagcg aggtgggcaa cgtgtacaac ttcctgatcg tgctgaccgc 4140
cctgcaggcc caggccttcc tgaccctgac cacctgtcgc aagctgctgg gcctggccga 4200
catcgactac accagcatca tgaacgagca cttgaacaag gagaaggagg agttccgcgt 4260
gaacatcctg ccgaccctga gcaacacctt cagcaacccg aactacgcca aggtgaaggg 4320
cagcgacgag gacgccaaga tgatcgtgga ggctaagccg ggccacgcgt tgatcggctt 4380
cgagatcagc aacgacagca tcaccgtgct gaaggtgtac gaggccaagc tgaagcagaa 4440
ctaccaggtg gacaaggaca gcttgagcga ggtgatctac ggcgacatgg acaagctgct 4500
gtgtccggac cagagcgagc aaatctacta caccaacaac atcgtgttcc cgaacgagta 4560
cgtgatcacc aagatcgact tcaccaagaa gatgaagacc ctgcgctacg aggtgaccgc 4620
caacttctac gacagcagca ccggcgagat cgacctgaac aagaagaagg tggagagcag 4680
cgaggccgag taccgcaccc tgagcgcgaa cgacgacggc gtctacatgc cactgggcgt 4740
gatcagcgag accttcctga ccccgatcaa cggctttggc ctgcaggccg acgagaacag 4800
ccgcctgatc accctgacct gtaagagcta cctgcgcgag ctgctgctag ccaccgacct 4860
gagcaacaag gagaccaagc tgatcgtgcc accgagcggc ttcatcagca acatcgtgga 4920
gaacggcagc atcgaggagg acaacctgga gccgtggaag gccaacaaca agaacgccta 4980
cgtggaccac accggcggcg tgaacggcac caaggccctg tacgtgcaca aggacggcgg 5040
catcagccag ttcatcggcg acaagctgaa gccgaagacc gagtacgtga tccagtacac 5100
cgtgaagggc aagccatcga ttcacctgaa ggacgagaac accggctaca tccactacga 5160
ggacaccaac aacaacctgg aggactacca gaccatcaac aagcgcttca ccaccggcac 5220
cgacctgaag ggcgtgtacc tgatcctgaa gagccagaac ggcgacgagg cctggggcga 5280
caacttcatc atcctggaga tcagcccgag cgagaagctg ctgagcccgg agctgatcaa 5340
caccaacaac tggaccagca ccggcagcac caacatcagc ggcaacaccc tgaccctgta 5400
ccagggcggc cgcggcatcc tgaagcagaa cctgcagctg gacagcttca gcacctaccg 5460
cgtgtacttc agcgtgagcg gcgacgccaa cgtgcgcatc cgcaactccc gcgaggtgct 5520
gttcgagaag aggtacatga gcggcgccaa ggacgtgagc gagatgttca ccaccaagtt 5580
cgagaaggac aacttctaca tcgagctgag ccagggcaac aacctgtacg gcggcccgat 5640
cgtgcacttc tacgacgtga gcatcaagta ggagctctag atctgttctg cacaaagtgg 5700
agtagtcagt catcgatcag gaaccagaca ccagactttt attcatacag tgaagtgaag 5760
tgaagtgcag tgcagtgagt tgctggtttt tgtacaactt agtatgtatt tgtatttgta 5820
aaatacttct atcaataaaa tttctaattc ctaaaaccat caaacatttg gcaataaagt 5880
ttcttaagat tgaatcctgt tgccggtctt gcgatgatta tcatataatt tctgttgaat 5940
tacgttaagc atgtaataat taacatgtaa tgcatgacgt tatttatgag atgggttttt 6000
atgattagag tcccgcaatt atacatttaa tacgcgatag aaaacaaaat atagcgcgca 6060
aactaggata aattatcgcg cgcggtgtca tctatgttac tagatccccg ggtctagaca 6120
attcagtaca ttaaaaacgt ccgccatggt ctgaaggcaa cagataaggc atactgggcc 6180
ttgtggtagt tgttttactg ggcctttttg tatgatctat aaaattcact gggatcaacc 6240
cggagaggaa tggcagcaga tgcagtcccc agggtcctcc gtcgccgcct gagcacccgg 6300

```
caccegcgct gaaccggaga gggacgcgcg gacgccgtgc agctggtgcg gagggggctg   6360
tggcagatga ggatgagacg cgtacgtggc tgggaaggcc agcaggccac cgggtcttcg   6420
tccagcccgg cgcgagtgga caggactaga gatggcaacg gttacaaacc cgctgggttt   6480
taccgtccca aacccgtacc cgtgaaaaat atctatgccc attaaaaaac ccgtacccat   6540
gacgggtttg agattttgcc caaacccgta cccatcgggt taacgggtac ccatgggtta   6600
cccgcgggtt tcatctccaa tatacctgtt cttctcataa tcaataagta tcgtaatgat   6660
taatgatatc atgatccaaa atctatgtaa tgaacaacga gttcatgatt tggtataaaa   6720
attattagta gagagaatga aatacaaata ataagttgta taattaagtg accttgcact   6780
aagttatcca tccatcacat atataacgct agtaaaaact ataatatcaa gcaagcaaca   6840
ctctcaccga ctactgatac attcaccaat tgataaaaaa tatgaagtaa ataaggaata   6900
acaagtttgt tgttcgttta taaaataaaa tgacaatatg cactaggttt ggtcgggttt   6960
aaaaaaccca cgggttcacg ggtttgggta ctataggaac aaacccgtac ccataaaccc   7020
attgggtaca gatttatgcc cgttaacaaa cccatgggta tgaaaattga cccaaaccta   7080
taccctaatg ggtaaaaac ccatcgggtt tcggatttcg ggtacccatt gccatctcta    7140
gacaggacaa cctcggccgg tcctgtatgt aggccaccag catcggccag ttggtacatc   7200
cagccggggt caggtcactt ttactcgtct caatcagaca atcaccgtcc accaacgaac   7260
gccaacgttg tcacttgtca ggtcggttga gacttgtatt ttttttgtc ctccgtaaaa    7320
atcggttcac cag                                                      7333
```

<210> SEQ ID NO 46
<211> LENGTH: 10579
<212> TYPE: DNA
<213> ORGANISM: Artificial
<220> FEATURE:
<223> OTHER INFORMATION: synthetic

<400> SEQUENCE: 46

```
tcctgtgttg ttggaacaga cttctgtctc ttctggtgat cataaatatt taaatgaacc     60
agttgtgttg gaaaatgttg ttttcttttg tctctagact ggaaagcgga gttctcgtca    120
acacggttct ttcaactagg gatgaaagtg gtaatccgaa ttgttagtac aaatttaata    180
ttttaaaata gatatgtata aaattttatg ttgatctttt ttatgttatc aagcacatta    240
gtataaatta gtataaatat gaataaaata ttacataaaa tgttttatgt attatttggt    300
ccctacaaca taaatagttg aaaaaattac taaatttgtt ttcgaatcta tatcgaagtt    360
tatatctatt atttaagaaa aatataggat gaaaaggttt atcttttatg aatctttaca    420
agctggatct tataaacaag aaaataaatt tatattgtag attttatatc ctatttattc    480
gcaatcaaag aaaagcgact aaaaaactga ttaccgagta aatactgttt ccaaccgttt    540
tcgtccctac tatcaacgcc ttctcccaac cgcagtcgat ctgtccgtct gtatcaggcg    600
cagcggcacc cctgctgttc gactatctag accatagaat attttaggta tacaataatt    660
ttagttccac gctagaacat tttagttaga ataataacaa gatttgctat tgatgtagga    720
ctcgcccgtc actgtctaaa aaagcattct gtcggtctta ttctttaggc atcagcgggt    780
gtactatctc atttttccta tcatattcct cagtactctg ttaagtataa atggtctatt    840
ttacatgatg aactaataaa actaattaag gatcctaact ttttgtgaag gtaatttgga    900
tcattatgca ttaccatcct acgtatacct gctgcagcag catctgcgta agcacagcct    960
```

agatatatgc ttctgtgtgg actgaaagga gactttgttt atcaattagt atactcccaa 1020
aaaactgatg acaccaatga tgcaaatagg ctgggaatag tctgtctaat agtttgagtg 1080
aatcatgtca ctgatagttt aaactgaagg cgggaaacga caatctgatc atgagcggag 1140
aattaaggga gtcacgttat gaccccgcc gatgacgcgg gacaagccgt tttacgtttg 1200
gaactgacag aaccgcaacg ttgaaggagc cactcagcaa gctggtacaa gcttgcatgc 1260
ctgcagtgca gcgtgacccg gtcgtgcccc tctctagaga taatgagcat tgcatgtcta 1320
agttataaaa aattaccaca tatttttttt gtcacacttg tttgaagtgc agtttatcta 1380
tctttataca tatatttaaa ctttactcta cgaataatat aatctatagt actacaataa 1440
tatcagtgtt ttagagaatc atataaatga acagttagac atggtctaaa ggacaattga 1500
gtattttgac aacaggactc tacagtttta tctttttagt gtgcatgtgt tctccttttt 1560
ttttgcaaat agcttcacct atataatact tcatccattt tattagtaca tccatttagg 1620
gtttagggtt aatggttttt atagactaat ttttttagta catctatttt attctatttt 1680
agcctctaaa ttaagaaaac taaaactcta ttttagtttt tttatttaat aatttagata 1740
taaaatagaa taaaataaag tgactaaaaa ttaaacaaat accctttaag aaattaaaaa 1800
aactaaggaa acatttttct tgtttcgagt agataatgcc agcctgttaa acgccgtcga 1860
cgagtctaac ggacaccaac cagcgaacca gcagcgtcgc gtcgggccaa gcgaagcaga 1920
cggcacggca tctctgtcgc tgcctctgga cccctctcga gagttccgct ccaccgttgg 1980
acttgctccg ctgtcggcat ccagaaattg cgtggcggag cggcagacgt gagccggcac 2040
ggcaggcggc ctcctcctcc tctcacggca ccggcagcta cgggggattc ctttcccacc 2100
gctccttcgc tttcccttcc tcgcccgccg taataaatag acaccccctc cacaccctct 2160
ttccccaacc tcgtgttgtt cggagcgcac acacacacaa ccagatctcc cccaaatcca 2220
cccgtcggca cctccgcttc aaggtacgcc gctcgtcctc cccccccccc cctctctacc 2280
ttctctagat cggcgttccg gtccatggtt agggcccggt agttctactt ctgttcatgt 2340
ttgtgttaga tccgtgtttg tgttagatcc gtgctgctag cgttcgtaca cggatgcgac 2400
ctgtacgtca gacacgttct gattgctaac ttgccagtgt ttctctttgg ggaatcctgg 2460
gatggctcta gccgttccgc agacgggatc gatttcatga ttttttttgt ttcgttgcat 2520
agggtttggt ttgccctttt cctttatttc aatatatgcc gtgcacttgt ttgtcgggtc 2580
atcttttcat gcttttttt gtcttggttg tgatgatgtg gtctggttgg gcggtcgttc 2640
tagatcggag tagaattctg tttcaaacta cctggtggat ttattaattt tggatctgta 2700
tgtgtgtgcc atacatattc atagttacga attgaagatg atggatggaa atatcgatct 2760
aggataggta tacatgttga tgcgggtttt actgatgcat atacagagat gctttttgtt 2820
cgcttggttg tgatgatgtg gtgtggttgg gcggtcgttc attcgttcta gatcggagta 2880
gaatactgtt tcaaactacc tggtgtattt attaattttg gaactgtatg tgtgtgtcat 2940
acatcttcat agttacgagt ttaagatgga tggaaatatc gatctaggat aggtatacat 3000
gttgatgtgg gttttactga tgcatataca tgatggcata tgcagcatct attcatatgc 3060
tctaaccttg agtacctatc tattataata aacaagtatg ttttataatt attttgatct 3120
tgatatactt ggatgatggc atatgcagca gctatatgtg gattttttta gccctgcctt 3180
catacgctat ttatttgctt ggtactgttt cttttgtcga tgctcaccct gttgtttggt 3240
gttacttctg caggtcgact ctagaggatc caccatgaac aagaacaaca ccaagctgag 3300
cacccgcgcc ctgccgagct tcatcgacta cttcaacggc atctacggct tcgccaccgg 3360

```
catcaaggac atcatgaaca tgatcttcaa gaccgacacc ggcggcgacc tgaccctgga   3420
cgagatcctg aagaaccagc agctgctgaa cgacatcagc ggcaagctgg acggcgtgaa   3480
cggcagcctg aacgacctga tcgcccaggg caacctgaac accgagctga gcaaggagat   3540
ccttaagatc gccaacgagc agaaccaggt gctgaacgac gtgaacaaca agctggacgc   3600
catcaacacc atgctgcgcg tgtacctgcc gaagatcacc agcatgctga gcgacgtgat   3660
taagcagaac tacgccctga gcctgcagat cgagtacctg agcaagcagc tgcaggagat   3720
cagcgacaag ctggacatca tcaacgtgaa cgtcctgatc aacagcaccc tgaccgagat   3780
caccccggcc taccagcgca tcaagtacgt gaacgagaag ttcgaagagc tgaccttcgc   3840
caccgagacc agcagcaagg tgaagaagga cggcagcccg gccgacatcc tggacgagct   3900
gaccgagctg accgagctgg cgaagagcgt gaccaagaac gacgtggacg gcttcgagtt   3960
ctacctgaac accttccacg acgtgatggt gggcaacaac ctgttcggcc gcagcgccct   4020
gaagaccgcc agcgagctga tcaccaagga gaacgtgaag accagcggca gcgaggtggg   4080
caacgtgtac aacttcctga tcgtgctgac cgccctgcag gcccaggcct tcctgaccct   4140
gaccacctgt cgcaagctgc tgggcctggc cgacatcgac tacaccagca tcatgaacga   4200
gcacttgaac aaggagaagg aggagttccg cgtgaacatc ctgccgaccc tgagcaacac   4260
cttcagcaac ccgaactacg ccaaggtgaa gggcagcgac gaggacgcca agatgatcgt   4320
ggaggctaag ccgggccacg cgttgatcgg cttcgagatc agcaacgaca gcatcaccgt   4380
gctgaaggtg tacgaggcca agctgaagca gaactaccag gtggacaagg acagcttgag   4440
cgaggtgatc tacggcgaca tggacaagct gctgtgtccg gaccagagcg agcaaatcta   4500
ctacaccaac aacatcgtgt tcccgaacga gtacgtgatc accaagatcg acttcaccaa   4560
gaagatgaag accctgcgct acgaggtgac cgccaacttc tacgacagca gcaccggcga   4620
gatcgacctg aacaagaaga aggtggagag cagcgaggcc gagtaccgca ccctgagcgc   4680
gaacgacgac ggcgtctaca tgccactggg cgtgatcagc gagaccttcc tgaccccgat   4740
caacggcttt ggcctgcagg ccgacgagaa cagccgcctg atcaccctga cctgtaagag   4800
ctacctgcgc gagctgctgc tagccaccga cctgagcaac aaggagacca agctgatcgt   4860
gccaccgagc ggcttcatca gcaacatcgt ggagaacggc agcatcgagg aggacaacct   4920
ggagccgtgg aaggccaaca acaagaacgc ctacgtcgac cacaccggcg gcgtgaacgg   4980
caccaaggcc ctgtacgtgc acaaggacgg cggcatcagc cagttcatcg gcgacaagct   5040
gaagccgaag accgagtacg tgatccagta caccgtgaag ggcaagccat cgattcacct   5100
gaaggacgag aacaccggct acatccacta cgaggacacc aacaacaacc tggaggacta   5160
ccagaccatc aacaagcgct tcaccaccgg caccgacctg aagggcgtgt acctgatcct   5220
gaagagccag aacggcgacg aggcctgggg cgacaacttc atcatcctgg agatcagccc   5280
gagcgagaag ctgctgagcc cggagctgat caacaccaac aactggacca gcaccggcag   5340
caccaacatc agcggcaaca ccctgaccct gtaccagggc ggccgcggca tcctgaagca   5400
gaacctgcag ctggacagct tcagcaccta ccgcgtgtac ttcagcgtga gcggcgacgc   5460
caacgtgcgc atccgcaact cccgcgaggt gctgttcgag aagaggtaca tgagcggcgc   5520
caaggacgtg agcgagatgt tcaccaccaa gttcgagaag gacaacttct acatcgagct   5580
gagccagggc aacaacctgt acggcggccc gatcgtgcac ttctacgacg tgagcatcaa   5640
gtaggagctc tagatctgtt ctgcacaaag tggagtagtc agtcatcgat caggaaccag   5700
```

```
acaccagact tttattcata cagtgaagtg aagtgaagtg cagtgcagtg agttgctggt   5760
ttttgtacaa cttagtatgt atttgtattt gtaaaatact tctatcaata aaatttctaa   5820
ttcctaaaac caaaatccag gggtaccagc ttgcatgcct gcagtgcagc gtgacccggt   5880
cgtgcccctc tctagagata atgagcattg catgtctaag ttataaaaaa ttaccacata   5940
tttttttgt cacacttgtt tgaagtgcag tttatctatc tttatacata tatttaaact   6000
ttactctacg aataatataa tctatagtac tacaataata tcagtgtttt agagaatcat   6060
ataaatgaac agttagacat ggtctaaagg acaattgagt attttgacaa caggactcta   6120
cagttttatc tttttagtgt gcatgtgttc tcctttttt ttgcaaatag cttcacctat   6180
ataatacttc atccatttta ttagtacatc catttagggt ttagggttaa tggtttttat   6240
agactaattt ttttagtaca tctattttat tctattttag cctctaaatt aagaaaacta   6300
aaactctatt ttagtttttt tatttaataa tttagatata aaatagaata aaataaagtg   6360
actaaaaatt aaacaaatac cctttaagaa attaaaaaaa ctaaggaaac atttttcttg   6420
tttcgagtag ataatgccag cctgttaaac gccgtcgacg agtctaacgg acaccaacca   6480
gcgaaccagc agcgtcgcgt cgggccaagc gaagcagacg gcacggcatc tctgtcgctg   6540
cctctggacc cctctcgaga gttccgctcc accgttggac ttgctccgct gtcggcatcc   6600
agaaattgcg tggcggagcg gcagacgtga gccggcacgg caggcggcct cctcctcctc   6660
tcacggcacc ggcagctacg gggattcct ttcccaccgc tccttcgctt tcccttcctc   6720
gcccgccgta ataaatagac acccctcca caccctcttt ccccaacctc gtgttgttcg   6780
gagcgcacac acacacaacc agatctcccc caaatccacc cgtcggcacc tccgcttcaa   6840
ggtacgccgc tcgtcctccc cccccccccc tctctacctt ctctagatcg gcgttccggt   6900
ccatggttag ggcccggtag ttctacttct gttcatgttt gtgttagatc cgtgtttgtg   6960
ttagatccgt gctgctagcg ttcgtacacg gatgcgacct gtacgtcaga cacgttctga   7020
ttgctaactt gccagtgttt ctctttgggg aatcctggga tggctctagc cgttccgcag   7080
acgggatcga tttcatgatt ttttttgttt cgttgcatag ggtttggttt gcccttttcc   7140
tttatttcaa tatatgccgt gcacttgttt gtcgggtcat cttttcatgc ttttttttgt   7200
cttggttgtg atgatgtggt ctggttgggc ggtcgttcta gatcggagta gaattctgtt   7260
tcaaactacc tggtggattt attaattttg gatctgtatg tgtgtgccat acatattcat   7320
agttacgaat tgaagatgat ggatggaaat atcgatctag gataggtata catgttgatg   7380
cgggttttac tgatgcatat acagagatgc tttttgttcg cttggttgtg atgatgtggt   7440
gtggttgggc ggtcgttcat tcgttctaga tcggagtaga atactgtttc aaactacctg   7500
gtgtatttat taattttgga actgtatgtg tgtgtcatac atcttcatag ttacgagttt   7560
aagatggatg gaaatatcga tctaggatag gtatacatgt tgatgtgggt tttactgatg   7620
catatacatg atggcatatg cagcatctat tcatatgctc taaccttgag tacctatcta   7680
ttataataaa caagtatgtt ttataattat tttgatcttg atatacttgg atgatggcat   7740
atgcagcagc tatatgtgga tttttttagc cctgccttca tacgctattt atttgcttgg   7800
tactgtttct tttgtcgatg ctcaccctgt tgtttggtgt tacttctgca gggatccccg   7860
atcatgcaaa aactcattaa ctcagtgcaa aactatgcct ggggcagcaa aacggcgttg   7920
actgaacttt atggtatgga aaatccgtcc agccagccga tggccgagct gtggatgggc   7980
gcacatccga aaagcagttc acgagtgcag aatgccgccg gagatatcgt ttcactgcgt   8040
gatgtgattg agagtgataa atcgactctg ctcggagagg ccgttgccaa acgctttggc   8100
```

gaactgcctt tcctgttcaa agtattatgc gcagcacagc cactctccat tcaggttcat 8160
ccaaacaaac acaattctga aatcggtttt gccaaagaaa atgccgcagg tatcccgatg 8220
gatgccgccg agcgtaacta taaagatcct aaccacaagc cggagctggt ttttgcgctg 8280
acgcctttcc ttgcgatgaa cgcgtttcgt gaattttccg agattgtctc cctactccag 8340
ccggtcgcag gtgcacatcc ggcgattgct cactttttac aacagcctga tgccgaacgt 8400
ttaagcgaac tgttcgccag cctgttgaat atgcagggtg aagaaaaatc ccgcgcgctg 8460
gcgattttaa aatcggccct cgatagccag cagggtgaac cgtggcaaac gattcgttta 8520
atttctgaat tttacccgga agacagcggt ctgttctccc cgctattgct gaatgtggtg 8580
aaattgaacc ctggcgaagc gatgttcctg ttcgctgaaa caccgcacgc ttacctgcaa 8640
ggcgtggcgc tggaagtgat ggcaaactcc gataacgtgc tgcgtgcggg tctgacgcct 8700
aaatacattg atattccgga actggttgcc aatgtgaaat tcgaagccaa accggctaac 8760
cagttgttga cccagccggt gaaacaaggt gcagaactgg acttcccgat tccagtggat 8820
gattttgcct tctcgctgca tgaccttagt gataaagaaa ccaccattag ccagcagagt 8880
gccgccattt tgttctgcgt cgaaggcgat gcaacgttgt ggaaaggttc tcagcagtta 8940
cagcttaaac cgggtgaatc agcgtttatt gccgccaacg aatcaccggt gactgtcaaa 9000
ggccacggcc gtttagcgcg tgtttacaac aagctgtaag agcttactga aaaaattaac 9060
atctcttgct aagctgggag ctcgatccgt cgacctgcag atcgttcaaa catttggcaa 9120
taaagtttct taagattgaa tcctgttgcc ggtcttgcga tgattatcat ataatttctg 9180
ttgaattacg ttaagcatgt aataattaac atgtaatgca tgacgttatt tatgagatgg 9240
gtttttatga ttagagtccc gcaattatac atttaatacg cgatagaaaa caaaatatag 9300
cgcgcaaact aggataaatt atcgcgcgcg gtgtcatcta tgttactaga tccccgggtc 9360
tagacaattc agtacattaa aaacgtccgc catggtctga aggcaacaga taaggcatac 9420
tgggccttgt ggtagttgtt ttactgggcc tttttgtatg atctataaaa ttcactggga 9480
tcaacccgga gaggaatggc agcagatgca gtccccaggg tcctccgtcg ccgcctgagc 9540
acccggcacc cgcgctgaac cggagaggga cgcgcggacg ccgtgcagct ggtgcggagg 9600
gggctgtggc agatgaggat gagacgcgta cgtggctggg aaggccagca ggccaccggg 9660
tcttcgtcca gcccggcgcg agtggacagg actagagatg gcaacggtta caaacccgct 9720
gggtttaccc gtcccaaacc cgtacccgtg aaaaatatct atgcccatta aaaaacccgt 9780
acccatgacg ggtttgagat tttgcccaaa cccgtaccca tcgggttaac gggtacccat 9840
gggttacccg cgggtttcat ctccaatata cctgttcttc tcataatcaa taagtatcgt 9900
aatgattaat gatatcatga tccaaaatct atgtaatgaa caacgagttc atgatttggt 9960
ataaaaatta ttagtagaga gaatgaaata caaataataa gttgtataat taagtgacct 10020
tgcactaagt tatccatcca tcacatatat aacgctagta aaaactataa tatcaagcaa 10080
gcaacactct caccgactac tgatacattc accaattgat aaaaaatatg aagtaaataa 10140
ggaataacaa gtttgttgtt cgtttataaa ataaaatgac aatatgcact aggtttggtc 10200
gggtttaaaa aacccacggg ttcacgggtt tgggtactat aggaacaaac ccgtacccat 10260
aaacccattg ggtacagatt tatgcccgtt aacaaaccca tgggtatgaa aattgaccca 10320
aacctatacc ctaatggggt aaaaacccat cgggtttcgg atttcgggta cccattgcca 10380
tctctagaca ggacaacctc ggccggtcct gtatgtaggc caccagcatc ggccagttgg 10440

-continued

```
tacatccagc cggggtcagg tcacttttac tcgtctcaat cagacaatca ccgtccacca  10500

acgaacgcca acgttgtcac ttgtcaggtc ggttgagact tgtatttttt tttgtcctcc  10560

gtaaaaatcg gttcaccag                                               10579


<210> SEQ ID NO 47
<211> LENGTH: 10606
<212> TYPE: DNA
<213> ORGANISM: Artificial
<220> FEATURE:
<223> OTHER INFORMATION: synthetic

<400> SEQUENCE: 47

tcctgtgttg ttggaacaga cttctgtctc ttctggtgat cataaatatt taaatgaacc     60

agttgtgttg gaaaatgttg ttttcttttg tctctagact ggaaagcgga gttctcgtca    120

acacggttct ttcaactagg gatgaaagtg gtaatccgaa ttgttagtac aaatttaata    180

ttttaaaata gatatgtata aaattttatg ttgatctttt ttatgttatc aagcacatta    240

gtataaatta gtataaatat gaataaaata ttacataaaa tgttttatgt attatttggt    300

ccctacaaca taaatagttg aaaaaattac taaatttgtt ttcgaatcta tatcgaagtt    360

tatatctatt atttaagaaa aatataggat gaaaaggttt atcttttatg aatctttaca    420

agctggatct tataaacaag aaaataaatt tatattgtag attttatatc ctatttattc    480

gcaatcaaag aaaagcgact aaaaaactga ttaccgagta aatactgttt ccaaccgttt    540

tcgtccctac tatcaacgcc ttctcccaac cgcagtcgat ctgtccgtct gtatcaggcg    600

cagcggcacc cctgctgttc gactatctag accatagaat attttaggta tacaataatt    660

ttagttccac gctagaacat tttagttaga ataataacaa gatttgctat tgatgtagga    720

ctcgcccgtc actgtctaaa aaagcattct gtcggtctta ttctttaggc atcagcgggt    780

gtactatctc atttttccta tcatattcct cagtactctg ttaagtataa atggtctatt    840

ttacatgatg aactaataaa actaattaag gatcctaact ttttgtgaag gtaatttgga    900

tcattatgca ttaccatcct acgtatacct gctgcagcag catctgcgta agcacagcct    960

agatatatgc ttctgtgtgg actgaaagga gactttgttt atcaattagt atactcccaa   1020

aaaactgatg acaccaatga tgcaaatagg ctgggaatag tctgtctaat agtttgagtg   1080

aatcatgtca ctgatttata gatcatacaa aaaggcccag ttagtttaaa ctgaaggcgg   1140

gaaacgacaa tctgatcatg agcggagaat taagggagtc acgttatgac cccgccgat    1200

gacgcgggac aagccgtttt acgtttggaa ctgacagaac cgcaacgttg aaggagccac   1260

tcagcaagct ggtacaagct tgcatgcctg cagtgcagcg tgacccggtc gtgcccctct   1320

ctagagataa tgagcattgc atgtctaagt tataaaaaat taccacatat tttttttgtc   1380

acacttgttt gaagtgcagt ttatctatct ttatacatat atttaaactt tactctacga   1440

ataatataat ctatagtact acaataatat cagtgtttta gagaatcata taaatgaaca   1500

gttagacatg gtctaaagga caattgagta ttttgacaac aggactctac agttttatct   1560

ttttagtgtg catgtgttct cctttttttt tgcaaatagc ttcacctata taatacttca   1620

tccattttat tagtacatcc atttagggtt tagggttaat ggtttttata gactaatttt   1680

tttagtacat ctattttatt ctattttagc ctctaaatta agaaaactaa aactctattt   1740

tagttttttt atttaataat ttagatataa aatagaataa aataaagtga ctaaaaatta   1800

aacaaatacc ctttaagaaa ttaaaaaaac taaggaaaca tttttcttgt ttcgagtaga   1860

taatgccagc ctgttaaacg ccgtcgacga gtctaacgga caccaaccag cgaaccagca   1920
```

```
gcgtcgcgtc gggccaagcg aagcagacgg cacggcatct ctgtcgctgc ctctggaccc   1980
ctctcgagag ttccgctcca ccgttggact tgctccgctg tcggcatcca gaaattgcgt   2040
ggcggagcgg cagacgtgag ccggcacggc aggcggcctc ctcctcctct cacggcaccg   2100
gcagctacgg gggattcctt tcccaccgct ccttcgcttt cccttcctcg cccgccgtaa   2160
taaatagaca ccccctccac accctctttc cccaacctcg tgttgttcgg agcgcacaca   2220
cacacaacca gatctccccc aaatccaccc gtcggcacct ccgcttcaag gtacgccgct   2280
cgtcctcccc cccccccct ctctaccttc tctagatcgg cgttccggtc catggttagg   2340
gcccggtagt tctacttctg ttcatgtttg tgttagatcc gtgtttgtgt tagatccgtg   2400
ctgctagcgt tcgtacacgg atgcgacctg tacgtcagac acgttctgat tgctaacttg   2460
ccagtgtttc tctttgggga atcctgggat ggctctagcc gttccgcaga cgggatcgat   2520
ttcatgattt tttttgtttc gttgcatagg gtttggtttg cccttttcct ttatttcaat   2580
atatgccgtg cacttgtttg tcgggtcatc ttttcatgct ttttttgtc ttggttgtga    2640
tgatgtggtc tggttgggcg gtcgttctag atcggagtag aattctgttt caaactacct   2700
ggtggattta ttaattttgg atctgtatgt gtgtgccata catattcata gttacgaatt   2760
gaagatgatg gatggaaata tcgatctagg ataggtatac atgttgatgc gggttttact   2820
gatgcatata cagagatgct tttgttcgc ttggttgtga tgatgtggtg tggttgggcg    2880
gtcgttcatt cgttctagat cggagtagaa tactgtttca aactacctgg tgtatttatt   2940
aattttggaa ctgtatgtgt gtgtcataca tcttcatagt tacgagttta agatggatgg   3000
aaatatcgat ctaggatagg tatacatgtt gatgtgggtt ttactgatgc atatacatga   3060
tggcatatgc agcatctatt catatgctct aaccttgagt acctatctat tataataaac   3120
aagtatgttt tataattatt ttgatcttga tatacttgga tgatggcata tgcagcagct   3180
atatgtggat ttttttagcc ctgccttcat acgctattta tttgcttggt actgtttctt   3240
ttgtcgatgc tcaccctgtt gtttggtgtt acttctgcag gtcgactcta gaggatccac   3300
catgaacaag aacaacacca agctgagcac ccgcgccctg ccgagcttca tcgactactt   3360
caacggcatc tacggcttcg ccaccggcat caaggacatc atgaacatga tcttcaagac   3420
cgacaccggc ggcgacctga ccctggacga gatcctgaag aaccagcagc tgctgaacga   3480
catcagcggc aagctggacg gcgtgaacgg cagcctgaac gacctgatcg cccagggcaa   3540
cctgaacacc gagctgagca aggagatcct taagatcgcc aacgagcaga accaggtgct   3600
gaacgacgtg aacaacaagc tggacgccat caacaccatg ctgcgcgtgt acctgccgaa   3660
gatcaccagc atgctgagcg acgtgattaa gcagaactac gccctgagcc tgcagatcga   3720
gtacctgagc aagcagctgc aggagatcag cgacaagctg gacatcatca acgtgaacgt   3780
cctgatcaac agcaccctga ccgagatcac cccggcctac cagcgcatca agtacgtgaa   3840
cgagaagttc gaagagctga ccttcgccac cgagaccagc agcaaggtga agaaggacgg   3900
cagcccggcc gacatcctgg acgagctgac cgagctgacc gagctggcga agagcgtgac   3960
caagaacgac gtggacggct tcgagttcta cctgaacacc ttccacgacg tgatggtggg   4020
caacaacctg ttcggccgca gcgccctgaa gaccgccagc gagctgatca ccaaggagaa   4080
cgtgaagacc agcggcagcg aggtgggcaa cgtgtacaac ttcctgatcg tgctgaccgc   4140
cctgcaggcc caggccttcc tgaccctgac cacctgtcgc aagctgctgg gcctggccga   4200
catcgactac accagcatca tgaacgagca cttgaacaag gagaaggagg agttccgcgt   4260
```

gaacatcctg ccgaccctga gcaacacctt cagcaacccg aactacgcca aggtgaaggg 4320
cagcgacgag gacgccaaga tgatcgtgga ggctaagccg ggccacgcgt tgatcggctt 4380
cgagatcagc aacgacagca tcaccgtgct gaaggtgtac gaggccaagc tgaagcagaa 4440
ctaccaggtg gacaaggaca gcttgagcga ggtgatctac ggcgacatgg acaagctgct 4500
gtgtccggac cagagcgagc aaatctacta caccaacaac atcgtgttcc cgaacgagta 4560
cgtgatcacc aagatcgact tcaccaagaa gatgaagacc ctgcgctacg aggtgaccgc 4620
caacttctac gacagcagca ccggcgagat cgacctgaac aagaagaagg tggagagcag 4680
cgaggccgag taccgcaccc tgagcgcgaa cgacgacggc gtctacatgc cactgggcgt 4740
gatcagcgag accttcctga ccccgatcaa cggctttggc ctgcaggccg acgagaacag 4800
ccgcctgatc accctgacct gtaagagcta cctgcgcgag ctgctgctag ccaccgacct 4860
gagcaacaag gagaccaagc tgatcgtgcc accgagcggc ttcatcagca acatcgtgga 4920
gaacggcagc atcgaggagg acaacctgga gccgtggaag gccaacaaca agaacgccta 4980
cgtcgaccac accggcggcg tgaacggcac caaggccctg tacgtgcaca aggacggcgg 5040
catcagccag ttcatcggcg acaagctgaa gccgaagacc gagtacgtga tccagtacac 5100
cgtgaagggc aagccatcga ttcacctgaa ggacgagaac accggctaca tccactacga 5160
ggacaccaac aacaacctgg aggactacca gaccatcaac aagcgcttca ccaccggcac 5220
cgacctgaag ggcgtgtacc tgatcctgaa gagccagaac ggcgacgagg cctggggcga 5280
caacttcatc atcctggaga tcagcccgag cgagaagctg ctgagcccgg agctgatcaa 5340
caccaacaac tggaccagca ccggcagcac caacatcagc ggcaacaccc tgaccctgta 5400
ccagggcggc cgcggcatcc tgaagcagaa cctgcagctg gacagcttca gcacctaccg 5460
cgtgtacttc agcgtgagcg gcgacgccaa cgtgcgcatc cgcaactccc gcgaggtgct 5520
gttcgagaag aggtacatga gcggcgccaa ggacgtgagc gagatgttca ccaccaagtt 5580
cgagaaggac aacttctaca tcgagctgag ccagggcaac aacctgtacg gcggcccgat 5640
cgtgcacttc tacgacgtga gcatcaagta ggagctctag atctgttctg cacaaagtgg 5700
agtagtcagt catcgatcag gaaccagaca ccagactttt attcatacag tgaagtgaag 5760
tgaagtgcag tgcagtgagt tgctggtttt tgtacaactt agtatgtatt tgtatttgta 5820
aaatacttct atcaataaaa tttctaattc ctaaaaccaa aatccagggg taccagcttg 5880
catgcctgca gtgcagcgtg acccggtcgt gcccctctct agagataatg agcattgcat 5940
gtctaagtta taaaaaatta ccacatattt tttttgtcac acttgtttga agtgcagttt 6000
atctatcttt atacatatat ttaaacttta ctctacgaat aatataatct atagtactac 6060
aataatatca gtgttttaga gaatcatata aatgaacagt tagacatggt ctaaaggaca 6120
attgagtatt ttgacaacag gactctacag ttttatcttt ttagtgtgca tgtgttctcc 6180
tttttttttg caaatagctt cacctatata atacttcatc cattttatta gtacatccat 6240
ttagggttta gggttaatgg tttttataga ctaatttttt tagtacatct attttattct 6300
attttagcct ctaaattaag aaaactaaaa ctctatttta gtttttttat ttaataattt 6360
agatataaaa tagaataaaa taaagtgact aaaaattaaa caaataccct ttaagaaatt 6420
aaaaaaacta aggaaacatt tttcttgttt cgagtagata atgccagcct gttaaacgcc 6480
gtcgacgagt ctaacggaca ccaaccagcg aaccagcagc gtcgcgtcgg gccaagcgaa 6540
gcagacggca cggcatctct gtcgctgcct ctggacccct ctcgagagtt ccgctccacc 6600
gttggacttg ctccgctgtc ggcatccaga aattgcgtgg cggagcggca gacgtgagcc 6660

```
ggcacggcag gcggcctcct cctcctctca cggcaccggc agctacgggg gattcctttc   6720
ccaccgctcc ttcgctttcc cttcctcgcc cgccgtaata aatagacacc ccctccacac   6780
cctctttccc caacctcgtg ttgttcggag cgcacacaca cacaaccaga tctcccccaa   6840
atccacccgt cggcacctcc gcttcaaggt acgccgctcg tcctcccccc cccccctct   6900
ctaccttctc tagatcggcg ttccggtcca tggttagggc ccggtagttc tacttctgtt   6960
catgtttgtg ttagatccgt gtttgtgtta gatccgtgct gctagcgttc gtacacggat   7020
gcgacctgta cgtcagacac gttctgattg ctaacttgcc agtgtttctc tttggggaat   7080
cctgggatgg ctctagccgt tccgcagacg ggatcgattt catgattttt tttgtttcgt   7140
tgcatagggt ttggtttgcc cttttccttt atttcaatat atgccgtgca cttgtttgtc   7200
gggtcatctt ttcatgcttt tttttgtctt ggttgtgatg atgtggtctg gttgggcggt   7260
cgttctagat cggagtagaa ttctgtttca aactacctgg tggatttatt aattttggat   7320
ctgtatgtgt gtgccataca tattcatagt tacgaattga agatgatgga tggaaatatc   7380
gatctaggat aggtatacat gttgatgcgg gttttactga tgcatataca gagatgcttt   7440
ttgttcgctt ggttgtgatg atgtggtgtg gttgggcggt cgttcattcg ttctagatcg   7500
gagtagaata ctgtttcaaa ctacctggtg tatttattaa ttttggaact gtatgtgtgt   7560
gtcatacatc ttcatagtta cgagtttaag atggatggaa atatcgatct aggataggta   7620
tacatgttga tgtgggtttt actgatgcat atacatgatg gcatatgcag catctattca   7680
tatgctctaa ccttgagtac ctatctatta taataaacaa gtatgtttta taattatttt   7740
gatcttgata tacttggatg atggcatatg cagcagctat atgtggattt ttttagccct   7800
gccttcatac gctatttatt tgcttggtac tgtttctttt gtcgatgctc accctgttgt   7860
ttggtgttac ttctgcaggg atccccgatc atgcaaaaac tcattaactc agtgcaaaac   7920
tatgcctggg gcagcaaaac ggcgttgact gaactttatg gtatggaaaa tccgtccagc   7980
cagccgatgg ccgagctgtg gatgggcgca catccgaaaa gcagttcacg agtgcagaat   8040
gccgccggag atatcgtttc actgcgtgat gtgattgaga gtgataaatc gactctgctc   8100
ggagaggccg ttgccaaacg ctttggcgaa ctgcctttcc tgttcaaagt attatgcgca   8160
gcacagccac tctccattca ggttcatcca aacaaacaca attctgaaat cggttttgcc   8220
aaagaaaatg ccgcaggtat cccgatggat gccgccgagc gtaactataa agatcctaac   8280
cacaagccgg agctggtttt tgcgctgacg cctttccttg cgatgaacgc gtttcgtgaa   8340
ttttccgaga ttgtctccct actccagccg gtcgcaggtg cacatccggc gattgctcac   8400
tttttacaac agcctgatgc cgaacgttta agcgaactgt tcgccagcct gttgaatatg   8460
cagggtgaag aaaaatcccg cgcgctggcg attttaaaat cggccctcga tagccagcag   8520
ggtgaaccgt ggcaaacgat tcgtttaatt tctgaatttt acccggaaga cagcggtctg   8580
ttctccccgc tattgctgaa tgtggtgaaa ttgaaccctg gcgaagcgat gttcctgttc   8640
gctgaaacac cgcacgctta cctgcaaggc gtggcgctgg aagtgatggc aaactccgat   8700
aacgtgctgc gtgcgggtct gacgcctaaa tacattgata ttccggaact ggttgccaat   8760
gtgaaattcg aagccaaacc ggctaaccag ttgttgaccc agccggtgaa acaaggtgca   8820
gaactggact tcccgattcc agtggatgat tttgccttct cgctgcatga ccttagtgat   8880
aaagaaacca ccattagcca gcagagtgcc gccattttgt tctgcgtcga aggcgatgca   8940
acgttgtgga aaggttctca gcagttacag cttaaaccgg gtgaatcagc gtttattgcc   9000
```

```
gccaacgaat caccggtgac tgtcaaaggc cacggccgtt tagcgcgtgt ttacaacaag   9060
ctgtaagagc ttactgaaaa aattaacatc tcttgctaag ctgggagctc gatccgtcga   9120
cctgcagatc gttcaaacat ttggcaataa agtttcttaa gattgaatcc tgttgccggt   9180
cttgcgatga ttatcatata atttctgttg aattacgtta agcatgtaat aattaacatg   9240
taatgcatga cgttatttat gagatgggtt tttatgatta gagtcccgca attatacatt   9300
taatacgcga tagaaaacaa aatatagcgc gcaaactagg ataaattatc gcgcgcggtg   9360
tcatctatgt tactagatcc ccgggtctag acaattcagt acattaaaaa cgtccgccat   9420
ggtctgaagg caacagataa ggcatactgg gccttgtggt agttgtttta ctgggccttt   9480
ttgtatgatc tataaaattc actgggatca acccggagag gaatggcagc agatgcagtc   9540
cccagggtcc tccgtcgccg cctgagcacc cggcacccgc gctgaaccgg agagggacgc   9600
gcggacgccg tgcagctggt gcggaggggg ctgtggcaga tgaggatgag acgcgtacgt   9660
ggctgggaag gccagcaggc caccgggtct tcgtccagcc cggcgcgagt ggacaggact   9720
agagatggca acggttacaa acccgctggg ttttaccgtc ccaaacccgt acccgtgaaa   9780
aatatctatg cccattaaaa aacccgtacc catgacgggt ttgagatttt gcccaaaccc   9840
gtacccatcg ggttaacggg tacccatggg ttacccgcgg gtttcatctc caatatacct   9900
gttcttctca taatcaataa gtatcgtaat gattaatgat atcatgatcc aaaatctatg   9960
taatgaacaa cgagttcatg atttggtata aaaattatta gtagagagaa tgaaatacaa  10020
ataataagtt gtataattaa gtgaccttgc actaagttat ccatccatca catatataac  10080
gctagtaaaa actataatat caagcaagca acactctcac cgactactga tacattcacc  10140
aattgataaa aaatatgaag taaataagga ataacaagtt tgttgttcgt ttataaaata  10200
aaatgacaat atgcactagg tttggtcggg tttaaaaaac ccacgggttc acgggtttgg  10260
gtactatagg aacaaacccg tacccataaa cccattgggt acagatttat gcccgttaac  10320
aaacccatgg gtatgaaaat tgacccaaac ctatacccta atggggtaaa aacccatcgg  10380
gtttcggatt tcgggtaccc attgccatct ctagacagga caacctcggc cggtcctgta  10440
tgtaggccac cagcatcggc cagttggtac atccagccgg ggtcaggtca cttttactcg  10500
tctcaatcag acaatcaccg tccaccaacg aacgccaacg ttgtcacttg tcaggtcggt  10560
tgagacttgt attttttttt gtcctccgta aaaatcggtt caccag                 10606
```

<210> SEQ ID NO 48
<211> LENGTH: 7333
<212> TYPE: DNA
<213> ORGANISM: Artificial
<220> FEATURE:
<223> OTHER INFORMATION: synthetic

<400> SEQUENCE: 48

```
tcctgtgttg ttggaacaga cttctgtctc ttctggtgat cataaatatt taaatgaacc     60
agttgtgttg gaaaatgttg ttttcttttg tctctagact ggaaagcgga gttctcgtca    120
acacggttct ttcaactagg gatgaaagtg gtaatccgaa ttgttagtac aaatttaata    180
ttttaaaata gatatgtata aaattttatg ttgatctttt ttatgttatc aagcacatta    240
gtataaatta gtataaatat gaataaaata ttacataaaa tgttttatgt attatttggt    300
ccctacaaca taaatagttg aaaaaattac taaatttgtt ttcgaatcta tatcgaagtt    360
tatatctatt atttaagaaa aatataggat gaaaaggttt atcttttatg aatctttaca    420
agctggatct tataaacaag aaaataaatt tatattgtag attttatatc ctatttattc    480
```

```
gcaatcaaag aaaagcgact aaaaaactga ttaccgagta aatactgttt ccaaccgttt    540
tcgtccctac tatcaacgcc ttctcccaac cgcagtcgat ctgtccgtct gtatcaggcg    600
cagcggcacc cctgctgttc gactatctag accatagaat attttaggta tacaataatt    660
ttagttccac gctagaacat tttagttaga ataataacaa gatttgctat tgatgtagga    720
ctcgcccgtc actgtctaaa aaagcattct gtcggtctta ttctttaggc atcagcgggt    780
gtactatctc atttttccta tcatattcct cagtactctg ttaagtataa atggtctatt    840
ttacatgatg aactaataaa actaattaag gatcctaact ttttgtgaag gtaatttgga    900
tcattatgca ttaccatcct acgtatacct gctgcagcag catctgcgta agcacagcct    960
agatatatgc ttctgtgtgg actgaaagga gactttgttt atcaattagt atactcccaa   1020
aaaactgatg acaccaatga tgcaaatagg ctgggaatag tctgtctaat agtttgagtg   1080
aatcatgtca ctgatttata gatcatacaa aaaggcccag ttagtttaaa ctgaaggcgg   1140
gaaacgacaa tctgatcatg agcggagaat taagggagtc acgttatgac ccccgccgat   1200
gacgcgggac aagccgtttt acgtttggaa ctgacagaac cgcaacgttg aaggagccac   1260
tcagcaagct ggtacaagct tgcatgcctg cagtgcagcg tgacccggtc gtgcccctct   1320
ctagagataa tgagcattgc atgtctaagt tataaaaaat taccacatat tttttttgtc   1380
acacttgttt gaagtgcagt ttatctatct ttatacatat atttaaactt tactctacga   1440
ataatataat ctatagtact acaataatat cagtgtttta gagaatcata taaatgaaca   1500
gttagacatg gtctaaagga caattgagta ttttgacaac aggactctac agttttatct   1560
ttttagtgtg catgtgttct cctttttttt tgcaaatagc ttcacctata taatacttca   1620
tccattttat tagtacatcc atttagggtt tagggttaat ggtttttata gactaatttt   1680
tttagtacat ctattttatt ctattttagc ctctaaatta agaaaactaa aactctattt   1740
tagttttttt atttaataat ttagatataa aatagaataa aataaagtga ctaaaaatta   1800
aacaaatacc ctttaagaaa ttaaaaaaac taaggaaaca tttttcttgt ttcgagtaga   1860
taatgccagc ctgttaaacg ccgtcgacga gtctaacgga caccaaccag cgaaccagca   1920
gcgtcgcgtc gggccaagcg aagcagacgg cacggcatct ctgtcgctgc ctctggaccc   1980
ctctcgagag ttccgctcca ccgttggact tgctccgctg tcggcatcca gaaattgcgt   2040
ggcggagcgg cagacgtgag ccggcacggc aggcggcctc ctcctcctct cacggcaccg   2100
gcagctacgg gggattcctt tcccaccgct ccttcgcttt cccttcctcg cccgccgtaa   2160
taaatagaca cccccctccac accctctttc cccaacctcg tgttgttcgg agcgcacaca   2220
cacacaacca gatctccccc aaatccaccc gtcggcacct ccgcttcaag gtacgccgct   2280
cgtcctcccc ccccccccct ctctaccttc tctagatcgg cgttccggtc catggttagg   2340
gcccggtagt tctacttctg ttcatgtttg tgttagatcc gtgtttgtgt tagatccgtg   2400
ctgctagcgt tcgtacacgg atgcgacctg tacgtcagac acgttctgat tgctaacttg   2460
ccagtgtttc tctttgggga atcctgggat ggctctagcc gttccgcaga cgggatcgat   2520
ttcatgattt tttttgtttc gttgcatagg gtttggtttg cccttttcct ttatttcaat   2580
atatgccgtg cacttgtttg tcgggtcatc ttttcatgct ttttttttgtc ttggttgtga   2640
tgatgtggtc tggttgggcg gtcgttctag atcggagtag aattctgttt caaactacct   2700
ggtggattta ttaattttgg atctgtatgt gtgtgccata catattcata gttacgaatt   2760
gaagatgatg gatggaaata tcgatctagg ataggtatac atgttgatgc gggttttact   2820
```

```
gatgcatata cagagatgct ttttgttcgc ttggttgtga tgatgtggtg tggttgggcg   2880
gtcgttcatt cgttctagat cggagtagaa tactgtttca aactacctgg tgtatttatt   2940
aattttggaa ctgtatgtgt gtgtcataca tcttcatagt tacgagttta agatggatgg   3000
aaatatcgat ctaggatagg tatacatgtt gatgtgggtt ttactgatgc atatacatga   3060
tggcatatgc agcatctatt catatgctct aaccttgagt acctatctat tataataaac   3120
aagtatgttt tataattatt ttgatcttga tatacttgga tgatggcata tgcagcagct   3180
atatgtggat ttttttagcc ctgccttcat acgctattta tttgcttggt actgtttctt   3240
ttgtcgatgc tcaccctgtt gtttggtgtt acttctgcag gtcgactcta gaggatccac   3300
catgaacaag aacaacacca agctgagcac ccgcgccctg ccgagcttca tcgactactt   3360
caacggcatc tacggcttcg ccaccggcat caaggacatc atgaacatga tcttcaagac   3420
cgacaccggc ggcgacctga ccctggacga gatcctgaag aaccagcagc tgctgaacga   3480
catcagcggc aagctggacg gcgtgaacgg cagcctgaac gacctgatcg cccagggcaa   3540
cctgaacacc gagctgagca aggagatcct taagatcgcc aacgagcaga accaggtgct   3600
gaacgacgtg aacaacaagc tggacgccat caacaccatg ctgcgcgtgt acctgccgaa   3660
gatcaccagc atgctgagcg acgtgattaa gcagaactac gccctgagcc tgcagatcga   3720
gtacctgagc aagcagctgc aggagatcag cgacaagctg gacatcatca acgtgaacgt   3780
cctgatcaac agcaccctga ccgagatcac cccggcctac cagcgcatca agtacgtgaa   3840
cgagaagttc gaagagctga ccttcgccac cgagaccagc agcaaggtga agaaggacgg   3900
cagcccggcc gacatcctgg acgagctgac cgagctgacc gagctggcga agagcgtgac   3960
caagaacgac gtggacggct tcgagttcta cctgaacacc ttccacgacg tgatggtggg   4020
caacaacctg ttcggccgca gcgccctgaa gaccgccagc gagctgatca ccaaggagaa   4080
cgtgaagacc agcggcagcg aggtgggcaa cgtgtacaac ttcctgatcg tgctgaccgc   4140
cctgcaggcc caggccttcc tgaccctgac cacctgtcgc aagctgctgg gcctggccga   4200
catcgactac accagcatca tgaacgagca cttgaacaag gagaaggagg agttccgcgt   4260
gaacatcctg ccgaccctga gcaacacctt cagcaacccg aactacgcca aggtgaaggg   4320
cagcgacgag gacgccaaga tgatcgtgga ggctaagccg ggccacgcgt tgatcggctt   4380
cgagatcagc aacgacagca tcaccgtgct gaaggtgtac gaggccaagc tgaagcagaa   4440
ctaccaggtg gacaaggaca gcttgagcga ggtgatctac ggcgacatgg acaagctgct   4500
gtgtccggac cagagcgagc aaatctacta caccaacaac atcgtgttcc cgaacgagta   4560
cgtgatcacc aagatcgact tcaccaagaa gatgaagacc ctgcgctacg aggtgaccgc   4620
caacttctac gacagcagca ccggcgagat cgacctgaac aagaagaagg tggagagcag   4680
cgaggccgag taccgcaccc tgagcgcgaa cgacgacggc gtctacatgc cactgggcgt   4740
gatcagcgag accttcctga ccccgatcaa cggctttggc ctgcaggccg acgagaacag   4800
ccgcctgatc accctgacct gtaagagcta cctgcgcgag ctgctgctag ccaccgacct   4860
gagcaacaag gagaccaagc tgatcgtgcc accgagcggc ttcatcagca acatcgtgga   4920
gaacggcagc atcgaggagg acaacctgga gccgtggaag gccaacaaca agaacgccta   4980
cgtcgaccac accggcggcg tgaacggcac caaggccctg tacgtgcaca aggacggcgg   5040
catcagccag ttcatcggcg acaagctgaa gccgaagacc gagtacgtga tccagtacac   5100
cgtgaagggc aagccatcga ttcacctgaa ggacgagaac accggctaca tccactacga   5160
ggacaccaac aacaacctgg aggactacca gaccatcaac aagcgcttca ccaccggcac   5220
```

```
cgacctgaag ggcgtgtacc tgatcctgaa gagccagaac ggcgacgagg cctggggcga   5280
caacttcatc atcctggaga tcagcccgag cgagaagctg ctgagcccgg agctgatcaa   5340
caccaacaac tggaccagca ccggcagcac caacatcagc ggcaacaccc tgaccctgta   5400
ccagggcggc cgcggcatcc tgaagcagaa cctgcagctg gacagcttca gcacctaccg   5460
cgtgtacttc agcgtgagcg gcgacgccaa cgtgcgcatc cgcaactccc gcgaggtgct   5520
gttcgagaag aggtacatga gcggcgccaa ggacgtgagc gagatgttca ccaccaagtt   5580
cgagaaggac aacttctaca tcgagctgag ccagggcaac aacctgtacg gcggcccgat   5640
cgtgcacttc tacgacgtga gcatcaagta ggagctctag atctgttctg cacaaagtgg   5700
agtagtcagt catcgatcag gaaccagaca ccagactttt attcatacag tgaagtgaag   5760
tgaagtgcag tgcagtgagt tgctggtttt tgtacaactt agtatgtatt tgtatttgta   5820
aaatacttct atcaataaaa tttctaattc ctaaaaccat caaacatttg gcaataaagt   5880
ttcttaagat tgaatcctgt tgccggtctt gcgatgatta tcatataatt tctgttgaat   5940
tacgttaagc atgtaataat taacatgtaa tgcatgacgt tatttatgag atgggttttt   6000
atgattagag tcccgcaatt atacatttaa tacgcgatag aaaacaaaat atagcgcgca   6060
aactaggata aattatcgcg cgcggtgtca tctatgttac tagatccccg ggtctagaca   6120
attcagtaca ttaaaaacgt ccgccatggt ctgaaggcaa cagataaggc atactgggcc   6180
ttgtggtagt tgttttactg ggcctttttg tatgatctat aaaattcact gggatcaacc   6240
cggagaggaa tggcagcaga tgcagtcccc agggtcctcc gtcgccgcct gagcacccgg   6300
cacccgcgct gaaccggaga gggacgcgcg gacgccgtgc agctggtgcg gagggggctg   6360
tggcagatga ggatgagacg cgtacgtggc tgggaaggcc agcaggccac cgggtcttcg   6420
tccagcccgg cgcgagtgga caggactaga gatggcaacg gttacaaacc cgctgggttt   6480
taccgtccca aacccgtacc cgtgaaaaat atctatgccc attaaaaaac ccgtacccat   6540
gacgggtttg agattttgcc caaacccgta cccatcgggt taacgggtac ccatgggtta   6600
cccgcgggtt tcatctccaa tatacctgtt cttctcataa tcaataagta tcgtaatgat   6660
taatgatatc atgatccaaa atctatgtaa tgaacaacga gttcatgatt tggtataaaa   6720
attattagta gagagaatga aatacaaata ataagttgta taattaagtg accttgcact   6780
aagttatcca tccatcacat atataacgct agtaaaaact ataatatcaa gcaagcaaca   6840
ctctcaccga ctactgatac attcaccaat tgataaaaaa tatgaagtaa ataaggaata   6900
acaagtttgt tgttcgttta taaaataaaa tgacaatatg cactaggttt ggtcgggttt   6960
aaaaaaccca cgggttcacg ggtttgggta ctataggaac aaacccgtac ccataaaccc   7020
attgggtaca gatttatgcc cgttaacaaa cccatgggta tgaaaattga cccaaaccta   7080
taccctaatg gggtaaaaac ccatcgggtt tcggatttcg ggtacccatt gccatctcta   7140
gacaggacaa cctcggccgg tcctgtatgt aggccaccag catcggccag ttggtacatc   7200
cagccggggt caggtcactt ttactcgtct caatcagaca atcaccgtcc accaacgaac   7260
gccaacgttg tcacttgtca ggtcggttga gacttgtatt tttttttgtc ctccgtaaaa   7320
atcggttcac cag                                                       7333
```

<210> SEQ ID NO 49
<211> LENGTH: 7302
<212> TYPE: DNA
<213> ORGANISM: Artificial
<220> FEATURE:

<223> OTHER INFORMATION: synthetic

<400> SEQUENCE: 49

```
tcctgtgttg ttggaacaga cttctgtctc ttctggtgat cataaatatt taaatgaacc     60
agttgtgttg gaaaatgttg ttttcttttg tctctagact ggaaagcgga gttctcgtca    120
acacggttct ttcaactagg gatgaaagtg gtaatccgaa ttgttagtac aaatttaata    180
ttttaaaata gatatgtata aaattttatg ttgatctttt ttatgttatc aagcacatta    240
gtataaatta gtataaatat gaataaaata ttacataaaa tgttttatgt attatttggt    300
ccctacaaca taaatagttg aaaaaattac taaatttgtt ttcgaatcta tatcgaagtt    360
tatatctatt atttaagaaa aatataggat gaaaaggttt atcttttatg aatctttaca    420
agctggatct tataaacaag aaaataaatt tatattgtag attttatatc ctatttattc    480
gcaatcaaag aaaagcgact aaaaaactga ttaccgagta aatactgttt ccaaccgttt    540
tcgtccctac tatcaacgcc ttctcccaac cgcagtcgat ctgtccgtct gtatcaggcg    600
cagcggcacc cctgctgttc gactatctag accatagaat atttaggta tacaataatt     660
ttagttccac gctagaacat tttagttaga ataataacaa gatttgctat tgatgtagga    720
ctcgcccgtc actgtctaaa aaagcattct gtcggtctta ttctttaggc atcagcgggt    780
gtactatctc atttttccta tcatattcct cagtactctg ttaagtataa atggtctatt    840
ttacatgatg aactaataaa actaattaag gatcctaact ttttgtgaag gtaatttgga    900
tcattatgca ttaccatcct acgtatacct gctgcagcag catctgcgta agcacagcct    960
agatatatgc ttctgtgtgg actgaaagga gactttgttt atcaattagt atactcccaa   1020
aaaactgatg acaccaatga tgcaaatagg ctgggaatag tctgtctaat agtttgagtg   1080
aatcatgtca ctgattaaac tgaaggcggg aaacgacaat ctgatcatga gcggagaatt   1140
aagggagtca cgttatgacc cccgccgatg acgcgggaca agccgtttta cgtttggaac   1200
tgacagaacc gcaacgttga aggagccact cagcaagctg gtacaagctt gcatgcctgc   1260
agtgcagcgt gacccggtcg tgcccctctc tagagataat gagcattgca tgtctaagtt   1320
ataaaaaatt accacatatt ttttttgtca cacttgtttg aagtgcagtt tatctatctt   1380
tatacatata tttaaacttt actctacgaa taatataatc tatagtacta caataatatc   1440
agtgttttag agaatcatat aaatgaacag ttagacatgg tctaaaggac aattgagtat   1500
tttgacaaca ggactctaca gttttatctt tttagtgtgc atgtgttctc cttttttttt   1560
gcaaatagct tcacctatat aatacttcat ccattttatt agtacatcca tttagggttt   1620
agggttaatg gtttttatag actaattttt ttagtacatc tattttattc tattttagcc   1680
tctaaattaa gaaaactaaa actctatttt agttttttta tttaataatt tagatataaa   1740
atagaataaa ataaagtgac taaaaattaa acaaataccc tttaagaaat taaaaaaact   1800
aaggaaacat ttttcttgtt tcgagtagat aatgccagcc tgttaaacgc cgtcgacgag   1860
tctaacggac accaaccagc gaaccagcag cgtcgcgtcg ggccaagcga agcagacggc   1920
acggcatctc tgtcgctgcc tctggacccc tctcgagagt tccgctccac cgttggactt   1980
gctccgctgt cggcatccag aaattgcgtg gcggagcggc agacgtgagc cggcacggca   2040
ggcggcctcc tcctcctctc acggcaccgg cagctacggg ggattccttt cccaccgctc   2100
cttcgctttc ccttcctcgc ccgccgtaat aaatagacac cccctccaca ccctctttcc   2160
ccaacctcgt gttgttcgga gcgcacacac acacaaccag atctccccca aatccacccg   2220
tcggcacctc cgcttcaagg tacgccgctc gtcctccccc ccccccccctc tctaccttct   2280
```

ctagatcggc gttccggtcc atggttaggg cccggtagtt ctacttctgt tcatgtttgt 2340
gttagatccg tgtttgtgtt agatccgtgc tgctagcgtt cgtacacgga tgcgacctgt 2400
acgtcagaca cgttctgatt gctaacttgc cagtgtttct ctttggggaa tcctgggatg 2460
gctctagccg ttccgcagac gggatcgatt tcatgatttt ttttgtttcg ttgcataggg 2520
tttggtttgc ccttttcctt tatttcaata tatgccgtgc acttgtttgt cgggtcatct 2580
tttcatgctt ttttttgtct tggttgtgat gatgtggtct ggttgggcgg tcgttctaga 2640
tcggagtaga attctgtttc aaactacctg gtggatttat taattttgga tctgtatgtg 2700
tgtgccatac atattcatag ttacgaattg aagatgatgg atggaaatat cgatctagga 2760
taggtataca tgttgatgcg ggttttactg atgcatatac agagatgctt tttgttcgct 2820
tggttgtgat gatgtggtgt ggttgggcgg tcgttcattc gttctagatc ggagtagaat 2880
actgtttcaa actacctggt gtatttatta attttggaac tgtatgtgtg tgtcatacat 2940
cttcatagtt acgagtttaa gatggatgga aatatcgatc taggataggt atacatgttg 3000
atgtgggttt tactgatgca tatacatgat ggcatatgca gcatctattc atatgctcta 3060
accttgagta cctatctatt ataataaaca agtatgtttt ataattattt tgatcttgat 3120
atacttggat gatggcatat gcagcagcta tatgtggatt tttttagccc tgccttcata 3180
cgctatttat ttgcttggta ctgtttcttt tgtcgatgct caccctgttg tttggtgtta 3240
cttctgcagg tcgactctag aggatccacc atgaacaaga acaacaccaa gctgagcacc 3300
cgcgccctgc cgagcttcat cgactacttc aacggcatct acggcttcgc caccggcatc 3360
aaggacatca tgaacatgat cttcaagacc gacaccggcg gcgacctgac cctggacgag 3420
atcctgaaga accagcagct gctgaacgac atcagcggca agctggacgg cgtgaacggc 3480
agcctgaacg acctgatcgc ccagggcaac ctgaacaccg agctgagcaa ggagatcctt 3540
aagatcgcca acgagcagaa ccaggtgctg aacgacgtga acaacaagct ggacgccatc 3600
aacaccatgc tgcgcgtgta cctgccgaag atcaccagca tgctgagcga cgtgattaag 3660
cagaactacg ccctgagcct gcagatcgag tacctgagca agcagctgca ggagatcagc 3720
gacaagctgg acatcatcaa cgtgaacgtc ctgatcaaca gcaccctgac cgagatcacc 3780
ccggcctacc agcgcatcaa gtacgtgaac gagaagttcg aagagctgac cttcgccacc 3840
gagaccagca gcaaggtgaa gaaggacggc agcccggccg acatcctgga cgagctgacc 3900
gagctgaccg agctggcgaa gagcgtgacc aagaacgacg tggacggctt cgagttctac 3960
ctgaacacct tccacgacgt gatggtgggc aacaacctgt tcggccgcag cgccctgaag 4020
accgccagcg agctgatcac caaggagaac gtgaagacca gcggcagcga ggtgggcaac 4080
gtgtacaact tcctgatcgt gctgaccgcc ctgcaggccc aggccttcct gaccctgacc 4140
acctgtcgca agctgctggg cctggccgac atcgactaca ccagcatcat gaacgagcac 4200
ttgaacaagg agaaggagga gttccgcgtg aacatcctgc cgaccctgag caacaccttc 4260
agcaacccga actacgccaa ggtgaagggc agcgacgagg acgccaagat gatcgtggag 4320
gctaagccgg gccacgcgtt gatcggcttc gagatcagca acgacagcat caccgtgctg 4380
aaggtgtacg aggccaagct gaagcagaac taccaggtgg acaaggacag cttgagcgag 4440
gtgatctacg gcgacatgga caagctgctg tgtccggacc agagcgagca aatctactac 4500
accaacaaca tcgtgttccc gaacgagtac gtgatcacca agatcgactt caccaagaag 4560
atgaagaccc tgcgctacga ggtgaccgcc aacttctacg acagcagcac cggcgagatc 4620

-continued

```
gacctgaaca agaagaaggt ggagagcagc gaggccgagt accgcaccct gagcgcgaac   4680
gacgacggcg tctacatgcc actgggcgtg atcagcgaga ccttcctgac cccgatcaac   4740
ggctttggcc tgcaggccga cgagaacagc cgcctgatca ccctgacctg taagagctac   4800
ctgcgcgagc tgctgctagc caccgacctg agcaacaagg agaccaagct gatcgtgcca   4860
ccgagcggct tcatcagcaa catcgtggag aacggcagca tcgaggagga caacctggag   4920
ccgtggaagg ccaacaacaa gaacgcctac gtcgaccaca ccggcggcgt gaacggcacc   4980
aaggccctgt acgtgcacaa ggacggcggc atcagccagt tcatcggcga caagctgaag   5040
ccgaagaccg agtacgtgat ccagtacacc gtgaagggca agccatcgat tcacctgaag   5100
gacgagaaca ccggctacat ccactacgag gacaccaaca acaacctgga ggactaccag   5160
accatcaaca agcgcttcac caccggcacc gacctgaagg gcgtgtacct gatcctgaag   5220
agccagaacg gcgacgaggc ctggggcgac aacttcatca tcctggagat cagcccgagc   5280
gagaagctgc tgagcccgga gctgatcaac accaacaact ggaccagcac cggcagcacc   5340
aacatcagcg gcaacaccct gaccctgtac cagggcggcc gcggcatcct gaagcagaac   5400
ctgcagctgg acagcttcag cacctaccgc gtgtacttca gcgtgagcgg cgacgccaac   5460
gtgcgcatcc gcaactcccg cgaggtgctg ttcgagaaga ggtacatgag cggcgccaag   5520
gacgtgagcg agatgttcac caccaagttc gagaaggaca acttctacat cgagctgagc   5580
cagggcaaca acctgtacgg cggcccgatc gtgcacttct acgacgtgag catcaagtag   5640
gagctctaga tctgttctgc acaaagtgga gtagtcagtc atcgatcagg aaccagacac   5700
cagactttta ttcatacagt gaagtgaagt gaagtgcagt gcagtgagtt gctggttttt   5760
gtacaactta gtatgtattt gtatttgtaa aatacttcta tcaataaaat ttctaattcc   5820
taaaaccatc aaacatttgg caataaagtt tcttaagatt gaatcctgtt gccggtcttg   5880
cgatgattat catataattt ctgttgaatt acgttaagca tgtaataatt aacatgtaat   5940
gcatgacgtt atttatgaga tgggttttta tgattagagt cccgcaatta tacatttaat   6000
acgcgataga aaacaaaata tagcgcgcaa actaggataa attatcgcgc gcggtgtcat   6060
ctatgttact agatccccgg gtctagacaa ttcagtacat taaaaacgtc cgccatggtc   6120
tgaaggcaac agataaggca tactgggcct tgtggtagtt gttttactgg gcctttttgt   6180
atgatctata aaattcactg ggatcaaccc ggagaggaat ggcagcagat gcagtcccca   6240
gggtcctccg tcgccgcctg agcacccggc acccgcgctg aaccggagag ggacgcgcgg   6300
acgccgtgca gctggtgcgg agggggctgt ggcagatgag gatgagacgc gtacgtggct   6360
gggaaggcca gcaggccacc gggtcttcgt ccagcccggc gcgagtggac aggactagag   6420
atggcaacgg ttacaaaccc gctgggtttt accgtcccaa acccgtaccc gtgaaaaata   6480
tctatgccca ttaaaaaacc cgtacccatg acgggtttga gattttgccc aaacccgtac   6540
ccatcgggtt aacgggtacc catgggttac ccgcgggttt catctccaat atacctgttc   6600
ttctcataat caataagtat cgtaatgatt aatgatatca tgatccaaaa tctatgtaat   6660
gaacaacgag ttcatgattt ggtataaaaa ttattagtag agagaatgaa atacaaataa   6720
taagttgtat aattaagtga ccttgcacta agttatccat ccatcacata tataacgcta   6780
gtaaaaacta taatatcaag caagcaacac tctcaccgac tactgataca ttcaccaatt   6840
gataaaaaat atgaagtaaa taaggaataa caagtttgtt gttcgtttat aaaataaaat   6900
gacaatatgc actaggtttg gtcgggttta aaaaacccac gggttcacgg gtttgggtac   6960
tataggaaca aacccgtacc cataaaccca ttgggtacag atttatgccc gttaacaaac   7020
```

```
ccatgggtat gaaaattgac ccaaacctat accctaatgg ggtaaaaacc catcgggttt   7080

cggatttcgg gtacccattg ccatctctag acaggacaac ctcggccggt cctgtatgta   7140

ggccaccagc atcggccagt tggtacatcc agccggggtc aggtcacttt tactcgtctc   7200

aatcagacaa tcaccgtcca ccaacgaacg ccaacgttgt cacttgtcag gtcggttgag   7260

acttgtattt ttttttgtcc tccgtaaaaa tcggttcacc ag                      7302


<210> SEQ ID NO 50
<211> LENGTH: 294
<212> TYPE: DNA
<213> ORGANISM: Artificial
<220> FEATURE:
<223> OTHER INFORMATION: synthetic

<400> SEQUENCE: 50

tacgtatacc tgctgcagca gcatctgcgt aagcacagcc tagatatatg cttctgtgtg     60

gactgaaagg agactttgtt tatcaattag tatactccca aaaaactgat gacaccaatg    120

atgcaaatag gctgggaata gtctgtctaa tagttaactg aaggcgggaa acgacaatct    180

gatcatgagc ggagaattaa gggagtcacg ttatgacccc cgccgatgac gcgggacaag    240

ccgttttacg tttggaactg acagaaccgc aacgttgaag gagccactca gcaa          294


<210> SEQ ID NO 51
<211> LENGTH: 295
<212> TYPE: DNA
<213> ORGANISM: Artificial
<220> FEATURE:
<223> OTHER INFORMATION: synthetic

<400> SEQUENCE: 51

tacgtatacc tgctgcagca gcatctgcgt aagcacagcc tagatatatg cttctgtgtg     60

gactgaaagg agactttgtt tatcaattag tatactccca aaaaactgat gacaccaatg    120

atgcaaatag gctgggaata gtctgtctaa tagtttcact gaaggcggga aacgacaatc    180

tgatcatgag cggagaatta agggagtcac gttatgaccc ccgccgatga cgcgggacaa    240

gccgttttac gtttggaact gacagaaccg caacgttgaa ggagccactc agcaa         295


<210> SEQ ID NO 52
<211> LENGTH: 296
<212> TYPE: DNA
<213> ORGANISM: Artificial
<220> FEATURE:
<223> OTHER INFORMATION: synthetic

<400> SEQUENCE: 52

tacgtatacc tgctgcagca gcatctgcgt aagcacagcc tagatatatg cttctgtgtg     60

gactgaaagg agactttgtt tatcaattag tatactccca aaaaactgat gacaccaatg    120

atgcaaatag gctgggaata gtctgtctaa tagtttgaac tgaaggcggg aaacgacaat    180

ctgatcatga gcggagaatt aagggagtca cgttatgacc cccgccgatg acgcgggaca    240

agccgtttta cgtttggaac tgacagaacc gcaacgttga aggagccact cagcaa        296


<210> SEQ ID NO 53
<211> LENGTH: 295
<212> TYPE: DNA
<213> ORGANISM: Artificial
<220> FEATURE:
<223> OTHER INFORMATION: synthetic
```

<400> SEQUENCE: 53
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa taggtagagt gaaggcggta aacgacaatc 180
tgatcatgag cggagaatta agggagtcac gttatgaccc ccgccgatga cgcgggacaa 240
gccgttttac gtttggaact tacagaaccg caacgttgaa ggagccactc agcaa 295

<210> SEQ ID NO 54
<211> LENGTH: 296
<212> TYPE: DNA
<213> ORGANISM: Artificial
<220> FEATURE:
<223> OTHER INFORMATION: synthetic

<400> SEQUENCE: 54
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gcagggaatc gtctgtcgga tagtttgagc ggaaggcggg aaacgacaat 180
ctgatcatga gcggagcatt aagggagtca cgttatgacc cccgccgatg acgcgggaca 240
agccgtttta cgtttggaac tgacagaacc gcaacgttga aggagccact cagcaa 296

<210> SEQ ID NO 55
<211> LENGTH: 300
<212> TYPE: DNA
<213> ORGANISM: Artificial
<220> FEATURE:
<223> OTHER INFORMATION: synthetic

<400> SEQUENCE: 55
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaactgaagg cgggaaacga 180
caatctgatc atgagcggag aattaaggga gtcacgttat gacccccgcc gatgacgcgg 240
gacaagccgt tttacgtttg gaactgacag aaccgcaacg ttgaaggagc cactcagcaa 300

<210> SEQ ID NO 56
<211> LENGTH: 304
<212> TYPE: DNA
<213> ORGANISM: Artificial
<220> FEATURE:
<223> OTHER INFORMATION: synthetic

<400> SEQUENCE: 56
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaataaactg aaggcgggaa 180
acgacaatct gatcatgagc ggagaattaa gggagtcacg ttatgacccc cgccgatgac 240
gcgggacaag ccgttttacg tttggaactg acagaaccgc aacgttgaag gagccactca 300
gcaa 304

<210> SEQ ID NO 57
<211> LENGTH: 299
<212> TYPE: DNA
<213> ORGANISM: Artificial

<220> FEATURE:
<223> OTHER INFORMATION: synthetic

<400> SEQUENCE: 57
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcaaggc gggaaacgac 180
aatctgatca tgagcggaga attaagggag tcacgttatg acccccgccg atgacgcggg 240
acaagccgtt ttacgtttgg aactgacaga accgcaacgt tgaaggagcc actcagcaa 299

<210> SEQ ID NO 58
<211> LENGTH: 304
<212> TYPE: DNA
<213> ORGANISM: Artificial
<220> FEATURE:
<223> OTHER INFORMATION: synthetic

<400> SEQUENCE: 58
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcaactg aaggcgggaa 180
acgacaatct gatcatgagc ggagaattaa gggagtcacg ttatgacccc cgccgatgac 240
gcgggacaag ccgttttacg tttggaactg acagaaccgc aacgttgaag gagccactca 300
gcaa 304

<210> SEQ ID NO 59
<211> LENGTH: 305
<212> TYPE: DNA
<213> ORGANISM: Artificial
<220> FEATURE:
<223> OTHER INFORMATION: synthetic

<400> SEQUENCE: 59
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcaaact gaaggcggga 180
aacgacaatc tgatcatgag cggagaatta agggagtcac gttatgaccc ccgccgatga 240
cgcgggacaa gccgttttac gtttggaact gacagaaccg caacgttgaa ggagccactc 300
agcaa 305

<210> SEQ ID NO 60
<211> LENGTH: 302
<212> TYPE: DNA
<213> ORGANISM: Artificial
<220> FEATURE:
<223> OTHER INFORMATION: synthetic

<400> SEQUENCE: 60
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgaa ggcgggaaac 180
gacaatctga tcatgagcgg agaattaagg gagtcacgtt atgacccccg ccgatgacgc 240
gggacaagcc gttttacgtt tggaactgac agaaccgcaa cgttgaagga gccactcagc 300
aa 302

<210> SEQ ID NO 61
<211> LENGTH: 306
<212> TYPE: DNA
<213> ORGANISM: Artificial
<220> FEATURE:
<223> OTHER INFORMATION: synthetic

<400> SEQUENCE: 61
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcaaaac tgaaggcggg 180
aaacgacaat ctgatcatga gcggagaatt aagggagtca cgttatgacc cccgccgatg 240
acgcgggaca agccgtttta cgtttggaac tgacagaacc gcaacgttga aggagccact 300
cagcaa 306

<210> SEQ ID NO 62
<211> LENGTH: 299
<212> TYPE: DNA
<213> ORGANISM: Artificial
<220> FEATURE:
<223> OTHER INFORMATION: synthetic

<400> SEQUENCE: 62
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatggc gggaaacgac 180
aatctgatca tgagcggaga attaagggag tcacgttatg acccccgccg atgacgcggg 240
acaagccgtt ttacgtttgg aactgacaga accgcaacgt tgaaggagcc actcagcaa 299

<210> SEQ ID NO 63
<211> LENGTH: 300
<212> TYPE: DNA
<213> ORGANISM: Artificial
<220> FEATURE:
<223> OTHER INFORMATION: synthetic

<400> SEQUENCE: 63
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatagg cgggaaacga 180
caatctgatc atgagcggag aattaaggga gtcacgttat gacccccgcc gatgacgcgg 240
gacaagccgt tttacgtttg gaactgacag aaccgcaacg ttgaaggagc cactcagcaa 300

<210> SEQ ID NO 64
<211> LENGTH: 311
<212> TYPE: DNA
<213> ORGANISM: Artificial
<220> FEATURE:
<223> OTHER INFORMATION: synthetic

<400> SEQUENCE: 64
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtt taaactgaag 180
gcgggaaacg acaatctgat catgagcgga gaattaaggg agtcacgtta tgaccccccgc 240 cgatgacgcg ggacaagccg ttttacgttt ggaactgaca gaaccgcaac gttgaaggag 300
ccactcagca a 311

<210> SEQ ID NO 65
<211> LENGTH: 305
<212> TYPE: DNA
<213> ORGANISM: Artificial
<220> FEATURE:
<223> OTHER INFORMATION: synthetic

<400> SEQUENCE: 65
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgct gaaggcggga 180
aacgacaatc tgatcatgag cggagaatta agggagtcac gttatgaccc ccgccgatga 240
cgcgggacaa gccgttttac gtttggaact gacagaaccg caacgttgaa ggagccactc 300
agcaa 305

<210> SEQ ID NO 66
<211> LENGTH: 307
<212> TYPE: DNA
<213> ORGANISM: Artificial
<220> FEATURE:
<223> OTHER INFORMATION: synthetic

<400> SEQUENCE: 66
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgaa ctgaaggcgg 180
gaaacgacaa tctgatcatg agcggagaat taagggagtc acgttatgac cccgccgat 240 gacgcgggac aagccgtttt acgtttggaa ctgacagaac cgcaacgttg aaggagccac 300
tcagcaa 307

<210> SEQ ID NO 67
<211> LENGTH: 308
<212> TYPE: DNA
<213> ORGANISM: Artificial
<220> FEATURE:
<223> OTHER INFORMATION: synthetic

<400> SEQUENCE: 67
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgaa actgaaggcg 180
ggaaacgaca atctgatcat gagcggagaa ttaagggagt cacgttatga cccccgccga 240
tgacgcggga caagccgttt tacgtttgga actgacagaa ccgcaacgtt gaaggagcca 300
ctcagcaa 308

<210> SEQ ID NO 68
<211> LENGTH: 309
<212> TYPE: DNA
<213> ORGANISM: Artificial
<220> FEATURE:

<223> OTHER INFORMATION: synthetic

<400> SEQUENCE: 68
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgta aactgaaggc 180
gggaaacgac aatctgatca tgagcggaga attaagggag tcacgttatg acccccgccg 240
atgacgcggg acaagccgtt ttacgtttgg aactgacaga accgcaacgt tgaaggagcc 300
actcagcaa 309

<210> SEQ ID NO 69
<211> LENGTH: 310
<212> TYPE: DNA
<213> ORGANISM: Artificial
<220> FEATURE:
<223> OTHER INFORMATION: synthetic

<400> SEQUENCE: 69
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtt aaactgaagg 180
cgggaaacga caatctgatc atgagcggag aattaaggga gtcacgttat gacccccgcc 240
gatgacgcgg gacaagccgt tttacgtttg gaactgacag aaccgcaacg ttgaaggagc 300
cactcagcaa 310

<210> SEQ ID NO 70
<211> LENGTH: 314
<212> TYPE: DNA
<213> ORGANISM: Artificial
<220> FEATURE:
<223> OTHER INFORMATION: synthetic

<400> SEQUENCE: 70
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgta gtttaaactg 180
aaggcgggaa acgacaatct gatcatgagc ggagaattaa gggagtcacg ttatgacccc 240
cgccgatgac gcgggacaag ccgttttacg tttggaactg acagaaccgc aacgttgaag 300
gagccactca gcaa 314

<210> SEQ ID NO 71
<211> LENGTH: 291
<212> TYPE: DNA
<213> ORGANISM: Artificial
<220> FEATURE:
<223> OTHER INFORMATION: synthetic

<400> SEQUENCE: 71
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtg acaatctgat 180
catgagcgga gaattaaggg agtcacgtta tgacccccgc cgatgacgcg ggacaagccg 240
ttttacgttt ggaactgaca gaaccgcaac gttgaaggag ccactcagca a 291

<210> SEQ ID NO 72
<211> LENGTH: 305
<212> TYPE: DNA
<213> ORGANISM: Artificial
<220> FEATURE:
<223> OTHER INFORMATION: synthetic

<400> SEQUENCE: 72
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtt gaaggcggga 180
aacgacaatc tgatcatgag cggagaatta agggagtcac gttatgaccc ccgccgatga 240
cgcgggacaa gccgttttac gtttggaact gacagaaccg caacgttgaa ggagccactc 300
agcaa 305

<210> SEQ ID NO 73
<211> LENGTH: 307
<212> TYPE: DNA
<213> ORGANISM: Artificial
<220> FEATURE:
<223> OTHER INFORMATION: synthetic

<400> SEQUENCE: 73
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgta ctgaaggcgg 180
gaaacgacaa tctgatcatg agcggagaat taagggagtc acgttatgac ccccgccgat 240
gacgcgggac aagccgtttt acgtttggaa ctgacagaac cgcaacgttg aaggagccac 300
tcagcaa 307

<210> SEQ ID NO 74
<211> LENGTH: 308
<212> TYPE: DNA
<213> ORGANISM: Artificial
<220> FEATURE:
<223> OTHER INFORMATION: synthetic

<400> SEQUENCE: 74
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgta actgaaggcg 180
ggaaacgaca atctgatcat gagcggagaa ttaagggagt cacgttatga cccccgccga 240
tgacgcggga caagccgttt tacgtttgga actgacagaa ccgcaacgtt gaaggagcca 300
ctcagcaa 308

<210> SEQ ID NO 75
<211> LENGTH: 312
<212> TYPE: DNA
<213> ORGANISM: Artificial
<220> FEATURE:
<223> OTHER INFORMATION: synthetic

<400> SEQUENCE: 75
tacgtatacc tgctgcagca gcatctgcgt aagcacagcc tagatatatg cttctgtgtg 60

```
gactgaaagg agactttgtt tatcaattag tatactccca aaaaactgat gacaccaatg    120

atgcaaatag gctgggaata gtctgtctaa tagtttgagt gaatcatgtt ttaaactgaa    180

ggcgggaaac gacaatctga tcatgagcgg agaattaagg gagtcacgtt atgacccccg    240

ccgatgacgc gggacaagcc gttttacgtt tggaactgac agaaccgcaa cgttgaagga    300

gccactcagc aa                                                        312
```

<210> SEQ ID NO 76
<211> LENGTH: 313
<212> TYPE: DNA
<213> ORGANISM: Artificial
<220> FEATURE:
<223> OTHER INFORMATION: synthetic

<400> SEQUENCE: 76

```
tacgtatacc tgctgcagca gcatctgcgt aagcacagcc tagatatatg cttctgtgtg     60

gactgaaagg agactttgtt tatcaattag tatactccca aaaaactgat gacaccaatg    120

atgcaaatag gctgggaata gtctgtctaa tagtttgagt gaatcatgtg tttaaactga    180

aggcgggaaa cgacaatctg atcatgagcg gagaattaag ggagtcacgt tatgaccccc    240

gccgatgacg cgggacaagc cgttttacgt ttggaactga cagaaccgca acgttgaagg    300

agccactcag caa                                                       313
```

<210> SEQ ID NO 77
<211> LENGTH: 294
<212> TYPE: DNA
<213> ORGANISM: Artificial
<220> FEATURE:
<223> OTHER INFORMATION: synthetic

<400> SEQUENCE: 77

```
tacgtatacc tgctgcagca gcatctgcgt aagcacagcc tagatatatg cttctgtgtg     60

gactgaaagg agactttgtt tatcaattag tatactccca aaaaactgat gacaccaatg    120

atgcaaatag gctgggaata gtctgtctaa tagtttgagt gaatcatgtc acgacaatct    180

gatcatgagc ggagaattaa gggagtcacg ttatgacccc cgccgatgac gcgggacaag    240

ccgttttacg tttggaactg acagaaccgc aacgttgaag gagccactca gcaa          294
```

<210> SEQ ID NO 78
<211> LENGTH: 296
<212> TYPE: DNA
<213> ORGANISM: Artificial
<220> FEATURE:
<223> OTHER INFORMATION: synthetic

<400> SEQUENCE: 78

```
tacgtatacc tgctgcagca gcatctgcgt aagcacagcc tagatatatg cttctgtgtg     60

gactgaaagg agactttgtt tatcaattag tatactccca aaaaactgat gacaccaatg    120

atgcaaatag gctgggaata gtctgtctaa tagtttgagt gaatcatgtc aaacgacaat    180

ctgatcatga gcggagaatt aagggagtca cgttatgacc cccgccgatg acgcgggaca    240

agccgtttta cgtttggaac tgacagaacc gcaacgttga aggagccact cagcaa        296
```

<210> SEQ ID NO 79
<211> LENGTH: 301
<212> TYPE: DNA
<213> ORGANISM: Artificial
<220> FEATURE:
<223> OTHER INFORMATION: synthetic

<400> SEQUENCE: 79
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc gcgggaaacg 180
acaatctgat catgagcgga gaattaaggg agtcacgtta tgacccccgc cgatgacgcg 240
ggacaagccg ttttacgttt ggaactgaca gaaccgcaac gttgaaggag ccactcagca 300
a 301

<210> SEQ ID NO 80
<211> LENGTH: 302
<212> TYPE: DNA
<213> ORGANISM: Artificial
<220> FEATURE:
<223> OTHER INFORMATION: synthetic

<400> SEQUENCE: 80
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc ggcgggaaac 180
gacaatctga tcatgagcgg agaattaagg gagtcacgtt atgacccccg ccgatgacgc 240
gggacaagcc gttttacgtt tggaactgac agaaccgcaa cgttgaagga gccactcagc 300
aa 302

<210> SEQ ID NO 81
<211> LENGTH: 303
<212> TYPE: DNA
<213> ORGANISM: Artificial
<220> FEATURE:
<223> OTHER INFORMATION: synthetic

<400> SEQUENCE: 81
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc aggcgggaaa 180
cgacaatctg atcatgagcg gagaattaag ggagtcacgt tatgaccccc gccgatgacg 240
cgggacaagc cgttttacgt ttggaactga cagaaccgca acgttgaagg agccactcag 300
caa 303

<210> SEQ ID NO 82
<211> LENGTH: 304
<212> TYPE: DNA
<213> ORGANISM: Artificial
<220> FEATURE:
<223> OTHER INFORMATION: synthetic

<400> SEQUENCE: 82
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc aaggcgggaa 180
acgacaatct gatcatgagc ggagaattaa gggagtcacg ttatgacccc cgccgatgac 240
gcgggacaag ccgttttacg tttggaactg acagaaccgc aacgttgaag gagccactca 300
gcaa 304

<210> SEQ ID NO 83
<211> LENGTH: 305
<212> TYPE: DNA
<213> ORGANISM: Artificial
<220> FEATURE:
<223> OTHER INFORMATION: synthetic

<400> SEQUENCE: 83
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc gaaggcggga 180
aacgacaatc tgatcatgag cggagaatta agggagtcac gttatgaccc ccgccgatga 240
cgcgggacaa gccgttttac gtttggaact gacagaaccg caacgttgaa ggagccactc 300
agcaa 305

<210> SEQ ID NO 84
<211> LENGTH: 308
<212> TYPE: DNA
<213> ORGANISM: Artificial
<220> FEATURE:
<223> OTHER INFORMATION: synthetic

<400> SEQUENCE: 84
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc actgaaggcg 180
ggaaacgaca atctgatcat gagcggagaa ttaagggagt cacgttatga cccccgccga 240
tgacgcggga caagccgttt tacgtttgga actgacagaa ccgcaacgtt gaaggagcca 300
ctcagcaa 308

<210> SEQ ID NO 85
<211> LENGTH: 309
<212> TYPE: DNA
<213> ORGANISM: Artificial
<220> FEATURE:
<223> OTHER INFORMATION: synthetic

<400> SEQUENCE: 85
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc aactgaaggc 180
gggaaacgac aatctgatca tgagcggaga attaagggag tcacgttatg acccccgccg 240
atgacgcggg acaagccgtt ttacgtttgg aactgacaga accgcaacgt tgaaggagcc 300
actcagcaa 309

<210> SEQ ID NO 86
<211> LENGTH: 310
<212> TYPE: DNA
<213> ORGANISM: Artificial
<220> FEATURE:
<223> OTHER INFORMATION: synthetic

<400> SEQUENCE: 86
tacgtatacc tgctgcagca gcatctgcgt aagcacagcc tagatatatg cttctgtgtg 60

```
gactgaaagg agactttgtt tatcaattag tatactccca aaaaactgat gacaccaatg    120

atgcaaatag gctgggaata gtctgtctaa tagtttgagt gaatcatgtc aaactgaagg    180

cgggaaacga caatctgatc atgagcggag aattaaggga gtcacgttat gacccccgcc    240

gatgacgcgg gacaagccgt tttacgtttg gaactgacag aaccgcaacg ttgaaggagc    300

cactcagcaa                                                           310


<210> SEQ ID NO 87
<211> LENGTH: 311
<212> TYPE: DNA
<213> ORGANISM: Artificial
<220> FEATURE:
<223> OTHER INFORMATION: synthetic

<400> SEQUENCE: 87

tacgtatacc tgctgcagca gcatctgcgt aagcacagcc tagatatatg cttctgtgtg     60

gactgaaagg agactttgtt tatcaattag tatactccca aaaaactgat gacaccaatg    120

atgcaaatag gctgggaata gtctgtctaa tagtttgagt gaatcatgtc taaactgaag    180

gcgggaaacg acaatctgat catgagcgga gaattaaggg agtcacgtta tgacccccgc    240

cgatgacgcg ggacaagccg ttttacgttt ggaactgaca gaaccgcaac gttgaaggag    300

ccactcagca a                                                         311


<210> SEQ ID NO 88
<211> LENGTH: 312
<212> TYPE: DNA
<213> ORGANISM: Artificial
<220> FEATURE:
<223> OTHER INFORMATION: synthetic

<400> SEQUENCE: 88

tacgtatacc tgctgcagca gcatctgcgt aagcacagcc tagatatatg cttctgtgtg     60

gactgaaagg agactttgtt tatcaattag tatactccca aaaaactgat gacaccaatg    120

atgcaaatag gctgggaata gtctgtctaa tagtttgagt gaatcatgtc ttaaactgaa    180

ggcgggaaac gacaatctga tcatgagcgg agaattaagg gagtcacgtt atgacccccg    240

ccgatgacgc gggacaagcc gttttacgtt tggaactgac agaaccgcaa cgttgaagga    300

gccactcagc aa                                                        312


<210> SEQ ID NO 89
<211> LENGTH: 313
<212> TYPE: DNA
<213> ORGANISM: Artificial
<220> FEATURE:
<223> OTHER INFORMATION: synthetic

<400> SEQUENCE: 89

tacgtatacc tgctgcagca gcatctgcgt aagcacagcc tagatatatg cttctgtgtg     60

gactgaaagg agactttgtt tatcaattag tatactccca aaaaactgat gacaccaatg    120

atgcaaatag gctgggaata gtctgtctaa tagtttgagt gaatcatgtc tttaaactga    180

aggcgggaaa cgacaatctg atcatgagcg gagaattaag ggagtcacgt tatgaccccc    240

gccgatgacg cgggacaagc cgttttacgt ttggaactga cagaaccgca acgttgaagg    300

agccactcag caa                                                       313


<210> SEQ ID NO 90
```

<211> LENGTH: 314
<212> TYPE: DNA
<213> ORGANISM: Artificial
<220> FEATURE:
<223> OTHER INFORMATION: synthetic

<400> SEQUENCE: 90
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc agtttaaact 180
gaaggcggga aacgacaatc tgatcatgag cggagaatta agggagtcac gttatgaccc 240
ccgccgatga cgcgggacaa gccgttttac gtttggaact gacagaaccg caacgttgaa 300
ggagccatca gcaa 314

<210> SEQ ID NO 91
<211> LENGTH: 315
<212> TYPE: DNA
<213> ORGANISM: Artificial
<220> FEATURE:
<223> OTHER INFORMATION: synthetic

<400> SEQUENCE: 91
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc agtttaaact 180
gaaggcggga aacgacaatc tgatcatgag cggagaatta agggagtcac gttatgaccc 240
ccgccgatga cgcgggacaa gccgttttac gtttggaact gacagaaccg caacgttgaa 300
ggagccactc agcaa 315

<210> SEQ ID NO 92
<211> LENGTH: 316
<212> TYPE: DNA
<213> ORGANISM: Artificial
<220> FEATURE:
<223> OTHER INFORMATION: synthetic

<400> SEQUENCE: 92
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc tagtttaaac 180
tgaaggcggg aaacgacaat ctgatcatga gcggagaatt aagggagtca cgttatgacc 240
cccgccgatg acgcgggaca agccgtttta cgtttggaac tgacagaacc gcaacgttga 300
aggagccact cagcaa 316

<210> SEQ ID NO 93
<211> LENGTH: 317
<212> TYPE: DNA
<213> ORGANISM: Artificial
<220> FEATURE:
<223> OTHER INFORMATION: synthetic

<400> SEQUENCE: 93
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc atagtttaaa 180
ctgaaggcgg gaaacgacaa tctgatcatg agcggagaat taagggagtc acgttatgac 240
ccccgccgat gacgcgggac aagccgtttt acgtttggaa ctgacagaac cgcaacgttg 300
aaggagccac tcagcaa 317

<210> SEQ ID NO 94
<211> LENGTH: 279
<212> TYPE: DNA
<213> ORGANISM: Artificial
<220> FEATURE:
<223> OTHER INFORMATION: synthetic

<400> SEQUENCE: 94
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc agagcggaga 180
attaagggag tcacgttatg acccccgccg atgacgcggg acaagccgtt ttacgtttgg 240
aactgacaga accgcaacgt tgaaggagcc actcagcaa 279

<210> SEQ ID NO 95
<211> LENGTH: 297
<212> TYPE: DNA
<213> ORGANISM: Artificial
<220> FEATURE:
<223> OTHER INFORMATION: synthetic

<400> SEQUENCE: 95
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc aaaacgacaa 180
tctgatcatg agcggagaat taagggagtc acgttatgac ccccgccgat gacgcgggac 240
aagccgtttt acgtttggaa ctgacagaac cgcaacgttg aaggagccac tcagcaa 297

<210> SEQ ID NO 96
<211> LENGTH: 302
<212> TYPE: DNA
<213> ORGANISM: Artificial
<220> FEATURE:
<223> OTHER INFORMATION: synthetic

<400> SEQUENCE: 96
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc agcgggaaac 180
gacaatctga tcatgagcgg agaattaagg gagtcacgtt atgacccccg ccgatgacgc 240
gggacaagcc gttttacgtt tggaactgac agaaccgcaa cgttgaagga gccactcagc 300
aa 302

<210> SEQ ID NO 97
<211> LENGTH: 307
<212> TYPE: DNA
<213> ORGANISM: Artificial
<220> FEATURE:
<223> OTHER INFORMATION: synthetic

<400> SEQUENCE: 97

```
tacgtatacc tgctgcagca gcatctgcgt aagcacagcc tagatatatg cttctgtgtg     60

gactgaaagg agactttgtt tatcaattag tatactccca aaaaactgat gacaccaatg    120

atgcaaatag gctgggaata gtctgtctaa tagtttgagt gaatcatgtc atgaaggcgg    180

gaaacgacaa tctgatcatg agcggagaat taagggagtc acgttatgac cccgccgat    240

gacgcgggac aagccgtttt acgtttggaa ctgacagaac cgcaacgttg aaggagccac    300

tcagcaa                                                              307
```

```
<210> SEQ ID NO 98
<211> LENGTH: 311
<212> TYPE: DNA
<213> ORGANISM: Artificial
<220> FEATURE:
<223> OTHER INFORMATION: synthetic

<400> SEQUENCE: 98

tacgtatacc tgctgcagca gcatctgcgt aagcacagcc tagatatatg cttctgtgtg     60

gactgaaagg agactttgtt tatcaattag tatactccca aaaaactgat gacaccaatg    120

atgcaaatag gctgggaata gtctgtctaa tagtttgagt gaatcatgtc aaaactgaag    180

gcgggaaacg acaatctgat catgagcgga gaattaaggg agtcacgtta tgaccccccgc    240

cgatgacgcg ggacaagccg ttttacgttt ggaactgaca gaaccgcaac gttgaaggag    300

ccactcagca a                                                         311
```

```
<210> SEQ ID NO 99
<211> LENGTH: 312
<212> TYPE: DNA
<213> ORGANISM: Artificial
<220> FEATURE:
<223> OTHER INFORMATION: synthetic

<400> SEQUENCE: 99

tacgtatacc tgctgcagca gcatctgcgt aagcacagcc tagatatatg cttctgtgtg     60

gactgaaagg agactttgtt tatcaattag tatactccca aaaaactgat gacaccaatg    120

atgcaaatag gctgggaata gtctgtctaa tagtttgagt gaatcatgtc ataaactgaa    180

ggcgggaaac gacaatctga tcatgagcgg agaattaagg gagtcacgtt atgacccccg    240

ccgatgacgc gggacaagcc gttttacgtt tggaactgac agaaccgcaa cgttgaagga    300

gccactcagc aa                                                        312
```

```
<210> SEQ ID NO 100
<211> LENGTH: 313
<212> TYPE: DNA
<213> ORGANISM: Artificial
<220> FEATURE:
<223> OTHER INFORMATION: synthetic

<400> SEQUENCE: 100

tacgtatacc tgctgcagca gcatctgcgt aagcacagcc tagatatatg cttctgtgtg     60

gactgaaagg agactttgtt tatcaattag tatactccca aaaaactgat gacaccaatg    120

atgcaaatag gctgggaata gtctgtctaa tagtttgagt gaatcatgtc agaaaactga    180

aggcgggaaa cgacaatctg atcatgagcg gagaattaag ggagtcacgt tatgaccccc    240

gccgatgacg cgggacaagc cgttttacgt ttggaactga cagaaccgca acgttgaagg    300

agccactcag caa                                                       313
```

<210> SEQ ID NO 101
<211> LENGTH: 314
<212> TYPE: DNA
<213> ORGANISM: Artificial
<220> FEATURE:
<223> OTHER INFORMATION: synthetic

<400> SEQUENCE: 101
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc atttaaactg 180
aaggcgggaa acgacaatct gatcatgagc ggagaattaa gggagtcacg ttatgacccc 240
cgccgatgac gcgggacaag ccgttttacg tttggaactg acagaaccgc aacgttgaag 300
gagccactca gcaa 314

<210> SEQ ID NO 102
<211> LENGTH: 309
<212> TYPE: DNA
<213> ORGANISM: Artificial
<220> FEATURE:
<223> OTHER INFORMATION: synthetic

<400> SEQUENCE: 102
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc acctgaaggc 180
gggaaacgac aatctgatca tgagcggaga attaagggag tcacgttatg acccccgccg 240
atgacgcggg acaagccgtt ttacgtttgg aactgacaga accgcaacgt tgaaggagcc 300
actcagcaa 309

<210> SEQ ID NO 103
<211> LENGTH: 311
<212> TYPE: DNA
<213> ORGANISM: Artificial
<220> FEATURE:
<223> OTHER INFORMATION: synthetic

<400> SEQUENCE: 103
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc acaactgaag 180
gcgggaaacg acaatctgat catgagcgga gaattaaggg agtcacgtta tgacccccgc 240
cgatgacgcg ggacaagccg ttttacgttt ggaactgaca gaaccgcaac gttgaaggag 300
ccactcagca a 311

<210> SEQ ID NO 104
<211> LENGTH: 312
<212> TYPE: DNA
<213> ORGANISM: Artificial
<220> FEATURE:
<223> OTHER INFORMATION: synthetic

<400> SEQUENCE: 104
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc acaaactgaa 180
ggcgggaaac gacaatctga tcatgagcgg agaattaagg gagtcacgtt atgaccccccg 240 ccgatgacgc gggacaagcc gttttacgtt tggaactgac agaaccgcaa cgttgaagga 300
gccactcagc aa 312

<210> SEQ ID NO 105
<211> LENGTH: 313
<212> TYPE: DNA
<213> ORGANISM: Artificial
<220> FEATURE:
<223> OTHER INFORMATION: synthetic

<400> SEQUENCE: 105
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc actaaactga 180
aggcgggaaa cgacaatctg atcatgagcg gagaattaag ggagtcacgt tatgaccccc 240
gccgatgacg cgggacaagc cgttttacgt ttggaactga cagaaccgca acgttgaagg 300
agccactcag caa 313

<210> SEQ ID NO 106
<211> LENGTH: 314
<212> TYPE: DNA
<213> ORGANISM: Artificial
<220> FEATURE:
<223> OTHER INFORMATION: synthetic

<400> SEQUENCE: 106
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc acttaaactg 180
aaggcgggaa acgacaatct gatcatgagc ggagaattaa gggagtcacg ttatgacccc 240
cgccgatgac gcgggacaag ccgttttacg tttggaactg acagaaccgc aacgttgaag 300
gagccactca gcaa 314

<210> SEQ ID NO 107
<211> LENGTH: 315
<212> TYPE: DNA
<213> ORGANISM: Artificial
<220> FEATURE:
<223> OTHER INFORMATION: synthetic

<400> SEQUENCE: 107
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc actttaaact 180
gaaggcggga aacgacaatc tgatcatgag cggagaatta agggagtcac gttatgaccc 240
ccgccgatga cgcgggacaa gccgttttac gtttggaact gacagaaccg caacgttgaa 300
ggagccactc agcaa 315

<210> SEQ ID NO 108
<211> LENGTH: 315
<212> TYPE: DNA
<213> ORGANISM: Artificial
<220> FEATURE:
<223> OTHER INFORMATION: synthetic

<400> SEQUENCE: 108
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc actataaact 180
gaaggcggga aacgacaatc tgatcatgag cggagaatta agggagtcac gttatgaccc 240
ccgccgatga cgcgggacaa gccgttttac gtttggaact gacagaaccg caacgttgaa 300
ggagccactc agcaa 315

<210> SEQ ID NO 109
<211> LENGTH: 318
<212> TYPE: DNA
<213> ORGANISM: Artificial
<220> FEATURE:
<223> OTHER INFORMATION: synthetic

<400> SEQUENCE: 109
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc actagtttaa 180
actgaaggcg ggaaacgaca atctgatcat gagcggagaa ttaagggagt cacgttatga 240
cccccgccga tgacgcggga caagccgttt tacgtttgga actgacagaa ccgcaacgtt 300
gaaggagcca ctcagcaa 318

<210> SEQ ID NO 110
<211> LENGTH: 312
<212> TYPE: DNA
<213> ORGANISM: Artificial
<220> FEATURE:
<223> OTHER INFORMATION: synthetic

<400> SEQUENCE: 110
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc actaactgaa 180
ggcgggaaac gacaatctga tcatgagcgg agaattaagg gagtcacgtt atgacccccg 240
ccgatgacgc gggacaagcc gttttacgtt tggaactgac agaaccgcaa cgttgaagga 300
gccactcagc aa 312

<210> SEQ ID NO 111
<211> LENGTH: 316
<212> TYPE: DNA
<213> ORGANISM: Artificial
<220> FEATURE:
<223> OTHER INFORMATION: synthetic

<400> SEQUENCE: 111
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc actatcaaac 180
tgaaggcggg aaacgacaat ctgatcatga gcggagaatt aagggagtca cgttatgacc 240
cccgccgatg acgcgggaca agccgtttta cgtttggaac tgacagaacc gcaacgttga 300
aggagccact cagcaa 316

<210> SEQ ID NO 112
<211> LENGTH: 317
<212> TYPE: DNA
<213> ORGANISM: Artificial
<220> FEATURE:
<223> OTHER INFORMATION: synthetic

<400> SEQUENCE: 112
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc actgattaaa 180
ctgaaggcgg gaaacgacaa tctgatcatg agcggagaat taagggagtc acgttatgac 240
ccccgccgat gacgcgggac aagccgtttt acgtttggaa ctgacagaac cgcaacgttg 300
aaggagccac tcagcaa 317

<210> SEQ ID NO 113
<211> LENGTH: 262
<212> TYPE: DNA
<213> ORGANISM: Artificial
<220> FEATURE:
<223> OTHER INFORMATION: synthetic

<400> SEQUENCE: 113
tacgtatacc tgctgcagca gcatctgcgt aagcacagcc tagatatatg cttctgtgtg 60
gactgaaagg agactttgtt tatcaattag tatactccca aaaaactgat gacacaaatg 120
atgcacatag ggcgggaatc gtctgtctga tcccgcgcgg agaatgaagg gagtcacgtt 180
atgacccccg ccgatgacgc gggacaagcc gttttacgtt tggaactgac agaaccgcaa 240
cgttgaagga gccactcagc aa 262

<210> SEQ ID NO 114
<211> LENGTH: 288
<212> TYPE: DNA
<213> ORGANISM: Artificial
<220> FEATURE:
<223> OTHER INFORMATION: synthetic

<400> SEQUENCE: 114
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa actgaaggcg ggaaacgaca atctgatcat 180
gagcggagaa ttaagggagt cacgttatga cccccgccga tgacgcggga caagccgttt 240
tacgtttgga actgacagaa ccgcaacgtt gaaggagcca ctcagcaa 288

<210> SEQ ID NO 115
<211> LENGTH: 296
<212> TYPE: DNA
<213> ORGANISM: Artificial
<220> FEATURE:
<223> OTHER INFORMATION: synthetic

<400> SEQUENCE: 115
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctggctga tagtttgagc tgaaggcggg aatcgacact 180
cttatcctga gcggagaatt aagggagtca cgttatgacc cccgccgatg acgcgggaca 240
agccgtttta cgtttggaac tgacagaacc gcaacgttga aggagccact cagcaa 296

<210> SEQ ID NO 116
<211> LENGTH: 262
<212> TYPE: DNA
<213> ORGANISM: Artificial
<220> FEATURE:
<223> OTHER INFORMATION: synthetic

<400> SEQUENCE: 116
tacgtatacc tgctgcagca gcatctgcgt aagcacagcc tagatatatg cttctgtgtg 60
gactgaaagg agactttgtt tatcaattag tatactccca aaaaactgat gacaccaagg 120
atgcaaatag gccgggaatc gtcagtctga tcgtttgagt ggaattaagg gagtcacgtt 180
atgacccccg ccgatgacgc gggacaagcc gttttacgtt tggaactgac agaaccgcaa 240
cgttgaagga gccactcagc aa 262

<210> SEQ ID NO 117
<211> LENGTH: 296
<212> TYPE: DNA
<213> ORGANISM: Artificial
<220> FEATURE:
<223> OTHER INFORMATION: synthetic

<400> SEQUENCE: 117
tacgtatacc tgctgcagca gcatctgcgt aagcacagcc tagatatatg cttctgtgtg 60
gactgaaagg agacttggtt tatcaattag tatactccca aaaaactgat gacaccaatg 120
atgcaattag gctgggaatc gtgtgtctga taggttgagt ggaaggcgcg aaacgacaat 180
ctgatcatga gcggagaaat aagggagtca cgttatgacc cccgccgatg actcgggaca 240
agccgtttta cgtttggaac tgacagaacc gcaacgttga aggagccact cagcaa 296

<210> SEQ ID NO 118
<211> LENGTH: 301
<212> TYPE: DNA
<213> ORGANISM: Artificial
<220> FEATURE:
<223> OTHER INFORMATION: synthetic

<400> SEQUENCE: 118
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaaactgaag gcgggaaacg 180
acaatctgat catgagcgga gaattaaggg agtcacgtta tgacccccgc cgatgacgcg 240
ggacaagccg ttttacgttt ggaactgaca gaaccgcaac gttgaaggag ccactcagca 300
a 301

<210> SEQ ID NO 119
<211> LENGTH: 303
<212> TYPE: DNA
<213> ORGANISM: Artificial
<220> FEATURE:
<223> OTHER INFORMATION: synthetic

<400> SEQUENCE: 119
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gttaaactga aggcgggaaa 180
cgacaatctg atcatgagcg gagaattaag ggagtcacgt tatgaccccc gccgatgacg 240
cgggacaagc cgttttacgt ttggaactga cagaaccgca acgttgaagg agccactcag 300
caa 303

<210> SEQ ID NO 120
<211> LENGTH: 296
<212> TYPE: DNA
<213> ORGANISM: Artificial
<220> FEATURE:
<223> OTHER INFORMATION: synthetic

<400> SEQUENCE: 120
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaaaggcggg aaacgacaat 180
ctgatcatga gcggagaatt aagggagtca cgttatgacc cccgccgatg acgcgggaca 240
agccgtttta cgtttggaac tgacagaacc gcaacgttga aggagccact cagcaa 296

<210> SEQ ID NO 121
<211> LENGTH: 303
<212> TYPE: DNA
<213> ORGANISM: Artificial
<220> FEATURE:
<223> OTHER INFORMATION: synthetic

<400> SEQUENCE: 121
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gataaactga aggcgggaaa 180
cgacaatctg atcatgagcg gagaattaag ggagtcacgt tatgaccccc gccgatgacg 240
cgggacaagc cgttttacgt ttggaactga cagaaccgca acgttgaagg agccactcag 300
caa 303

<210> SEQ ID NO 122
<211> LENGTH: 304
<212> TYPE: DNA
<213> ORGANISM: Artificial
<220> FEATURE:
<223> OTHER INFORMATION: synthetic

<400> SEQUENCE: 122
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaataaactg aaggcgggaa 180
acgacaatct gatcatgagc ggagaattaa gggagtcacg ttatgacccc cgccgatgac 240
gcgggacaag ccgttttacg tttggaactg acagaaccgc aacgttgaag gagccactca 300
gcaa 304

<210> SEQ ID NO 123
<211> LENGTH: 300

<212> TYPE: DNA
<213> ORGANISM: Artificial
<220> FEATURE:
<223> OTHER INFORMATION: synthetic

<400> SEQUENCE: 123
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaattgaagg cgggaaacga 180
caatctgatc atgagcggag aattaaggga gtcacgttat gaccccgcc gatgacgcgg 240 gacaagccgt tttacgtttg gaactgacag aaccgcaacg ttgaaggagc cactcagcaa 300

<210> SEQ ID NO 124
<211> LENGTH: 315
<212> TYPE: DNA
<213> ORGANISM: Artificial
<220> FEATURE:
<223> OTHER INFORMATION: synthetic

<400> SEQUENCE: 124
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgat agtttaaact 180
gaaggcggga aacgacaatc tgatcatgag cggagaatta agggagtcac gttatgaccc 240
ccgccgatga cgcgggacaa gccgttttac gtttggaact gacagaaccg caacgttgaa 300
ggagccactc agcaa 315

<210> SEQ ID NO 125
<211> LENGTH: 311
<212> TYPE: DNA
<213> ORGANISM: Artificial
<220> FEATURE:
<223> OTHER INFORMATION: synthetic

<400> SEQUENCE: 125
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtt taaactgaag 180
gcgggaaacg acaatctgat catgagcgga gaattaaggg agtcacgtta tgaccccgc 240 cgatgacgcg ggacaagccg ttttacgttt ggaactgaca gaaccgcaac gttgaaggag 300
ccactcagca a 311

<210> SEQ ID NO 126
<211> LENGTH: 309
<212> TYPE: DNA
<213> ORGANISM: Artificial
<220> FEATURE:
<223> OTHER INFORMATION: synthetic

<400> SEQUENCE: 126
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgta aactgaaggc 180
gggaaacgac aatctgatca tgagcggaga attaagggag tcacgttatg acccccgccg 240
atgacgcggg acaagccgtt ttacgtttgg aactgacaga accgcaacgt tgaaggagcc 300
actcagcaa 309

<210> SEQ ID NO 127
<211> LENGTH: 310
<212> TYPE: DNA
<213> ORGANISM: Artificial
<220> FEATURE:
<223> OTHER INFORMATION: synthetic

<400> SEQUENCE: 127
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtt aaactgaagg 180
cgggaaacga caatctgatc atgagcggag aattaaggga gtcacgttat gacccccgcc 240
gatgacgcgg gacaagccgt tttacgtttg gaactgacag aaccgcaacg ttgaaggagc 300
cactcagcaa 310

<210> SEQ ID NO 128
<211> LENGTH: 306
<212> TYPE: DNA
<213> ORGANISM: Artificial
<220> FEATURE:
<223> OTHER INFORMATION: synthetic

<400> SEQUENCE: 128
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc tgaaggcggg 180
aaacgacaat ctgatcatga gcggagaatt aagggagtca cgttatgacc cccgccgatg 240
acgcgggaca agccgtttta cgtttggaac tgacagaacc gcaacgttga aggagccact 300
cagcaa 306

<210> SEQ ID NO 129
<211> LENGTH: 312
<212> TYPE: DNA
<213> ORGANISM: Artificial
<220> FEATURE:
<223> OTHER INFORMATION: synthetic

<400> SEQUENCE: 129
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtt ttaaactgaa 180
ggcgggaaac gacaatctga tcatgagcgg agaattaagg gagtcacgtt atgacccccg 240
ccgatgacgc gggacaagcc gttttacgtt tggaactgac agaaccgcaa cgttgaagga 300
gccactcagc aa 312

<210> SEQ ID NO 130
<211> LENGTH: 259
<212> TYPE: DNA
<213> ORGANISM: Artificial
<220> FEATURE:
<223> OTHER INFORMATION: synthetic

<400> SEQUENCE: 130

```
tacgtatacc tgctgcagca gcatctgcgt aagcacagcc tagatatatg cttctgtgtg     60

gactgaaagg agactttgtt tatcaattag tatactccca aaaaactgat gacaccaatg    120

atgcaaatag gctgggaata gtctgtctaa tagtttgagt gaatcatgtc tcacgttatg    180

acccccgccg atgacgcggg acaagccgtt ttacgtttgg aactgacaga accgcaacgt    240

tgaaggagcc actcagcaa                                                 259
```

<210> SEQ ID NO 131
<211> LENGTH: 302
<212> TYPE: DNA
<213> ORGANISM: Artificial
<220> FEATURE:
<223> OTHER INFORMATION: synthetic

<400> SEQUENCE: 131

```
tacgtatacc tgctgcagca gcatctgcgt aagcacagcc tagatatatg cttctgtgtg     60

gactgaaagg agactttgtt tatcaattag tatactccca aaaaactgat gacaccaatg    120

atgcaaatag gctgggaata gtctgtctaa tagtttgagt gaatcatgtc ggcgggaaac    180

gacaatctga tcatgagcgg agaattaagg gagtcacgtt atgacccccg ccgatgacgc    240

gggacaagcc gttttacgtt tggaactgac agaaccgcaa cgttgaagga gccactcagc    300

aa                                                                   302
```

<210> SEQ ID NO 132
<211> LENGTH: 303
<212> TYPE: DNA
<213> ORGANISM: Artificial
<220> FEATURE:
<223> OTHER INFORMATION: synthetic

<400> SEQUENCE: 132

```
tacgtatacc tgctgcagca gcatctgcgt aagcacagcc tagatatatg cttctgtgtg     60

gactgaaagg agactttgtt tatcaattag tatactccca aaaaactgat gacaccaatg    120

atgcaaatag gctgggaata gtctgtctaa tagtttgagt gaatcatgtc aggcgggaaa    180

cgacaatctg atcatgagcg gagaattaag ggagtcacgt tatgaccccc gccgatgacg    240

cgggacaagc cgttttacgt ttggaactga cagaaccgca acgttgaagg agccactcag    300

caa                                                                  303
```

<210> SEQ ID NO 133
<211> LENGTH: 308
<212> TYPE: DNA
<213> ORGANISM: Artificial
<220> FEATURE:
<223> OTHER INFORMATION: synthetic

<400> SEQUENCE: 133

```
tacgtatacc tgctgcagca gcatctgcgt aagcacagcc tagatatatg cttctgtgtg     60

gactgaaagg agactttgtt tatcaattag tatactccca aaaaactgat gacaccaatg    120

atgcaaatag gctgggaata gtctgtctaa tagtttgagt gaatcatgtc actgaaggcg    180

ggaaacgaca atctgatcat gagcggagaa ttaagggagt cacgttatga cccccgccga    240

tgacgcggga caagccgttt tacgtttgga actgacagaa ccgcaacgtt gaaggagcca    300

ctcagcaa                                                             308
```

<210> SEQ ID NO 134

<211> LENGTH: 309
<212> TYPE: DNA
<213> ORGANISM: Artificial
<220> FEATURE:
<223> OTHER INFORMATION: synthetic

<400> SEQUENCE: 134
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc aactgaaggc 180
gggaaacgac aatctgatca tgagcggaga attaagggag tcacgttatg acccccgccg 240
atgacgcggg acaagccgtt ttacgtttgg aactgacaga accgcaacgt tgaaggagcc 300
actcagcaa 309

<210> SEQ ID NO 135
<211> LENGTH: 310
<212> TYPE: DNA
<213> ORGANISM: Artificial
<220> FEATURE:
<223> OTHER INFORMATION: synthetic

<400> SEQUENCE: 135
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc aaactgaagg 180
cgggaaacga caatctgatc atgagcggag aattaaggga gtcacgttat gacccccgcc 240
gatgacgcgg gacaagccgt tttacgtttg gaactgacag aaccgcaacg ttgaaggagc 300
cactcagcaa 310

<210> SEQ ID NO 136
<211> LENGTH: 311
<212> TYPE: DNA
<213> ORGANISM: Artificial
<220> FEATURE:
<223> OTHER INFORMATION: synthetic

<400> SEQUENCE: 136
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc taaactgaag 180
gcgggaaacg acaatctgat catgagcgga gaattaaggg agtcacgtta tgacccccgc 240
cgatgacgcg ggacaagccg ttttacgttt ggaactgaca gaaccgcaac gttgaaggag 300
ccactcagca a 311

<210> SEQ ID NO 137
<211> LENGTH: 312
<212> TYPE: DNA
<213> ORGANISM: Artificial
<220> FEATURE:
<223> OTHER INFORMATION: synthetic

<400> SEQUENCE: 137
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc ttaaactgaa 180
ggcgggaaac gacaatctga tcatgagcgg agaattaagg gagtcacgtt atgacccccg 240
ccgatgacgc gggacaagcc gttttacgtt tggaactgac agaaccgcaa cgttgaagga 300
gccactcagc aa 312

<210> SEQ ID NO 138
<211> LENGTH: 315
<212> TYPE: DNA
<213> ORGANISM: Artificial
<220> FEATURE:
<223> OTHER INFORMATION: synthetic

<400> SEQUENCE: 138
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc agtttaaact 180
gaaggcggga aacgacaatc tgatcatgag cggagaatta agggagtcac gttatgaccc 240
ccgccgatga cgcgggacaa gccgttttac gtttggaact gacagaaccg caacgttgaa 300
ggagccactc agcaa 315

<210> SEQ ID NO 139
<211> LENGTH: 259
<212> TYPE: DNA
<213> ORGANISM: Artificial
<220> FEATURE:
<223> OTHER INFORMATION: synthetic

<400> SEQUENCE: 139
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc acacgttatg 180
acccccgccg atgacgcggg acaagccgtt ttacgtttgg aactgacaga accgcaacgt 240
tgaaggagcc actcagcaa 259

<210> SEQ ID NO 140
<211> LENGTH: 305
<212> TYPE: DNA
<213> ORGANISM: Artificial
<220> FEATURE:
<223> OTHER INFORMATION: synthetic

<400> SEQUENCE: 140
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc aaaggcggga 180
aacgacaatc tgatcatgag cggagaatta agggagtcac gttatgaccc ccgccgatga 240
cgcgggacaa gccgttttac gtttggaact gacagaaccg caacgttgaa ggagccactc 300
agcaa 305

<210> SEQ ID NO 141
<211> LENGTH: 311
<212> TYPE: DNA
<213> ORGANISM: Artificial
<220> FEATURE:
<223> OTHER INFORMATION: synthetic

<400> SEQUENCE: 141
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc aaaactgaag 180
gcgggaaacg acaatctgat catgagcgga gaattaaggg agtcacgtta tgacccccgc 240
cgatgacgcg ggacaagccg ttttacgttt ggaactgaca gaaccgcaac gttgaaggag 300
ccactcagca a 311

<210> SEQ ID NO 142
<211> LENGTH: 311
<212> TYPE: DNA
<213> ORGANISM: Artificial
<220> FEATURE:
<223> OTHER INFORMATION: synthetic

<400> SEQUENCE: 142
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc aaaactgaag 180
gcgggaaacg acaatctgat catgagcgga gaattaaggg agtcacgtta tgacccccgc 240
cgatgacgcg ggacaagccg ttttacgttt ggaactgaca gaaccgcaac gttgaaggag 300
ccactcagca a 311

<210> SEQ ID NO 143
<211> LENGTH: 312
<212> TYPE: DNA
<213> ORGANISM: Artificial
<220> FEATURE:
<223> OTHER INFORMATION: synthetic

<400> SEQUENCE: 143
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc ataaactgaa 180
ggcgggaaac gacaatctga tcatgagcgg agaattaagg gagtcacgtt atgacccccg 240
ccgatgacgc gggacaagcc gttttacgtt tggaactgac agaaccgcaa cgttgaagga 300
gccactcagc aa 312

<210> SEQ ID NO 144
<211> LENGTH: 313
<212> TYPE: DNA
<213> ORGANISM: Artificial
<220> FEATURE:
<223> OTHER INFORMATION: synthetic

<400> SEQUENCE: 144
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc attaaactga 180
aggcgggaaa cgacaatctg atcatgagcg gagaattaag ggagtcacgt tatgaccccc 240
gccgatgacg cgggacaagc cgttttacgt ttggaactga cagaaccgca acgttgaagg 300
agccactcag caa 313

<210> SEQ ID NO 145
<211> LENGTH: 306
<212> TYPE: DNA
<213> ORGANISM: Artificial
<220> FEATURE:
<223> OTHER INFORMATION: synthetic

<400> SEQUENCE: 145
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc acaaggcggg 180
aaacgacaat ctgatcatga gcggagaatt aagggagtca cgttatgacc cccgccgatg 240
acgcgggaca agccgtttta cgtttggaac tgacagaacc gcaacgttga aggagccact 300
cagcaa 306

<210> SEQ ID NO 146
<211> LENGTH: 307
<212> TYPE: DNA
<213> ORGANISM: Artificial
<220> FEATURE:
<223> OTHER INFORMATION: synthetic

<400> SEQUENCE: 146
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc acgaaggcgg 180
gaaacgacaa tctgatcatg agcggagaat taagggagtc acgttatgac ccccgccgat 240
gacgcgggac aagccgtttt acgtttggaa ctgacagaac cgcaacgttg aaggagccac 300
tcagcaa 307

<210> SEQ ID NO 147
<211> LENGTH: 309
<212> TYPE: DNA
<213> ORGANISM: Artificial
<220> FEATURE:
<223> OTHER INFORMATION: synthetic

<400> SEQUENCE: 147
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc acctgaaggc 180
gggaaacgac aatctgatca tgagcggaga attaagggag tcacgttatg acccccgccg 240
atgacgcggg acaagccgtt ttacgtttgg aactgacaga accgcaacgt tgaaggagcc 300
actcagcaa 309

<210> SEQ ID NO 148
<211> LENGTH: 310
<212> TYPE: DNA
<213> ORGANISM: Artificial
<220> FEATURE:
<223> OTHER INFORMATION: synthetic

<400> SEQUENCE: 148
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc acactgaagg 180
cgggaaacga caatctgatc atgagcggag aattaaggga gtcacgttat gaccccccgcc 240 gatgacgcgg gacaagccgt tttacgtttg gaactgacag aaccgcaacg ttgaaggagc 300
cactcagcaa 310

<210> SEQ ID NO 149
<211> LENGTH: 311
<212> TYPE: DNA
<213> ORGANISM: Artificial
<220> FEATURE:
<223> OTHER INFORMATION: synthetic

<400> SEQUENCE: 149
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc acaactgaag 180
gcgggaaacg acaatctgat catgagcgga gaattaaggg agtcacgtta tgacccccgc 240
cgatgacgcg ggacaagccg ttttacgttt ggaactgaca gaaccgcaac gttgaaggag 300
ccactcagca a 311

<210> SEQ ID NO 150
<211> LENGTH: 312
<212> TYPE: DNA
<213> ORGANISM: Artificial
<220> FEATURE:
<223> OTHER INFORMATION: synthetic

<400> SEQUENCE: 150
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc acaaactgaa 180
ggcgggaaac gacaatctga tcatgagcgg agaattaagg gagtcacgtt atgacccccg 240
ccgatgacgc gggacaagcc gttttacgtt tggaactgac agaaccgcaa cgttgaagga 300
gccactcagc aa 312

<210> SEQ ID NO 151
<211> LENGTH: 313
<212> TYPE: DNA
<213> ORGANISM: Artificial
<220> FEATURE:
<223> OTHER INFORMATION: synthetic

<400> SEQUENCE: 151
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc actaaactga 180
aggcgggaaa cgacaatctg atcatgagcg gagaattaag ggagtcacgt tatgaccccc 240
gccgatgacg cgggacaagc cgttttacgt ttggaactga cagaaccgca acgttgaagg 300
agccactcag caa 313

<210> SEQ ID NO 152
<211> LENGTH: 314

<212> TYPE: DNA
<213> ORGANISM: Artificial
<220> FEATURE:
<223> OTHER INFORMATION: synthetic

<400> SEQUENCE: 152
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc acttaaactg 180
aaggcgggaa acgacaatct gatcatgagc ggagaattaa gggagtcacg ttatgacccc 240
cgccgatgac gcgggacaag ccgttttacg tttggaactg acagaaccgc aacgttgaag 300
gagccactca gcaa 314

<210> SEQ ID NO 153
<211> LENGTH: 315
<212> TYPE: DNA
<213> ORGANISM: Artificial
<220> FEATURE:
<223> OTHER INFORMATION: synthetic

<400> SEQUENCE: 153
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc actttaaact 180
gaaggcggga aacgacaatc tgatcatgag cggagaatta agggagtcac gttatgaccc 240
ccgccgatga cgcgggacaa gccgttttac gtttggaact gacagaaccg caacgttgaa 300
ggagccactc agcaa 315

<210> SEQ ID NO 154
<211> LENGTH: 318
<212> TYPE: DNA
<213> ORGANISM: Artificial
<220> FEATURE:
<223> OTHER INFORMATION: synthetic

<400> SEQUENCE: 154
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc actagtttaa 180
actgaaggcg ggaaacgaca atctgatcat gagcggagaa ttaagggagt cacgttatga 240
cccccgccga tgacgcggga caagccgttt tacgtttgga actgacagaa ccgcaacgtt 300
gaaggagcca ctcagcaa 318

<210> SEQ ID NO 155
<211> LENGTH: 305
<212> TYPE: DNA
<213> ORGANISM: Artificial
<220> FEATURE:
<223> OTHER INFORMATION: synthetic

<400> SEQUENCE: 155
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc actggcggga 180
aacgacaatc tgatcatgag cggagaatta agggagtcac gttatgaccc ccgccgatga 240
cgcgggacaa gccgttttac gtttggaact gacagaaccg caacgttgaa ggagccactc 300
agcaa 305

<210> SEQ ID NO 156
<211> LENGTH: 309
<212> TYPE: DNA
<213> ORGANISM: Artificial
<220> FEATURE:
<223> OTHER INFORMATION: synthetic

<400> SEQUENCE: 156
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc acttgaaggc 180
gggaaacgac aatctgatca tgagcggaga attaagggag tcacgttatg acccccgccg 240
atgacgcggg acaagccgtt ttacgtttgg aactgacaga accgcaacgt tgaaggagcc 300
actcagcaa 309

<210> SEQ ID NO 157
<211> LENGTH: 311
<212> TYPE: DNA
<213> ORGANISM: Artificial
<220> FEATURE:
<223> OTHER INFORMATION: synthetic

<400> SEQUENCE: 157
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc actactgaag 180
gcgggaaacg acaatctgat catgagcgga gaattaaggg agtcacgtta tgacccccgc 240
cgatgacgcg ggacaagccg ttttacgttt ggaactgaca gaaccgcaac gttgaaggag 300
ccactcagca a 311

<210> SEQ ID NO 158
<211> LENGTH: 312
<212> TYPE: DNA
<213> ORGANISM: Artificial
<220> FEATURE:
<223> OTHER INFORMATION: synthetic

<400> SEQUENCE: 158
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc actaactgaa 180
ggcgggaaac gacaatctga tcatgagcgg agaattaagg gagtcacgtt atgacccccg 240
ccgatgacgc gggacaagcc gttttacgtt tggaactgac agaaccgcaa cgttgaagga 300
gccactcagc aa 312

<210> SEQ ID NO 159
<211> LENGTH: 316
<212> TYPE: DNA
<213> ORGANISM: Artificial
<220> FEATURE:
<223> OTHER INFORMATION: synthetic

<400> SEQUENCE: 159
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc acttttaaac 180
tgaaggcggg aaacgacaat ctgatcatga gcggagaatt aagggagtca cgttatgacc 240
cccgccgatg acgcgggaca agccgtttta cgtttggaac tgacagaacc gcaacgttga 300
aggagccact cagcaa 316

<210> SEQ ID NO 160
<211> LENGTH: 317
<212> TYPE: DNA
<213> ORGANISM: Artificial
<220> FEATURE:
<223> OTHER INFORMATION: synthetic

<400> SEQUENCE: 160
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc actgtttaaa 180
ctgaaggcgg gaaacgacaa tctgatcatg agcggagaat taagggagtc acgttatgac 240
ccccgccgat gacgcgggac aagccgtttt acgtttggaa ctgacagaac cgcaacgttg 300
aaggagccac tcagcaa 317

<210> SEQ ID NO 161
<211> LENGTH: 314
<212> TYPE: DNA
<213> ORGANISM: Artificial
<220> FEATURE:
<223> OTHER INFORMATION: synthetic

<400> SEQUENCE: 161
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc actgaaactg 180
aaggcgggaa acgacaatct gatcatgagc ggagaattaa gggagtcacg ttatgacccc 240
cgccgatgac gcgggacaag ccgttttacg tttggaactg acagaaccgc aacgttgaag 300
gagccactca gcaa 314

<210> SEQ ID NO 162
<211> LENGTH: 315
<212> TYPE: DNA
<213> ORGANISM: Artificial
<220> FEATURE:
<223> OTHER INFORMATION: synthetic

<400> SEQUENCE: 162
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc actgaaaact 180
gaaggcggga aacgacaatc tgatcatgag cggagaatta agggagtcac gttatgaccc 240
ccgccgatga cgcgggacaa gccgttttac gtttggaact gacagaaccg caacgttgaa 300
ggagccactc agcaa 315

<210> SEQ ID NO 163
<211> LENGTH: 317
<212> TYPE: DNA
<213> ORGANISM: Artificial
<220> FEATURE:
<223> OTHER INFORMATION: synthetic

<400> SEQUENCE: 163
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc actgattaaa 180
ctgaaggcgg gaaacgacaa tctgatcatg agcggagaat taagggagtc acgttatgac 240
ccccgccgat gacgcgggac aagccgtttt acgtttggaa ctgacagaac cgcaacgttg 300
aaggagccac tcagcaa 317

<210> SEQ ID NO 164
<211> LENGTH: 318
<212> TYPE: DNA
<213> ORGANISM: Artificial
<220> FEATURE:
<223> OTHER INFORMATION: synthetic

<400> SEQUENCE: 164
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc actgatttaa 180
actgaaggcg ggaaacgaca atctgatcat gagcggagaa ttaagggagt cacgttatga 240
cccccgccga tgacgcggga caagccgttt tacgtttgga actgacagaa ccgcaacgtt 300
gaaggagcca ctcagcaa 318

<210> SEQ ID NO 165
<211> LENGTH: 317
<212> TYPE: DNA
<213> ORGANISM: Artificial
<220> FEATURE:
<223> OTHER INFORMATION: synthetic

<400> SEQUENCE: 165
tacgtatacc tgctgcagca gcatctgcgt aagcacagcc tagatatatg cttctgtgtg 60
gactgaaagg agactttgtt tatcaattag tatactccca aaaaactgat gacaccaatg 120
atgcaaatag gctgggaata gtctgtctaa tagtttgagt gaatcatgtc actgataaaa 180
ctgaaggcgg gaaacgacaa tctgatcatg agcggagaat taagggagtc acgttatgac 240
ccccgccgat gacgcgggac aagccgtttt acgtttggaa ctgacagaac cgcaacgttg 300
aaggagccac tcagcaa 317

<210> SEQ ID NO 166
<211> LENGTH: 319
<212> TYPE: DNA
<213> ORGANISM: Artificial
<220> FEATURE:
<223> OTHER INFORMATION: synthetic

<400> SEQUENCE: 166
tacgtatacc tgctgcagca gcatctgcgt aagcacagcc tagatatatg cttctgtgtg 60

-continued

```
gactgaaagg agactttgtt tatcaattag tatactccca aaaaactgat gacaccaatg    120

atgcaaatag gctgggaata gtctgtctaa tagtttgagt gaatcatgtc actgatagta    180

aactgaaggc gggaaacgac aatctgatca tgagcggaga attaagggag tcacgttatg    240

acccccgccg atgacgcggg acaagccgtt ttacgtttgg aactgacaga accgcaacgt    300

tgaaggagcc actcagcaa                                                 319


<210> SEQ ID NO 167
<211> LENGTH: 320
<212> TYPE: DNA
<213> ORGANISM: Artificial
<220> FEATURE:
<223> OTHER INFORMATION: synthetic

<400> SEQUENCE: 167

tacgtatacc tgctgcagca gcatctgcgt aagcacagcc tagatatatg cttctgtgtg     60

gactgaaagg agactttgtt tatcaattag tatactccca aaaaactgat gacaccaatg    120

atgcaaatag gctgggaata gtctgtctaa tagtttgagt gaatcatgtc actgatagtt    180

aaactgaagg cgggaaacga caatctgatc atgagcggag aattaaggga gtcacgttat    240

gacccccgcc gatgacgcgg gacaagccgt tttacgtttg gaactgacag aaccgcaacg    300

ttgaaggagc cactcagcaa                                                320
```

INIR12 TRANSGENIC MAIZE

REFERENCE TO SEQUENCE LISTING SUBMITTED ELECTRONICALLY

The sequence listing contained in the file named "P13420US05_ST25", which is 236,668 bytes in size and which was created on Jun. 8, 2022 and electronically filed on Jun. 10, 2022, is incorporated herein by reference in its entirety.

BACKGROUND

Transgenes which are placed into different positions in the plant genome through non-site specific integration can exhibit different levels of expression (Weising et al., 1988, Ann. Rev. Genet. 22:421-477). Such transgene insertion sites can also contain various undesirable rearrangements of the foreign DNA elements that include deletions and/or duplications. Furthermore, many transgene insertion sites can also comprise selectable or scoreable marker genes which in some instances are no longer required once a transgenic plant event containing the linked transgenes which confer desirable traits are selected.

Commercial transgenic plants typically comprise one or more independent insertions of transgenes at specific locations in the host plant genome that have been selected for features that include expression of the transgene(s) of interest and the transgene-conferred trait(s), absence or minimization of rearrangements, and normal Mendelian transmission of the trait(s) to progeny. An example of a selected transgenic maize event which confers tolerance to certain lepidopteran insect pests is the MIR162 transgenic maize event disclosed in U.S. Pat. No. 8,455,720. MIR162 transgenic maize plants express a VIP3Aa20 protein which can confer resistance to fall armyworm (*Spodoptera frugiperda*), corn earworm (*Helicoverpa zea*), western bean cutworm (*Striacosta albicosta*), and black cutworm (*Agrotis ipsilon*) infestations. MIR162 transgenic maize plants also express a phosphomannose isomerase selectable marker protein.

Methods for removing selectable marker genes and/or duplicated transgenes in transgene insertion sites in plant genomes involving use of site-specific recombinase systems (e.g., cre-lox) as well as for insertion of new genes into transgene insertion sites have been disclosed (Srivastava and Ow; Methods Mol Biol, 2015, 1287:95-103; Dale and Ow, 1991, *Proc. Natl Acad. Sci. USA* 88, 10558-10562; Srivastava and Thomson, Plant Biotechnol J, 2016; 14(2):471-82). Such methods typically require incorporation of the recombination site sequences recognized by the recombinase at particular locations within the transgene.

SUMMARY

Transgenic maize plant cells comprising a first ZmUbiInt promoter, a vip3Aa19 or vip3Aa20 coding region which is operably linked to said promoter, a CaMV 35S terminator element which is operably linked to said vip3Aa19 or vip3Aa20 coding region, and a nopaline synthase terminator element, wherein said cell does not contain a second ZmUbiInt promoter and an operably linked phosphomannose isomerase coding region between said terminator elements are provided. Transgenic maize plant cell comprising a nucleotide sequence comprising a first ZmUbiInt promoter, a vip3Aa19 or vip3Aa20 coding region which is operably linked to said promoter, a CaMV 35S terminator element which is operably linked to said vip3Aa19 or vip3Aa20 coding region, and a nopaline synthase terminator element, wherein said nucleotide sequence does not contain a second ZmUbiInt promoter and an operably linked phosphomannose isomerase coding region between said terminator elements are provided. Transgenic maize plant cells comprising a nucleotide sequence comprising a ZmUbiInt promoter, a vip3Aa19 or vip3Aa20 coding region which is operably linked to said promoter, a CaMV 35S terminator element which is operably linked to said vip3Aa19 or vip3Aa20 coding region, and a nopaline synthase terminator element, wherein said nucleotide sequence does not contain a phosphomannose isomerase coding region between said terminator elements are provided. Transgenic maize plant cells comprising a nucleotide sequence comprising a first ZmUbiInt promoter, a vip3Aa19 or vip3Aa20 coding region which is operably linked to said promoter, a CaMV 35S terminator element which is operably linked to said vip3Aa19 or vip3Aa20 coding region, and a nopaline synthase terminator element, wherein said nucleotide sequence does not contain a second ZmUbiInt promoter and an operably linked phosphomannose isomerase coding region are provided. Transgenic maize plant cell comprising a nucleotide sequence comprising a ZmUbiInt promoter, a vip3Aa19 or vip3Aa20 coding region which is operably linked to said promoter, a CaMV 35S terminator element which is operably linked to said vip3Aa19 or vip3Aa20 coding region, and a nopaline synthase terminator element, wherein said nucleotide sequence does not contain a phosphomannose isomerase coding region are provided. In certain embodiments, aforementioned transgenic maize plant cells wherein: (i) the ZmUbiInt promoter, the vip3Aa19 or vip3Aa20 coding region which is operably linked to said promoter, the CaMV 35S terminator element which is operably linked to said vip3Aa19 or vip3Aa20 coding region are located in the maize plant cell genomic location of the MIR162 transgenic locus; (ii) wherein a selectable marker or scoreable is absent from said maize plant cell genomic location, and/or (iii) wherein the nopaline synthase terminator element is not separated from the CaMV 35S terminator element by DNA encoding a selectable marker protein, a scoreable marker protein, or a protein conferring a useful trait are provided. Transgenic maize plant cells comprising an INIR12 transgenic locus comprising the first ZmUbiInt promoter, the vip3Aa19 or vip3Aa20 coding region which is operably linked to said promoter, the CaMV 35S terminator element which is operably linked to said vip3Aa19 or vip3Aa20 coding region, and the nopaline synthase terminator element of an original MIR162 transgenic locus allelic variants thereof, or other variants thereof, wherein DNA of said original MIR162 transgenic locus, allelic variants thereof, or other variants thereof comprising a second ZmUbiInt promoter and an operably linked phosphomannose isomerase coding region is absent are provided. In certain embodiments, the original MIR162 transgenic locus is set forth in SEQ ID NO: 1, is present in seed deposited at the ATCC under accession No. PTA-8166 (SEQ ID NO: 46) or progeny thereof, is an allelic variant thereof, or is another variant thereof. In certain embodiments, an INIR12 transgenic locus comprises or further comprises an insertion and/or substitution of a DNA element comprising a cognate guide RNA recognition site (CgRRS) in a junction polynucleotide of said INIR12 transgenic locus, wherein the CgRRS optionally comprises SEQ ID NO: 37. In certain embodiments, transgenic maize plant cells comprising a INIR12 transgenic locus set forth in SEQ ID NO: 2, 3, 4, 5, 6, 29, 43, 44, 45, 47, 48, or 49 are provided. Also provided are transgenic maize plants and parts thereof including seeds which comprise the aforementioned transgenic maize plant cells. INIR12 transgenic maize plants provided herein can exhibit resistance to fall armyworm (*Spodoptera frugiperda*), corn earworm (*Helicoverpa zea*), western bean cutworm (*Striacosta albicosta*), and black cutworm (*Agrotis ipsilon*) infestations in comparison to control maize plants which lack the Vip3Aa protein.

Methods or obtaining a bulked population of inbred seed comprising selfing any of the aforementioned INIR12 transgenic maize plants and harvesting seed comprising the INIR12 transgenic locus from the selfed maize plant are provided.

Methods of obtaining hybrid maize seed comprising crossing any of the aforementioned INIR12 transgenic maize plant to a second maize plant which is genetically distinct from the first maize plant and harvesting seed comprising the INIR12 transgenic locus from the cross are provided.

DNA molecules comprising any one of SEQ ID NO: 7, 8, 9, 10, 11, 12, 13, 14, 15, 16, 17, 18, 19, 25, 37, 40, 41, 42, 43, 44, 45, 47, 48, 49, or 50-167 are provided. Processed transgenic maize plant products and biological samples comprising the aforementioned DNA molecules are also provided. Methods of detecting a maize plant cell comprising a INIR12 transgenic locus comprising the step of detecting a DNA molecule comprising SEQ ID NO: 7, 8, 9, 10, 11, 12, 13, 14, 15, 16, 17, 18, 19, 25, 37, 39, 40, 41, 42, 43, 44, 45, 47, 48, 49, or 50-167 are also provided.

Also provided are methods of excising a INIR12 transgenic locus comprising an CgRRS and an originator guide RNA recognition site (OgRRS) from the genome of a maize plant cell comprising the steps of: (a) contacting a transgenic plant genome of a maize plant cell comprising the INIR12 transgenic locus with: (i) an RNA dependent DNA endonuclease (RdDe); and (ii) a guide RNA (gRNA) capable of hybridizing to the guide RNA hybridization site of the OgRRS and the CgRRS; wherein the RdDe recognizes a OgRRS/gRNA and a CgRRS/gRNA hybridization complex; and, (b) selecting a transgenic plant cell, transgenic plant part, or transgenic plant wherein the INIR12 transgenic locus flanked by the OgRRS and the CgRRS has been excised. In certain embodiments of the methods, the INIR12 locus comprising the CgRRS comprises the DNSA sequence set forth in SEQ ID NO: 47 or SEQ ID NO; 48.

Also provided are methods of making transgenic maize plant cell comprising an INIR12 transgenic locus comprising: (a) contacting the transgenic plant genome of a maize MIR162 plant cell with: (i) a first set of gene editing molecules comprising a first site-specific nuclease which introduces a first double stranded DNA break in a 5' junction polynucleotide of an MIR162 transgenic locus; and (ii) a second set of gene editing molecules comprising a second site-specific nuclease which introduces a second double stranded DNA break between the CaMV35S terminator element and the ZmUbi promoter of said MIR162 transgenic locus which is operably linked to DNA encoding a phosphomannose isomerase (pmi) and a third site specific nuclease which introduces a third double stranded DNA break between the DNA encoding the pmi and DNA encoding the nopaline synthase (nos) terminator element of said MIR162 transgenic locus; and (b) selecting a transgenic maize plant cell, transgenic maize callus, and/or a transgenic maize plant comprising an INIR12 transgenic locus wherein one or more nucleotides of said 5' junction polynucleotide have been deleted and/or substituted, wherein the first ZmUbiInt promoter, the vip3Aa19 or vip3Aa20 coding region which is operably linked to the first ZmUbiInt promoter, the CaMV 35S terminator element which is operably linked to said vip3Aa19 or vip3Aa20 coding region, and the nos terminator element of said MIR162 transgenic locus are present, and wherein DNA of said MIR162 transgenic locus comprising a second ZmUbiInt promoter and an operably linked phosphomannose isomerase coding region is absent, thereby making a transgenic maize plant cell comprising an INIR12 transgenic locus. Transgenic maize plant cells, transgenic maize plant callus, transgenic maize plants, and transgenic maize plant seeds comprising an INIR12 transgenic locus made by the aforementioned methods are also provided. Also provided are methods of modifying a transgenic maize plant cell comprising: obtaining a MIR162 maize event plant cell, a representative sample of which was deposited at the ATCC under accession No. PTA-8166, comprising a nucleotide sequence comprising a first ZmUbiInt promoter, a vip3Aa19 or vip3Aa20 coding region which is operably linked to said promoter, a CaMV 35S terminator element which is operably linked to said vip3Aa19 or vip3Aa20 coding region, a second ZmUbiInt promoter and an operably linked phosphomannose isomerase coding region, and a nopaline synthase terminator element; and modifying said nucleotide sequence to eliminate functionality of said phosphomannose isomerase coding region and/or to substantially, essentially, or completely remove said phosphomannose isomerase coding region, and optionally to eliminate functionality of, or substantially, essentially, or completely remove, said second ZmUbiInt promoter. Also provided are methods of modifying a transgenic maize plant cell comprising: obtaining a MIR162 maize event plant cell, a representative sample of which was deposited at the ATCC under accession No. PTA-8166, comprising a nucleotide sequence comprising a first ZmUbiInt promoter, a vip3Aa19 or vip3Aa20 coding region which is operably linked to said promoter, a CaMV 35S terminator element which is operably linked to said vip3Aa19 or vip3Aa20 coding region, a second ZmUbiInt promoter and an operably linked phosphomannose isomerase coding region, and a nopaline synthase terminator element; and modifying said nucleotide sequence to substantially, essentially, or completely remove said phosphomannose isomerase coding region, and optionally substantially, essentially, or completely remove said second ZmUniInt promoter.

BRIEF DESCRIPTION OF THE DRAWINGS/FIGURES

FIG. 1 shows a diagram of transgene expression cassettes and selectable markers in the MIR162 transgenic locus in the deposited seed of ATCC accession No. PTA-8166.

Figure 2:
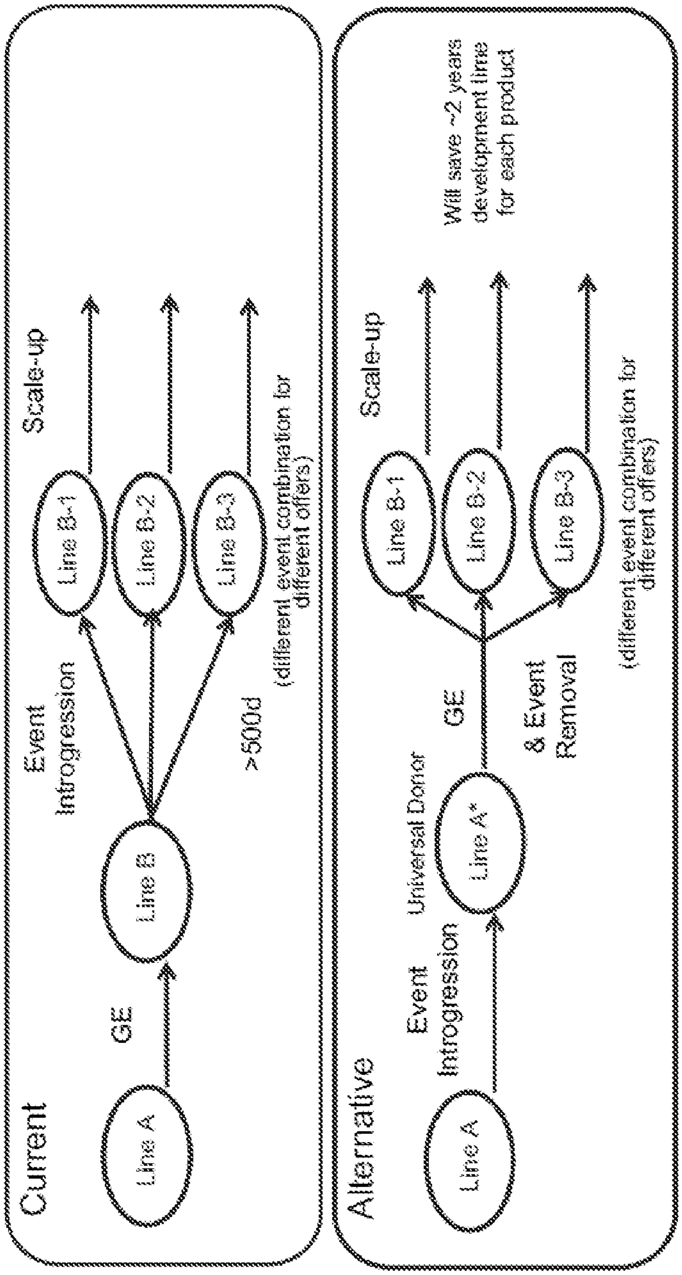

FIG. 2 shows a schematic diagram which compares current breeding strategies for introgression of transgenic events (i.e., transgenic loci) to alternative breeding strategies for introgression of transgenic events where the transgenic events (i.e., transgenic loci) can be removed following introgression to provide different combinations of transgenic traits. In FIG. 2, "GE" refers to genome editing (e.g., including introduction of targeted genetic changes with genome editing molecules and "Event Removal" refers to excision of a transgenic locus (i.e., an "Event") or portion thereof with genome editing molecules.

Figure 3A:
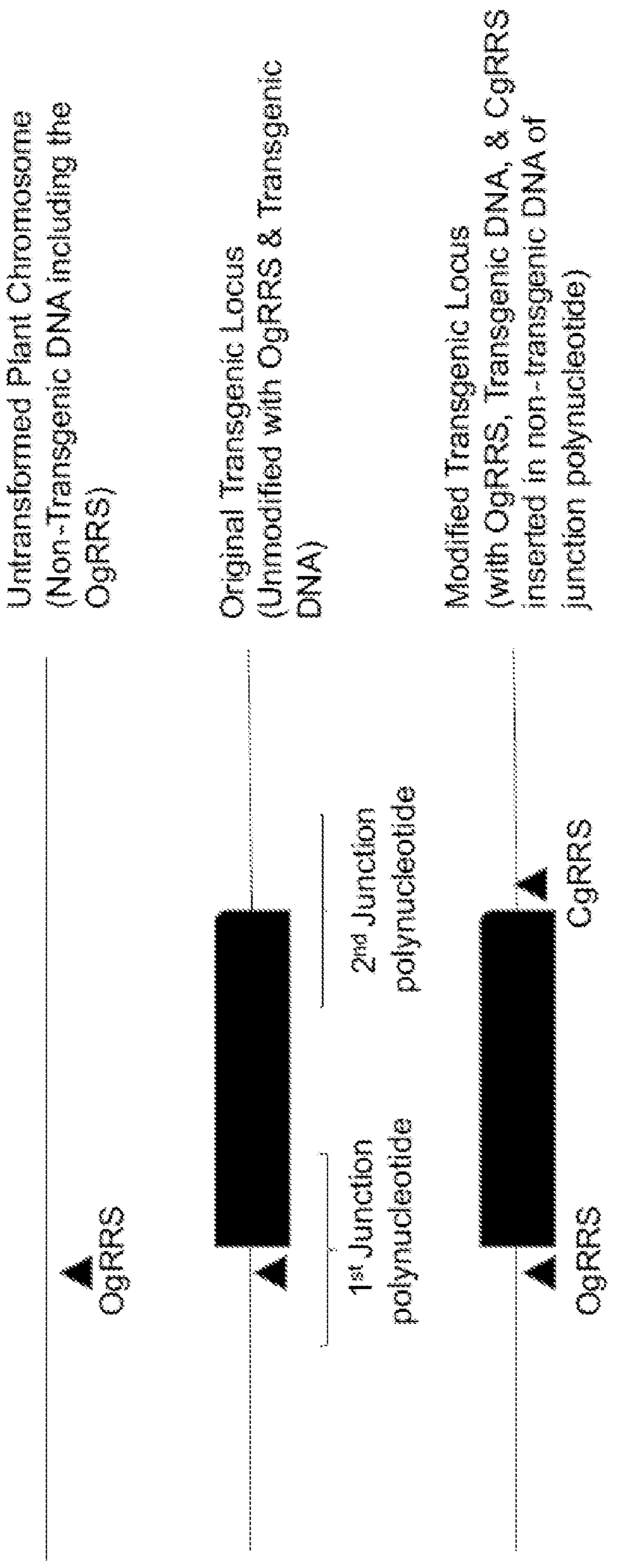
Figure 3B:
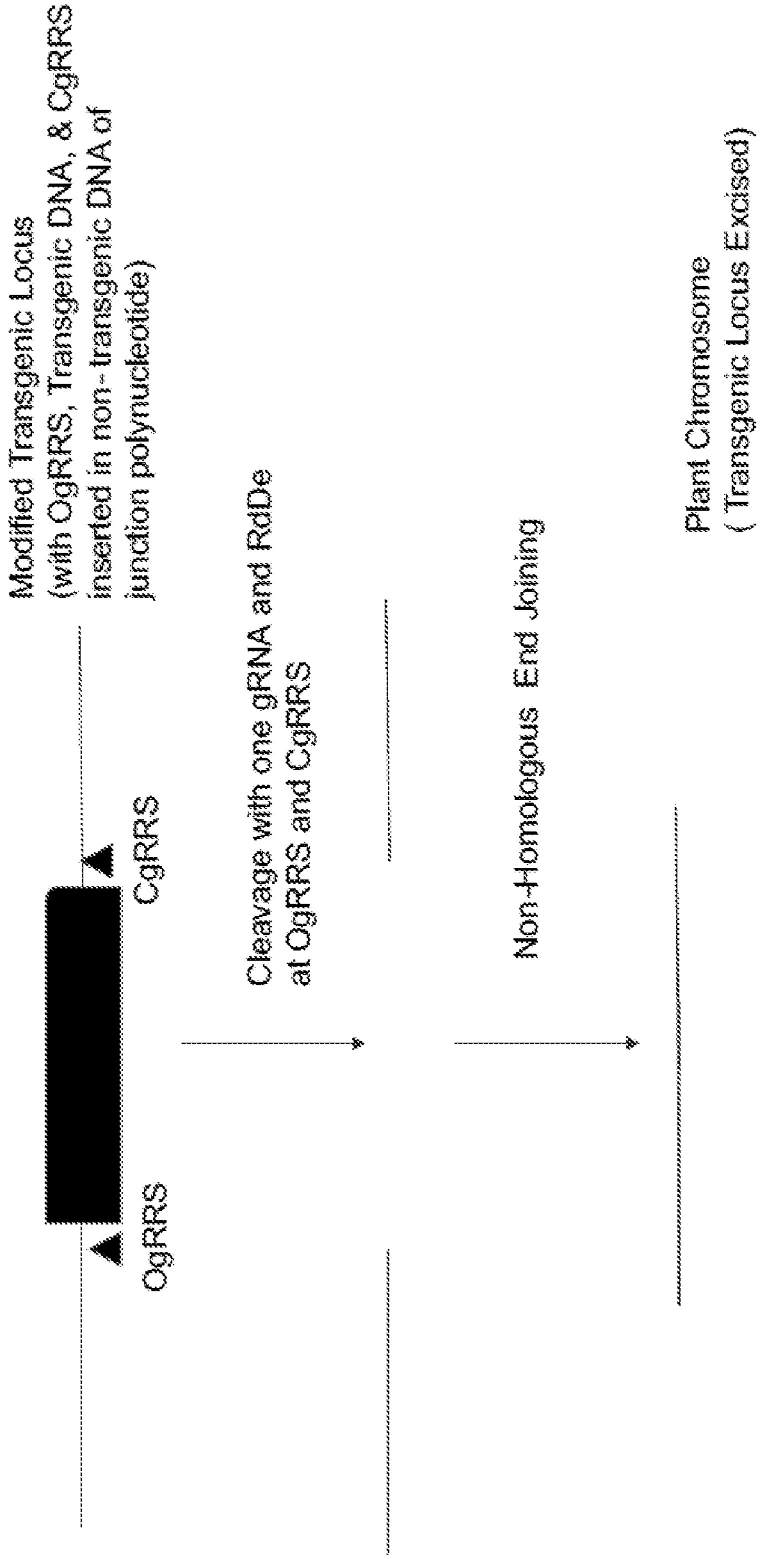
Figure 3C:
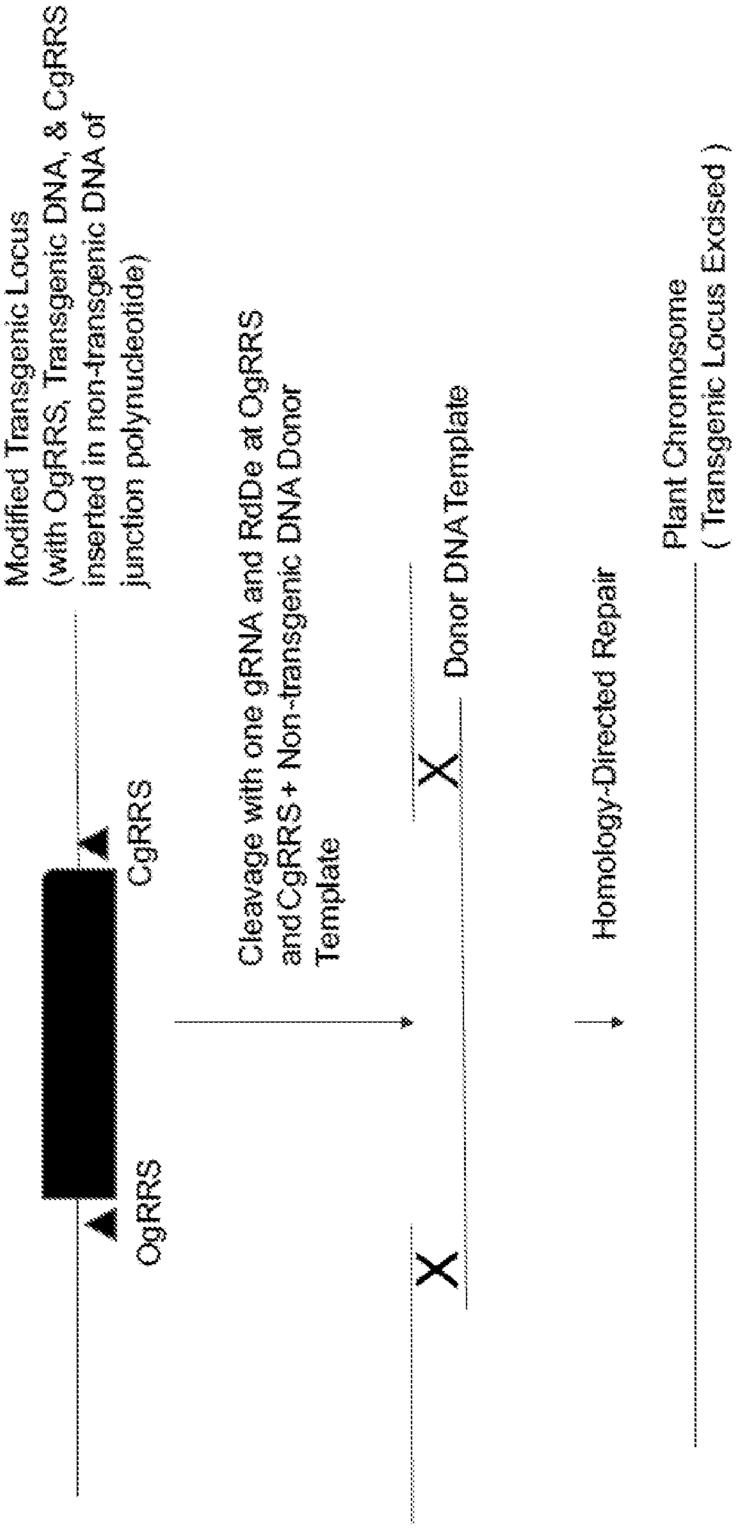

FIG. 3A, B, C. FIG. 3A shows a schematic diagram of a non-limiting example of: (i) an untransformed plant chromosome containing non-transgenic DNA which includes the originator guide RNA recognition site (OgRRS) (top); (ii) the original transgenic locus with the OgRRS in the non-transgenic DNA of the $1^{st}$ junction polynucleotide (middle);

and (iii) the modified transgenic locus with a cognate guide RNA inserted into the non-transgenic DNA of the $2^{nd}$ junction polynucleotide (bottom). FIG. 3B shows a schematic diagram of a non-limiting example of a process where a modified transgenic locus with a cognate guide RNA inserted into the non-transgenic DNA of the $2^{nd}$ junction polynucleotide (top) is subjected to cleavage at the OgRRS and CgRRS with one guide RNA (gRNA) that hybridizes to gRNA hybridization site in both the OgRRS and the CgRRS and an RNA dependent DNA endonuclease (RdDe) that recognizes and cleaves the gRNA/OgRRS and the gRNA/CgRRS complex followed by non-homologous end joining processes to provide a plant chromosome where the transgenic locus is excised. FIG. 3C shows a schematic diagram of a non-limiting example of a process where a modified transgenic locus with a cognate guide RNA inserted into the non-transgenic DNA of the $2^{nd}$ junction polynucleotide (top) is subjected to cleavage at the OgRRS and CgRRS with one guide RNA (gRNA) that hybridizes to the gRNA hybridization site in both the OgRRS and the CgRRS and an RNA dependent DNA endonuclease (RdDe) that recognizes and cleaves the gRNA/OgRRS and the gRNA/CgRRS complex in the presence of a donor DNA template. In FIG. 3C, cleavage of the modified transgenic locus in the presence of the donor DNA template which has homology to non-transgenic DNA but lacks the OgRRS in the $1^{st}$ and $2^{nd}$ junction polynucleotides followed by homology-directed repair processes to provide a plant chromosome where the transgenic locus is excised and non-transgenic DNA present in the untransformed plant chromosome is at least partially restored.

FIG. 4 shows a schematic diagram of the hybridization sites for gRNAs of SEQ ID NO: 20, 21, and 22. The 5' junction polynucleotide sequence set forth in FIG. 4 corresponds to nucleotides 920 to 1240 of SEQ ID NO: 1 and SEQ ID NO: 46.

FIG. 5A, B, C shows the sequence (SEQ ID NO: 46) of the MIR162 locus in the deposited seed of ATCC accession No. PTA-8166 which encodes the Vip3Aa20 protein. The endogenous genomic DNA (uppercase), transgenic insert DNA (lowercase) and 5' and 3' junction sequences at both ends of the transgenic insert DNA are shown. The OgRRS sequence in the 3' junction sequence (comprising SEQ ID NO: 27 in the complementary DNA strand) is shown in bold and underlined.

FIG. 6A, B, C shows the sequence (SEQ ID NO: 47) of an INIR12 transgenic locus obtained by insertion of a CgRRS in the 5' DNA junction polynucleotide sequence of an MIR 162 transgenic locus in the ATCC accession no. PTA-8166 deposit which encodes the Vip3Aa20 protein. The endogenous genomic DNA (uppercase) and transgenic insert DNA (lowercase) as well as the 5' and 3' junction sequences at both ends of the inserted transgenic DNA are shown. The CgRRS sequence comprising the PAM site and gRNA hybridization site in the 5' junction polynucleotide sequence is shown in bold, lowercase, and underlined. The OgRRS sequence in the 3' junction polynucleotide sequence (comprising SEQ ID NO: 27 in the complementary DNA strand) is shown in bold, uppercase, and underlined.

FIG. 7A, B shows the sequence (SEQ ID NO: 49) of an INIR12 transgenic locus obtained by deletion of a 5' DNA junction polynucleotide sequence of an MIR 162 transgenic locus in the ATCC accession no. PTA-8166 deposit which encodes the Vip3Aa20 protein. The endogenous genomic DNA (uppercase) and transgenic insert DNA (lowercase) as well as the 5' and 3' junction sequences at both ends of the inserted transgenic DNA are shown.

DETAILED DESCRIPTION

Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as well as necessarily defines the exact complements, as is known to one of ordinary skill in the art.

Where a term is provided in the singular, the inventors also contemplate embodiments described by the plural of that term.

The term "about" as used herein means a value or range of values which would be understood as an equivalent of a stated value and can be greater or lesser than the value or range of values stated by 10 percent. Each value or range of values preceded by the term "about" is also intended to encompass the embodiment of the stated absolute value or range of values.

The phrase "allelic variant" as used herein refers to a polynucleotide or polypeptide sequence variant that occurs in a different strain, variety, or isolate of a given organism.

The term "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the phrase "approved transgenic locus" is a genetically modified plant event which has been authorized, approved, and/or de-regulated for any one of field testing, cultivation, human consumption, animal consumption, and/or import by a governmental body. Illustrative and non-limiting examples of governmental bodies which provide such approvals include the Ministry of Agriculture of Argentina, Food Standards Australia New Zealand, National Biosafety Technical Committee (CTNBio) of Brazil, Canadian Food Inspection Agency, China Ministry of Agriculture Biosafety Network, European Food Safety Authority, US Department of Agriculture, US Department of Environmental Protection, and US Food and Drug Administration.

The term "backcross", as used herein, refers to crossing an F1 plant or plants with one of the original parents. A backcross is used to maintain or establish the identity of one parent (species) and to incorporate a particular trait from a second parent (species). The term "backcross generation", as used herein, refers to the offspring of a backcross.

As used herein, the phrase "biological sample" refers to either intact or non-intact (e.g. milled seed or plant tissue, chopped plant tissue, lyophilized tissue) plant tissue. It may also be an extract comprising intact or non-intact seed or plant tissue. The biological sample can comprise flour, meal, syrup, oil, starch, and cereals manufactured in whole or in part to contain crop plant by-products. In certain embodiments, the biological sample is "non-regenerable" (i.e., incapable of being regenerated into a plant or plant part). In certain embodiments, the biological sample refers to a homogenate, an extract, or any fraction thereof containing genomic DNA of the organism from which the biological sample was obtained, wherein the biological sample does not comprise living cells.

As used herein, the terms "correspond," "corresponding," and the like, when used in the context of an nucleotide position, mutation, and/or substitution in any given polynucleotide (e.g., an allelic variant of SEQ ID NO: 1 or SEQ ID NO: 46) with respect to the reference polynucleotide sequence (e.g., SEQ ID NO: 1 or SEQ ID NO: 46) all refer to the position of the polynucleotide residue in the given sequence that has identity to the residue in the reference nucleotide sequence when the given polynucleotide is aligned to the reference polynucleotide sequence using a pairwise alignment algorithm (e.g., CLUSTAL O 1.2.4 with default parameters).

As used herein, the terms "Cpf1" and "Cas12a" are used interchangeably to refer to the same RNA dependent DNA endonuclease (RdDe). Cas12a proteins include the protein provided herein as SEQ ID NO: 38.

The term "crossing" as used herein refers to the fertilization of female plants (or gametes) by male plants (or gametes). The term "gamete" refers to the haploid reproductive cell (egg or pollen) produced in plants by meiosis from a gametophyte and involved in sexual reproduction, during which two gametes of opposite sex fuse to form a diploid zygote. The term generally includes reference to a pollen (including the sperm cell) and an ovule (including the ovum). When referring to crossing in the context of achieving the introgression of a genomic region or segment, the skilled person will understand that in order to achieve the introgression of only a part of a chromosome of one plant into the chromosome of another plant, random portions of the genomes of both parental lines recombine during the cross due to the occurrence of crossing-over events in the production of the gametes in the parent lines. Therefore, the genomes of both parents must be combined in a single cell by a cross, where after the production of gametes from the cell and their fusion in fertilization will result in an introgression event.

As used herein, the phrases "DNA junction polynucleotide" and "junction polynucleotide" refers to a polynucleotide of about 18 to about 500 base pairs in length comprised of both endogenous chromosomal DNA of the plant genome and heterologous transgenic DNA which is inserted in the plant genome. A junction polynucleotide can thus comprise about 8, 10, 20, 50, 100, 200, 250, 500, or 1000 base pairs of endogenous chromosomal DNA of the plant genome and about 8, 10, 20, 50, 100, 200, 250, 500, or 1000 base pairs of heterologous transgenic DNA which span the one end of the transgene insertion site in the plant chromosomal DNA. Transgene insertion sites in chromosomes will typically contain both a 5' junction polynucleotide and a 3' junction polynucleotide. In embodiments set forth herein in SEQ ID NO: 1, the 5' junction polynucleotide is located at the 5' end of the sequence and the 3' junction polynucleotide is located at the 3' end of the sequence. In a non-limiting and illustrative example, a 5' junction polynucleotide of a transgenic locus is telomere proximal in a chromosome arm and the 3' junction polynucleotide of the transgenic locus is centromere proximal in the same chromosome arm. In another non-limiting and illustrative example, a 5' junction polynucleotide of a transgenic locus is centromere proximal in a chromosome arm and the 3' junction polynucleotide of the transgenic locus is telomere proximal in the same chromosome arm. The junction polynucleotide which is telomere proximal and the junction polynucleotide which is centromere proximal can be determined by comparing non-transgenic genomic sequence of a sequenced non-transgenic plant genome to the non-transgenic DNA in the junction polynucleotides.

The term "donor," as used herein in the context of a plant, refers to the plant or plant line from which the trait, transgenic event, or genomic segment originates, wherein the donor can have the trait, introgression, or genomic segment in either a heterozygous or homozygous state.

As used herein, the terms "excise" and "delete," when used in the context of a DNA molecule, are used interchangeably to refer to the removal of a given DNA segment or element (e.g., transgene element or transgenic locus or portion thereof) of the DNA molecule.

As used herein, the phrase "elite crop plant" refers to a plant which has undergone breeding to provide one or more trait improvements. Elite crop plant lines include plants which are an essentially homozygous, e.g. inbred or doubled haploid. Elite crop plants can include inbred lines used as is or used as pollen donors or pollen recipients in hybrid seed production (e.g. used to produce F1 plants). Elite crop plants can include inbred lines which are selfed to produce non-hybrid cultivars or varieties or to produce (e.g., bulk up) pollen donor or recipient lines for hybrid seed production. Elite crop plants can include hybrid F1 progeny of a cross between two distinct elite inbred or doubled haploid plant lines.

As used herein, an "event," "a transgenic event," "a transgenic locus" and related phrases refer to an insertion of one or more transgenes at a unique site in the genome of a plant as well as to DNA fragments, plant cells, plants, and plant parts (e.g., seeds) comprising genomic DNA containing the transgene insertion. Such events typically comprise both a 5' and a 3' DNA junction polynucleotide and confer one or more useful traits including herbicide tolerance, insect resistance, male sterility, and the like.

As used herein, the phrases "endogenous sequence," "endogenous gene," "endogenous DNA," "endogenous polynucleotide," and the like refer to the native form of a polynucleotide, gene or polypeptide in its natural location in the organism or in the genome of an organism.

The terms "exogenous" and "heterologous" as are used synonymously herein to refer to any polynucleotide (e.g. DNA molecule) that has been inserted into a new location in the genome of a plant. Non-limiting examples of an exogenous or heterologous DNA molecule include a synthetic DNA molecule, a non-naturally occurring DNA molecule, a DNA molecule found in another species, a DNA molecule found in a different location in the same species, and/or a DNA molecule found in the same strain or isolate of a species, where the DNA molecule has been inserted into a new location in the genome of a plant.

As used herein, the term "F1" refers to any offspring of a cross between two genetically unlike individuals.

The term "gene," as used herein, refers to a hereditary unit consisting of a sequence of DNA that occupies a specific location on a chromosome and that contains the genetic instruction for a particular characteristics or trait in an organism. The term "gene" thus includes a nucleic acid (for example, DNA or RNA) sequence that comprises coding sequences necessary for the production of an RNA, or a polypeptide or its precursor. A functional polypeptide can be encoded by a full length coding sequence or by any portion of the coding sequence as long as the desired activity or functional properties (e.g., enzymatic activity, pesticidal activity, ligand binding, and/or signal transduction) of the RNA or polypeptide are retained.

The term "identifying," as used herein with respect to a plant, refers to a process of establishing the identity or distinguishing character of a plant, including exhibiting a certain trait, containing one or more transgenes, and/or containing one or more molecular markers.

As used herein, the term "INIR12" is used herein to refer either individually or collectively to items that include any or all of the MIR162 transgenic maize loci which have been modified as disclosed herein, transgenic maize plants and parts thereof including seed that comprise the modified MIR162 transgenic loci, and DNA obtained therefrom.

The term "isolated" as used herein means having been removed from its natural environment.

As used herein, the terms "include," "includes," and "including" are to be construed as at least having the features to which they refer while not excluding any additional unspecified features.

As used herein, the phrase "introduced transgene" is a transgene not present in the original transgenic locus in the genome of an initial transgenic event or in the genome of a progeny line obtained from the initial transgenic event. Examples of introduced transgenes include exogenous transgenes which are inserted in a resident original transgenic locus.

As used herein, the terms "introgression", "introgressed" and "introgressing" refer to both a natural and artificial process, and the resulting plants, whereby traits, genes or DNA sequences of one species, variety or cultivar are moved into the genome of another species, variety or cultivar, by crossing those species. The process may optionally be completed by backcrossing to the recurrent parent. Examples of introgression include entry or introduction of a gene, a transgene, a regulatory element, a marker, a trait, a trait locus, or a chromosomal segment from the genome of one plant into the genome of another plant.

The phrase "marker-assisted selection", as used herein, refers to the diagnostic process of identifying, optionally followed by selecting a plant from a group of plants using the presence of a molecular marker as the diagnostic characteristic or selection criterion. The process usually involves detecting the presence of a certain nucleic acid sequence or polymorphism in the genome of a plant.

As used herein, the term "MIR162" is used to refer to items that include a transgenic maize locus, transgenic maize plants and parts thereof including seed set forth in U.S. Pat. No. 8,455,720, which is incorporated herein by reference in its entirety. Representative MIR162 transgenic maize seed have been deposited at the American Type Culture Collection (ATCC, Manassas, VA, USA) as accession No. PTA-8166. MIR162 transgenic loci include loci having the sequence of SEQ ID NO:1, the sequence of the MIR162 locus in the deposited seed of accession No. PTA-8166 (SEQ ID NO: 46) and any progeny thereof, as well as allelic variants and other variants of SEQ ID NO:1 or SEQ ID NO: 46. Other variants of a MIR162 locus can include variants in MIR162 other than those disclosed herein obtained by gene editing techniques (e.g., by use of RdDe, CBE, or ABE and gRNAs, TALENs, and/or ZFN).

The phrase "molecular marker", as used herein, refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), microsatellite markers (e.g. SSRs), sequence-characterized amplified region (SCAR) markers, Next Generation Sequencing (NGS) of a molecular marker, cleaved amplified polymorphic sequence (CAPS) markers or isozyme markers or combinations of the markers described herein which defines a specific genetic and chromosomal location.

As used herein the terms "native" or "natural" define a condition found in nature. A "native DNA sequence" is a DNA sequence present in nature that was produced by natural means or traditional breeding techniques but not generated by genetic engineering (e.g., using molecular biology/transformation techniques).

The term "offspring", as used herein, refers to any progeny generation resulting from crossing, selfing, or other propagation technique.

The phrase "operably linked" refers to a juxtaposition wherein the components so described are in a relationship permitting them to function in their intended manner. For instance, a promoter is operably linked to a coding sequence if the promoter affects its transcription or expression. When the phrase "operably linked" is used in the context of a PAM site and a guide RNA hybridization site, it refers to a PAM site which permits cleavage of at least one strand of DNA in a polynucleotide with an RNA dependent DNA endonuclease or RNA dependent DNA nickase which recognize the PAM site when a guide RNA complementary to guide RNA hybridization site sequences adjacent to the PAM site is present. A OgRRS and its CgRRS, sPAM sites, or sigRNAR sites are operably linked to junction polynucleotides when they can be recognized by a gRNA and an RdDe to provide for excision of the transgenic locus or portion thereof flanked by the junction polynucleotides. When the phrase "operably linked" is used in the context of a signature PAM site and a DNA junction polynucleotide, it refers to a PAM site which permits cleavage of at least one strand of DNA in the junction polynucleotide with an RNA dependent DNA endonuclease, RNA dependent DNA binding protein, or RNA dependent DNA nickase which recognizes the PAM site when a guide RNA complementary to sequences adjacent to the PAM site is present. When the phrase "operably linked" is used in the context of a sigRNAR site and a DNA junction polynucleotide, it refers to a sigRNAR site which permits cleavage of at least one strand of DNA in the junction polynucleotide with an RNA dependent DNA endonuclease, RNA dependent DNA binding protein, or RNA dependent DNA nickase which recognizes the sigRNAR site when a guide RNA complementary to the heterologous sequences adjacent in the sigRNAR site is present.

As used herein, the term "plant" includes a whole plant and any descendant, cell, tissue, or part of a plant. The term "plant parts" include any part(s) of a plant, including, for example and without limitation: seed (including mature seed and immature seed); a plant cutting; a plant cell; a plant cell culture; or a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. Regenerable cells in a plant cell or tissue culture may be embryos, protoplasts, meristematic cells, callus, pollen, leaves, anthers, roots, root tips, silk, flowers, kernels, ears, cobs, husks, or stalks. In contrast, some plant cells are not capable of being regenerated to produce plants and are referred to herein as "non-regenerable" plant cells.

The term "purified," as used herein defines an isolation of a molecule or compound in a form that is substantially free of contaminants normally associated with the molecule or compound in a native or natural environment and means having been increased in purity as a result of being separated from other components of the original composition. The term “purified nucleic acid” is used herein to describe a nucleic acid sequence which has been separated from other compounds including, but not limited to polypeptides, lipids and carbohydrates.

The term “recipient”, as used herein, refers to the plant or plant line receiving the trait, transgenic event or genomic segment from a donor, and which recipient may or may not have the have trait, transgenic event or genomic segment itself either in a heterozygous or homozygous state.

As used herein the term “recurrent parent” or “recurrent plant” describes an elite line that is the recipient plant line in a cross and which will be used as the parent line for successive backcrosses to produce the final desired line.

As used herein the term “recurrent parent percentage” relates to the percentage that a backcross progeny plant is identical to the recurrent parent plant used in the backcross. The percent identity to the recurrent parent can be determined experimentally by measuring genetic markers such as SNPs and/or RFLPs or can be calculated theoretically based on a mathematical formula.

The terms “selfed,” “selfing,” and “self,” as used herein, refer to any process used to obtain progeny from the same plant or plant line as well as to plants resulting from the process. As used herein, the terms thus include any fertilization process wherein both the ovule and pollen are from the same plant or plant line and plants resulting therefrom. Typically, the terms refer to self-pollination processes and progeny plants resulting from self-pollination.

The term “selecting”, as used herein, refers to a process of picking out a certain individual plant from a group of individuals, usually based on a certain identity, trait, characteristic, and/or molecular marker of that individual.

As used herein, the phrase “originator guide RNA recognition site” or the acronym “OgRRS” refers to an endogenous DNA polynucleotide comprising a protospacer adjacent motif (PAM) site operably linked to a guide RNA hybridization site. In certain embodiments, an OgRRS can be located in an untransformed plant chromosome or in non-transgenic DNA of a DNA junction polynucleotide of both an original transgenic locus and a modified transgenic locus. In certain embodiments, an OgRRS can be located in transgenic DNA of a DNA junction polynucleotide of both an original transgenic locus and a modified transgenic locus. In certain embodiments, an OgRRS can be located in both transgenic DNA and non-transgenic DNA of a DNA junction polynucleotide of both an original transgenic locus and a modified transgenic locus (i.e., can span transgenic and non-transgenic DNA in a DNA junction polynucleotide).

As used herein the phrase “cognate guide RNA recognition site” or the acronym “CgRRS” refer to a DNA polynucleotide comprising a PAM site operably linked to a guide RNA hybridization site, where the CgRRS is absent from transgenic plant genomes comprising a first original transgenic locus that is unmodified and where the CgRRS and its corresponding OgRRS can hybridize to a single gRNA. A CgRRS can be located in transgenic DNA of a DNA junction polynucleotide of a modified transgenic locus, in transgenic DNA of a DNA junction polynucleotide of a modified transgenic locus, or in both transgenic and non-transgenic DNA of a modified transgenic locus (i.e., can span transgenic and non-transgenic DNA in a DNA junction polynucleotide).

As used herein, the phrase “a transgenic locus excision site” refers to the DNA which remains in the genome of a plant or in a DNA molecule (e.g., an isolated or purified DNA molecule) wherein a segment comprising, consisting essentially of, or consisting of a transgenic locus or portion thereof has been deleted. In a non-limiting and illustrative example, a transgenic locus excision site can thus comprise a contiguous segment of DNA comprising at least 10 base pairs of DNA that is telomere proximal to the deleted transgenic locus or to the deleted segment of the transgenic locus and at least 10 base pairs of DNA that is centromere proximal to the deleted transgenic locus or to the deleted segment of the transgenic locus.

As used herein, the phrase “signature protospacer adjacent motif (sPAM)” or acronym “sPAM” refer to a PAM which has been introduced into a transgenic plant genome by genome editing, wherein the sPAM is absent from a transgenic plant genome comprising the original transgenic locus. A sPAM can be introduced by an insertion, deletion, and or substitution of one or more nucleotides in genomic DNA.

As used herein the phrase “signature guide RNA Recognition site” or acronym “sigRNAR site” refer to a DNA polynucleotide comprising a heterologous crRNA (CRISPR RNA) binding sequence located immediately 5' or 3' to a PAM site, wherein the sigRNAR site has been introduced into a transgenic plant genome by genome editing and wherein at least the heterologous crRNA binding sequence is absent from a transgenic plant genome comprising the original transgenic locus. In certain embodiments, the heterologous crRNA binding sequence is operably linked to a pre-existing PAM site in the transgenic plant genome. In other embodiments, the heterologous crRNA binding sequence is operably linked to a sPAM site in the transgenic plant genome.

As used herein, the phrase “transgene element” refers to a segment of DNA comprising, consisting essentially of, or consisting of a promoter, a 5' UTR, an intron, a coding region, a 3'UTR, or a polyadenylation signal. Polyadenylation signals include transgene elements referred to as “terminators” (e.g., NOS, pinII, rbcs, Hsp17, TubA).

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Genome editing molecules can permit introduction of targeted genetic change conferring desirable traits in a variety of crop plants (Zhang et al. Genome Biol. 2018; 19: 210; Schindele et al. FEBS Lett. 2018; 592(12):1954). Desirable traits introduced into crop plants such as maize include herbicide tolerance, improved food and/or feed characteristics, male-sterility, and drought stress tolerance. Nonetheless, full realization of the potential of genome editing methods for crop improvement will entail efficient incorporation of the targeted genetic changes in germplasm of different elite crop plants adapted for distinct growing conditions. Such elite crop plants will also desirably comprise useful transgenic loci which confer various traits including herbicide tolerance, pest resistance (e.g.; insect, nematode, fungal disease, and bacterial disease resistance), conditional male sterility systems for hybrid seed production, abiotic stress tolerance (e.g., drought tolerance), improved food and/or feed quality, and improved industrial use (e.g., biofuel).

INIR12 transgenic loci comprising modifications of a MIR162 transgenic loci in a maize plant genome by directed insertion, deletion, and/or substitution of DNA within or adjacent to such MIR162 transgenic loci as well as methods of making and using such INIR12 transgenic loci are provided herein. In certain embodiments, the INIR12 transgenic loci comprise the first ZmUbiInt promoter, the vip3Aa19 or vip3Aa20 coding region which is operably linked to said promoter, the CaMV 35S terminator element which is operably linked to said vip3Aa19 or vip3Aa20 coding region, and the nopaline synthase terminator element of an MIR162 transgenic locus, wherein DNA of said MIR162 transgenic locus comprising a second ZmUbiInt promoter and an operably linked phosphomannose isomerase (pmi) coding region is absent. Such INIR12 transgenic loci can thus comprise a vip3Aa19 or vip3Aa20 expression cassette having two tandemly arrayed terminator elements (i.e., a CaMV35S and a NOS terminator) while lacking non-essential DNA elements (i.e., the duplicate copy of the ZmUbiInt promoter and pmi selectable marker gene which is operably linked thereto). Examples of an INIR12 transgenic locus comprising a vip3Aa20 expression cassette and tandemly arrayed CaMV35S and a NOS terminators include the INIR12 transgenic loci comprising the DNA sequence of SEQ ID NO: 48 and SEQ ID NO: 49.

In certain embodiments, INIR12 transgenic loci provided herein can thus comprise deletions of selectable marker genes and/or repetitive sequences. In its unmodified form (in certain embodiments, the "unmodified form" is the "original form," "original transgenic locus," etc.) a MIR162 transgenic locus comprises a phosphomannose isomerase (pmi)-encoding selectable marker gene which confers the ability to grow on mannose as a carbon source. In embodiments provided herein, the selectable marker gene which is deleted comprises, consists essentially of, or consists of a DNA molecule encoding: (i) the phosphomannose isomerase (pmi) of a MIR162 transgenic locus and the ZmUbi promoter that is operably linked thereto; or (ii) the phosphomannose isomerase (pmi) of a MIR162 transgenic locus and both the ZmUbi promoter and NOS terminator that are operably linked thereto. In certain embodiments, DNA elements comprising the ZmUbi promoter and operably linked pmi coding region corresponding to at least nucleotides 5837, 5838, 5840, 5845, or 5850 to 8040, 9060, 9080, 9090, 9100, or 9105 of SEQ ID NO:1 or SEQ ID NO:46 can be absent from an INIR12 locus. In certain embodiments, the INIR12 locus comprising a deletion of DNA encoding the pmi gene and the operably linked ZmUbi promoter is set forth in SEQ ID NO: 2, wherein nucleotides designated n in the sequence are either absent, independently selected from a guanine, a cytosine, an adenine residue, or a thymine, comprise or consist of 1 or more nucleotides corresponding to nucleotides 5831 to 5836 of SEQ ID NO:1 or SEQ ID NO:46 and/or comprise or consist of 1 or more nucleotides corresponding to nucleotides 9102 to 9107 of SEQ ID NO:1 or SEQ ID NO:46. In certain embodiments, the deletion junction sequence present in an INIR12 transgenic locus comprises a DNA molecule set forth in SEQ ID NO: 25 which corresponds to nucleotides 5821 to 5850 of SEQ ID NO: 6. In certain embodiments, the DNA comprising the ZmUbi promoter and operably linked pmi coding region to be deleted is flanked by operably linked protospacer adjacent motif (PAM) sites in a MIR162 transgenic locus which are recognized by an RNA dependent DNA endonuclease (RdDe); for example, a class 2 type II or class 2 type V RdDe. In certain embodiments, the deleted selectable marker gene is replaced in an INIR12 transgenic locus by an introduced DNA sequence as discussed in further detail elsewhere herein. For example, in certain embodiments, the introduced DNA sequence comprises a trait expression cassette such as a trait expression cassette of another transgenic locus. In addition to the deletion of a selectable marker gene, in certain embodiments at least one copy of a repetitive sequence has also been deleted with genome editing molecules from an MIR162 transgenic locus. In certain embodiments, the repetitive sequence comprises, consists essentially of, or consists of the two distinct ZmUbiInt promoters which are each operably linked to the VIP3Aa20 gene and to the pmi selectable marker gene within the MIR162 transgenic locus (e.g., as depicted in FIG. 1). In certain embodiments, the repetitive sequence which comprises, consists essentially of, or consists of the second ZmUbiInt promoter and which is operably linked to the pmi selectable maker of an MIR162 transgenic locus is absent from the INIR12 transgenic locus. In certain embodiments, any of the aforementioned INIR12 transgenic loci can optionally further comprise: (i) an OgRRS and a CgRRS which are operably linked to a $1^{st}$ and a $2^{nd}$ junction sequence of the INIR12 transgenic locus; (ii) one or more signature protospacer adjacent motif (sPAM) sites which are operably linked to a $1^{st}$ and a $2^{nd}$ junction sequence of the INIR12 transgenic locus; or (iii) signature guide RNA Recognition site (sigRNAR) sites which are operably linked to a $1^{st}$ and a $2^{nd}$ junction sequence of the INIR12 transgenic locus. Also provided herein are plants comprising any of aforementioned INIR12 transgenic loci.

In certain embodiments, an INIR12 transgenic locus can further comprise modifications of a 5' or 3' junction polynucleotide of an MIR162 transgenic locus (e.g., as set forth in SEQ ID NO:1 or SEQ ID NO:46 and in FIG. 1). Such modifications of junction polynucleotides include deletions of DNA segments comprising non-essential transgenic DNA in the junction polynucleotide. In certain embodiments, such deletions of non-essential DNA of a 5' junction polynucleotide of an INIR12 transgenic locus include those set forth in SEQ ID NO: 3, wherein one or more nucleotides in a segment corresponding to nucleotides 1089 to 1098 are absent or independently selected from A, C, G, or T, with the proviso that the nucleotides 1089 to 1098 of SEQ ID NO:3 are not identical to nucleotides 1089 to 1098 of SEQ ID NO:1 or SEQ ID NO:46. In certain embodiments, such deletions of non-essential DNA of a 5' junction polynucleotide of an INIR12 transgenic locus include those wherein nucleotides corresponding to nucleotides 1081 to 1104 of SEQ ID NO:3 are: (i) each either absent or independently selected from a guanine, a cytosine, an adenine residue, or a thymine residue; (ii) comprise about 2 to 8 consecutive residues of nucleotides 1,081 to 1092 of SEQ ID NO:1 or SEQ ID NO:46 and/or about 2 to 8 consecutive residues of nucleotides 1093 to 1104 of SEQ ID NO:1 or SEQ ID NO:46; or (iii) any combination of (i) and (ii), wherein each of (i), (ii), and (iii) are with the proviso that the nucleotides corresponding to nucleotides 1081 to 1104 of SEQ ID NO: 3 are not identical to nucleotides 1081 to 1104 of SEQ ID NO:1 or SEQ ID NO:46. In certain embodiments, such deletions of non-essential DNA of a 5' junction polynucleotide of an INIR12 transgenic locus include those wherein nucleotides corresponding to nucleotides 1081 to 1104 of SEQ ID NO:3 are set forth in SEQ ID NO: 7, wherein n is absent, is independently selected from A, C, G, or T, correspond to 1 to 10 residues of nucleotides 1083 to 1092 of SEQ ID NO:1 or SEQ ID NO:46, and/or correspond to 1 to 10 residues of nucleotides 1093 to 1102 of SEQ ID NO:1 or SEQ ID NO:46 with the proviso that nucleotides corresponding to nucleotide 3 to 22 of SEQ ID NO: 7 are not identical to residues 1083 to 1102 of SEQ ID NO:1 or SEQ ID NO:46. In certain embodiments, such deletions of non-essential DNA of a 5' junction polynucleotide of an INIR12 transgenic locus include those wherein nucleotides corresponding to nucleotides 1081 to 1104 of SEQ ID NO:3 are set forth in SEQ ID NO: 8, wherein n is absent, is independently selected from A, C, G, or T, correspond to 1 to 5 residues of nucleotides 1088 to 1092 of SEQ ID NO:1 or SEQ ID NO:46, and/or correspond to 1 to 5 residues of nucleotides 1093 to 1097 of SEQ ID NO:1 or SEQ ID NO:46 with the proviso that nucleotides corresponding to residues 8 to 17 of SEQ ID NO: 8 are not identical to residues 1088 to 1097 of SEQ ID NO:1 or SEQ ID NO:46. In certain embodiments, such deletions of non-essential DNA of a 5' junction polynucleotide of an INIR12 transgenic locus include those wherein nucleotides corresponding to nucleotides 1081 to 1104 of SEQ ID NO:3 are set forth in SEQ ID NO: 9; wherein n is absent, is independently selected from A, C, G, or T, correspond to 1 to 3 residues of nucleotides 1090-1092 of SEQ ID NO:1 or SEQ ID NO:46, and/or correspond to 1 to 3 residues of nucleotides 1093 to 1095 of SEQ ID NO:1 or SEQ ID NO:46 with the proviso that nucleotides corresponding to residues 1090 to 1095 of SEQ ID NO: 9 are not identical to nucleotides 1090 to 1095 of SEQ ID NO:1 or SEQ ID NO:46. In certain embodiments, such deletions of non-essential DNA of a 5' junction polynucleotide of an INIR12 transgenic locus include those wherein nucleotides corresponding to nucleotides 1081 to 1104 of SEQ ID NO:3 are set forth in SEQ ID NO: 10, 11, 12, 13, 14, 15, 16, 17, 18, or 19. In certain embodiments, such deletions of non-essential DNA of a 5' junction polynucleotide of an INIR12 transgenic locus include those set forth in SEQ ID NO: 39, 40, and SEQ ID NO: 50-167. INIR12 transgenic loci comprising deletions of the non-essential DNA of a 5' junction polynucleotide are set forth in SEQ ID NO: 43 and 49.

Also provided herein are methods whereby targeted genetic changes are efficiently combined with desired subsets of transgenic loci in elite progeny plant lines (e.g., elite inbreds used for hybrid seed production or for inbred varietal production). Examples of such methods include those illustrated in FIG. 2. In certain embodiments, INIR12 transgenic loci provided here are characterized by polynucleotide sequences that can facilitate as necessary the removal of the INIR12 transgenic loci from the genome. Useful applications of such INIR12 transgenic loci and related methods of making include targeted excision of a INIR12 transgenic locus or portion thereof in certain breeding lines to facilitate recovery of germplasm with subsets of transgenic traits tailored for specific geographic locations and/or grower preferences. Other useful applications of such INIR12 transgenic loci and related methods of making include removal of transgenic traits from certain breeding lines when it is desirable to replace the trait in the breeding line without disrupting other transgenic loci and/or non-transgenic loci. In certain embodiments, maize genomes containing INIR12 transgenic loci or portions thereof which can be selectively excised with one or more gRNA molecules and RdDe (RNA dependent DNA endonucleases) which form gRNA/target DNA complexes. Such selectively excisable INIR12 transgenic loci can comprise an originator guide RNA recognition site (OgRRS) which is identified in non-transgenic DNA, transgenic DNA, or a combination thereof in of a first junction polynucleotide of the transgenic locus and cognate guide RNA recognition site (CgRRS) which is introduced (e.g., by genome editing methods) into a second junction polynucleotide of the transgenic locus and which can hybridize to the same gRNA as the OgRRS, thereby permitting excision of the modified transgenic locus or portions thereof with a single guide RNA (e.g., as shown in FIGS. 3A and B). In certain embodiments, an originator guide RNA recognition site (OgRRS) comprises endogenous DNA found in untransformed plants and in endogenous non-transgenic DNA of junction polynucleotides of transgenic plants containing a modified or unmodified transgenic locus. In certain embodiments, an originator guide RNA recognition site (OgRRS) comprises exogenous transgenic DNA of junction polynucleotides of transgenic plants containing a modified or unmodified transgenic locus. The OgRRS located in non-transgenic DNA, transgenic DNA, or a combination thereof in of a first DNA junction polynucleotide is used to design a related cognate guide RNA recognition site (CgRRS) which is introduced (e.g., by genome editing methods) into the second junction polynucleotide of the transgenic locus. A CgRRS is thus present in junction polynucleotides of modified transgenic loci provided herein and is absent from endogenous DNA found in untransformed plants and absent from junction sequences of transgenic plants containing an unmodified transgenic locus. A CgRRS is also absent from a combination of non-transgenic and transgenic DNA found in junction sequences of transgenic plants containing an unmodified transgenic locus. In certain embodiments such as those illustrated in the non-limiting example of FIG. 3, the OgRRS is located in non-transgenic DNA of a 5' junction polynucleotide and the CgRRS is introduced into non-transgenic DNA of a 3' junction polynucleotide. In other embodiments, the OgRRS can be located in non-transgenic DNA of a 3' junction polynucleotide and the CgRRS is introduced into non-transgenic DNA, transgenic DNA, or a combination thereof in a 5' junction polynucleotide. Examples of OgRRS polynucleotide sequences in or near a 3' junction polynucleotide in an MIR162 transgenic locus include SEQ ID NO: 26, 27, and 28. OgRRS polynucleotide sequences located in a first junction polynucleotide can be introduced into the second junction polynucleotide using donor DNA templates as illustrated in FIG. 3A and as elsewhere described herein. A donor DNA template for introducing the SEQ ID NO: 27 OgRRS into the 5' junction polynucleotide of an MIR162 locus includes the donor DNA template of SEQ ID NO: 32. Integration of the SEQ ID NO: 32 donor DNA template into the 5' junction polynucleotide of an MIR162 locus can provide an INIR12 locus comprising the CgRRS sequence set forth in SEQ ID NO: 37. Integration of the SEQ ID NO: 32 donor DNA template into the 5' junction polynucleotide of an MIR162 locus can provide an INIR12 locus set forth in SEQ ID NO: 44 or 47, wherein the entire phosphomannose isomerase (pmi)-encoding selectable marker gene is retained. An INIR12 transgenic locus of SEQ ID NO: 47 comprising the CgRRS sequence set forth in SEQ ID NO: 37 in its 5' junction polynucleotide is shown in FIG. 6. Integration of the SEQ ID NO: 32 donor DNA template into the 5' junction polynucleotide of an MIR162 locus can provide an INIR12 locus set forth in SEQ ID NO: 45 (encoding Vip3Aa19) or SEQ ID NO: 48 (encoding Vip3Aa20), wherein the ZmUbiInt promoter and an operably linked phosphomannose isomerase coding region of the pmi-encoding selectable marker gene are absent.

Such selectively excisable INIR12 transgenic loci can also comprise signature protospacer adjacent motif (sPAM) sites and/or signature guide RNA recognition (sigRNAR) sites, wherein the sPAM and/or sigRNAR sites are operably linked to both DNA junction polynucleotides of the INIR12 transgenic locus. Such sigRNAR sites can be recognized by RdDe and suitable guide RNAs containing crRNA complementary to heterologous DNA sequences adjacent to a PAM or sPAM site to provide for cleavage within or near the two junction polynucleotides. Such heterologous sequences which introduced at the sigRNAR site are at least 17 or 18 nucleotides in length and are complementary to the crRNA of a guide RNA. In certain embodiments, the heterologous polynucleotide of the sigRNAR is about 17 or 18 to about 24 nucleotides in length. Non-limiting features of the heterologous DNA sequences in the sigRNAR include: (i) absence of significant homology or sequence identity (e.g., less than 50% sequence identity across the entire length of the heterologous sequence) to any other endogenous or transgenic sequences present in the transgenic plant genome or in other transgenic genomes of the maize plant being edited (ii) absence of significant homology or sequence identity (e.g., less than 50% sequence identity across the entire length of the heterologous sequence) of a heterologous sequence of a first sigRNAR site to a heterologous sequence of a second or third sigRNAR site; and/or (ii) optimization of the heterologous sequence for recognition by the RdDe and guide RNA when used in conjunction with a particular PAM sequence. In certain embodiments, the sigRNAR sites which are created are recognized by the same class of RdDe (e.g., Class 2 type II or Class 2 type V) or by the same RdDe (e.g., both sPAMs or PAMs of the sigRNAR recognized by the same RdDe (e.g., Cas9 or Cas 12 RdDe). In certain embodiments, the same sigRNAR sites can be introduced in both 5' and 3' junction polynucleotides to permit excision of the INIR12 transgenic locus by a single guide RNA and a single RdDe. In certain embodiments, different sets of distinct sigRNAR sites can be introduced in the 5' and 3' junction polynucleotides of different transgenic loci to permit selective excision of any single transgenic locus by a single guide RNA and a single RdDe directed to the distinct sigRNAR sites that flank the transgenic locus. A sigRNAR site can be created in the plant genome by inserting the heterologous sequence adjacent to a pre-existing PAM sequence using genome editing molecules. A sigRNAR site can be created in the plant genome by inserting the heterologous sequence adjacent to a preexisting PAM sequence using genome editing molecules. A sigRNAR site also can be created in the plant genome by inserting both the heterologous sequence and an associated PAM or sPAM site in a junction polynucleotide. Such insertions can be made in non-transgenic plant genomic DNA of the junction polynucleotide, in the inserted transgenic DNA of the junction polynucleotide, or can span the junction comprising both non-transgenic plant genomic DNA and inserted transgenic DNA of the junction polynucleotide. Such nucleotide insertions can be effected in the plant genome by using gene editing molecules (e.g., RdDe and guide RNAs, RNA dependent nickases and guide RNAs, Zinc Finger nucleases or nickases, or TALE nucleases or nickases) which introduce blunt double stranded breaks or staggered double stranded breaks in the DNA junction polynucleotides. In the case of DNA insertions, the genome editing molecules can also in certain embodiments further comprise a donor DNA template or other DNA template which comprises the heterologous nucleotides for insertion. Guide RNAs can be directed to the junction polynucleotides by using a pre-existing PAM site located within or adjacent to a junction polynucleotide of the transgenic locus.

Also provided herein are allelic variants of any of the INIR12 transgenic loci or DNA molecules provided herein. In certain embodiments, such allelic variants of INIR12 transgenic loci include sequences having at least 85%, 90%, 95%, 98%, or 99% sequence identity across the entire length or at least 20, 40, 100, 500, 1,000, 2,000, 4,000, 6,000, 8,000, 9,000, 10,000, or 10,500 nucleotides of SEQ ID NO: 2, 3, 4, 5, 6, 29, 43, 44, 45, 47, 48, or 49. In certain embodiments, such allelic variants of INIR12 DNA molecules include sequences having at least 85%, 90%, 95%, 98%, or 99% sequence identity across the entire length of SEQ ID NO: 2, 3, 4, 5, 6, 10, 11, 12, 13, 14, 15, 16, 17, 18, 19, 29, 39, 40, 41, 42, 43, 44, 45, 47, 48, 49, or, 50-167.

Also provided are unique transgenic locus excision sites created by excision of INIR12 transgenic loci or selectively excisable INIR12 transgenic loci, DNA molecules comprising the INIR12 transgenic loci or unique fragments thereof (i.e., fragments of an INIR12 locus which are not found in an MIR162 transgenic locus), INIR12 plants comprising the same, biological samples containing the DNA, nucleic acid markers adapted for detecting the DNA molecules, and related methods of identifying maize plants comprising unique INIR12 transgenic locus excision sites and unique fragments of a INIR12 transgenic locus. DNA molecules comprising unique fragments of an INIR12 transgenic locus are diagnostic for the presence of an INIR12 transgenic locus or fragments thereof in a maize plant, maize cell, maize seed, products obtained therefrom (e.g., seed meal or stover), and biological samples. DNA molecules comprising unique fragments of an INIR12 transgenic locus include DNA molecules comprising modified 5' junction polynucleotides. Unique 5' junction polynucleotides of an INIR12 transgenic locus include: (i) a DNA molecule comprising nucleotides corresponding to nucleotides 1080 or 1082 to 1102 or 1104 of SEQ ID NO:1 or SEQ ID NO:46 with the proviso that the DNA molecules is not identical to residues 1080 or 1082 to 1102 or 1104 of SEQ ID NO:1 or SEQ ID NO:46); or (ii) any one of SEQ ID NO: 7, 8, or 9, with the proviso that the DNA molecules is not identical to residues 1080 or 1082 to 1102 or 1104 of SEQ ID NO:1 or SEQ ID NO:46; or (iii) or SEQ ID NO: 10, 11, 12, 13, 14, 15, 16, 17, 18, 19, 39, or 40. DNA molecules comprising unique fragments of an INIR12 transgenic locus also include DNA molecules comprising modified junction polynucleotides containing CgRRS sequences comprising insertions of OgRRS sequences (e.g., a CgRRS element comprising SEQ ID NO: 37). DNA molecules comprising unique fragments of an INIR12 transgenic locus also include DNA molecules comprising deletion junctions corresponding to residues spanning the deletion of the phosphomannose isomerase coding region and operably linked ZmUbiInt promoter in the INIR12 transgenic locus. Such deletion junctions thus comprise one or more nucleotides located between the 35S terminator element and the 5' end of the ZmUbiInt promoter (e.g., nucleotides 5839 to 5858 of SEQ ID NO:1 or SEQ ID NO:46) which are directly joined to (i.e., are contiguous with) nucleotides located between or at the 3' terminus of the pmi coding region and the 5' end of the NOS terminator in a MIR162 locus (e.g., nucleotides 9040 to 9105 of SEQ ID NO:1 or SEQ ID NO:46). Examples of unique INIR12 DNA fragment comprising a such deletion include nucleotides 5821 to 5850 of SEQ ID NO: 2, wherein one or more nucleotides designated n are absent, independently selected from a guanine, a cytosine, an adenine residue, or a thymine residue, comprise or consist of 1 or more nucleotides corresponding to nucleotides 5831 to 5836 of SEQ ID NO:1 or SEQ ID NO:46 and/or comprise or consist of 1 or more nucleotides corresponding to nucleotides 9102 to 9107 of SEQ ID NO:1 or SEQ ID NO:46 junction. Another example of a unique INIR12 DNA fragment comprising such a deletion junction include SEQ ID NO: 25, which corresponds to residues 5821 to 5850 of an INIR12 locus set forth in SEQ ID NO: 6. Another example of a unique INIR12 DNA fragment comprising such a deletion junction include SEQ ID NO: 41 and 42. In certain embodiments, any of the aforementioned unique fragments of an INIR12 transgenic locus comprise DNA molecules of at least about 18, 20, or 24 nucleotides to about 30, 50, 100, or 200 nucleotides in length. Also provided herein are nucleic acid hybridization probes and primers (e.g., for SNP analysis) adapted for detection of INIR12 transgenic loci which can comprise all or part of any of the aforementioned DNA molecules and optionally a detectable label. Methods and reagents (e.g., nucleic acid markers including nucleic acid probes and/or primers) for detecting plants, edited plant genomes, and biological samples containing DNA molecules comprising the transgenic loci excision sites and/or non-essential DNA deletions are also provided herein. Detection of the DNA molecules can be achieved by any combination of nucleic acid amplification (e.g., PCR amplification), hybridization, sequencing, and/or mass-spectrometry based techniques. Methods set forth for detecting junction nucleic acids in unmodified transgenic loci set forth in US 20190136331 and U.S. Pat. No. 9,738,904, both incorporated herein by reference in their entireties, can be adapted for use in detection of the nucleic acids provided herein. In certain embodiments, such detection is achieved by amplification and/or hybridization-based detection methods using a method (e.g., selective amplification primers) and/or probe (e.g., capable of selective hybridization or generation of a specific primer extension product) which specifically recognizes the target DNA molecule (e.g., transgenic locus excision site) but does not recognize DNA from an unmodified transgenic locus. In certain embodiments, the hybridization probes can comprise detectable labels (e.g., fluorescent, radioactive, epitope, and chemiluminescent labels). In certain embodiments, a single nucleotide polymorphism detection assay can be adapted for detection of the target DNA molecule (e.g., transgenic locus excision site). Detection of any of the aforementioned unique DNA fragments comprising SEQ ID NO: 10, 11, 12, 13, 14, 15, 16, 17, 18, 19, 39, 40, 41, and/or 42 in a biological sample indicates that the sample contains material from a INIR12 plant or seed.

Methods provided herein can be used to excise any transgenic locus where the first and second junction sequences comprising the endogenous non-transgenic genomic DNA and the heterologous transgenic DNA which are joined at the site of transgene insertion in the plant genome are known or have been determined. In certain embodiments provided herein, transgenic loci can be removed from crop plant lines to obtain crop plant lines with tailored combinations of transgenic loci and optionally targeted genetic changes. Such first and second junction sequences are readily identified in new transgenic events by inverse PCR techniques using primers which are complementary the inserted transgenic sequences. In certain embodiments, the first and second junction sequences of transgenic loci are published. An example of a transgenic locus which can be improved and used in the methods provided herein is the maize MIR162 transgenic locus. The maize MIR162 transgenic locus and its transgenic junction sequences are also depicted in FIG. 1. Maize plants comprising the MIR162 transgenic locus and seed thereof have been cultivated, been placed in commerce, and have been described in a variety of publications by various governmental bodies. Databases which have compiled descriptions of the MIR162 transgenic locus include the International Service for the Acquisition of Agri-biotech Applications (ISAAA) database (available on the world wide web internet site "isaaa.org/gmapprovaldatabase/event"), the GenBit LLC database (available on the world wide web internet site "genbitgroup.com/en/gmo/gmodatabase"), and the Biosafety Clearing-House (BCH) database (available on the http internet site "bch.cbd.int/database/organisms").

Sequences of the junction polynucleotides as well as the transgenic insert(s) of an original MIR162 transgenic locus which can be improved by the methods provided herein are set forth or otherwise provided in SEQ ID NO: 1, U.S. Pat. No. 8,455,720, the sequence of the MIR162 locus in the deposited seed of ATCC accession No. PTA-8166 (SEQ ID NO: 46), and elsewhere in this disclosure. In certain embodiments provided herein, the MIR162 transgenic locus set forth in SEQ ID NO: 1 or present in the deposited seed of ATCC accession No. PTA-8166 (SEQ ID NO: 46) is referred to as an original MIR162 transgenic locus. The MIR162 transgenic locus set forth in SEQ ID NO:1 encodes the Vip3Aa19 protein. The MIR162 transgenic locus in the deposited seed of ATCC accession No. PTA-8166 (SEQ ID NO: 46) encodes the Vip3Aa20 protein. The Vip3Aa19 and Vip3Aa20 proteins differ by one amino acid residue. The vip3Aa20 gene in SEQ ID NO: 46 encodes isoleucine at position 129 of the Vip3Aa20 protein rather than the methionine residue at position 129 of the Vip3Aa19 protein encoded by the vip3Aa19 gene of SEQ ID NO: 1. Allelic or other variants of the sequence set forth in SEQ ID NO: 1 or SEQ ID NO:46, the patent references set forth therein and incorporated herein by reference in their entireties, and elsewhere in this disclosure which may be present in certain variant MIR162 transgenic plant loci (e.g., progeny of deposited seed of accession No. PTA-8166 which contain allelic variants of SEQ ID NO:1 or SEQ ID NO:46 or progeny originating from transgenic plant cells comprising the original MIR162 transgenic set forth in U.S. Pat. No. 8,455,720 which contain allelic variants of SEQ ID NO:1 or SEQ ID NO:46) can also be improved by identifying sequences in the variants that correspond to the sequences of SEQ ID NO: 1 or SEQ ID NO: 46 by performing a pairwise alignment (e.g., using CLUSTAL O 1.2.4 with default parameters) and making corresponding changes in the allelic or other variant sequences. Such allelic or other variant sequences include sequences having at least 85%, 90%, 95%, 98%, or 99% sequence identity across the entire length or at least 20, 40, 100, 500, 1,000, 2,000, 4,000, 8,000, 10,000, or 10,579 nucleotides of SEQ ID NO: 1 or SEQ ID NO: 46. Also provided are plants, plant parts including seeds, genomic DNA, and/or DNA obtained from INIR12 plants which comprise one or more modifications (e.g., via insertion of a CgRRS in a junction polynucleotide sequence) which provide for selective excision of the INIR12 transgenic locus or a portion thereof (e.g., the Vip3A coding region and operably linked promoter). Such INIR12 transgenic loci can be treated with gene editing molecules (e.g., RdDe and gRNA(s)) to obtain plants wherein a segment comprising, consisting essentially of, or consisting of the INIR12 transgenic locus or a portion thereof (e.g., the Vip3A coding region and operably linked promoter) is deleted. In certain embodiments, the MIR162 transgenic loci set forth in SEQ ID NO:1 or SEQ ID NO:46 and allelic variants thereof are further modified by deletion of a segment of DNA comprising, consisting essentially of, or consisting of a selectable marker gene or portions thereof (e.g, the pmi coding region and operably linked ZmUbi promoter) and/or non-essential DNA (e.g., T-DNA border sequences or anything other than the ZmUbi1::VIP3a::t35S expression cassette) to obtain INIR12 transgenic loci. In certain embodiments, the INIR12 transgenic locus comprises a deletion of the phosphomannose isomerase (PMI) coding region and operably linked ZmUbi promoter which are in a MIR162 transgenic locus. Also provided herein are methods of detecting plants, genomic DNA, and/or DNA obtained from plants comprising a INIR12 transgenic locus which contains one or more of a CgRRS, deletions of selectable marker genes, deletions of non-essential DNA, and/or a transgenic locus excision site. A first junction polynucleotide of a MIR162 transgenic locus can comprise either one of the junction polynucleotides found at the 5' end or the 3' end of any one of the sequences set forth in SEQ ID NO:1 or SEQ ID NO:46, allelic variants thereof, or other variants thereof. An OgRRS can be found within non-transgenic DNA, transgenic DNA, or a combination thereof in either one of the junction polynucleotides of any one of SEQ ID NO:1 or SEQ ID NO:46, allelic variants thereof, or other variants thereof. A second junction polynucleotide of a transgenic locus can comprise either one of the junction polynucleotides found at the 5' or 3' end of any one of the sequences set forth in SEQ ID NO:1 or SEQ ID NO:46, allelic variants thereof, or other variants thereof. A CgRRS can be introduced within transgenic, non-transgenic DNA, or a combination thereof of either one of the junction polynucleotides of any one of SEQ ID NO:1 or SEQ ID NO:46, allelic variants thereof, or other variants thereof to obtain an INIR12 transgenic locus. In certain embodiments, the OgRRS is found in non-transgenic DNA or transgenic DNA of the 5' junction polynucleotide of a transgenic locus of any one of SEQ ID NO:1 or SEQ ID NO:46, allelic variants thereof, or other variants thereof and the corresponding CgRRS is introduced into the transgenic DNA, non-transgenic DNA, or a combination thereof in the 3' junction polynucleotide of the MIR162 transgenic locus of SEQ ID NO: 1, SEQ ID NO: 46, allelic variants thereof, or other variants thereof to obtain an INIR12 transgenic locus. In other embodiments, the OgRRS is found in non-transgenic DNA or transgenic DNA of the 3' junction polynucleotide of the MIR162 transgenic locus of any one of SEQ ID NO: 1, SEQ ID NO: 46, allelic variants thereof, or other variants thereof and the corresponding CgRRS is introduced into the transgenic DNA, non-transgenic DNA, or a combination thereof in the 5' junction polynucleotide of the transgenic locus of SEQ ID NO: 1, SEQ ID NO: 46, allelic variants thereof, or other variants thereof to obtain an INIR12 transgenic locus. Examples of INIR12 transgenic loci comprising a CgRRS insertion in a 5' junction polynucleotide include those set forth in SEQ ID NO: 44 (encoding Vip3Aa19), SEQ ID NO: 47 (encoding Vip3Aa20), and SEQ ID NO: 48 (encoding Vip3Aa20).

In certain embodiments, the CgRRS is comprised in whole or in part of an exogenous DNA molecule that is introduced into a DNA junction polynucleotide by genome editing. In certain embodiments, the guide RNA hybridization site of the CgRRS is operably linked to a pre-existing PAM site in the transgenic DNA or non-transgenic DNA of the transgenic plant genome. In other embodiments, the guide RNA hybridization site of the CgRRS is operably linked to a new PAM site that is introduced in the DNA junction polynucleotide by genome editing. A CgRRS can be located in non-transgenic plant genomic DNA of a DNA junction polynucleotide of an INIR12 transgenic locus, in transgenic DNA of a DNA junction polynucleotide of an INIR12 transgenic locus or can span the junction of the transgenic and non-transgenic DNA of a DNA junction polynucleotide of an INIR12 transgenic locus. An OgRRS can likewise be located in non-transgenic plant genomic DNA of a DNA junction polynucleotide of an INIR12 transgenic locus, in transgenic DNA of a DNA junction polynucleotide of an INIR12 transgenic locus or can span the junction of the transgenic and non-transgenic DNA of a DNA junction polynucleotide of an INIR12 transgenic locus.

Methods provided herein can be used in a variety of breeding schemes to obtain elite crop plants comprising subsets of desired modified transgenic loci comprising an OgRRS and a CgRRS operably linked to junction polynucleotide sequences and transgenic loci excision sites where undesired transgenic loci or portions thereof have been removed (e.g., by use of the OgRRS and a CgRRS). Such methods are useful at least insofar as they allow for production of distinct useful donor plant lines each having unique sets of modified transgenic loci and, in some instances, targeted genetic changes that are tailored for distinct geographies and/or product offerings. In an illustrative and non-limiting example, a different product lines comprising transgenic loci conferring only two of three types of herbicide tolerance (e.g., glyphosate, glufosinate, and dicamba) can be obtained from a single donor line comprising three distinct transgenic loci conferring resistance to all three herbicides. In certain aspects, plants comprising the subsets of undesired transgenic loci and transgenic loci excision sites can further comprise targeted genetic changes. Such elite crop plants can be inbred plant lines or can be hybrid plant lines. In certain embodiments, at least two transgenic loci (e.g., transgenic loci including an INIR12 and another modified transgenic locus wherein an OgRRS and a CgRRS site is operably linked to a first and a second junction sequence and optionally a selectable marker gene and/or non-essential DNA are deleted) are introgressed into a desired donor line comprising elite crop plant germplasm and then subjected to genome editing molecules to recover plants comprising one of the two introgressed transgenic loci as well as a transgenic loci excision site introduced by excision of the other transgenic locus or portion thereof by the genome editing molecules. In certain embodiments, the genome editing molecules can be used to remove a transgenic locus and introduce targeted genetic changes in the crop plant genome. Introgression can be achieved by backcrossing plants comprising the transgenic loci to a recurrent parent comprising the desired elite germplasm and selecting progeny with the transgenic loci and recurrent parent germplasm. Such backcrosses can be repeated and/or supplemented by molecular assisted breeding techniques using SNP or other nucleic acid markers to select for recurrent parent germplasm until a desired recurrent parent percentage is obtained (e.g., at least about 95%, 96%, 97%, 98%, or 99% recurrent parent percentage). A non-limiting, illustrative depiction of a scheme for obtaining plants with both subsets of transgenic loci and the targeted genetic changes is shown in the FIG. 2 (bottom "Alternative" panel), where two or more of the transgenic loci ("Event" in FIG. 2) are provided in Line A and then moved into elite crop plant germplasm by introgression. In the non-limiting FIG. 2 illustration, introgression can be achieved by crossing a "Line A" comprising two or more of the modified transgenic loci to the elite germplasm and then backcrossing progeny of the cross comprising the transgenic loci to the elite germplasm as the recurrent parent) to obtain a "Universal Donor" (e.g. Line A+ in FIG. 2) comprising two or more of the modified transgenic loci. This elite germplasm containing the modified transgenic loci (e.g. "Universal Donor" of FIG. 2) can then be subjected to genome editing molecules which can excise at least one of the transgenic loci ("Event Removal" in FIG. 2) and introduce other targeted genetic changes ("GE" in FIG. 2) in the genomes of the elite crop plants containing one of the transgenic loci and a transgenic locus excision site corresponding to the removal site of one of the transgenic loci. Such selective excision of transgenic loci or portion thereof can be effected by contacting the genome of the plant comprising two transgenic loci with gene editing molecules (e.g., RdDe and gRNAs, TALENS, and/or ZFN) which recognize one transgenic loci but not another transgenic loci. Genome editing molecules that provide for selective excision of a first modified transgenic locus comprising an OgRRS and a CgRRS include a gRNA that hybridizes to the OgRRS and CgRRS of the first modified transgenic locus and an RdDe that recognizes the gRNA/OgRRS and gRNA/CgRRS complexes. Distinct plant lines with different subsets of transgenic loci and desired targeted genetic changes are thus recovered (e.g., "Line B-1," "Line B-2," and "Line B-3" in FIG. 2). In certain embodiments, it is also desirable to bulk up populations of inbred elite crop plants or their seed comprising the subset of transgenic loci and a transgenic locus excision site by selfing. In certain embodiments, inbred progeny of the selfed maize plants comprising the INIR12 transgenic loci can be used as a pollen donor or recipient for hybrid seed production. Such hybrid seed and the progeny grown therefrom can comprise a subset of desired transgenic loci and a transgenic loci excision site.

Hybrid plant lines comprising elite crop plant germplasm, at least one transgenic locus and at least one transgenic locus excision site, and in certain aspects, additional targeted genetic changes are also provided herein. Methods for production of such hybrid seed can comprise crossing elite crop plant lines where at least one of the pollen donor or recipient comprises at least the transgenic locus and a transgenic locus excision site and/or additional targeted genetic changes. In certain embodiments, the pollen donor and recipient will comprise germplasm of distinct heterotic groups and provide hybrid seed and plants exhibiting heterosis. In certain embodiments, the pollen donor and recipient can each comprise a distinct transgenic locus which confers either a distinct trait (e.g., herbicide tolerance or insect resistance), a different type of trait (e.g., tolerance to distinct herbicides or to distinct insects such as coleopteran or lepidopteran insects), or a different mode-of-action for the same trait (e.g., resistance to coleopteran insects by two distinct modes-of-action or resistance to lepidopteran insects by two distinct modes-of-action). In certain embodiments, the pollen recipient will be rendered male sterile or conditionally male sterile. Methods for inducing male sterility or conditional male sterility include emasculation (e.g., detasseling), cytoplasmic male sterility, chemical hybridizing agents or systems, a transgenes or transgene systems, and/or mutation(s) in one or more endogenous plant genes. Descriptions of various male sterility systems that can be adapted for use with the elite crop plants provided herein are described in Wan et al. Molecular Plant; 12, 3, (2019):321-342 as well as in U.S. Pat. No. 8,618,358; US 20130031674; and US 2003188347.

In certain embodiments, it will be desirable to use genome editing molecules to make modified transgenic loci by introducing a CgRRS into the transgenic loci, to excise modified transgenic loci comprising an OgRRS and a CgRRS, and/or to make targeted genetic changes in elite crop plant or other germplasm. Techniques for effecting genome editing in crop plants (e.g., maize) include use of morphogenic factors such as Wuschel (WUS), Ovule Development Protein (ODP), and/or Babyboom (BBM) which can improve the efficiency of recovering plants with desired genome edits. In some aspects, the morphogenic factor comprises WUS1, WUS2, WUS3, WOX2A, WOX4, WOX5, WOX9, BBM2, BMN2, BMN3, and/or ODP2. In certain embodiments, compositions and methods for using WUS, BBM, and/or ODP, as well as other techniques which can be adapted for effecting genome edits in elite crop plant and other germplasm, are set forth in US 20030082813, US 20080134353, US 20090328252, US 20100100981, US 20110165679, US 20140157453, US 20140173775, and US 20170240911, which are each incorporated by reference in their entireties. In certain embodiments, the genome edits can be effected in regenerable plant parts (e.g., plant embryos) of elite crop plants by transient provision of gene editing molecules or polynucleotides encoding the same and do not necessarily require incorporating a selectable marker gene into the plant genome (e.g., US 20160208271 and US 20180273960, both incorporated herein by reference in their entireties; Svitashev et al. Nat Commun. 2016; 7:13274).

In certain embodiments, edited transgenic plant genomes, transgenic plant cells, parts, or plants containing those genomes, and DNA molecules obtained therefrom, can comprise a desired subset of transgenic loci and/or comprise at least one transgenic locus excision site. In certain embodiments, a segment comprising an INIR12 transgenic locus comprising an OgRRS in non-transgenic DNA of a 1$^{st}$ junction polynucleotide sequence and a CgRRS in a 2$^{nd}$ junction polynucleotide sequence is deleted with a gRNA and RdDe that recognize the OgRRS and the CgRRS to produce an INIR12 transgenic locus excision site. In certain embodiments, a segment comprising an INIR12 transgenic locus comprising a sPAM and/or a sigRNAR site in a 1$^{st}$ junction polynucleotide sequence and a sPAM and/or a sigRNAR in a 2$^{nd}$ junction polynucleotide sequence is deleted with at least one gRNA and RdDe that recognize the sPAM and/or a sigRNAR to produce an INIR12 transgenic locus excision site. In certain embodiments, the transgenic locus excision site can comprise a contiguous segment of DNA comprising at least 10 base pairs of DNA that is telomere proximal to the deleted segment of the transgenic locus and at least 10 base pairs of DNA that is centromere proximal to the deleted segment of the transgenic locus wherein the transgenic DNA (i.e., the heterologous DNA) that has been inserted into the crop plant genome has been deleted. In certain embodiments where a segment comprising a transgenic locus has been deleted, the transgenic locus excision site can comprise a contiguous segment of DNA comprising at least 10 base pairs DNA that is telomere proximal to the deleted segment of the transgenic locus and at least 10 base pairs of DNA that is centromere proximal DNA to the deleted segment of the transgenic locus wherein the heterologous transgenic DNA and at least 1, 2, 5, 10, 20, 50, or more base pairs of endogenous DNA located in a 5' junction sequence and/or in a 3' junction sequence of the original transgenic locus that has been deleted. In such embodiments where DNA comprising the transgenic locus is deleted, a transgenic locus excision site can comprise at least 10 base pairs of DNA that is telomere proximal to the deleted segment of the transgenic locus and at least 10 base pairs of DNA that is centromere proximal to the deleted segment of the transgenic locus wherein all of the transgenic DNA is absent and either all or less than all of the endogenous DNA flanking the transgenic DNA sequences are present. In certain embodiments where a segment consisting essentially of an original transgenic locus has been deleted, the transgenic locus excision site can be a contiguous segment of at least 10 base pairs of DNA that is telomere proximal to the deleted segment of the transgenic locus and at least 10 base pairs of DNA that is centromere proximal to the deleted segment of the transgenic locus wherein less than all of the heterologous transgenic DNA that has been inserted into the crop plant genome is excised. In certain aforementioned embodiments where a segment consisting essentially of an original transgenic locus has been deleted, the transgenic locus excision site can thus contain at least 1 base pair of DNA or 1 to about 2 or 5, 8, 10, 20, or 50 base pairs of DNA comprising the telomere proximal and/or centromere proximal heterologous transgenic DNA that has been inserted into the crop plant genome. In certain embodiments where a segment consisting of an original transgenic locus has been deleted, the transgenic locus excision site can contain a contiguous segment of DNA comprising at least 10 base pairs of DNA that is telomere proximal to the deleted segment of the transgenic locus and at least 10 base pairs of DNA that is centromere proximal to the deleted segment of the transgenic locus wherein the heterologous transgenic DNA that has been inserted into the crop plant genome is deleted. In certain embodiments where DNA consisting of the transgenic locus is deleted, a transgenic locus excision site can comprise at least 10 base pairs of DNA that is telomere proximal to the deleted segment of the transgenic locus and at least 10 base pairs of DNA that is centromere proximal to the deleted segment of the transgenic locus wherein all of the heterologous transgenic DNA that has been inserted into the crop plant genome is deleted and all of the endogenous DNA flanking the heterologous sequences of the transgenic locus is present. In any of the aforementioned embodiments or in other embodiments, the continuous segment of DNA comprising the transgenic locus excision site can further comprise an insertion of 1 to about 2, 5, 10, 20, or more nucleotides between the DNA that is telomere proximal to the deleted segment of the transgenic locus and the DNA that is centromere proximal to the deleted segment of the transgenic locus. Such insertions can result either from endogenous DNA repair and/or recombination activities at the double stranded breaks introduced at the excision site and/or from deliberate insertion of an oligonucleotide. Plants, edited plant genomes, biological samples, and DNA molecules (e.g., including isolated or purified DNA molecules) comprising the INIR12 transgenic loci excision sites are provided herein.

In other embodiments, a segment comprising a INIR12 transgenic locus (e.g., a transgenic locus comprising an OgRRS in non-transgenic DNA of a $1^{st}$ junction sequence and a CgRRS in a $2^{nd}$ junction sequence) can be deleted with a gRNA and RdDe that recognize the OgRRS and the CgRRS and replaced with DNA comprising the endogenous non-transgenic plant genomic DNA present in the genome prior to transgene insertion. A non-limiting example of such replacements can be visualized in FIG. 3C, where the donor DNA template can comprise the endogenous non-transgenic plant genomic DNA present in the genome prior to transgene insertion along with sufficient homology to non-transgenic DNA on each side of the excision site to permit homology-directed repair. In certain embodiments, the endogenous non-transgenic plant genomic DNA present in the genome prior to transgene insertion can be at least partially restored. In certain embodiments, the endogenous non-transgenic plant genomic DNA present in the genome prior to transgene insertion can be essentially restored such that no more than about 5, 10, or 20 to about 50, 80, or 100 nucleotides are changed relative to the endogenous DNA at the essentially restored excision site.

In certain embodiments, edited transgenic plant genomes and transgenic plant cells, plant parts, or plants containing those edited genomes, comprising a modification of an original transgenic locus, where the modification comprises an OgRRS and a CgRRS which are operably linked to a $1^{st}$ and a $2^{nd}$ junction sequence, respectively or irrespectively, and optionally further comprise a deletion of a segment of the original transgenic locus. In certain embodiments, the modification comprises two or more separate deletions and/or there is a modification in two or more original transgenic plant loci. In certain embodiments, the deleted segment comprises, consists essentially of, or consists of a segment of non-essential DNA in the transgenic locus. Illustrative examples of non-essential DNA include but are not limited to synthetic cloning site sequences, duplications of transgene sequences; fragments of transgene sequences, and *Agrobacterium* right and/or left border sequences. In certain embodiments, the non-essential DNA is a duplication and/or fragment of a promoter sequence and/or is not the promoter sequence operably linked in the cassette to drive expression of a transgene. In certain embodiments, excision of the non-essential DNA improves a characteristic, functionality, and/or expression of a transgene of the transgenic locus or otherwise confers a recognized improvement in a transgenic plant comprising the edited transgenic plant genome. In certain embodiments, the non-essential DNA does not comprise DNA encoding a selectable marker gene. In certain embodiments of an edited transgenic plant genome, the modification comprises a deletion of the non-essential DNA and a deletion of a selectable marker gene. The modification producing the edited transgenic plant genome could occur by excising both the non-essential DNA and the selectable marker gene at the same time, e.g., in the same modification step, or the modification could occur step-wise. For example, an edited transgenic plant genome in which a selectable marker gene has previously been removed from the transgenic locus can comprise an original transgenic locus from which a non-essential DNA is further excised and vice versa. In certain embodiments, the modification comprising deletion of the non-essential DNA and deletion of the selectable marker gene comprises excising a single segment of the original transgenic locus that comprises both the non-essential DNA and the selectable marker gene. Such modification would result in one excision site in the edited transgenic genome corresponding to the deletion of both the non-essential DNA and the selectable marker gene. In certain embodiments, the modification comprising deletion of the non-essential DNA and deletion of the selectable marker gene comprises excising two or more segments of the original transgenic locus to achieve deletion of both the non-essential DNA and the selectable marker gene. Such modification would result in at least two excision sites in the edited transgenic genome corresponding to the deletion of both the non-essential DNA and the selectable marker gene. In certain embodiments of an edited transgenic plant genome, prior to excision, the segment to be deleted is flanked by operably linked protospacer adjacent motif (PAM) sites in the original or unmodified transgenic locus and/or the segment to be deleted encompasses an operably linked PAM site in the original or unmodified transgenic locus. In certain embodiments, following excision of the segment, the resulting edited transgenic plant genome comprises PAM sites flanking the deletion site in the modified transgenic locus. In certain embodiments of an edited transgenic plant genome, the modification comprises a modification of a MIR162 transgenic locus.

In certain embodiments, improvements in a transgenic plant locus are obtained by introducing a new cognate guide RNA recognition site (CgRRS) which is operably linked to a DNA junction polynucleotide of the transgenic locus in the transgenic plant genome. Such CgRRS sites can be recognized by RdDe and a single suitable guide RNA directed to the CgRRS and the originator gRNA Recognition Site (OgRRS) to provide for cleavage within the junction polynucleotides which flank an INIR12 transgenic locus. In certain embodiments, the CgRRS/gRNA and OgRRS/gRNA hybridization complexes are recognized by the same class of RdDe (e.g., Class 2 type II or Class 2 type V) or by the same RdDe (e.g., both the CgRRS/gRNA and OgRRS/gRNA hybridization complexes recognized by the same Cas9 or Cas 12 RdDe). Such CgRRS and OgRRS can be recognized by RdDe and suitable guide RNAs containing crRNA sufficiently complementary to the guide RNA hybridization site DNA sequences adjacent to the PAM site of the CgRRS and the OgRRS to provide for cleavage within or near the two junction polynucleotides. Suitable guide RNAs can be in the form of a single gRNA comprising a crRNA or in the form of a crRNA/tracrRNA complex. In the case of the OgRRS site, the PAM and guide RNA hybridization site are endogenous DNA polynucleotide molecules found in the plant genome. In certain embodiments where the CgRRS is introduced into the plant genome by genome editing, gRNA hybridization site polynucleotides introduced at the CgRRS are at least 17 or 18 nucleotides in length and are complementary to the crRNA of a guide RNA. In certain embodiments, the gRNA hybridization site sequence of the OgRRS and/or the CgRRS is about 17 or 18 to about 24 nucleotides in length. The gRNA hybridization site sequence of the OgRRS and the gRNA hybridization site of the CgRRS can be of different lengths or comprise different sequences so long as there is sufficient complementarity to permit hybridization by a single gRNA and recognition by a RdDe that recognizes and cleaves DNA at the gRNA/OgRRS and gRNA/CgRRS complex. In certain embodiments, the guide RNA hybridization site of the CgRRS comprise about a 17 or 18 to about 24 nucleotide sequence which is identical to the guide RNA hybridization site of the OgRRS. In other embodiments, the guide RNA hybridization site of the CgRRS comprise about a 17 or 18 to about 24 nucleotide sequence which has one, two, three, four, or five nucleotide insertions, deletions or substitutions when compared to the guide RNA hybridization site of the OgRRS. Certain CgRRS comprising a gRNA hybridization site containing has one, two, three, four, or five nucleotide insertions, deletions or substitutions when compared to the guide RNA hybridization site of the OgRRS can undergo hybridization with a gRNA which is complementary to the OgRRS gRNA hybridization site and be cleaved by certain RdDe. Examples of mismatches between gRNAs and guide RNA hybridization sites which allow for RdDe recognition and cleavage include mismatches resulting from both nucleotide insertions and deletions in the DNA which is hybridized to the gRNA (e.g., Lin et al., doi: 10.1093/nar/gku402). In certain embodiments, an operably linked PAM site is co-introduced with the gRNA hybridization site polynucleotide at the CgRRS. In certain embodiments, the gRNA hybridization site polynucleotides are introduced at a position adjacent to a resident endogenous PAM sequence in the junction polynucleotide sequence to form a CgRRS where the gRNA hybridization site polynucleotides are operably linked to the endogenous PAM site. In certain embodiments, non-limiting features of the OgRRS, CgRRS, and/or the gRNA hybridization site polynucleotides thereof include: (i) absence of significant homology or sequence identity (e.g., less than 50% sequence identity across the entire length of the OgRRS, CgRRS, and/or the gRNA hybridization site sequence) to any other endogenous or transgenic sequences present in the transgenic plant genome or in other transgenic genomes of the maize plant being transformed and edited; (ii) absence of significant homology or sequence identity (e.g., less than 50% sequence identity across the entire length of the sequence) of a sequence of a first OgRRS and a first CgRRS to a second OgRRS and a second CgRRS which are operably linked to junction polynucleotides of a distinct transgenic locus; (iii) the presence of some sequence identity (e.g., about 25%, 40%, or 50% to about 60%, 70%, or 80%) between the OgRRS sequence and endogenous sequences present at the site where the CgRRS sequence is introduced; and/or (iv) optimization of the gRNA hybridization site polynucleotides for recognition by the RdDe and guide RNA when used in conjunction with a particular PAM sequence. In certain embodiments, the first and second OgRRS as well as the first and second CgRRS are recognized by the same class of RdDe (e.g., Class 2 type II or Class 2 type V) or by the same RdDe (e.g., Cas9 or Cas 12 RdDe). In certain embodiments, the first OgRRS site in a first junction polynucleotide and the CgRRS introduced in the second junction polynucleotide to permit excision of a first transgenic locus by a first single guide RNA and a single RdDe. Such nucleotide insertions or genome edits used to introduce CgRRS in a transgenic plant genome can be effected in the plant genome by using gene editing molecules (e.g., RdDe and guide RNAs, RNA dependent nickases and guide RNAs, Zinc Finger nucleases or nickases, or TALE nucleases or nickases) which introduce blunt double stranded breaks or staggered double stranded breaks in the DNA junction polynucleotides. In the case of DNA insertions, the genome editing molecules can also in certain embodiments further comprise a donor DNA template or other DNA template which comprises the heterologous nucleotides for insertion to form the CgRRS. Guide RNAs can be directed to the junction polynucleotides by using a pre-existing PAM site located within or adjacent to a junction polynucleotide of the transgenic locus. Non-limiting examples of such pre-existing PAM sites present in junction polynucleotides, which can be used either in conjunction with an inserted heterologous sequence to form a CgRRS or which can be used to create a double stranded break to insert or create a CgRRS, include PAM sites recognized by a Cas12a enzyme. Non-limiting examples where a CgRRS are created in a DNA sequence are illustrated in Example 2.

Transgenic loci comprising OgRRS and CgRRS in a first and a second junction polynucleotides can be excised from the genomes of transgenic plants by contacting the transgenic loci with RdDe or RNA directed nickases, and a suitable guide RNA directed to the OgRRS and CgRRS. A non-limiting example where a modified transgenic locus is excised from a plant genome by use of a gRNA and an RdDe that recognizes an OgRRS/gRNA and a CgRRS/gRNA complex and introduces dsDNA breaks in both junction polynucleotides and repaired by NHEJ is depicted in FIG. 3B. In the depicted example set forth in FIG. 3B, the OgRRS site and the CgRRS site are absent from the plant chromosome comprising the transgene excision site that results from the process. In other embodiments provided herein where a modified transgenic locus is excised from a plant genome by use of a gRNA and an RdDe that recognizes an OgRRS/gRNA and a CgRRS/gRNA complex and repaired by NHEJ or microhomology-mediated end joining (MMEJ), the OgRRS and/or other non-transgenic sequences that were originally present prior to transgene insertion are at least partially or essentially restored.

In certain embodiments, edited transgenic plant genomes provided herein can lack one or more selectable and/or scoreable markers found in an original event (transgenic locus). Original MIR162 transgenic loci (events), including those set forth in SEQ ID NO: 1), U.S. Pat. No. 8,455,720, the sequence of the MIR162 locus in the deposited seed of accession No. PTA-8166 (SEQ ID NO: 46) and progeny thereof, contain a selectable phosphomannose isomerase (pmi) transgene marker conferring an ability to grow on mannose. Transgenes encoding a phosphomannose isomerase (pmi) can confer the ability to grow on mannose. In certain embodiments provided herein, the DNA element comprising, consisting essentially of, or consisting of the ZmUbi promoter which is operably linked to a pmi coding region of an MIR162 transgenic locus is absent from an INIR12 transgenic locus, or scoreable marker transgenes can be excised from an original transgenic locus by contacting the transgenic locus with one or more gene editing molecules which introduce double stranded breaks in the transgenic locus at the 5' and 3' end of the expression cassette comprising the selectable marker transgene (e.g., an RdDe and guide RNAs directed to PAM sites located at the 5' and 3' end of the expression cassette comprising the selectable marker transgenes) and selecting for plant cells, plant parts, or plants wherein the selectable or scoreable marker has been excised. In certain embodiments, the selectable or scoreable marker transgene can be inactivated. Inactivation can be achieved by modifications including insertion, deletion, and/or substitution of one or more nucleotides in a promoter element, 5' or 3' untranslated region (UTRs), intron, coding region, and/or 3' terminator and/or polyadenylation site of the selectable marker transgene. Such modifications can inactivate the selectable or scoreable marker transgene by eliminating or reducing promoter activity, introducing a missense mutation, and/or introducing a premature stop codon. In certain embodiments, the selectable and/or scoreable marker transgene can be replaced by an introduced transgene. In certain embodiments, an original transgenic locus that was contacted with gene editing molecules which introduce double stranded breaks in the transgenic locus at the 5' and 3' end of the expression cassette comprising the selectable marker and/or scoreable transgene can also be contacted with a suitable donor DNA template comprising an expression cassette flanked by DNA homologous to remaining DNA in the transgenic locus located 5' and 3' to the selectable marker excision site. In certain embodiments, a coding region of the selectable and/or scoreable marker transgene can be replaced with another coding region such that the replacement coding region is operably linked to the promoter and 3' terminator or polyadenylation site of the selectable and/or scoreable marker transgene.

In certain embodiments, edited transgenic plant genomes provided herein can comprise additional new introduced transgenes (e.g., expression cassettes) inserted into the transgenic locus of a given event. Introduced transgenes inserted at the transgenic locus of an event subsequent to the event's original isolation can be obtained by inducing a double stranded break at a site within an original transgenic locus (e.g., with genome editing molecules including an RdDe and suitable guide RNA(s); a suitable engineered zinc-finger nuclease; a TALEN protein and the like) and providing an exogenous transgene in a donor DNA template which can be integrated at the site of the double stranded break (e.g. by homology-directed repair (HDR) or by non-homologous end-joining (NHEJ)). In certain embodiments, an OgRRS and a CgRRS located in a 1st junction polynucleotide and a 2nd junction polynucleotide, respectively, can be used to delete the transgenic locus and replace it with one or more new expression cassettes. In certain embodiments, such deletions and replacements are effected by introducing dsDNA breaks in both junction polynucleotides and providing the new expression cassettes on a donor DNA template (e.g., in FIG. 3C, the donor DNA template can comprise an expression cassette flanked by DNA homologous to non-transgenic DNA located telomere proximal and centromere proximal to the excision site). Suitable expression cassettes for insertion include DNA molecules comprising promoters which are operably linked to DNA encoding proteins and/or RNA molecules which confer useful traits which are in turn operably linked to polyadenylation sites or terminator elements. In certain embodiments, such expression cassettes can also comprise 5' UTRs, 3' UTRs, and/or introns. Useful traits include biotic stress tolerance (e.g., insect resistance, nematode resistance, or disease resistance), abiotic stress tolerance (e.g., heat, cold, drought, and/or salt tolerance), herbicide tolerance, and quality traits (e.g., improved fatty acid compositions, protein content, starch content, and the like). Suitable expression cassettes for insertion include expression cassettes which confer insect resistance, herbicide tolerance, biofuel use, or male sterility traits contained in any of the transgenic events set forth in US Patent Application Public. Nos. 20090038026, 20130031674, 20150361446, 20170088904, 20150267221, 201662346688, and 20200190533 as well as in U.S. Pat. Nos. 6,342,660, 7,323,556, 8,575,434, 6,040,497, 8,759,618, 7,157,281, 6,852,915, 7,705,216, 10,316,330, 8,618,358, 8,450,561, 8,212,113, 9,428,765, 7,897,748, 8,273,959, 8,093,453, 8,901,378, 9,994,863, 7,928,296, and 8,466,346, each of which are incorporated herein by reference in their entireties.

In certain embodiments, INIR12 plants provided herein, including plants with one or more transgenic loci, modified transgenic loci, and/or comprising transgenic loci excision sites can further comprise one or more targeted genetic changes introduced by one or more of gene editing molecules or systems. Also provided are methods where the targeted genetic changes are introduced and one or more transgenic loci are removed from plants either in series or in parallel (e.g., as set forth in the non-limiting illustration in FIG. 2, bottom "Alternative" panel, where "GE" can represent targeted genetic changes induced by gene editing molecules and "Event Removal" represents excision of one or more transgenic loci with gene editing molecules). Such targeted genetic changes include those conferring traits such as improved yield, improved food and/or feed characteristics (e.g., improved oil, starch, protein, or amino acid quality or quantity), improved nitrogen use efficiency, improved biofuel use characteristics (e.g., improved ethanol production), male sterility/conditional male sterility systems (e.g., by targeting endogenous MS26, MS45 and MSCA1 genes), herbicide tolerance (e.g., by targeting endogenous ALS, EPSPS, HPPD, or other herbicide target genes), delayed flowering, non-flowering, increased biotic stress resistance (e.g., resistance to insect, nematode, bacterial, or fungal damage), increased abiotic stress resistance (e.g., resistance to drought, cold, heat, metal, or salt), enhanced lodging resistance, enhanced growth rate, enhanced biomass, enhanced tillering, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and increased meristem size in comparison to a control plant lacking the targeted genetic change. Types of targeted genetic changes that can be introduced include insertions, deletions, and substitutions of one or more nucleotides in the crop plant genome. Sites in endogenous plant genes for the targeted genetic changes include promoter, coding, and non-coding regions (e.g., 5' UTRs, introns, splice donor and acceptor sites and 3' UTRs). In certain embodiments, the targeted genetic change comprises an insertion of a regulatory or other DNA sequence in an endogenous plant gene. Non-limiting examples of regulatory sequences which can be inserted into endogenous plant genes with gene editing molecules to effect targeted genetic changes which confer useful phenotypes include those set forth in US Patent Application Publication 20190352655, which is incorporated herein by reference in its entirety, such as: (a) auxin response element (AuxRE) sequence; (b) at least one D1-4 sequence (Ulmasov et al. (1997) Plant Cell, 9:1963-1971), (c) at least one DR5 sequence (Ulmasov et al. (1997) Plant Cell, 9:1963-1971); (d) at least one m5-DR5 sequence (Ulmasov et al. (1997) Plant Cell, 9:1963-1971); (e) at least one P3 sequence; (f) a small RNA recognition site sequence bound by a corresponding small RNA (e.g., an siRNA, a microRNA (miRNA), a trans-acting siRNA as described in U.S. Pat. No. 8,030,473, or a phased sRNA as described in U.S. Pat. No. 8,404,928; both of these cited patents are incorporated by reference herein); (g) a microRNA (miRNA) recognition site sequence; (h) the sequence recognizable by a specific binding agent includes a microRNA (miRNA) recognition sequence for an engineered miRNA wherein the specific binding agent is the corresponding engineered mature miRNA; (i) a transposon recognition sequence; (j) a sequence recognized by an ethylene-responsive element binding-factor-associated amphiphilic repression (EAR) motif; (k) a splice site sequence (e.g., a donor site, a branching site, or an acceptor site; see, for example, the splice sites and splicing signals set forth in the internet site lemur[dot]amu[dot]edu[dot]pl/share/ERISdb/home.html); (l) a recombinase recognition site sequence that is recognized by a site-specific recombinase; (m) a sequence encoding an RNA or amino acid aptamer or an RNA riboswitch, the specific binding agent is the corresponding ligand, and the change in expression is upregulation or downregulation; (n) a hormone responsive element recognized by a nuclear receptor or a hormone-binding domain thereof; (o) a transcription factor binding sequence; and (p) a polycomb response element (see Xiao et al. (2017) Nature Genetics, 49:1546-1552, doi: 10.1038/ng.3937). Non limiting examples of target maize genes that can be subjected to targeted gene edits to confer useful traits include: (a) ZmIPK1 (herbicide tolerant and phytate reduced maize; Shukla et al., Nature. 2009; 459:437-41); (b) ZmGL2 (reduced epicuticular wax in leaves; Char et al. Plant Biotechnol J. 2015; 13:1002); (c) ZmMTL (induction of haploid plants; Kelliher et al. Nature. 2017; 542:105); (d) Wx1 (high amylopectin content; US 20190032070; incorporated herein by reference in its entirety); (e) TMS5 (thermosensitive male sterile; Li et al. J Genet Genomics. 2017; 44:465-8); (f) ALS (herbicide tolerance; Svitashev et al.; Plant Physiol. 2015; 169:931-45); and (g) ARGOS8 (drought stress tolerance; Shi et al., Plant Biotechnol J. 2017; 15:207-16). Non-limiting examples of target genes in crop plants including maize which can be subjected to targeted genetic changes which confer useful phenotypes include those set forth in US Patent Application Nos. 20190352655, 20200199609, 20200157554, and 20200231982, which are each incorporated herein in their entireties; and Zhang et al. (Genome Biol. 2018; 19: 210).

Gene editing molecules of use in methods provided herein include molecules capable of introducing a double-strand break ("DSB") or single-strand break ("SSB") in double-stranded DNA, such as in genomic DNA or in a target gene located within the genomic DNA as well as accompanying guide RNA or donor DNA template polynucleotides. Examples of such gene editing molecules include: (a) a nuclease comprising an RNA-guided nuclease, an RNA-guided DNA endonuclease or RNA directed DNA endonuclease (RdDe), a class 1 CRISPR type nuclease system, a type II Cas nuclease, a Cas9, a nCas9 nickase, a type V Cas nuclease, a Cas12a nuclease, a nCas12a nickase, a Cas12d (CasY), a Cas12e (CasX), a Cas12b (C2c1), a Cas12c (C2c3), a Cas12i, a Cas12j, a Cas14, an engineered nuclease, a codon-optimized nuclease, a zinc-finger nuclease (ZFN) or nickase, a transcription activator-like effector nuclease (TAL-effector nuclease or TALEN) or nickase (TALE-nickase), an Argonaute, and a meganuclease or engineered meganuclease; (b) a polynucleotide encoding one or more nucleases capable of effectuating site-specific alteration (including introduction of a DSB or SSB) of a target nucleotide sequence; (c) a guide RNA (gRNA) for an RNA-guided nuclease, or a DNA encoding a gRNA for an RNA-guided nuclease; (d) donor DNA template polynucleotides; and (e) other DNA templates (dsDNA, ssDNA, or combinations thereof) suitable for insertion at a break in genomic DNA (e.g., by non-homologous end joining (NHEJ) or microhomology-mediated end joining (MMEJ).

CRISPR-type genome editing can be adapted for use in the plant cells and methods provided herein in several ways. CRISPR elements, e.g., gene editing molecules comprising CRISPR endonucleases and CRISPR guide RNAs including single guide RNAs or guide RNAs in combination with tracrRNAs or scoutRNA, or polynucleotides encoding the same, are useful in effectuating genome editing without remnants of the CRISPR elements or selective genetic markers occurring in progeny. In certain embodiments, the CRISPR elements are provided directly to the eukaryotic cell (e.g., plant cells), systems, methods, and compositions as isolated molecules, as isolated or semi-purified products of a cell free synthetic process (e.g., in vitro translation), or as isolated or semi-purified products of in a cell-based synthetic process (e.g., such as in a bacterial or other cell lysate). In certain embodiments, genome-inserted CRISPR elements are useful in plant lines adapted for use in the methods provide herein. In certain embodiments, plants or plant cells used in the systems, methods, and compositions provided herein can comprise a transgene that expresses a CRISPR endonuclease (e.g., a Cas9, a Cpf1-type or other CRISPR endonuclease). In certain embodiments, one or more CRISPR endonucleases with unique PAM recognition sites can be used. Guide RNAs (sgRNAs or crRNAs and a tracrRNA) to form an RNA-guided endonuclease/guide RNA complex which can specifically bind sequences in the gDNA target site that are adjacent to a protospacer adjacent motif (PAM) sequence. The type of RNA-guided endonuclease typically informs the location of suitable PAM sites and design of crRNAs or sgRNAs. G-rich PAM sites, e.g., 5'-NGG are typically targeted for design of crRNAs or sgRNAs used with Cas9 proteins. Examples of PAM sequences include 5'-NGG (*Streptococcus pyogenes*), 5'-NNAGAA (*Streptococcus thermophilus* CRISPR1), 5'-NGGNG (*Streptococcus thermophilus* CRISPR3), 5'-NNGRRT or 5'-NNGRR (*Staphylococcus aureus* Cas9, SaCas9), and 5'-NNNNGATT (*Neisseria meningitidis*). T-rich PAM sites (e.g., 5'-TTN or 5'-TTTV, where "V" is A, C, or G) are typically targeted for design of crRNAs or sgRNAs used with Cas12a proteins. In some instances, Cas12a can also recognize a 5'-CTA PAM motif. Other examples of potential Cas12a PAM sequences include TTN, CTN, TCN, CCN, TTTN, TCTN, TTCN, CTTN, ATTN, TCCN, TTGN, GTTN, CCCN, CCTN, TTAN, TCGN, CTCN, ACTN, GCTN, TCAN, GCCN, and CCGN (wherein N is defined as any nucleotide). Cpf1 (i.e., Cas12a) endonuclease and corresponding guide RNAs and PAM sites are disclosed in US Patent Application Publication 2016/0208243 A1, which is incorporated herein by reference for its disclosure of DNA encoding Cpf1 endonucleases and guide RNAs and PAM sites. Introduction of one or more of a wide variety of CRISPR guide RNAs that interact with CRISPR endonucleases integrated into a plant genome or otherwise provided to a plant is useful for genetic editing for providing desired phenotypes or traits, for trait screening, or for gene editing mediated trait introgression (e.g., for introducing a trait into a new genotype without backcrossing to a recurrent parent or with limited backcrossing to a recurrent parent). Multiple endonucleases can be provided in expression cassettes with the appropriate promoters to allow multiple genome site editing.

CRISPR technology for editing the genes of eukaryotes is disclosed in US Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1. Other CRISPR nucleases useful for editing genomes include Cas12b and Cas12c (see Shmakov et al. (2015) Mol. Cell, 60:385-397; Harrington et al. (2020) Molecular Cell doi: 10.1016/j.molcel.2020.06.022) and CasX and CasY (see Burstein et al. (2016) Nature, doi:10.1038/nature21059; Harrington et al. (2020) Molecular Cell doi:10.1016/j.molcel.2020.06.022), or Cas12j (Pausch et al, (2020) Science 10.1126/science.abb1400). Plant RNA promoters for expressing CRISPR guide RNA and plant codon-optimized CRISPR Cas9 endonuclease are disclosed in International Patent Application PCT/US2015/018104 (published as WO 2015/131101 and claiming priority to U.S. Provisional Patent Application 61/945,700). Methods of using CRISPR technology for genome editing in plants are disclosed in US Patent Application Publications US 2015/0082478A1 and US 2015/0059010A1 and in International Patent Application PCT/US2015/038767 A1 (published as WO 2016/007347 and claiming priority to U.S. Provisional Patent Application 62/023,246). All of the patent publications referenced in this paragraph are incorporated herein by reference in their entirety. In certain embodiments, an RNA-guided endonuclease that leaves a blunt end following cleavage of the target site is used. Blunt-end cutting RNA-guided endonucleases include Cas9, Cas12c, and Cas 12h (Yan et al., 2019). In certain embodiments, an RNA-guided endonuclease that leaves a staggered single stranded DNA overhanging end following cleavage of the target site following cleavage of the target site is used. Staggered-end cutting RNA-guided endonucleases include Cas12a, Cas12b, and Cas12e.

The methods can also use sequence-specific endonucleases or sequence-specific endonucleases and guide RNAs that cleave a single DNA strand in a dsDNA target site. Such cleavage of a single DNA strand in a dsDNA target site is also referred to herein and elsewhere as “nicking” and can be effected by various “nickases” or systems that provide for nicking. Nickases that can be used include nCas9 (Cas9 comprising a D10A amino acid substitution), nCas12a (e.g., Cas12a comprising an R1226A amino acid substitution; Yamano et al., 2016), Cas12i (Yan et al. 2019), a zinc finger nickase e.g., as disclosed in Kim et al., 2012), a TALE nickase (e.g., as disclosed in Wu et al., 2014), or a combination thereof. In certain embodiments, systems that provide for nicking can comprise a Cas nuclease (e.g., Cas9 and/or Cas12a) and guide RNA molecules that have at least one base mismatch to DNA sequences in the target editing site (Fu et al., 2019). In certain embodiments, genome modifications can be introduced into the target editing site by creating single stranded breaks (i.e., “nicks”) in genomic locations separated by no more than about 10, 20, 30, 40, 50, 60, 80, 100, 150, or 200 base pairs of DNA. In certain illustrative and non-limiting embodiments, two nickases (i.e., a CAS nuclease which introduces a single stranded DNA break including nCas9, nCas12a, Cas12i, zinc finger nickases, TALE nickases, combinations thereof, and the like) or nickase systems can directed to make cuts to nearby sites separated by no more than about 10, 20, 30, 40, 50, 60, 80 or 100 base pairs of DNA. In instances where an RNA guided nickase and an RNA guide are used, the RNA guides are adjacent to PAM sequences that are sufficiently close (i.e., separated by no more than about 10, 20, 30, 40, 50, 60, 80, 100, 150, or 200 base pairs of DNA). For the purposes of gene editing, CRISPR arrays can be designed to contain one or multiple guide RNA sequences corresponding to a desired target DNA sequence; see, for example, Cong et al. (2013) *Science,* 339:819-823; Ran et al. (2013) *Nature Protocols,* 8:2281-2308. At least 16 or 17 nucleotides of gRNA sequence are required by Cas9 for DNA cleavage to occur; for Cpf1 at least 16 nucleotides of gRNA sequence are needed to achieve detectable DNA cleavage and at least 18 nucleotides of gRNA sequence were reported necessary for efficient DNA cleavage in vitro; see Zetsche et al. (2015) *Cell,* 163:759-771. In practice, guide RNA sequences are generally designed to have a length of 17-24 nucleotides (frequently 19, 20, or 21 nucleotides) and exact complementarity (i.e., perfect base-pairing) to the targeted gene or nucleic acid sequence; guide RNAs having less than 100% complementarity to the target sequence can be used (e.g., a gRNA with a length of 20 nucleotides and 1-4 mismatches to the target sequence) but can increase the potential for off-target effects. The design of effective guide RNAs for use in plant genome editing is disclosed in US Patent Application Publication 2015/0082478 A1, the entire specification of which is incorporated herein by reference. More recently, efficient gene editing has been achieved using a chimeric “single guide RNA” (“sgRNA”), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing); see, for example, Cong et al. (2013) *Science,* 339:819-823; Xing et al. (2014) *BMC Plant Biol.,* 14:327-340. Chemically modified sgRNAs have been demonstrated to be effective in genome editing; see, for example, Hendel et al. (2015) *Nature Biotechnol.,* 985-991. The design of effective gRNAs for use in plant genome editing is disclosed in US Patent Application Publication 2015/0082478 A1, the entire specification of which is incorporated herein by reference.

Genomic DNA may also be modified via base editing. Both adenine base editors (ABE) which convert A/T base pairs to G/C base pairs in genomic DNA as well as cytosine base pair editors (CBE) which effect C to T substitutions can be used in certain embodiments of the methods provided herein. In certain embodiments, useful ABE and CBE can comprise genome site specific DNA binding elements (e.g., RNA-dependent DNA binding proteins including catalytically inactive Cas9 and Cas12 proteins or Cas9 and Cas12 nickases) operably linked to adenine or cytidine deaminases and used with guide RNAs which position the protein near the nucleotide targeted for substitution. Suitable ABE and CBE disclosed in the literature (Kim, Nat Plants, 2018 March; 4(3):148-151) can be adapted for use in the methods set forth herein. In certain embodiments, a CBE can comprise a fusion between a catalytically inactive Cas9 (dCas9) RNA dependent DNA binding protein fused to a cytidine deaminase which converts cytosine (C) to uridine (U) and selected guide RNAs, thereby effecting a C to T substitution; see Komor et al. (2016) *Nature,* 533:420-424. In other embodiments, C to T substitutions are effected with Cas9 nickase [Cas9n(D10A)] fused to an improved cytidine deaminase and optionally a bacteriophage Mu dsDNA (double-stranded DNA) end-binding protein Gam; see Komor et al., *Sci Adv.* 2017 August; 3(8):eaao4774. In other embodiments, adenine base editors (ABEs) comprising an adenine deaminase fused to catalytically inactive Cas9 (dCas9) or a Cas9 D10A nickase can be used to convert A/T base pairs to G/C base pairs in genomic DNA (Gaudelli et al., (2017) *Nature* 551(7681):464-471.

In certain embodiments, zinc finger nucleases or zinc finger nickases can also be used in the methods provided herein. Zinc-finger nucleases are site-specific endonucleases comprising two protein domains: a DNA-binding domain, comprising a plurality of individual zinc finger repeats that each recognize between 9 and 18 base pairs, and a DNA-cleavage domain that comprises a nuclease domain (typically Fokl). The cleavage domain dimerizes in order to cleave DNA; therefore, a pair of ZFNs are required to target non-palindromic target polynucleotides. In certain embodiments, zinc finger nuclease and zinc finger nickase design methods which have been described (Umov et al. (2010) *Nature Rev. Genet.,* 11:636-646; Mohanta et al. (2017) *Genes* vol. 8, 12: 399; Ramirez et al. Nucleic Acids Res. (2012); 40(12): 5560-5568; Liu et al. (2013) *Nature Communications,* 4: 2565) can be adapted for use in the methods set forth herein. The zinc finger binding domains of the zinc finger nuclease or nickase provide specificity and can be engineered to specifically recognize any desired target DNA sequence. The zinc finger DNA binding domains are derived from the DNA-binding domain of a large class of eukaryotic transcription factors called zinc finger proteins (ZFPs). The DNA-binding domain of ZFPs typically contains a tandem array of at least three zinc "fingers" each recognizing a specific triplet of DNA. A number of strategies can be used to design the binding specificity of the zinc finger binding domain. One approach, termed "modular assembly", relies on the functional autonomy of individual zinc fingers with DNA. In this approach, a given sequence is targeted by identifying zinc fingers for each component triplet in the sequence and linking them into a multifinger peptide. Several alternative strategies for designing zinc finger DNA binding domains have also been developed. These methods are designed to accommodate the ability of zinc fingers to contact neighboring fingers as well as nucleotide bases outside their target triplet. Typically, the engineered zinc finger DNA binding domain has a novel binding specificity, compared to a naturally-occurring zinc finger protein. Engineering methods include, for example, rational design and various types of selection. Rational design includes, for example, the use of databases of triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, e.g., U.S. Pat. Nos. 6,453,242 and 6,534,261, both incorporated herein by reference in their entirety. Exemplary selection methods (e.g., phage display and yeast two-hybrid systems) can be adapted for use in the methods described herein. In addition, enhancement of binding specificity for zinc finger binding domains has been described in U.S. Pat. No. 6,794,136, incorporated herein by reference in its entirety. In addition, individual zinc finger domains may be linked together using any suitable linker sequences. Examples of linker sequences are publicly known, e.g., see U.S. Pat. Nos. 6,479,626; 6,903,185; and 7,153,949, incorporated herein by reference in their entirety. The nucleic acid cleavage domain is non-specific and is typically a restriction endonuclease, such as Fokl. This endonuclease must dimerize to cleave DNA. Thus, cleavage by Fokl as part of a ZFN requires two adjacent and independent binding events, which must occur in both the correct orientation and with appropriate spacing to permit dimer formation. The requirement for two DNA binding events enables more specific targeting of long and potentially unique recognition sites. Fokl variants with enhanced activities have been described and can be adapted for use in the methods described herein; see, e.g., Guo et al. (2010) *J Mol. Biol.,* 400:96-107.

Transcription activator like effectors (TALEs) are proteins secreted by certain *Xanthomonas* species to modulate gene expression in host plants and to facilitate the colonization by and survival of the bacterium. TALEs act as transcription factors and modulate expression of resistance genes in the plants. Recent studies of TALEs have revealed the code linking the repetitive region of TALEs with their target DNA-binding sites. TALEs comprise a highly conserved and repetitive region consisting of tandem repeats of mostly 33 or 34 amino acid segments. The repeat monomers differ from each other mainly at amino acid positions 12 and 13. A strong correlation between unique pairs of amino acids at positions 12 and 13 and the corresponding nucleotide in the TALE-binding site has been found. The simple relationship between amino acid sequence and DNA recognition of the TALE binding domain allows for the design of DNA binding domains of any desired specificity. TALEs can be linked to a non-specific DNA cleavage domain to prepare genome editing proteins, referred to as TAL-effector nucleases or TALENs. As in the case of ZFNs, a restriction endonuclease, such as Fokl, can be conveniently used. Methods for use of TALENs in plants have been described and can be adapted for use in the methods described herein, see Mahfouz et al. (2011) Proc. Natl. Acad. Sci. USA, 108:2623-2628; Mahfouz (2011) GM Crops, 2:99-103; and Mohanta et al. (2017) *Genes* vol. 8, 12: 399). TALE nickases have also been described and can be adapted for use in methods described herein (Wu et al.; Biochem Biophys Res Commun. (2014); 446(1):261-6; Luo et al; *Scientific Reports* 6, Article number: 20657 (2016)).

Embodiments of the donor DNA template molecule having a sequence that is integrated at the site of at least one double-strand break (DSB) in a genome include double-stranded DNA, a single-stranded DNA, a single-stranded DNA/RNA hybrid, and a double-stranded DNA/RNA hybrid. In embodiments, a donor DNA template molecule that is a double-stranded (e.g., a dsDNA or dsDNA/RNA hybrid) molecule is provided directly to the plant protoplast or plant cell in the form of a double-stranded DNA or a double-stranded DNA/RNA hybrid, or as two single-stranded DNA (ssDNA) molecules that are capable of hybridizing to form dsDNA, or as a single-stranded DNA molecule and a single-stranded RNA (ssRNA) molecule that are capable of hybridizing to form a double-stranded DNA/RNA hybrid; that is to say, the double-stranded polynucleotide molecule is not provided indirectly, for example, by expression in the cell of a dsDNA encoded by a plasmid or other vector. In various non-limiting embodiments of the method, the donor DNA template molecule that is integrated (or that has a sequence that is integrated) at the site of at least one double-strand break (DSB) in a genome is double-stranded and blunt-ended; in other embodiments the donor DNA template molecule is double-stranded and has an overhang or "sticky end" consisting of unpaired nucleotides (e.g., 1, 2, 3, 4, 5, or 6 unpaired nucleotides) at one terminus or both termini. In an embodiment, the DSB in the genome has no unpaired nucleotides at the cleavage site, and the donor DNA template molecule that is integrated (or that has a sequence that is integrated) at the site of the DSB is a blunt-ended double-stranded DNA or blunt-ended double-stranded DNA/RNA hybrid molecule, or alternatively is a single-stranded DNA or a single-stranded DNA/RNA hybrid molecule. In another embodiment, the DSB in the genome has one or more unpaired nucleotides at one or both sides of the cleavage site, and the donor DNA template molecule that is integrated (or that has a sequence that is integrated) at the site of the DSB is a double-stranded DNA or double-stranded DNA/RNA hybrid molecule with an overhang or "sticky end" consisting of unpaired nucleotides at one or both termini, or alternatively is a single-stranded DNA or a single-stranded DNA/RNA hybrid molecule; in embodiments, the donor DNA template molecule DSB is a double-stranded DNA or double-stranded DNA/RNA hybrid molecule that includes an overhang at one or at both termini, wherein the overhang consists of the same number of unpaired nucleotides as the number of unpaired nucleotides created at the site of a DSB by a nuclease that cuts in an off-set fashion (e.g., where a Cas12 nuclease effects an off-set DSB with 5-nucleotide overhangs in the genomic sequence, the donor DNA template molecule that is to be integrated (or that has a sequence that is to be integrated) at the site of the DSB is double-stranded and has 5 unpaired nucleotides at one or both termini). In certain embodiments, one or both termini of the donor DNA template molecule contain no regions of sequence homology (identity or complementarity) to genomic regions flanking the DSB; that is to say, one or both termini of the donor DNA template molecule contain no regions of sequence that is sufficiently complementary to permit hybridization to genomic regions immediately adjacent to the location of the DSB. In embodiments, the donor DNA template molecule contains no homology to the locus of the DSB, that is to say, the donor DNA template molecule contains no nucleotide sequence that is sufficiently complementary to permit hybridization to genomic regions immediately adjacent to the location of the DSB. In embodiments, the donor DNA template molecule is at least partially double-stranded and includes 2-20 base-pairs, e. g., 2, 3, 4, 5, 6, 7, 8, 9, 10, 11, 12, 13, 14, 15, 16, 17, 18, 19, or 20 base-pairs; in embodiments, the donor DNA template molecule is double-stranded and blunt-ended and consists of 2-20 base-pairs, e.g., 2, 3, 4, 5, 6, 7, 8, 9, 10, 11, 12, 13, 14, 15, 16, 17, 18, 19, or 20 base-pairs; in other embodiments, the donor DNA template molecule is double-stranded and includes 2-20 base-pairs, e.g., 2, 3, 4, 5, 6, 7, 8, 9, 10, 11, 12, 13, 14, 15, 16, 17, 18, 19, or 20 base-pairs and in addition has at least one overhang or "sticky end" consisting of at least one additional, unpaired nucleotide at one or at both termini. In an embodiment, the donor DNA template molecule that is integrated (or that has a sequence that is integrated) at the site of at least one double-strand break (DSB) in a genome is a blunt-ended double-stranded DNA or a blunt-ended double-stranded DNA/RNA hybrid molecule of about 18 to about 300 base-pairs, or about 20 to about 200 base-pairs, or about 30 to about 100 base-pairs, and having at least one phosphorothioate bond between adjacent nucleotides at a 5' end, 3' end, or both 5' and 3' ends. In embodiments, the donor DNA template molecule includes single strands of at least 11, at least 18, at least 20, at least 30, at least 40, at least 60, at least 80, at least 100, at least 120, at least 140, at least 160, at least 180, at least 200, at least 240, at about 280, or at least 320 nucleotides. In embodiments, the donor DNA template molecule has a length of at least 2, at least 3, at least 4, at least 5, at least 6, at least 7, at least 8, at least 9, at least 10, or at least 11 base-pairs if double-stranded (or nucleotides if single-stranded), or between about 2 to about 320 base-pairs if double-stranded (or nucleotides if single-stranded), or between about 2 to about 500 base-pairs if double-stranded (or nucleotides if single-stranded), or between about 5 to about 500 base-pairs if double-stranded (or nucleotides if single-stranded), or between about 5 to about 300 base-pairs if double-stranded (or nucleotides if single-stranded), or between about 11 to about 300 base-pairs if double-stranded (or nucleotides if single-stranded), or about 18 to about 300 base-pairs if double-stranded (or nucleotides if single-stranded), or between about 30 to about 100 base-pairs if double-stranded (or nucleotides if single-stranded). In embodiments, the donor DNA template molecule includes chemically modified nucleotides (see, e.g., the various modifications of internucleotide linkages, bases, and sugars described in Verma and Eckstein (1998) Annu. Rev. Biochem., 67:99-134); in embodiments, the naturally occurring phosphodiester backbone of the donor DNA template molecule is partially or completely modified with phosphorothioate, phosphorodithioate, or methylphosphonate internucleotide linkage modifications, or the donor DNA template molecule includes modified nucleoside bases or modified sugars, or the donor DNA template molecule is labelled with a fluorescent moiety (e.g., fluorescein or rhodamine or a fluorescent nucleoside analogue) or other detectable label (e.g., biotin or an isotope). In another embodiment, the donor DNA template molecule contains secondary structure that provides stability or acts as an aptamer. Other related embodiments include double-stranded DNA/RNA hybrid molecules, single-stranded DNA/RNA hybrid donor molecules, and single-stranded donor DNA template molecules (including single-stranded, chemically modified donor DNA template molecules), which in analogous procedures are integrated (or have a sequence that is integrated) at the site of a double-strand break. Donor DNA templates provided herein include those comprising CgRRS sequences flanked by DNA with homology to a donor DNA template (e.g., SEQ ID NO: 32). In certain embodiments, integration of the donor DNA templates can be facilitated by use of a bacteriophage lambda exonuclease, a bacteriophage lambda beta SSAP protein, and an *E. coli* SSB essentially as set forth in US Patent Application Publication 20200407754, which is incorporated herein by reference in its entirety.

Donor DNA template molecules used in the methods provided herein include DNA molecules comprising, from 5' to 3', a first homology arm, a replacement DNA, and a second homology arm, wherein the homology arms containing sequences that are partially or completely homologous to genomic DNA (gDNA) sequences flanking a target site-specific endonuclease cleavage site in the gDNA. In certain embodiments, the replacement DNA can comprise an insertion, deletion, or substitution of 1 or more DNA base pairs relative to the target gDNA. In an embodiment, the donor DNA template molecule is double-stranded and perfectly base-paired through all or most of its length, with the possible exception of any unpaired nucleotides at either terminus or both termini. In another embodiment, the donor DNA template molecule is double-stranded and includes one or more non-terminal mismatches or non-terminal unpaired nucleotides within the otherwise double-stranded duplex. In an embodiment, the donor DNA template molecule that is integrated at the site of at least one double-strand break (DSB) includes between 2-20 nucleotides in one (if single-stranded) or in both strands (if double-stranded), e. g., 2, 3, 4, 5, 6, 7, 8, 9, 10, 11, 12, 13, 14, 15, 16, 17, 18, 19, or 20 nucleotides on one or on both strands, each of which can be base-paired to a nucleotide on the opposite strand (in the case of a perfectly base-paired double-stranded polynucleotide molecule). Such donor DNA templates can be integrated in genomic DNA containing blunt and/or staggered double stranded DNA breaks by homology-directed repair (HDR). In certain embodiments, a donor DNA template homology arm can be about 20, 50, 100, 200, 400, or 600 to about 800, or 1000 base pairs in length. In certain embodiments, a donor DNA template molecule can be delivered to a plant cell) in a circular (e.g., a plasmid or a viral vector including a geminivirus vector) or a linear DNA molecule. In certain embodiments, a circular or linear DNA molecule that is used can comprise a modified donor DNA template molecule comprising, from 5' to 3', a first copy of the target sequence-specific endonuclease cleavage site sequence, the first homology arm, the replacement DNA, the second homology arm, and a second copy of the target sequence-specific endonuclease cleavage site sequence. Without seeking to be limited by theory, such modified donor DNA template molecules can be cleaved by the same sequence-specific endonuclease that is used to cleave the target site gDNA of the eukaryotic cell to release a donor DNA template molecule that can participate in HDR-mediated genome modification of the target editing site in the plant cell genome. In certain embodiments, the donor DNA template can comprise a linear DNA molecule comprising, from 5' to 3', a cleaved target sequence-specific endonuclease cleavage site sequence, the first homology arm, the replacement DNA, the second homology arm, and a cleaved target sequence-specific endonuclease cleavage site sequence. In certain embodiments, the cleaved target sequence-specific endonuclease sequence can comprise a blunt DNA end or a blunt DNA end that can optionally comprise a 5' phosphate group. In certain embodiments, the cleaved target sequence-specific endonuclease sequence comprises a DNA end having a single-stranded 5' or 3' DNA overhang. Such cleaved target sequence-specific endonuclease cleavage site sequences can be produced by either cleaving an intact target sequence-specific endonuclease cleavage site sequence or by synthesizing a copy of the cleaved target sequence-specific endonuclease cleavage site sequence. Donor DNA templates can be synthesized either chemically or enzymatically (e.g., in a polymerase chain reaction (PCR)). Donor DNA templates provided herein include those comprising CgRRS sequences flanked by DNA with homology to a donor DNA template e (e.g., SEQ ID NO: 32).

Various treatments are useful in delivery of gene editing molecules and/or other molecules to a MIR162 or INIR12 plant cell. In certain embodiments, one or more treatments is employed to deliver the gene editing or other molecules (e.g., comprising a polynucleotide, polypeptide or combination thereof) into a eukaryotic or plant cell, e.g., through barriers such as a cell wall, a plasma membrane, a nuclear envelope, and/or other lipid bilayer. In certain embodiments, a polynucleotide-, polypeptide-, or RNP-containing composition comprising the molecules are delivered directly, for example by direct contact of the composition with a plant cell. Aforementioned compositions can be provided in the form of a liquid, a solution, a suspension, an emulsion, a reverse emulsion, a colloid, a dispersion, a gel, liposomes, micelles, an injectable material, an aerosol, a solid, a powder, a particulate, a nanoparticle, or a combination thereof can be applied directly to a plant, plant part, plant cell, or plant explant (e.g., through abrasion or puncture or otherwise disruption of the cell wall or cell membrane, by spraying or dipping or soaking or otherwise directly contacting, by microinjection). For example, a plant cell or plant protoplast is soaked in a liquid genome editing molecule-containing composition, whereby the agent is delivered to the plant cell. In certain embodiments, the agent-containing composition is delivered using negative or positive pressure, for example, using vacuum infiltration or application of hydrodynamic or fluid pressure. In certain embodiments, the agent-containing composition is introduced into a plant cell or plant protoplast, e.g., by microinjection or by disruption or deformation of the cell wall or cell membrane, for example by physical treatments such as by application of negative or positive pressure, shear forces, or treatment with a chemical or physical delivery agent such as surfactants, liposomes, or nanoparticles; see, e.g., delivery of materials to cells employing microfluidic flow through a cell-deforming constriction as described in US Published Patent Application 2014/0287509, incorporated by reference in its entirety herein. Other techniques useful for delivering the agent-containing composition to a eukaryotic cell, plant cell or plant protoplast include: ultrasound or sonication; vibration, friction, shear stress, vortexing, cavitation; centrifugation or application of mechanical force; mechanical cell wall or cell membrane deformation or breakage; enzymatic cell wall or cell membrane breakage or permeabilization; abrasion or mechanical scarification (e.g., abrasion with carborundum or other particulate abrasive or scarification with a file or sandpaper) or chemical scarification (e.g., treatment with an acid or caustic agent); and electroporation. In certain embodiments, the agent-containing composition is provided by bacterially mediated (e.g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection of the plant cell or plant protoplast with a polynucleotide encoding the genome editing molecules (e.g., RNA dependent DNA endonuclease, RNA dependent DNA binding protein, RNA dependent nickase, ABE, or CBE, and/or guide RNA); see, e.g., Broothaerts et al. (2005) *Nature,* 433:629-633). Any of these techniques or a combination thereof are alternatively employed on the plant explant, plant part or tissue or intact plant (or seed) from which a plant cell is optionally subsequently obtained or isolated; in certain embodiments, the agent-containing composition is delivered in a separate step after the plant cell has been isolated.

In some embodiments, one or more polynucleotides or vectors driving expression of one or more genome editing molecules or trait-conferring genes (e.g.; herbicide tolerance, insect resistance, and/or male sterility) are introduced into a MIR162 or INIR12 plant cell. In certain embodiments, a polynucleotide vector comprises a regulatory element such as a promoter operably linked to one or more polynucleotides encoding genome editing molecules and/or trait-conferring genes. In such embodiments, expression of these polynucleotides can be controlled by selection of the appropriate promoter, particularly promoters functional in a eukaryotic cell (e.g., plant cell); useful promoters include constitutive, conditional, inducible, and temporally or spatially specific promoters (e.g., a tissue specific promoter, a developmentally regulated promoter, or a cell cycle regulated promoter). Developmentally regulated promoters that can be used in plant cells include Phospholipid Transfer Protein (PLTP), fructose-1,6-bisphosphatase protein, NAD (P)-binding Rossmann-Fold protein, adipocyte plasma membrane-associated protein-like protein, Rieske [2Fe-2S] iron-sulfur domain protein, chlororespiratory reduction 6 protein, D-glycerate 3-kinase, chloroplastic-like protein, chlorophyll a-b binding protein 7, chloroplastic-like protein, ultraviolet-B-repressible protein, Soul heme-binding family protein, Photosystem I reaction center subunit psi-N protein, and short-chain dehydrogenase/reductase protein that are disclosed in US Patent Application Publication No. 20170121722, which is incorporated herein by reference in its entirety and specifically with respect to such disclosure. In certain embodiments, the promoter is operably linked to nucleotide sequences encoding multiple guide RNAs, wherein the sequences encoding guide RNAs are separated by a cleavage site such as a nucleotide sequence encoding a microRNA recognition/cleavage site or a self-cleaving ribozyme (see, e.g., Ferré-D'Amaré and Scott (2014) Cold Spring Harbor Perspectives Biol., 2:a003574). In certain embodiments, the promoter is an RNA polymerase III promoter operably linked to a nucleotide sequence encoding one or more guide RNAs. In certain embodiments, the RNA polymerase III promoter is a plant U6 spliceosomal RNA promoter, which can be native to the genome of the plant cell or from a different species, e.g., a U6 promoter from maize, tomato, or soybean such as those disclosed U.S. Patent Application Publication 2017/0166912, or a homologue thereof; in an example, such a promoter is operably linked to DNA sequence encoding a first RNA molecule including a Cas12a gRNA followed by an operably linked and suitable 3' element such as a U6 poly-T terminator. In another embodiment, the RNA polymerase III promoter is a plant U3, 7SL (signal recognition particle RNA), U2, or U5 promoter, or chimerics thereof, e.g., as described in U.S. Patent Application Publication 20170166912. In certain embodiments, the promoter operably linked to one or more polynucleotides is a constitutive promoter that drives gene expression in eukaryotic cells (e.g., plant cells). In certain embodiments, the promoter drives gene expression in the nucleus or in an organelle such as a chloroplast or mitochondrion. Examples of constitutive promoters for use in plants include a CaMV 35S promoter as disclosed in U.S. Pat. Nos. 5,858,742 and 5,322,938, a rice actin promoter as disclosed in U.S. Pat. No. 5,641,876, a maize chloroplast aldolase promoter as disclosed in U.S. Pat. No. 7,151,204, and the nopaline synthase (NOS) and octopine synthase (OCS) promoters from *Agrobacterium tumefaciens*. In certain embodiments, the promoter operably linked to one or more polynucleotides encoding elements of a genome-editing system is a promoter from figwort mosaic virus (FMV), a RUBISCO promoter, or a pyruvate phosphate dikinase (PPDK) promoter, which is active in photosynthetic tissues. Other contemplated promoters include cell-specific or tissue-specific or developmentally regulated promoters, for example, a promoter that limits the expression of the nucleic acid targeting system to germline or reproductive cells (e.g., promoters of genes encoding DNA ligases, recombinases, replicases, or other genes specifically expressed in germline or reproductive cells). In certain embodiments, the genome alteration is limited only to those cells from which DNA is inherited in subsequent generations, which is advantageous where it is desirable that expression of the genome-editing system be limited in order to avoid genotoxicity or other unwanted effects. All of the patent publications referenced in this paragraph are incorporated herein by reference in their entirety.

Expression vectors or polynucleotides provided herein may contain a DNA segment near the 3' end of an expression cassette that acts as a signal to terminate transcription and directs polyadenylation of the resultant mRNA and may also support promoter activity. Such a 3' element is commonly referred to as a "3'-untranslated region" or "3'-UTR" or a "polyadenylation signal." In some cases, plant gene-based 3' elements (or terminators) consist of both the 3'-UTR and downstream non-transcribed sequence (Nuccio et al., 2015). Useful 3' elements include: *Agrobacterium tumefaciens* nos 3', tml 3', tmr 3', tms 3', ocs 3', and tr7 3' elements disclosed in U.S. Pat. No. 6,090,627, incorporated herein by reference, and 3' elements from plant genes such as the heat shock protein 17, ubiquitin, and fructose-1,6-biphosphatase genes from wheat (*Triticum aestivum*), and the glutelin, lactate dehydrogenase, and beta-tubulin genes from rice (*Oryza sativa*), disclosed in US Patent Application Publication 2002/0192813 A1. All of the patent publications referenced in this paragraph are incorporated herein by reference in their entireties.

In certain embodiments, the MIR162 or INIR12 plant cells used herein can comprise haploid, diploid, or polyploid plant cells or plant protoplasts, for example, those obtained from a haploid, diploid, or polyploid plant, plant part or tissue, or callus. In certain embodiments, plant cells in culture (or the regenerated plant, progeny seed, and progeny plant) are haploid or can be induced to become haploid; techniques for making and using haploid plants and plant cells are known in the art, see, e.g., methods for generating haploids in *Arabidopsis thaliana* by crossing of a wild-type strain to a haploid-inducing strain that expresses altered forms of the centromere-specific histone CENH3, as described by Maruthachalam and Chan in "How to make haploid *Arabidopsis thaliana*", protocol available at www [dot]openwetware[dot]org/images/d/d3/Haploid_Arabidopsis_protocol[dot]pdf; (Ravi et al. (2014) *Nature Communications,* 5:5334, doi: 10.1038/ncomms6334). Haploids can also be obtained in a wide variety of monocot plants (e.g., maize, wheat, rice, sorghum, barley) by crossing a plant comprising a mutated CENH3 gene with a wildtype diploid plant to generate haploid progeny as disclosed in U.S. Pat. No. 9,215,849, which is incorporated herein by reference in its entirety. Haploid-inducing maize lines that can be used to obtain haploid maize plants and/or cells include Stock 6, MHI (Moldovian Haploid Inducer), indeterminate gametophyte (ig) mutation, KEMS, RWK, ZEM, ZMS, KMS, and well as transgenic haploid inducer lines disclosed in U.S. Pat. No. 9,677,082, which is incorporated herein by reference in its entirety. Examples of haploid cells include but are not limited to plant cells obtained from haploid plants and plant cells obtained from reproductive tissues, e.g., from flowers, developing flowers or flower buds, ovaries, ovules, megaspores, anthers, pollen, megagametophyte, and microspores. In certain embodiments where the plant cell or plant protoplast is haploid, the genetic complement can be doubled by chromosome doubling (e.g., by spontaneous chromosomal doubling by meiotic non-reduction, or by using a chromosome doubling agent such as colchicine, oryzalin, trifluralin, pronamide, nitrous oxide gas, anti-microtubule herbicides, anti-microtubule agents, and mitotic inhibitors) in the plant cell or plant protoplast to produce a doubled haploid plant cell or plant protoplast wherein the complement of genes or alleles is homozygous; yet other embodiments include regeneration of a doubled haploid plant from the doubled haploid plant cell or plant protoplast. Another embodiment is related to a hybrid plant having at least one parent plant that is a doubled haploid plant provided by this approach. Production of doubled haploid plants provides homozygosity in one generation, instead of requiring several generations of self-crossing to obtain homozygous plants. The use of doubled haploids is advantageous in any situation where there is a desire to establish genetic purity (i.e., homozygosity) in the least possible time. Doubled haploid production can be particularly advantageous in slow-growing plants or for producing hybrid plants that are offspring of at least one doubled-haploid plant.

In certain embodiments, the MIR162 or INIR12 plant cells used in the methods provided herein can include non-dividing cells. Such non-dividing cells can include plant cell protoplasts, plant cells subjected to one or more of a genetic and/or pharmaceutically-induced cell-cycle blockage, and the like.

In certain embodiments, the MIR162 or INIR12 plant cells in used in the methods provided herein can include dividing cells. Dividing cells can include those cells found in various plant tissues including leaves, meristems, and embryos. These tissues include but are not limited to dividing cells from young maize leaf, meristems and scutellar tissue from about 8 or 10 to about 12 or 14 days after pollination (DAP) embryos. The isolation of maize embryos has been described in several publications (Brettschneider, Becker, and Lörz 1997; Leduc et al. 1996; Frame et al. 2011; K. Wang and Frame 2009). In certain embodiments, basal leaf tissues (e.g., leaf tissues located about 0 to 3 cm from the ligule of a maize plant; Kirienko, Luo, and Sylvester 2012) are targeted for HDR-mediated gene editing. Methods for obtaining regenerable plant structures and regenerating plants from the NHEJ-, MMEJ-, or HDR-mediated gene editing of plant cells provided herein can be adapted from methods disclosed in US Patent Application Publication No. 20170121722, which is incorporated herein by reference in its entirety and specifically with respect to such disclosure. In certain embodiments, single plant cells subjected to the HDR-mediated gene editing will give rise to single regenerable plant structures. In certain embodiments, the single regenerable plant cell structure can form from a single cell on, or within, an explant that has been subjected to the NHEJ-, MMEJ-, or HDR-mediated gene editing.

In some embodiments, methods provided herein can include the additional step of growing or regenerating an INIR12 plant from a INIR12 plant cell that had been subjected to the gene editing or from a regenerable plant structure obtained from that INIR12 plant cell. In certain embodiments, the plant can further comprise an inserted transgene, a target gene edit, or genome edit as provided by the methods and compositions disclosed herein. In certain embodiments, callus is produced from the plant cell, and plantlets and plants produced from such callus. In other embodiments, whole seedlings or plants are grown directly from the plant cell without a callus stage. Thus, additional related aspects are directed to whole seedlings and plants grown or regenerated from the plant cell or plant protoplast having a target gene edit or genome edit, as well as the seeds of such plants. In certain embodiments wherein the plant cell or plant protoplast is subjected to genetic modification (for example, genome editing by means of, e.g., an RdDe), the grown or regenerated plant exhibits a phenotype associated with the genetic modification. In certain embodiments, the grown or regenerated plant includes in its genome two or more genetic or epigenetic modifications that in combination provide at least one phenotype of interest. In certain embodiments, a heterogeneous population of plant cells having a target gene edit or genome edit, at least some of which include at least one genetic or epigenetic modification, is provided by the method; related aspects include a plant having a phenotype of interest associated with the genetic or epigenetic modification, provided by either regeneration of a plant having the phenotype of interest from a plant cell or plant protoplast selected from the heterogeneous population of plant cells having a target gene or genome edit, or by selection of a plant having the phenotype of interest from a heterogeneous population of plants grown or regenerated from the population of plant cells having a targeted genetic edit or genome edit. Examples of phenotypes of interest include herbicide resistance, improved tolerance of abiotic stress (e.g., tolerance of temperature extremes, drought, or salt) or biotic stress (e.g., resistance to nematode, bacterial, or fungal pathogens), improved utilization of nutrients or water, modified lipid, carbohydrate, or protein composition, improved flavor or appearance, improved storage characteristics (e.g., resistance to bruising, browning, or softening), increased yield, altered morphology (e.g., floral architecture or color, plant height, branching, root structure). In an embodiment, a heterogeneous population of plant cells having a target gene edit or genome edit (or seedlings or plants grown or regenerated therefrom) is exposed to conditions permitting expression of the phenotype of interest; e.g., selection for herbicide resistance can include exposing the population of plant cells having a target gene edit or genome edit (or seedlings or plants grown or regenerated therefrom) to an amount of herbicide or other substance that inhibits growth or is toxic, allowing identification and selection of those resistant plant cells (or seedlings or plants) that survive treatment. Methods for obtaining regenerable plant structures and regenerating plants from plant cells or regenerable plant structures can be adapted from published procedures (Roest and Gilissen, Acta Bot. Neerl., 1989, 38(1), 1-23; Bhaskaran and Smith, Crop Sci. 30(6):1328-1337; Ikeuchi et al., Development, 2016, 143: 1442-1451). Methods for obtaining regenerable plant structures and regenerating plants from plant cells or regenerable plant structures can also be adapted from US Patent Application Publication No. 20170121722, which is incorporated herein by reference in its entirety and specifically with respect to such disclosure. Also provided are heterogeneous or homogeneous populations of such plants or parts thereof (e.g., seeds), succeeding generations or seeds of such plants grown or regenerated from the plant cells or plant protoplasts, having a target gene edit or genome edit. Additional related aspects include a hybrid plant provided by crossing a first plant grown or regenerated from a plant cell or plant protoplast having a target gene edit or genome edit and having at least one genetic or epigenetic modification, with a second plant, wherein the hybrid plant contains the genetic or epigenetic modification; also contemplated is seed produced by the hybrid plant. Also envisioned as related aspects are progeny seed and progeny plants, including hybrid seed and hybrid plants, having the regenerated plant as a parent or ancestor. The plant cells and derivative plants and seeds disclosed herein can be used for various purposes useful to the consumer or grower. In other embodiments, processed products are made from the INIR12 plant or its seeds, including: (a) maize seed meal (defatted or non-defatted); (b) extracted proteins, oils, sugars, and starches; (c) fermentation products; (d) animal feed or human food products (e.g., feed and food comprising maize seed meal (defatted or non-defatted) and other ingredients (e.g., other cereal grains, other seed meal, other protein meal, other oil, other starch, other sugar, a binder, a preservative, a humectant, a vitamin, and/or mineral; (e) a pharmaceutical; (f) raw or processed biomass (e.g., cellulosic and/or lignocellulosic material); and (g) various industrial products.

EMBODIMENTS

Various embodiments of the plants, genomes, methods, biological samples, and other compositions described herein are set forth in the following sets of numbered embodiments.

1a. A transgenic maize plant cell comprising a first ZmUbiInt promoter, a vip3Aa19 or vip3Aa20 coding region which is operably linked to said promoter, a CaMV 35S terminator element which is operably linked to said vip3Aa19 or vip3Aa20 coding region, and a nopaline synthase terminator element, wherein said cell does not contain a second ZmUbiInt promoter and an operably linked phosphomannose isomerase coding region between said terminator elements, optionally wherein: (i) the ZmUbiInt promoter, the vip3Aa19 or vip3Aa20 coding region which is operably linked to said promoter, the CaMV 35S terminator element which is operably linked to said vip3Aa19 or vip3Aa20 coding region are located in the maize plant cell genomic location of the MIR162 transgenic locus; (ii) wherein a selectable marker or scoreable is absent from said maize plant cell genomic location, and/or (iii) wherein the nopaline synthase terminator element is not separated from the CaMV 35S terminator element by DNA encoding a selectable marker protein, a scoreable marker protein, or a protein conferring a useful trait.

1b. A transgenic maize plant cell comprising a nucleotide sequence comprising a first ZmUbiInt promoter, a vip3Aa19 or vip3Aa20 coding region which is operably linked to said promoter, a CaMV 35S terminator element which is operably linked to said vip3Aa19 or vip3Aa20 coding region, and a nopaline synthase terminator element, wherein said nucleotide sequence does not contain a second ZmUbiInt promoter and an operably linked phosphomannose isomerase coding region between said terminator elements optionally wherein: (i) the ZmUbiInt promoter, the vip3Aa19 or vip3Aa20 coding region which is operably linked to said promoter, the CaMV 35S terminator element which is operably linked to said vip3Aa19 or vip3Aa20 coding region are located in the maize plant cell genomic location of the MIR162 transgenic locus; (ii) wherein a selectable marker or scoreable is absent from said maize plant cell genomic location, and/or (iii) wherein the nopaline synthase terminator element is not separated from the CaMV 35S terminator element by DNA encoding a selectable marker protein, a scoreable marker protein, or a protein conferring a useful trait.

1c. A transgenic maize plant cell comprising a nucleotide sequence comprising a ZmUbiInt promoter, a vip3Aa19 or vip3Aa20 coding region which is operably linked to said promoter, a CaMV 35S terminator element which is operably linked to said vip3Aa19 or vip3Aa20 coding region, and a nopaline synthase terminator element, wherein said nucleotide sequence does not contain a phosphomannose isomerase coding region between said terminator elements, optionally wherein: (i) the ZmUbiInt promoter, the vip3Aa19 or vip3Aa20 coding region which is operably linked to said promoter, the CaMV 35S terminator element which is operably linked to said vip3Aa19 or vip3Aa20 coding region are located in the maize plant cell genomic location of the MIR162 transgenic locus; (ii) wherein a selectable marker or scoreable is absent from said maize plant cell genomic location, and/or (iii) wherein the nopaline synthase terminator element is not separated from the CaMV 35S terminator element by DNA encoding a selectable marker protein, a scoreable marker protein, or a protein conferring a useful trait.

1d. A transgenic maize plant cell comprising a nucleotide sequence comprising a first ZmUbiInt promoter, a vip3Aa19 or vip3Aa20 coding region which is operably linked to said promoter, a CaMV 35S terminator element which is operably linked to said vip3Aa19 or vip3Aa20 coding region, and a nopaline synthase terminator element, wherein said nucleotide sequence does not contain a second ZmUbiInt promoter and an operably linked phosphomannose isomerase coding region, optionally wherein: (i) the ZmUbiInt promoter, the vip3Aa19 or vip3Aa20 coding region which is operably linked to said promoter, the CaMV 35S terminator element which is operably linked to said vip3Aa19 or vip3Aa20 coding region are located in the maize plant cell genomic location of the MIR162 transgenic locus; (ii) wherein a selectable marker or scoreable is absent from said maize plant cell genomic location, and/or (iii) wherein the nopaline synthase terminator element is not separated from the CaMV 35S terminator element by DNA encoding a selectable marker protein, a scoreable marker protein, or a protein conferring a useful trait.

1e. A transgenic maize plant cell comprising a nucleotide sequence comprising a ZmUbiInt promoter, a vip3Aa19 or vip3Aa20 coding region which is operably linked to said promoter, a CaMV 35S terminator element which is operably linked to said vip3Aa19 or vip3Aa20 coding region, and a nopaline synthase terminator element, wherein said nucleotide sequence does not contain a phosphomannose isomerase coding region, optionally wherein: (i) the ZmUbiInt promoter, the vip3Aa19 or vip3Aa20 coding region which is operably linked to said promoter, the CaMV 35S terminator element which is operably linked to said vip3Aa19 or vip3Aa20 coding region are located in the maize plant cell genomic location of the MIR162 transgenic locus; (ii) wherein a selectable marker or scoreable is absent from said maize plant cell genomic location, and/or (iii) wherein the nopaline synthase terminator element is not separated from the CaMV 35S terminator element by DNA encoding a selectable marker protein, a scoreable marker protein, or a protein conferring a useful trait.

1f. A transgenic maize plant cell comprising an INIR12 transgenic locus comprising the first ZmUbiInt promoter, the vip3Aa19 or vip3Aa20 coding region which is operably linked to said promoter, the CaMV 35S terminator element which is operably linked to said vip3Aa19 or vip3Aa20 coding region, and the nopaline synthase terminator element of a MIR162 transgenic locus, allelic variants thereof, or other variants thereof, wherein DNA of said original MIR162 transgenic locus, allelic variants thereof, or other variants thereof comprising a second ZmUbiInt promoter and an operably linked phosphomannose isomerase coding region is absent.

1g. A transgenic maize plant cell comprising an INIR12 transgenic locus comprising an insertion and/or substitution of a DNA element comprising a cognate guide RNA recognition site (CgRRS) in a DNA junction polynucleotide of said INIR12 transgenic locus.

2. The transgenic maize plant cell of embodiment 1a, 1b, 1c, 1d, 1e, or 1f, wherein said INIR12 transgenic locus comprises DNA corresponding to at least nucleotide number 1101 to 5830 of SEQ ID NO:1 or SEQ ID NO:46 and nucleotide number 9111 to 9360 of SEQ ID NO:1 or SEQ ID NO:46, wherein nucleotides corresponding to at least 5850 to 9090 of SEQ ID NO:1 or SEQ ID NO:46 are absent.

3. The transgenic maize plant cell of embodiment 1a, 1b, 1c, 1d, 1e, 1f, or 1g, wherein said INIR12 transgenic locus comprises the DNA molecule set forth in SEQ ID NO: 2, 6, 29, 43, 44, 45, 47, 48, 49, or an allelic variant thereof.

4. The transgenic maize plant cell of embodiment 1a, 1b, 1c, 1d, 1e, or 1f, wherein said INIR12 transgenic locus comprises:

(a) the DNA molecule set forth in SEQ ID NO: 3 wherein nucleotide residues 1081 to 1104 are: (i) each either absent or independently selected from a guanine, a cytosine, an adenine residue, or a thymine residue, with the proviso that nucleotides corresponding to residues 1081 to 1104 of SEQ ID NO: 3 are not identical to residues 1081 to 1104 of SEQ ID NO:1 or SEQ ID NO:46; (ii) comprise about 2 to 8 consecutive residues of nucleotides 1081 to 1092 of SEQ ID NO:1 or SEQ ID NO:46 and/or about 2 to 8 consecutive residues of nucleotides 1093 to 1104 of SEQ ID NO:1 or SEQ ID NO:46, with the proviso that nucleotides corresponding to residues 1081 to 1104 of SEQ ID NO: 3 are not identical to residues 1081 to 1104 of SEQ ID NO:1 or SEQ ID NO:46; (iii) any combination of (i) and (ii); (v) are set forth in SEQ ID NO: 7, wherein n is absent, is independently selected from A, C, G, or T, correspond to 1 to 10 residues of nucleotides 1083 to 1092 of SEQ ID NO:1 or SEQ ID NO:46, and/or correspond to 1 to 10 residues of nucleotides 1093 to 1102 of SEQ ID NO:1 or SEQ ID NO:46 with the proviso that nucleotides corresponding to nucleotide 3 to 22 of SEQ ID NO: 7 are not identical to residues 1083 to 1102 of SEQ ID NO:1 or SEQ ID NO:46; (vi) are set forth in SEQ ID NO: 8; wherein n is absent, is independently selected from A, C, G, or T, correspond to 1 to 5 residues of nucleotides 1088 to 1092 of SEQ ID NO:1 or SEQ ID NO:46, and/or correspond to 1 to 5 residues of nucleotides 1093 to 1097 of SEQ ID NO:1 or SEQ ID NO:46 with the proviso that nucleotides corresponding to residues 8 to 17 of SEQ ID NO: 8 are not identical to residues 1088 to 1097 of SEQ ID NO:1 or SEQ ID NO:46; (vii) are set forth in SEQ ID NO: 9; wherein n is absent, is independently selected from A, C, G, or T, correspond to 1 to 3 residues of nucleotides 1090-1092 of SEQ ID NO:1 or SEQ ID NO:46, and/or correspond to 1 to 3 residues of nucleotides 1093 to 1095 of SEQ ID NO:1 or SEQ ID NO:46 with the proviso that nucleotides corresponding to residues 1090 to 1095 of SEQ ID NO: 9 are not identical to nucleotides 1090 to 1095 of SEQ ID NO:1 or SEQ ID NO:46); or (viii) are set forth in SEQ ID NO:1 or SEQ ID NO:46, 11, 12, 13, 14, 15, 16, 17, 18, or 19 and wherein nucleotides 5831 to 5842 of SEQ ID NO: 3 are each either absent, independently selected from a guanine, a cytosine, an adenine residue, or a thymine residue, comprise or consist of 1 or more nucleotides corresponding to nucleotides 5831 to 5836 of SEQ ID NO:1 or SEQ ID NO:46, and/or comprise or consist of 1 or more nucleotides corresponding to nucleotides 9102 to 9107 of SEQ ID NO:1 or SEQ ID NO:46.

5. The transgenic maize plant cell of embodiment 1a, 1b, 1c, 1d, 1e, or 1f, wherein said INIR12 transgenic locus further comprises an insertion and/or substitution of a DNA element comprising a cognate guide RNA recognition site (CgRRS) in a DNA junction polynucleotide of said INIR12 transgenic locus.

6. The transgenic maize plant cell of embodiment 1g or 5, wherein said cognate guide RNA recognition site (CgRRS) comprises SEQ ID NO: 26, 27, or 28, wherein the insertion and/or substitution is in a 5' junction polynucleotide of said INIR12 transgenic locus and optionally wherein the insertion and/or substitution is in a 5' junction polynucleotide of the INIR12 transgenic locus corresponding to at least one of nucleotides 1079 to 1098 of SEQ ID NO:1 or SEQ ID NO:46.

7. The transgenic maize plant cell of embodiment 6, wherein said CgRRS comprises the DNA molecule set forth in SEQ ID NO: 37.

8. The transgenic maize plant cell of embodiment 1a, 1b, 1c, 1d, 1e, 1f, or 1g, wherein said INIR12 transgenic locus comprises the DNA molecule set forth in SEQ ID NO: 2, 3, 4, 5, 6, 29, 43, 44, 45, 47, 48, 49, or an allelic variant thereof, or wherein said MIR162 transgenic locus is set forth in SEQ ID NO:1 or SEQ ID NO:46, is present in seed deposited at the ATCC under accession No. PTA-8166, is present in progeny thereof, is present in allelic variants thereof, or is present in other variants thereof.

9. A transgenic maize plant part comprising the maize plant cell of any one of embodiments 1a, 1b, 1c, 1d, 1e, 1f, 1g, 2, 3, 4, 5, 6, 7, or 8, wherein said maize plant part is optionally a seed.

10. A transgenic maize plant comprising the maize plant cell of any one of embodiments 1a, 1b, 1c, 1d, 1e, 1f, 1g, 2, 3, 4, 5, 6, 7, 8, or 8.

11. A method for obtaining a bulked population of inbred seed comprising selfing the transgenic maize plant of embodiment 10 and harvesting seed comprising the INIR12 transgenic locus from the selfed maize plant.

12. A method of obtaining hybrid maize seed comprising crossing the transgenic maize plant of embodiment 10 to a second maize plant which is genetically distinct from the first maize plant and harvesting seed comprising the INIR12 transgenic locus from the cross.

13. A DNA molecule comprising SEQ ID NO: 7, 8, 9, 10, 11, 12, 13, 14, 15, 16, 17, 18, 19, 25, 37, 39, 40, 41, 42, 43, 44, 45, 47, 48, 49, 50-167, or an allelic variant thereof.

14. A processed transgenic maize plant product comprising the DNA molecule of embodiment 13.

15. A biological sample containing the DNA molecule of embodiment 13.

16. A nucleic acid molecule adapted for detection of genomic DNA comprising the DNA molecule of embodiment 13, wherein said nucleic acid molecule optionally comprises a detectable label.

17. A method of detecting a plant cell comprising the INIR12 transgenic locus of any one of embodiments 1 a, b, c, d, e, or f to 8, comprising the step of detecting DNA molecule comprising SEQ ID NO: 7, 8, 9, 10, 11, 12, 13, 14, 15, 16, 17, 18, 19, 25, 37, 39, 40, 41, 42, 43, 44, 45, 47, 48, 49, 50-167, or an allelic variant thereof.

18. A method of excising the INIR12 transgenic locus from the genome of the maize plant cell of any one of embodiments 5, 6, 7, or 8, comprising the steps of:

(a) contacting the edited transgenic plant genome of the plant cell of embodiment 5, 6, 7, or 8 with: (i) an RNA dependent DNA endonuclease (RdDe); and (ii) a guide RNA (gRNA) capable of hybridizing to the guide RNA hybridization site of the OgRRS and the CgRRS; wherein the RdDe recognizes a OgRRS/gRNA and a CgRRS/gRNA hybridization complex; and, (b) selecting a transgenic plant cell, transgenic plant part, or transgenic plant wherein the INIR12 transgenic locus flanked by the OgRRS and the CgRRS has been excised.

19. The method of embodiment 18, wherein the OgRRS is located in a 3' flanking DNA junction polynucleotide and comprises SEQ ID NO: 26, 27, or 28 and wherein the CgRRS comprises an insertion or substitution of SEQ ID NO: 26, 27, or 28 in a 5' junction polynucleotide of said INIR12 transgenic locus.

20. The method of embodiment 19, wherein the insertion and/or substitution is in a 5' junction polynucleotide of the INIR12 transgenic locus corresponding to at least one of nucleotides 1079 to 1098 of SEQ ID NO:1 or SEQ ID NO:46.

21. The method of embodiment 19, wherein the CgRRS comprises the DNA molecule set forth in SEQ ID NO: 37.

20a. A method of modifying a transgenic maize plant cell comprising: obtaining a MIR162 maize event plant cell, a representative sample of which was deposited at the ATCC under accession No. PTA-8166, comprising a nucleotide sequence comprising a first ZmUbiInt promoter, a vip3Aa19 or vip3Aa20 coding region which is operably linked to said promoter, a CaMV 35S terminator element which is operably linked to said vip3Aa19 or vip3Aa20 coding region, a second ZmUbiInt promoter and an operably linked phosphomannose isomerase coding region, and a nopaline synthase terminator element; and modifying said nucleotide sequence to eliminate functionality of said phosphomannose isomerase coding region and/or to substantially, essentially, or completely remove said phosphomannose isomerase coding region, and optionally to eliminate functionality of, or substantially, essentially, or completely remove, said second ZmUbiInt promoter.

20b. A method of modifying a transgenic maize plant cell comprising: obtaining a MIR162 maize event plant cell, a representative sample of which was deposited at the ATCC under accession No. PTA-8166, comprising a nucleotide sequence comprising a first ZmUbiInt promoter, a vip3Aa19 or vip3Aa20 coding region which is operably linked to said promoter, a CaMV 35S terminator element which is operably linked to said vip3Aa19 or vip3Aa20 coding region, a second ZmUbiInt promoter and an operably linked phosphomannose isomerase coding region, and a nopaline synthase terminator element; and modifying said nucleotide sequence to substantially, essentially, or completely remove said phosphomannose isomerase coding region, and optionally substantially, essentially, or completely remove said second ZmUniInt promoter.

20c. A method of making transgenic maize plant cell comprising an INIR12 transgenic locus comprising:

(a) contacting the transgenic plant genome of a maize MIR162 plant cell with: (i) a first set of gene editing molecules comprising a first site-specific nuclease which introduces a first double stranded DNA break in a 5' junction polynucleotide of an MIR162 transgenic locus; and (ii) a second set of gene editing molecules comprising a second site-specific nuclease which introduces a second double stranded DNA break between the CaMV35S terminator element and the ZmUbi promoter of said MIR162 transgenic locus which is operably linked to DNA encoding a phosphomannose isomerase (pmi) and a third site specific nuclease which introduces a third double stranded DNA break between the DNA encoding the pmi and DNA encoding the nopaline synthase (nos) terminator element of said MIR162 transgenic locus; and (b) selecting a transgenic maize plant cell, transgenic maize callus, and/or a transgenic maize plant comprising an INIR12 transgenic locus wherein one or more nucleotides of said 5' junction polynucleotide have been deleted and/or substituted, wherein the first ZmUbiInt promoter, the vip3Aa19 or vip3Aa20 coding region which is operably linked to the first ZmUbiInt promoter, the CaMV 35S terminator element which is operably linked to said vip3Aa19 or vip3Aa20 coding region, and the nos terminator element of said MIR162 transgenic locus are present, and wherein DNA of said MIR162 transgenic locus comprising a second ZmUbiInt promoter and an operably linked phosphomannose isomerase coding region is absent, thereby making a transgenic maize plant cell comprising an INIR12 transgenic locus.

21. The method of embodiment 20c, comprising:

(a) contacting the transgenic plant genome of a maize MIR162 plant cell with: (i) a first set of gene editing molecules comprising a first site-specific nuclease which introduces a first double stranded DNA break between nucleotide residues corresponding to nucleotide number 1079 to 1098 of SEQ ID NO:1 or SEQ ID NO:46; and (ii) a second set of gene editing molecules comprising a second site-specific nuclease which introduces a second double stranded DNA break between nucleotide residues corresponding to nucleotide number 5838 to 5858 of SEQ ID NO:1 or SEQ ID NO:46 and a third site specific nuclease which introduces a third double stranded DNA break between nucleotide residues corresponding to nucleotide number 9040 to 9105 of SEQ ID NO:1 or SEQ ID NO:46; and (b) selecting a transgenic maize plant cell, transgenic maize plant callus, and/or a transgenic maize plant wherein one or more nucleotides corresponding to nucleotide number 1081 to 1104 of SEQ ID NO:1 or SEQ ID NO:46 have been deleted and/or substituted, wherein nucleotides corresponding to at least nucleotide number 5858 to 9040 of SEQ ID NO:1 or SEQ ID NO:46 have been deleted and/or replaced, and wherein nucleotides corresponding to at least nucleotide number 1105 to 5837 of SEQ ID NO:1 or SEQ ID NO:46 are retained.

22. The method of embodiment 20c or 21, further comprising contacting the transgenic plant genome of the maize MIR162 plant cell with a donor DNA template comprising a cognate guide RNA recognition site (CgRRS), wherein said CgRRS optionally comprises a polynucleotide set forth in SEQ ID NO: 26, 27, 28, or 37; and selecting a transgenic plant cell wherein said CgRRS has integrated into and/or replaced one or more nucleotides corresponding to at least one of nucleotides 1079 to 1098 of SEQ ID NO:1 or SEQ ID NO:46.

23. The method of any one of embodiments 20c or 21, wherein the gene editing molecules comprise: (i) a zinc finger nuclease; (ii) a TALEN; and/or (iii) an RNA dependent DNA endonuclease (RdDe) and a guide RNA.

24. The method of embodiment 23, wherein the RNA dependent DNA endonuclease (RdDe) comprises a Cas12a RdDe and wherein the guide RNA of said first set of gene editing molecules comprises SEQ ID NO: 20, the guide RNA of said second set of gene-editing molecules comprises SEQ ID NO: 21, and the guide RNA of said third set of gene-editing molecules comprises SEQ ID NO: 23.

25. The method of any one of embodiments 20a, b, or c to 24, further comprising the step of regenerating transgenic maize plant callus and/or a transgenic maize plant comprising the modification or the INIR12 transgenic locus from said transgenic maize plant cell selected in step (c).

26. The method of any one of embodiments 20a, b, or c to 25, further comprising the step of harvesting a transgenic maize plant seed comprising the modification or the INIR12 transgenic locus from the transgenic maize plant comprising the modification or the INIR12 transgenic locus.

27. A transgenic maize plant cell comprising a modification or an INIR12 transgenic locus made by the method of any one of embodiments 20a, b, or c to 25.

28. Transgenic maize plant callus comprising a modification or an INIR12 transgenic locus made by the method of any one of embodiments 20a, b, or c to 25.

29. A transgenic maize plant comprising a modification or an INIR12 transgenic locus made by the method of any one of embodiments 20a, b, or c to 25.

30. A transgenic maize plant seed comprising a modification or an INIR12 transgenic locus made by the method of embodiment 26.

31. A method of using the maize plant cell of any one of embodiments 1a, b, c, d, e, f, h, or g; 2-8, or 27, the maize plant callus of embodiment 28, the maize plant of embodiment 10 or 29, maize plant part of embodiment 9, or maize plant seed of embodiment 30 for collecting nucleic acid analysis data; wherein said method comprises: (a) isolating the nucleic acids from the maize plant cell, the maize plant callus, the maize plant, the maize plant part, or the maize plant seed of and analyzing said nucleic acids, and (c) recording data based on the analysis of the nucleic acids; wherein the nucleic acid analysis data are optionally nucleic acid sequence data or nucleic acid abundance data.

32. A method of collecting nucleic acid analysis data comprising: (a) isolating nucleic acids from the maize plant cell of any one of embodiments 1a, b, c, d, e, f, h, or g, 2-8, or 27, the maize plant callus of embodiment 28, the maize plant of embodiment 10 or 29, maize plant part of embodiment 9, or maize plant seed of embodiment 30; (b) analyzing said nucleic acids; and (c) recording data based on the analysis of the nucleic acids; wherein the nucleic acid analysis data are optionally nucleic acid sequence data or nucleic acid abundance data.

33. A method of plant breeding comprising: (a) isolating nucleic acids from the maize plant cell of any one of embodiments 1a, b, c, d, e, f, h, or g, 2-8, or 27, the maize plant callus of embodiment 28, the maize plant of embodiment 10 or 29, maize plant part of embodiment 9, or maize plant seed of embodiment 30; (b) identifying one or more nucleic acid polymorphisms from the isolated nucleic acids; and (c) selecting a plant having one or more of the identified nucleic acid polymorphisms.

EXAMPLES

Example 1. Application of a Cas12a and Guide RNAs to Change or Excise the 5'-T-DNA Junction Sequence in the MIR162 Event The MIR162 5'-junction sequence shown in FIG. 4 is flanked by three Cas12a recognition sequences, gRNA-1 (SEQ ID NO: 20), gRNA-2 (SEQ ID NO: 21), and gRNA-3 (SEQ ID NO: 22) that can be used to modify some of the 5' junction sequence or eliminate most of it. There are four possible iterations of this approach. The first two depend on gRNA-1 and gRNA-3 alone to disrupt the MIR162 5'-junction sequence. The second two combine gRNA-2 with either gRNA-1 or gRNA-3 to eliminate most of the MIR162 junction sequence. In certain instances, gRNA-1 (SEQ ID NO: 20) is used to modify the 5' DNA junction polynucleotide and obtain a modified 5' junction polynucleotide comprising SEQ ID NO: 39 or 40.

The Cas12a nuclease and the single or combined gRNAs are introduced into the MIR162 event. This can be accomplished in different ways that are familiar to those with ordinary skill in the art. The first is to encode expression of the Cas12a nuclease and gRNA(s) on a T-DNA and transform it into the MIR162 event via *Agrobacterium*-mediated transformation. Alternatively, the T-DNA can be transformed into any convenient maize line, and then crossed with the MIR162 event to combine the Cas12a ribonucleoprotein expressing T-DNA with the MIR162 event. The Cas12a nuclease and gRNAs can also be assembled in vitro then delivered to MIR162 explants as ribonucleoprotein complexes using a biolistic approach (Svitashev et al., 2016; doi: 10.1038/ncomms13274). Also, a plasmid encoding a Cas12a nuclease and the gRNA(s) can be delivered to MIR162 explants using a biolistic approach. This will produce plant cells that have a high likelihood of incurring mutations that disrupt the MIR162 junction sequence. To use the *Agrobacterium* approach a binary vector that contains a strong constitutive expression cassette like the ZmUbi1 promoter::ZmUbi1 terminator driving Cas12a, a PolII or PolIII gene cassette driving the Cas12a gRNA(s) and a CaMV 35S:PAT:NOS or other suitable plant selectable marker is constructed. An expression cassette driving a fluorescent protein like mScarlet may also be useful to the plant transformation process. Constructs are transformed into *Agrobacterium* strain LBA4404.

Maize transformations are performed based on published methods (Ishida et. al, Nature Protocols 2007; 2, 1614-1621). Briefly, immature embryos from inbred line GIBE0104, approximately 1.8-2.2 mm in size, are isolated from surface sterilized ears 10-14 days after pollination. Embryos are placed in an *Agrobacterium* suspension made with infection medium at a concentration of OD 600=1.0. Acetosyringone (200 μM) is added to the infection medium at the time of use. Embryos and *Agrobacterium* are placed on a rocker shaker at slow speed for 15 minutes. Embryos are then poured onto the surface of a plate of co-culture medium. Excess liquid media is removed by tilting the plate and drawing off all liquid with a pipette. Embryos are flipped as necessary to maintain a scutelum up orientation. Coculture plates are placed in a box with a lid and cultured in the dark at 22° C. for 3 days. Embryos are then transferred to resting medium, maintaining the scutellum up orientation. Embryos remain on resting medium for 7 days at 27-28° C. Embryos that produce callus are transferred to Selection 1 medium with 7.5 mg/L phosphinothricin (PPT) and cultured for an additional 7 days. Callused embryos are placed on Selection 2 medium with 10 mg/L PPT and cultured for 14 days at 27-28° C. Growing calli resistant to the selection agent are transferred to Pre-Regeneration media with 10 mg/L PPT to initiate shoot development. Calli remain on Pre-Regeneration media for 7 days. Calli beginning to initiate shoots are transferred to Regeneration medium with 7.5 mg/L PPT in Phytatrays and cultured in light at 27-28° C. Shoots that reach the top of the Phytatray with intact roots are transferred to Shoot Elongation medium prior to transplant into soil and gradual acclimatization to greenhouse conditions.

When a sufficient amount of viable tissue is obtained, it can be screened for mutations at the MIR162 junction sequence, using a PCR-based approach. One way to screen is to design DNA oligonucleotide primers that flank and amplify the MIR162 junction plus surrounding sequence. For example, the primers (5'-tttgcatcattggtgtcatcagttttt-3'; SEQ ID NO: 30) and (5'-tttcccgccttcagtttaaactatcag-3'; SEQ ID NO: 31) will produce a ~310 bp product that can be analyzed for edits at the target site. The size of this product will vary based on the nature of the edit. Amplicons can be sequenced directly using an amplicon sequencing approach or ligated to a convenient plasmid vector for Sanger sequencing. Those plants in which the MIR162 5'-junction sequence is disrupted are selected and grown to maturity.

The DNA encoding the Cas12a reagents can be segregated away from the modified junction sequence in a subsequent generation.

Example 2. Insertion of a CgRRS Element in the 5'-Junction of the MIR162 Event

This example describes the construction of plant expression vectors for *Agrobacterium* mediated maize transformation. Two plant gene expression vectors are prepared. Plant expression cassettes for expressing a Bacteriophage lambda exonuclease, a bacteriophage lambda beta SSAP protein, and an *E. coli* SSB are constructed essentially as set forth in US Patent Application Publication 20200407754, which is incorporated herein by reference in its entirety. A DNA sequence encoding a tobacco c2 nuclear localization signal (NLS) is fused in-frame to the DNA sequences encoding the exonuclease, the bacteriophage lambda beta SSAP protein, and the *E. coli* SSB to provide a DNA sequence encoding the c2 NLS-Exo, c2 NLS lambda beta SSAP, and c2 NLS-SSB fusion proteins that are set forth in SEQ ID NO: 135, SEQ ID NO: 134, and SEQ ID NO: 133 of US Patent Application Publication 20200407754, respectively, and incorporated herein by reference in its entirety. DNA sequences encoding the c2 NLS-Exo, c2 NLS lambda beta SSAP, and c2NLS-SSB fusion proteins are operably linked to a OsUBI1, ZmUBI1, OsACT promoter and a OsUbi1, ZmUBI1, OsACT polyadenylation site respectively, to provide the exonuclease, SSAP, and SSB plant expression cassettes.

A donor DNA template sequence (SEQ ID NO: 32) that targets the 5'-T-DNA junction of the MIR162 event for insertion of a 27 base pair heterologous sequence, that is identical to a Cas12a recognition site at the 3'-junction of the MIR162 T-DNA insert, by HDR is constructed. The donor DNA template sequence includes a replacement template with desired insertion region (27 base pair long sequence of SEQ ID NO: 27) flanked on both sides by homology arms about 500-635 bp in length. The homology arms match (i.e., are homologous to) gDNA (genomic DNA) regions flanking the target gDNA insertion site. The replacement template region comprising the donor DNA template is flanked at each end by DNA sequences identical to the MIR162 5' polynucleotide sequence recognized by an RNA-guided nuclease and one or more gRNA(s) (e.g. gRNAs comprising SEQ ID NO: 20, 21, and 22). In certain cases, a deletion is made in the targeted MIR162 5' polynucleotide sequence (e.g., using gRNAs comprising SEQ ID NO: 20 and 21 in combination or by using gRNAs comprising SEQ ID NO: 21 and 22 in combination).

A plant expression cassette that provides for expression of the RNA-guided sequence-specific Cas12a endonuclease is constructed. A plant expression cassette that provides for expression of a guide RNA complementary to sequences adjacent to the insertion site (e.g. gRNAs comprising SEQ ID NO: 20, 21, and 22) is constructed. An *Agrobacterium* superbinary plasmid transformation vector containing a cassette that provides for the expression of the phosphinothricin N-acetyltransferasesynthase (PAT) protein is constructed. Once the cassettes, donor sequence and *Agrobacterium* superbinary plasmid transformation vector are constructed, they were combined to generate two maize transformation plasmids.

A maize transformation plasmid is constructed with the PAT cassette, the RNA-guided sequence-specific endonuclease cassette, the guide RNA cassette, and the MIR162 5'-junction polynucleotide donor DNA template sequence into the *Agrobacterium* superbinary plasmid transformation vector (the control vector).

A maize transformation plasmid is constructed with the PAT cassette, the RNA-guided sequence-specific endonuclease cassette, the guide RNA cassette, the SSB cassette, the lambda beta SSAP cassette, the Exo cassette, and the MIR162 5'-junction polynucleotide donor DNA template into the *Agrobacterium* superbinary plasmid transformation vector (the lambda red vector).

All constructs are delivered from superbinary vectors in *Agrobacterium* strain LBA4404.

Maize transformations are performed based on published methods (Ishida et. al, Nature Protocols 2007; 2, 1614-1621). Briefly, immature embryos from inbred line GIBE0104, approximately 1.8-2.2 mm in size, are isolated from surface sterilized ears 10-14 days after pollination. Embryos are placed in an *Agrobacterium* suspension made with infection medium at a concentration of $OD_{600}$=1.0. Acetosyringone (200 μM) is added to the infection medium at the time of use. Embryos and *Agrobacterium* are placed on a rocker shaker at slow speed for 15 minutes. Embryos are then poured onto the surface of a plate of co-culture medium. Excess liquid media is removed by tilting the plate and drawing off all liquid with a pipette. Embryos are flipped as necessary to maintain a scutelum up orientation. Co-culture plates are placed in a box with a lid and cultured in the dark at 22° C. for 3 days. Embryos are then transferred to resting medium, maintaining the scutellum up orientation. Embryos remain on resting medium for 7 days at 27-28° C. Embryos that produced callus are transferred to Selection 1 medium with 7.5 mg/L phosphinothricin (PPT) and cultured for an additional 7 days. Callused embryos are placed on Selection 2 medium with 10 mg/L PPT and cultured for 14 days at 27-28° C. Growing calli resistant to the selection agent are transferred to Pre-Regeneration media with 10 mg/L PPT to initiate shoot development. Calli remained on Pre-Regeneration media for 7 days. Calli beginning to initiate shoots are transferred to Regeneration medium with 7.5 mg/L PPT in Phytatrays and cultured in light at 27-28° C. Shoots that reached the top of the Phytatray with intact roots are isolated into Shoot Elongation medium prior to transplant into soil and gradual acclimatization to greenhouse conditions.

When a sufficient amount of viable tissue is obtained, it can be screened for insertion at the MIR162 junction sequence, using a PCR-based approach. The PCR primer on the 5'-end can be 5'-ttttatgtattatttggtccctaca-3' (SEQ ID NO: 33) and the PCR primer on the 3'-end is 5'-gtcgacggcgtttaacaggctggca-3' (SEQ ID NO: 34). These primers that flank donor DNA homology arms are used to amplify the MIR162 5'-junction sequence. The correct donor sequence insertion will produce a 1579 bp product. Amplicons can be sequenced directly using an amplicon sequencing approach or ligated to a convenient plasmid vector for Sanger sequencing. Those plants in which the MIR162 5' junction polynucleotide sequence now contains the intended CgRRS (e.g., Cas12a recognition sequence in SEQ ID NO: 37) are selected and grown to maturity. The T-DNA encoding the Cas12a reagents can be segregated away from the modified junction sequence in a subsequent generation. The resultant INIR12 transgenic locus comprising the CgRRS and OgRRS (e.g. which each comprise SEQ ID NO: 27 and an operably linked PAM site) can be excised using Cas12a and a suitable gRNA which hybridizes to DNA comprising SEQ ID NO: 27 at both the OgRRS and the CgRRS. An example of an INIR12 locus comprising the intended CgRRS in SEQ ID NO: 37 is provided as SEQ ID NO: 44. Another example of an INIR12 locus comprising the intended CgRRS in SEQ ID NO: 37 is provided as SEQ ID NO: 47 and is illustrated in FIG. 6.

Example 3. Deletion of the MIR162 PMI Gene Cassette

The ZmUbi1::PMI coding sequence in MIR162 transgenic maize performs no useful function with respect to field productivity. It can be removed using a Cas12a-mediated genomic DNA deletion approach. The procedure calls for creating an *Agrobacterium* transformation vector encoding the Cas12a nuclease, the MIR162 PMI 5' guide RNA (5'-taattcctaaaaccaaaatccag-3'; SEQ ID NO: 23), the MIR162 PMI 3' guide RNA (5'-ttgccaaatgtttgaacgatctg-3'; SEQ ID NO: 24), and a plant selectable marker gene.

A binary vector that contains a strong constitutive expression cassette like the ZmUbi1 promoter::ZmUbi1 terminator driving Cas12a, a PolII or PolIII gene cassette driving the Cas12a gRNAs and a CaMV 35S:PAT:NOS or other suitable plant selectable marker is constructed. An expression cassette driving a fluorescent protein like mScarlet may also be useful to the plant transformation process and included in the binary vector.

The aforementioned binary vector is transformed into maize using the procedure essentially as outlined in Example 1. The regenerated plants can be screened with the primer set below to identify individuals that have lost the ZmUbi1::PMI fragment. The primers span 3820 bases in the intact insert. If both cuts occur and the ends are ligated together, this will produce a ~555 bp amplicon. This is verified by DNA sequence analysis. The primer set includes 162-PMI-ampseq-5' (5'-ggcaacaacctgtacggcggcccga-3'; SEQ ID NO: 35) and 162-PMI-ampseq-3' (5'-gttgccttcagaccatggcggacgt-3'; SEQ ID NO: 36).

Example 4. Introduction of a CgRRS into an INIR12 Maize Plant Comprising a Deletion of the MIR162 ZmUbi1::PMI Fragment Maize Plants comprising the deletion of the MIR162 ZmUbi1:PMI fragment are subjected to the procedures for integration of the SEQ ID NO: 32 donor DNA template set forth in Example 2 to provide for a resultant INIR12 transgenic locus comprising the CgRRS and OgRRS (e.g. which each comprise SEQ ID NO: 27 and an operably linked PAM site) where the ZmUbi1::PMI fragment is absent. This resultant INIR12 transgenic locus can be excised using Cas12a and a suitable gRNA which hybridizes to DNA comprising SEQ ID NO: 27 at both the OgRRS and the CgRRS. An example of a INIR12 transgenic locus comprising the deletion of the MIR162 ZmUbi1:PMI fragment, the CgRRS sequence, and the OgRRS sequence (e.g. which each comprise SEQ ID NO: 27 and an operably linked PAM site) is set forth in SEQ ID NO: 48.

Example 5. Application of Cas12a and SEQ ID NO: 20 and SEQ ID NO: 22 Guide RNAs to Change or Excise the 5'-T-DNA Junction Sequence in the MIR162 Event Cas12a and SEQ ID NO: 20 and SEQ ID NO: 22 guide RNAs to are used to excise portions of a 5' junction sequence in the MIR162 event as follows.

Maize protoplasts were prepared essentially as described in a preparation protocol modified from one publicly available at molbio[dot]mgh[dot]harvard.edu/sheenweb/protocols_reg[dot]html. Healthy leaf tissue minus the midveins from the third leaf of 10 day old plants were sliced into 0.5 mm segments using a fresh scalpel in Enzyme Solution (0.6 M mannitol, 10 mM MES, 20 mM KCl, 20 mM $CaCl_2$), 0.1% BSA, 1.5% Cellulase RS, 0.3% Macerozyme RO at pH 5.7 and sterilized using a 0.2 micron filter). The tissued was vacuum infiltrated for 30 minutes, and up to 8 leaves were processed in 20 mL Enzyme Solution. Continue digestion for 2.5 hours at 26° C. on shaking incubator at 60 rpm. Samples were sealed with parafilm and incubated in the dark for 2.5 hours at 26° C. while shaking at 60 rpm. The Enzyme solution containing protoplasts was passed through a 40 μm sterile cell strainer into a conical 50 ml falcon tube. The dish was rinsed with 10 mL PVB1 solution (0.6 M mannitol, 10 mM MES, 20 mM KCl, 20 mM $CaCl_2$), 0.1% BSA at pH 5.7 and sterilized using a 0.2 micron filter) which was also passed through the 40 μm sterile cell strainer. The protoplast solution was transferred to a conical round bottom centrifuge tube and gently centrifuged at 200×g for 2 minutes in a swinging bucket rotor. The protoplasts were gently resuspended in 20 mL PVB1 solution then centrifuged as before. This wash step was repeated once more, then the protoplasts were suspended in PVB1 solution at 1000000 protoplasts/mL.

Each plasmid vector encoding genome editing reagents and the fluorescent marker mScarlet (see Sample column in Table 1) was transfected into protoplasts by adding approximately $2\times10^{12}$ copies of plasmid DNA (in 20 μL, TE buffer) to 200 μL, of cells (~250000). Then 220 μL, of PEG solution (200 mM mannitol, 100 mM $CaCl_2$), 40% PEG) was added and the mixture was incubated for 5 minutes at room temperature. Then 1 mL of W5 solution (10 mM MES, 154 mM NaCl, 125 mM $CaCl_2$), 5 mM KCl, 0.1% BSA at pH 5.8 and sterilized using a 0.2 micron filter) was gently added, and the protoplast solution was centrifuged at 200×g for 3 minutes. The protoplast pellet was gently resuspended in 1.7 mL W5 solution and centrifuged cells at 200× g for 2 minutes. The protoplasts were resuspended in W5 buffer, then transferred to a 24 well cell culture plate, at 50000 cells in 500 μL W5 buffer per well. The plates were sealed with Parafilm, wrapped in aluminum foil, and incubated overnight at 28° in an incubator with zero agitation.

Approximately 44 hours after transfection viable protoplasts were assessed by Fluorescein Diacetate (FDA) staining and dead cells were assessed by SytoxGreen staining using standard procedures. The transfection efficiency is the ratio of viable protoplasts to mScarlet positive protoplasts.

Results for a typical experiment are in Table 1. Flow cytometry was used to isolate viable transfected cells expressing mScarlet. Identical cell samples were pooled and stored at −80° C. until DNA extraction.

TABLE 1

Typical Transfection Analysis

| | | Protoplasts | | FDA+ events | | mScarlet+ | |
|---|---|---|---|---|---|---|---|
| Sample | Type | Events | % of total | Events | % of total | Events | % of FDA + |
| B104 with TE buffer no fda | wt control | 9273 | 47.0 | 0 | 0 | 0 | 0 |
| B104 with TE buffer | wt control | 9228 | 51.6 | 2761 | 29.9 | 0 | 0 |
| MIR162 with TE buffer no fda | buffer control | 9299 | 68.7 | 0 | 0 | 0 | 0 |
| MIR162 with TE buffer no fda | buffer control | 9340 | 66.3 | 1368 | 14.6 | 1 | 0.0 |
| MIR162 with Cas12a sample 1 no FDA | vector control | 9237 | 67.5 | 2 | 0.0 | 2 | 100.0 |
| MIR162 with Cas12a sample 1 | vector control | 9408 | 69.1 | 1839 | 19.5 | 329 | 17.9 |
| MIR162 with Cas12a sample 2 | vector control | 9250 | 64.5 | 1474 | 15.9 | 320 | 21.7 |
| MIR162 with SEQ ID NO: 22 vector sample 1 | Edit 1 | 9266 | 67.3 | 1435 | 15.5 | 238 | 16.6 |
| MIR162 with SEQ ID NO: 22 vector sample 2 | Edit 1 | 9081 | 64.4 | 1619 | 17.8 | 251 | 15.5 |
| MIR162 with SEQ ID NO: 22 vector sample 3 | Edit 1 | 9275 | 66.1 | 1547 | 16.7 | 269 | 17.4 |
| MIR162 with SEQ ID NO: 20 vector sample 1 | Edit 2 | 9292 | 67.9 | 1417 | 15.2 | 291 | 20.5 |
| MIR162 with SEQ ID NO: 20 vector sample 2 | Edit 2 | 9364 | 64.9 | 1404 | 15.0 | 242 | 17.2 |
| MIR162 with SEQ ID NO: 20 vector sample 3 | Edit 2 | 9320 | 65.6 | 1457 | 15.6 | 204 | 14.0 |

The gDNA isolation procedure combines the Qiagen DNeasy® plant mini kit protocol with a magnetic bead based nucleic acid clean-up protocol similar to the MAGBIO (Gaithersburg, MD, USA) HighPrep™ PCR Clean-up System. Added 400 μL buffer AP1 and 4 μL RNase A to each sample, thoroughly vortexed and incubate at 65° C. for 10 minutes. The tubes were inverted 2-3 times during incubation. Added 130 μL buffer P3, mixed and incubated for 5 minutes on ice. Centrifuged the lysate for 5 minutes at 20000× g, then added the lysate into a Qiagen QIAshredder spin column and centrifuged for 2 minutes at 20000× g.

A U-bottom 96 well plate was prepared by adding 50 μL resuspended magnetic beads per well. Then 50 μL plant leaf lysate was added to the beads and mixed by pipetting. The remaining lysate was transferred to a new 2 mL Eppendorf tube, mixed with 1.5 volume of AW1 buffer and stored at −20° C. If necessary this sample can be used to extracted gDNA according to the Qiagen DNeasy® plant mini kit protocol (starting at step 7). The bead mixture was incubated for 5 minutes at room temperature, then the U-bottom plate was placed on a magnetic separation device for 3 minutes or until the solution cleared completely. The supernatant was removed and discarded. The beads were washed by adding 200 μL of 80% ethanol and incubating for 30 seconds on the magnetic separation device. The supernatant removed and the 80% ethanol wash was repeated. The beads were air dried at room temperature on the magnetic separation device. The gDNA was eluted by adding in 50 μL EB and incubating for 2 minutes at room temperature.

The plate was placed on the magnetic separation device for 3 minutes or until the solution cleared completely. The supernatant was transferred to a new 96 well plate and stored at either 20° C. (long term) or at 4° C. (short time). Typically 1-2 μL is suitable template for PCR.

The amplicons were produced in 50 μL PCR reaction mixtures containing 50] μL Q5 High-Fidelity 5× buffer, 1 μL 10 mM dNTP mix, 0.5 μL Q5 polymerase, 2.5 μL 10 μM forward primer, 2.5 μL 10 μM reverse primer and 5 μL template DNA. The forward PCR primer for amplicon production is set forth in SEQ ID NO: 168 and the reverse PCT primer for amplicon production is set forth in SEQ ID NO: 169. The thermocycling program was 98° C. for 30 seconds followed by 37 cycles of 98° C. for 10 seconds, 63° C. for 30 seconds and 72° C. for 30 seconds. The final extension was 72° C. for 2 minutes. Products (10 μL) were analyzed on a 2% TAE agarose gel. Each reaction produced a single dominant band at the expected size (about 386 nucleotides). The remaining reaction products were pooled (approx. 2×35 μL) and 400 μL PB buffer (Qiagen) was added. The reaction products were isolated using the Qiagen QIAquick PCR purification kit and each amplicon was eluted in 38 μL EB. The DNA concentration was quantified and adjusted to 20 ng/μL. Amplicon sequencing data were generated and analyzed by standard procedures.

Results of the SEQ ID NO: 20 gRNA mediated deletions of the 5' junction polynucleotide of the MIR162 locus are provided in SEQ ID NO: 50-112, which correspond to the region located between nucleotides 920 to 1240 in the MIR162 locus sequence of SEQ ID NO: 46. Results of the SEQ ID NO: 22 gRNA mediated deletions of the 5' junction polynucleotide in the MIR162 locus are provided in SEQ ID NO: 113-167, which correspond to the region located between nucleotides 920 to 1240 in the MIR162 locus sequence of SEQ ID NO: 46. The amplicon sequence set forth in SEQ ID NO: 112 shows the deletion of the TAGT sequence located at position 1095 to 1098 of SEQ ID NO: 46. A full length sequence of an INIR12 locus comprising the deletion shown in the SEQ ID NO: 112 amplicon sequence is shown in SEQ ID NO: 49.

The breadth and scope of the present disclosure should not be limited by any of the above-described embodiments.

What is claimed is:

1. A transgenic maize plant cell comprising a modified MIR162 transgenic locus;

wherein an unmodified MIR162 transgenic locus comprises an original MIR162 transgenic locus comprising SEQ ID NO: 46;

wherein the modified MIR162 transgenic locus comprises the first ZmUbiInt promoter operably linked to the Vip3Aa20 gene, the CaMV35S terminator, and the NOS terminator of the original MIR162 transgenic locus and;

wherein the DNA molecule encoding the second ZmUbiInt promoter and operably linked phosphomannose isomerase coding region of the original MIR162 transgenic locus are deleted from the modified MIR162 transgenic locus; and wherein the 5' junction polynucleotide of the modified MIR162 transgenic locus comprises the DNA molecule of any one of SEQ ID NO: 50-121, 123-124, 128, 130, 139-140, 142, 144-146, 148, 155-157, 159-162, 164-166.

2. A transgenic maize plant part comprising the maize plant cell of claim 1, wherein said maize plant part is optionally a seed.

3. A transgenic maize plant comprising the maize plant cell of claim 1.

4. A method for obtaining a bulked population of inbred seed comprising selfing the transgenic maize plant of claim 3 and harvesting seed comprising the transgenic locus from the selfed maize plant.

5. A method of obtaining hybrid maize seed comprising crossing the transgenic maize plant of claim 3 to a second maize plant which is genetically distinct from the first maize plant and harvesting seed comprising the transgenic locus from the cross.

6. The transgenic maize plant cell of claim 1, wherein the 5' junction polynucleotide of the modified MIR162 transgenic locus comprises the DNA molecule of any one of SEQ ID NO: 64, 70, 75, 76, 88, 89, 90, 91, 92, 93, 101, 107, 109, 119, 124, 144, 159, 160, or 164.

* * * * *